US010736551B2

(12) United States Patent
Rogers

(10) Patent No.: US 10,736,551 B2
(45) Date of Patent: Aug. 11, 2020

(54) EPIDERMAL PHOTONIC SYSTEMS AND METHODS

(71) Applicant: The Board of Trustees of the University of Illinois, Urbana, IL (US)

(72) Inventor: John A. Rogers, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 230 days.

(21) Appl. No.: 15/501,364

(22) PCT Filed: Aug. 11, 2015

(86) PCT No.: PCT/US2015/044573
§ 371 (c)(1),
(2) Date: Feb. 2, 2017

(87) PCT Pub. No.: WO2016/025430
PCT Pub. Date: Feb. 18, 2016

(65) Prior Publication Data
US 2017/0224257 A1    Aug. 10, 2017

Related U.S. Application Data

(60) Provisional application No. 62/142,877, filed on Apr. 3, 2015, provisional application No. 62/035,823, filed
(Continued)

(51) Int. Cl.
*A61B 5/00* (2006.01)
*A61B 5/1455* (2006.01)
(Continued)

(52) U.S. Cl.
CPC ............ *A61B 5/1455* (2013.01); *A61B 5/002* (2013.01); *A61B 5/0022* (2013.01); *A61B 5/01* (2013.01);
(Continued)

(58) Field of Classification Search
CPC ... A61B 5/1455; A61B 5/1468; A61B 5/6833; A61B 5/0059; A61B 5/0071; A61B 5/01;
(Continued)

(56) References Cited

U.S. PATENT DOCUMENTS 3,822,115 A    7/1974  Morin et al.
3,852,092 A   12/1974  Patterson et al.
(Continued)

FOREIGN PATENT DOCUMENTS

DE        1087752        8/1960
WO    WO 1996/004876     2/1996
(Continued)

OTHER PUBLICATIONS

Åberg et al. (2004) "Skin cancer identification using multifrequency electrical impedance—a potential screening tool," IEEE Transactions on Biomedical Engineering. 51(12):2097-2102.
(Continued)

*Primary Examiner* — Max F Hindenburg
(74) *Attorney, Agent, or Firm* — Leydig, Voit & Mayer, Ltd.

(57) ABSTRACT

The invention provides systems and methods for tissue-mounted photonics. Devices of some embodiments implement photonic sensing and actuation in flexible and/stretchable device architectures compatible with achieving long term, mechanically robust conformal integration with a range of tissue classes, including in vivo biometric sensing for internal and external tissues. Tissue-mounted photonic systems of some embodiments include colorimetric, fluorometric and/or spectroscopic photonics sensors provided in pixelated array formats on soft, elastomeric substrates to achieve spatially and/or or temporally resolved sensing of tissue and/or environmental properties, while minimize adverse physical effects to the tissue. Tissue-mounted pho-
(Continued)

tonic systems of some embodiments enable flexible passive or active optical sensing modalities, including sensing compatible with optical readout using a mobile electronic devices such as a mobile phone or tablet computer.

70 Claims, 53 Drawing Sheets

Related U.S. Application Data on Aug. 11, 2014, provisional application No. 62/035,866, filed on Aug. 11, 2014.

(51) Int. Cl.
   A61B 5/145     (2006.01)
   A61B 10/00     (2006.01)
   A61B 5/1468    (2006.01)
   A61B 5/053     (2006.01)
   A61B 5/01      (2006.01)
   A61B 5/026     (2006.01)

(52) U.S. Cl.
   CPC .......... *A61B 5/0261* (2013.01); *A61B 5/0537* (2013.01); *A61B 5/1451* (2013.01); *A61B 5/1468* (2013.01); *A61B 5/14521* (2013.01); *A61B 5/14532* (2013.01); *A61B 5/14539* (2013.01); *A61B 5/14546* (2013.01); *A61B 5/4875* (2013.01); *A61B 10/0041* (2013.01); A61B 2560/0214 (2013.01); A61B 2560/0223 (2013.01); A61B 2560/0242 (2013.01); A61B 2562/0233 (2013.01); A61B 2562/164 (2013.01)

(58) Field of Classification Search
   CPC .... A61B 2560/0242; A61B 2562/0242; A61B 10/0045; A61B 10/0064; A61B 2010/008
   See application file for complete search history.

(56) References Cited

U.S. PATENT DOCUMENTS

| | | | |
|---|---|---|---|
| 3,951,133 A | 4/1976 | Reese | |
| 3,993,809 A | 11/1976 | Schranz et al. | |
| 4,327,742 A | 5/1982 | Meyers et al. | |
| 4,393,142 A | 7/1983 | Stephens | |
| 4,433,637 A | 2/1984 | Buirley et al. | |
| 5,032,506 A | 7/1991 | Palmer et al. | |
| 5,053,339 A | 10/1991 | Patel | |
| 5,096,671 A | 3/1992 | Kane et al. | |
| 5,207,227 A | 5/1993 | Powers | |
| 5,290,519 A | 3/1994 | Bar-Or et al. | |
| 5,678,566 A | 10/1997 | Dribbon | |
| 5,763,282 A | 6/1998 | Zhang | |
| 7,195,733 B2 | 3/2007 | Rogers et al. | |
| 7,383,072 B2 | 6/2008 | Edmonson et al. | |
| 7,521,292 B2 | 4/2009 | Rogers et al. | |
| 7,557,367 B2 | 7/2009 | Rogers et al. | |
| 7,622,367 B1 | 11/2009 | Nuzzo et al. | |
| 7,635,362 B2 | 12/2009 | Hwang et al. | |
| 7,704,684 B2 | 4/2010 | Rogers et al. | |
| 7,705,280 B2 | 4/2010 | Nuzzo et al. | |
| 7,799,699 B2 | 9/2010 | Nuzzo et al. | |
| 7,932,123 B2 | 4/2011 | Rogers et al. | |
| 7,943,491 B2 | 5/2011 | Nuzzo et al. | |
| 7,969,307 B2 * | 6/2011 | Peeters ................ | A61B 5/0002 340/572.1 |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,357,335 B1 | 1/2013 | Harvey et al. | |
| 8,367,035 B2 | 2/2013 | Rogers et al. | |
| 8,394,706 B2 | 3/2013 | Nuzzo et al. | |
| 8,440,546 B2 | 5/2013 | Nuzzo et al. | |
| 8,470,701 B2 | 6/2013 | Rogers et al. | |
| 8,552,299 B2 | 10/2013 | Rogers et al. | |
| 8,562,095 B2 | 10/2013 | Alleyene et al. | |
| 8,664,699 B2 | 3/2014 | Nuzzo et al. | |
| 8,666,471 B2 | 3/2014 | Rogers et al. | |
| 8,679,888 B2 | 3/2014 | Rogers et al. | |
| 8,722,458 B2 | 5/2014 | Rogers et al. | |
| 8,729,524 B2 | 5/2014 | Rogers et al. | |
| 8,754,396 B2 | 6/2014 | Rogers et al. | |
| 8,865,489 B2 | 10/2014 | Rogers et al. | |
| 8,895,406 B2 | 11/2014 | Rogers et al. | |
| 8,905,772 B2 | 12/2014 | Rogers et al. | |
| 8,934,965 B2 | 1/2015 | Rogers et al. | |
| 8,946,683 B2 | 2/2015 | Rogers et al. | |
| 9,057,994 B2 | 6/2015 | Rogers et al. | |
| 9,061,494 B2 | 6/2015 | Rogers et al. | |
| 9,095,291 B2 * | 8/2015 | Soller ................ | A61B 5/14552 |
| 9,105,555 B2 | 8/2015 | Rogers et al. | |
| 9,105,782 B2 | 8/2015 | Rogers et al. | |
| 9,117,940 B2 | 8/2015 | Rogers et al. | |
| 9,133,024 B2 * | 9/2015 | Phan ................ | B01L 3/502738 |
| 9,278,522 B2 | 3/2016 | Rogers et al. | |
| 9,324,733 B2 | 4/2016 | Rogers et al. | |
| 9,349,900 B2 | 5/2016 | Rogers et al. | |
| 9,372,123 B2 * | 6/2016 | Li ............... | G01K 1/14 |
| 9,420,952 B2 * | 8/2016 | Paquet ................ | A61B 5/0008 |
| 9,442,285 B2 | 9/2016 | Rogers | |
| 9,450,043 B2 | 9/2016 | Nuzzo et al. | |
| 9,487,002 B2 | 11/2016 | Rogers et al. | |
| 9,496,229 B2 | 11/2016 | Rogers et al. | |
| 9,515,025 B2 | 12/2016 | Rogers et al. | |
| 9,554,484 B2 | 1/2017 | Rogers et al. | |
| 9,555,644 B2 | 1/2017 | Rogers et al. | |
| 9,579,040 B2 * | 2/2017 | Rafferty ............ | A61B 5/112 |
| 9,587,991 B2 * | 3/2017 | Padiy ............ | A61B 5/01 |
| 9,601,671 B2 | 3/2017 | Rogers et al. | |
| 9,603,531 B2 * | 3/2017 | Natarajan ............ | A61B 5/026 |
| 9,613,911 B2 | 4/2017 | Rogers et al. | |
| 9,647,171 B2 | 5/2017 | Rogers et al. | |
| 9,691,873 B2 | 6/2017 | Rogers et al. | |
| 9,761,444 B2 | 9/2017 | Nuzzo et al. | |
| 9,765,934 B2 | 9/2017 | Rogers et al. | |
| 9,768,086 B2 | 9/2017 | Nuzzo et al. | |
| 9,782,082 B2 * | 10/2017 | Gannon ............ | A61B 5/002 |
| 9,825,229 B2 | 11/2017 | Rogers et al. | |
| 9,848,815 B2 * | 12/2017 | Abreu ............ | A61B 5/0008 |
| 9,875,974 B2 | 1/2018 | Rogers et al. | |
| 10,022,089 B2 * | 7/2018 | Lechot ............ | A61B 5/6832 |
| 2002/0135772 A1 | 9/2002 | Bornhop et al. | |
| 2002/0156471 A1 | 10/2002 | Stern et al. | |
| 2005/0048571 A1 | 3/2005 | Danielson et al. | |
| 2005/0238967 A1 | 10/2005 | Rogers et al. | |
| 2006/0038182 A1 | 2/2006 | Rogers et al. | |
| 2006/0117859 A1 | 6/2006 | Liu et al. | |
| 2006/0286488 A1 | 12/2006 | Rogers et al. | |
| 2006/0286785 A1 | 12/2006 | Rogers et al. | |
| 2007/0032089 A1 | 2/2007 | Nuzzo et al. | |
| 2008/0055581 A1 | 3/2008 | Rogers et al. | |
| 2008/0108171 A1 | 5/2008 | Rogers et al. | |
| 2008/0157235 A1 | 7/2008 | Rogers et al. | |
| 2008/0212102 A1 | 9/2008 | Nuzzo et al. | |
| 2008/0275319 A1 | 11/2008 | Van Gogh et al. | |
| 2009/0199960 A1 | 8/2009 | Nuzzo et al. | |
| 2009/0204100 A1 | 8/2009 | Van Pieterson et al. | |
| 2009/0294803 A1 | 12/2009 | Nuzzo et al. | |
| 2010/0002402 A1 | 1/2010 | Rogers et al. | |
| 2010/0052112 A1 | 3/2010 | Rogers et al. | |
| 2010/0059863 A1 | 3/2010 | Rogers et al. | |
| 2010/0072577 A1 | 3/2010 | Nuzzo et al. | |
| 2010/0113894 A1 | 5/2010 | Padiy | |
| 2010/0283069 A1 | 11/2010 | Rogers et al. | |
| 2010/0289124 A1 | 11/2010 | Nuzzo et al. | |
| 2010/0302040 A1 | 12/2010 | Davidowitz | |
| 2010/0317132 A1 | 12/2010 | Rogers et al. | |
| 2011/0147715 A1 | 6/2011 | Rogers et al. | |
| 2011/0152643 A1 | 6/2011 | Xue et al. | |

(56) References Cited

U.S. PATENT DOCUMENTS

| | | |
|---|---|---|
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0245713 A1 | 10/2011 | Rensen et al. |
| 2011/0266561 A1 | 11/2011 | Rogers et al. |
| 2011/0277813 A1 | 11/2011 | Rogers et al. |
| 2011/0316120 A1 | 12/2011 | Rogers et al. |
| 2012/0024833 A1 | 2/2012 | Klewer et al. |
| 2012/0071783 A1 | 3/2012 | Klee et al. |
| 2012/0083099 A1 | 4/2012 | Nuzzo et al. |
| 2012/0105528 A1 | 5/2012 | Alleyne et al. |
| 2012/0157804 A1 | 6/2012 | Rogers et al. |
| 2012/0165759 A1 | 6/2012 | Rogers et al. |
| 2012/0190989 A1 | 7/2012 | Kaiser et al. |
| 2012/0238901 A1 | 9/2012 | Augustine |
| 2012/0261551 A1 | 10/2012 | Rogers |
| 2012/0320581 A1 | 12/2012 | Rogers et al. |
| 2012/0321785 A1 | 12/2012 | Rogers et al. |
| 2012/0327608 A1 | 12/2012 | Rogers et al. |
| 2013/0036928 A1 | 2/2013 | Rogers et al. |
| 2013/0041235 A1 | 2/2013 | Rogers et al. |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0150685 A1 | 6/2013 | Toth |
| 2013/0218046 A1 | 8/2013 | Bowman et al. |
| 2013/0245546 A1 | 9/2013 | Hayn |
| 2013/0320503 A1 | 12/2013 | Nuzzo et al. |
| 2013/0333094 A1 | 12/2013 | Rogers et al. |
| 2014/0025000 A1 | 1/2014 | Currie et al. |
| 2014/0092158 A1 | 4/2014 | Alleyne et al. |
| 2014/0140020 A1 | 5/2014 | Rogers et al. |
| 2014/0163390 A1 | 6/2014 | Rogers et al. |
| 2014/0191236 A1 | 7/2014 | Nuzzo et al. |
| 2014/0216524 A1 | 8/2014 | Rogers et al. |
| 2014/0220422 A1 | 8/2014 | Rogers et al. |
| 2014/0305900 A1 | 10/2014 | Rogers et al. |
| 2014/0323968 A1 | 10/2014 | Rogers et al. |
| 2014/0361409 A1 | 12/2014 | Rogers et al. |
| 2014/0373898 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Rogers et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0050750 A1 | 2/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0381789 A1 | 12/2016 | Rogers et al. |
| 2017/0020402 A1 | 1/2017 | Rogers et al. |
| 2017/0128015 A1 | 5/2017 | Rogers et al. |
| 2017/0164482 A1 | 6/2017 | Rogers et al. |
| 2017/0179085 A1 | 6/2017 | Rogers et al. |
| 2017/0179100 A1 | 6/2017 | Rogers et al. |
| 2017/0179356 A1 | 6/2017 | Rogers et al. |
| 2017/0181704 A1 | 6/2017 | Rogers et al. |
| 2017/0200679 A1 | 7/2017 | Rogers et al. |
| 2017/0200707 A1 | 7/2017 | Rogers et al. |
| 2017/0210117 A1 | 7/2017 | Rogers et al. |
| 2017/0224257 A1 | 8/2017 | Rogers et al. |
| 2017/0291817 A1 | 10/2017 | Rogers et al. |
| 2017/0309733 A1 | 10/2017 | Nuzzo et al. |
| 2017/0347891 A1 | 12/2017 | Rogers et al. |
| 2017/0365557 A1 | 12/2017 | Rogers et al. |
| 2018/0014734 A1 | 1/2018 | Rogers et al. |
| 2018/0064377 A1 | 3/2018 | Rogers et al. |

FOREIGN PATENT DOCUMENTS

| | | |
|---|---|---|
| WO | WO 2001/083027 | 11/2001 |
| WO | WO 2005/057467 | 6/2005 |
| WO | WO 2009/144615 | 12/2009 |
| WO | WO 2010/045247 | 4/2010 |
| WO | WO 2013/152087 | 10/2013 |
| WO | WO 2016/196673 | 12/2016 |
| WO | WO 2016/196675 | 12/2016 |
| WO | WO 2017/004531 | 1/2017 |
| WO | WO 2017/004576 | 1/2017 |

OTHER PUBLICATIONS

Agache et al. (1980) Mechanical properties and Young's modulus of human skin in vivo. Arch. Dermatol. Res. 269:221-232.
Ahn et al. (2012) "Stretchable electronics: materials, architectures and integrations," J. Phys. D: Appl. Phys. 45:103001.
Aitken et al. (1996) "Textile applications of thermochromic systems," Rev. Prog. Coloration. 26:1-8.
Akhtar et al. (2010) "Sensitivity of digital thermal monitoring parameters to reactive hyperemia," J. Biomech. Eng. 132:051005.
Alanen et al. (2004) "Measurement of hydration in the stratum corneum with the MoistureMeter and comparison with the Corneometer," Skin Research and Technology. 10(1):32-37.
Alba (Jul. 11, 2014) "Startup Builds Sensors that Will Analyze Sweat to Track Your Health," WIRED. Accessible on the Internet at URL: https://www.wired.com/2014/11/sweat-sensors. [Last Accessed Feb. 27, 2015] 2 pgs.
Allen (2007) "Photoplethysmography and its application in clinical physiological measurement," Physiol. Meas. 28:R1-R39.
Allen et al. (2002) "Microvascular blood flow and skin temperature changes in the fingers following a deep nspiratory gasp," Physiol. Meas. 23:365-373.
Anderson et al. (2005) "Liquid-crystal thermography: Illumination spectral effects. Part 1—Experiments," J. Heat. Trans. 127:581-587.
Armstrong (2007) "Assessing hydration status: the elusive gold standard," Journal of the American College of Nutrition. 26(Suppl 5): 575S-584S.
Armstrong et al. (1997) "Bioimpedance spectroscopy technique: intra-, extracellular, and total body water," Med. Sci. Sports Exerc. 29:1657-1663.
Arnaud et al. (1994) "A micro thermal diffusion sensor for non-invasive skin characterization," Sensors and Actuators: A. Physical. 41:240-243.
Arora et al. (2008) "Effectiveness of a noninvasive digital infrared thermal imaging system in the detection of breast cancer," Am. J. Surg. 196:523-526.
Arora et al. (2008) "Micro-scale devices for transdermal drug delivery," International Journal of Pharmaceutics. 364(2):227-236.
Arumugam et al. (1994) "Effect of strain-rate on the fracture-behavior of skin," Journal of Biosciences. 19:307-313.
Asada et al. (2003) "Hutchinson, Mobile monitoring with wearable photoplethysmographic biosensors," IEEE engineering in medicine and biology magazine: The quarterly magazine of the Engineering in Medicine & Biology Society. 22:28-40.
Badugu et al. (2003) "A Glucose Sensing Contact Lens: A Non-Invasive Technique for Continuous Physiological Glucose Monitoring," J. Fluoresc. 13:371-374.
Badugu et al. (2003) "Non-invasive continuous monitoring of physiological glucose using a monosaccharide-sensing contact lens," Anal. Chem. 76:610-618.
Bakan et al. (1984) "Liquid-crystal microcapsule medical device used for thermographic examination of the human female breast," Appl. Biochem. Biotechnol. 10:289-299.
Bandodkar et al. (2012) "Tattoo-based potentiometric ion-selective sensors for epidermal pH monitoring," Analyst. 138:123-128.

(56) References Cited

OTHER PUBLICATIONS

Bandodkar et al. (Apr. 15, 2014) "Epidermal tattoo potentiometric sodium sensors with wireless signal transduction for continuous non-invasive sweat monitoring," Biosensors and Bioelectronics. 54:603-609.
Bandodkar et al. (Dec. 12, 2014) "Tattoo-Based Noninvasive Glucose Monitoring: A Proof-of-Concept Study," Analytical Chemistry. 87(1):394-398.
Bandodkar et al. (Jul. 18, 2013) "Solid-state Forensic Finger sensor for integrated sampling and detection of gunshot residue and explosives: towards 'Lab-on-a-finger'," Analyst. 138:5288-5295.
Bandodkar et al. (Jul. 2014) "Non-invasive wearable electrochemical sensors: a review," Trends in Biotech. 32(7):363-371.
Barone et al. (1992) "Blood-flow measurements of injured peripheral nerves by laser Doppler flowmetry," J. Reconstr. Microsurg. 8(4):319-323.
Batt et al. (1986) "Hydration of the stratum corneum," International Journal of Cosmetic Science. 8(6):253-264.
Benelam et al. (2010) "Hydration and Health: A Review," Nutr. Bull. 35:3-25.
Bernjak et al. (2008) "Low-frequency blood flow oscillations in congestive heart failure and after beta1-blockade treatment," Microvasc. Res. 76:224-232.
Bhadra et al. (2011) "Wireless Passive Sensor for Remote pH Monitoring," J. Nanotechnol. Eng. Med. 2:011011.
Biagi et al. (2012) "Simultaneous determination of lactate and pyruvate in human sweat using reversed-phase high-performance liquid chromatography: a noninvasive approach," Biomedical Chromatography. 26(11):1408-1415.
Birklein et al. (2008) "Neuropeptides, neurogenic inflammation and complex regional pain syndrome (CRPS)," Neurosci. Lett. 437(3):199-202.
Boas et al. (2010) "Laser speckle contrast imaging in biomedical optics," J. Biomed. Opt. 15(1):011109.
Bohling et al. (Jun. 12, 2013) "Comparison of the stratum corneum thickness measured in vivo with confocal Raman spectroscopy and confocal reflectance microscopy," Skin Res. Technol. 20(1):50-57.
Bonato (2010) "Wearable sensors and systems. From enabling technology to clinical applications," IEEE Eng. Med. Biol. Mag. 29:25-36.
Brenner et al. (1995) "A quantitative test for copper using bicinchoninic acid," Anal. Biochem. 226(1):80-84.
Brull et al. (1990) "Comparison of crystalline skin temperature to esophageal temperatures during anesthesia," Anesthesiology. 73(3A):A472.
Caduff et al. (2009) "Non-invasive glucose monitoring in patients with Type 1 diabetes: a Multisensor system combining sensors for dielectric and optical characterisation of skin," Biosens. Bioelectron. 24:2778-84.
Cameron et al. (1991) "Liquid-crystal thermography as a screening-test for deep-vein thrombosis in patients with cerebral infarction," Eur. J. Clin. Invest. 21:548-550.
Cametti et al. (2011) "Dielectric Relaxation Spectroscopy of Lysozyme Aqueous Solutions: Analysis of the δ-Dispersion and the Contribution of the Hydration Water," J. Phys. Chem. B. 115:7144-7153.
Carmichael et al. (2008) "Activation of the 5-HT1B/D receptor reduces hindlimb neurogenic inflammation caused by sensory nerve stimulation and capsaicin," Pain. 134(1-2):97-105.
Celermajer et al. (1992) "Non-invasive detection of endothelial dysfunction in children and adults at risk of atherosclerosis," Lancet. 340:1111-1115.
Chan et al. (2012) "Smart wearable systems: current status and future challenges," Artif. Intell. Med. 56:137-156.
Cheng et al. (Sep. 6, 2013) "Analysis of a concentric coplanar capacitor for epidermal hydration sensing," Sensors and Actuators A: Physical. 203:149-153.
Ching et al. (2008) "Simultaneous Transdermal Extraction of Glucose and Lactate From Human Subjects by Reverse Iontophoresis," Int. J. Nanomedicine. 3(2):211-223.

Chowdhury et al. (2012) "Application of thermochromic colorants on textiles: temperature dependence of colorimetric properties," Color. Technol. 129:232-237.
Chowdhury et al. (Jan. 2014) "Photochromic and thermochromic colorants in textile applications," J. Eng. Fiber. Fabr. 9:107-123.
clinicaltrials.gov (First Received Sep. 24, 2011) "Genetics and Pain Severity in Sickle Cell Disease," National Institutes of Health. Accessible on the Internet at URL: https://clinicaltrials.gov/ct2/show/NCT01441141. [Last Accessed Sep. 5, 2017].
Cohen (1977) "Measurement of thermal-properties of human-skin—review," J. Invest Dermatol. 69:333-338.
Coyle et al. (2010) "BIOTEX—Biosensing Textiles for Personalized Healthcare Management," IEEE Trans. Inf. Technol. Biomed. 14(2):364-370.
Coyle et al. (2010) "On-Body Chemical Sensors for Monitoring Sweat," In; Lecture Notes in Electrical Engineering: Wearable and Autonomous Biomedical Devices and Systems for Smart Environment. Eds.: Lay-Ekuakille et al. vol. 75. Springer. pp. 177-193.
Crandall et al. (2005) "Palmar skin blood flow and temperature responses throughout endoscopic sympathectomy," Anesth. Anal. 100:277-283.
Curto et al. (2012) "Real-Time Sweat pH Monitoring Based on a Wearable Chemical Barcode Micro-fluidic Platform Incorporating Ionic Liquids," Sensors and Actuators B. 171-172:327-1334.
Davison et al. (1972) "Detection of breast-cancer by liquid-crystal thermography—preliminary report," Cancer 29:1123-1132.
De La Hera et al. (1988) "Co-expression of Mac-1 and p150,95 on CD5+ B cells. Structural and functional characterization in a human chronic lymphocytic leukemia," Eur. J. Immunol. 18(7):1131-4.
Deshmukh (2012) "Enhancing clinical measures of postural stability with wearable sensors," Presented at Engineering in Medicine and Biology Society (EMBC), 2012 Annual International Conference of the IEEE, Aug. 28, 2012-Sep. 1, 2012.
Deshpande (2007) "Thermal analysis of vascular reactivity," MS thesis, Texas A&M University.
Dolphin et al. (1973) "Low-temperature chiral nematic liquid-crystals derived from beta-methylbutylaniline," J. Chem. Phys. 58:413-419.
Drack et al. (Oct. 20, 2014) "An imperceptible plastic electronic wrap," Adv. Mater. 27:34-40.
Draijer et al. (2009) "Review of laser speckle contrast techniques for visualizing tissue perfusion," Lasers in Medical Science. 24:639-651.
Ducharme et al. (1991) "In vivo thermal conductivity of the human forearm tissues," Journal of Applied Physiology. 70:2682-2690.
Dunn et al. (2001) "Dynamic imaging of cerebral blood flow using laser speckle," Journal of Cerebral Blood Flow and Metabolism. 21:195-201.
Egawa et al. (2007) "In vivo estimation of stratum corneum thickness from water concentration profiles obtained with Raman spectroscopy," Acta Derm. Venereol. 87(1):4-8.
El-Brawany et al. (2009) "Measurement of thermal and ultrasonic properties of some biological tissues," Journal of Medical Engineering and Technology. 33:249-256.
Farina et al. (1994) "Illuminant invariant calibration of thermochromic liquid-crystals," Exp. Therm. Fluid. Sci. 9:1-12.
Fiala et al. (1999) "computer model of human thermoregulation for a wide range of environmental conditions: The passive system," J. App. Physiol. 87:1957-1972.
Flammer et al. (2012) "The assessment of endothelial function: from research into clinical practice," Circulation. 126:753-767.
Fonseca et al. (2002) "Wireless micromachined ceramic pressure sensor for high-temperature application," J. Microelectromech. Syst. 11:337-343.
Fujikawa et al. (2009) "Measurement of hemodynamics during postural changes using a new wearable cephalic laser blood flowmeter," Circ. J. 73:1950-1955.
Gao et al. (Sep. 19, 2014) "Epidermal photonic devices for quantitative imaging of temperature and thermal transport characteristics of the skin," Nat. Commun. 5:4938.
Gorbach et al. (2012) "Infrared imaging of nitric oxide-mediated blood flow in human sickle cell disease," Microvasc. Res. 84:262-269.

(56) References Cited

OTHER PUBLICATIONS

Guidotti et al. (2008) "The interpretation of trace element analysis in body fluids," Indian J. Med. Res. 128:524-532.

Guinovart et al. (Sep. 26, 2013) "A potentiometric tattoo sensor for monitoring ammonium in sweat," Analyst. 138:7031-7038.

Gustafsson (1991) "Transient plane source techniques for thermal conductivity and thermal diffusivity measurements of solid materials," Review of Scientific Instruments. 62:797-804.

Hamraoui et al. (2002) "Analytical Approach for the Lucas-Washburn Equation," J. Colloid Interf. Sci. 250:415-421.

Harpster et al. (2002) "A passive wireless integrated humidity sensor," Sens. Actuators A. 95:100-107.

Hassan et al. (2001) "Observation of skin thermal inertia distribution during reactive hyperaemia using a single-hood measurement system," Physiol. Meas. 22:187-200.

Heikenfeld (Oct. 22, 2014) "Sweat Sensors Will Change How Wearables Track Your Health," IEEE Spectrum. Accessible on the Internet at URL: http://spectrum.ieee.org/biomedical/diagnostics/sweat-sensors-will-change-how-wearables-track-your-health. [Last Accessed Feb. 27, 2015] 4 pgs.

Higurashi et al. (2003) "An integrated laser blood flowmeter," Journal of Lightwave Technology. 21:591-595.

Holowatz et al. (2008) "The human cutaneous circulation as a model of generalized microvascular function," J. App. Physiol. 105:370-372.

Hu et al. (2006) "Human body fluid proteome analysis," Proteomics. 6(23):6326-53.

Huang et al. (2007) "Predictive value of reactive hyperemia for cardiovascular events in patients with peripheral arterial disease undergoing vascular surgery," Arterioscl. Throm. Vasc. 27:2113-2119.

Huang et al. (Apr. 6, 2014) "Stretchable, Wireless Sensors and Functional Substrates for Epidermal Characterization of Sweat," Small. 10(15):3083-3090.

Huang et al. (May 31, 2013) "Epidermal impedance sensing sheets for precision hydration assessment and spatial mapping," IEEE Trans. Biomed. Eng. 60(10):2848-57.

Ikeda et al. (1997) "Influence of thermoregulatory vasomotion and ambient temperature variation on the accuracy of core-temperature estimates by cutaneous liquid crystal thermometers," Anesthesiology. 86:603-612.

Ikeda et al. (1998) "Local radiant heating increases subcutaneous oxygen tension," Am. J. Surg. 175:33-37.

Intaglietta (1972) "On-line measurement of microvascular dimensions by television microscopy," J. Appl. Physiol. 32:546-551.

Ireland et al. (1987) "The response-time of a surface thermometer employing encapsulated thermochromic liquid-crystals," J. Phys. E. Sci. Instrum. 20:1195-1199.

Ishibashi et al. (2006) "Short duration of reactive hyperemia in the forearm of subjects with multiple cardiovascular risk factors," Circ. J. 70:115-123.

Jang et al. (Sep. 3, 2014) "Rugged and breathable forms of stretchable electronics with adherent composite substrates for transcutaneous monitoring," Nat. Commun. 5:4779.

Jansky et al. (2003) "Skin temperature changes in humans induced by local peripheral cooling," J. Therm. Biol. 28:429-437.

Jia et al. (Jul. 5, 2013) "Electrochemical tattoo biosensors for real-time noninvasive lactate monitoring in human perspiration," Anal. Chem. 85(14):6553-60.

Jin et al. (2012) "A feasible method for measuring the blood flow velocity in superficial artery based on the laser induced dynamic thermography," Infrared Physics and Technology. 55:462-468.

Kakade et al. (2009) "Accurate heat transfer measurements using thermochromic liquid crystal. Part 1: Calibration and characteristics of crystals," Int. J. Heat. Fluid Fl. 30:939-949.

Kaltenbrunner et al. (Jul. 25, 2013) "An ultra-lightweight design for imperceptible plastic electronics," Nature. 499:458-463.

Kathirgamanathan et al. (2009) "Delineation of distal ulnar nerve anatomy using ultrasound in volunteers to identify an optimum approach for neural blockade," Eur. J. Anaesth. 26:43-46.

Kehoe et al. (Aug. 9, 2013) "Introducing Colorimetric Analysis with Camera Phones and Digital Cameras: An Activity for High School or General Chemistry," J. Chem. Educ. 90:1191-1195.

Kennedy et al. (2009) "A Comparative Review of Thermography as a Breast Cancer Screening Technique," Integr. Cancer Ther. 8:9-16.

Kerr (2004) "Review of the effectiveness of infrared thermal imaging (thermography) for population screening and diagnostic testing of breast cancer," NZHTA Tech Brief Series. vol. 3. No. 3. pp. 1-49.

Khodagholy et al. (2012) "Organic electrochemical transistor incorporating an ionogel as a solid state electrolyte for lactate sensing," J. Mater. Chem. 22:4440-4443.

Kim et al. (2011) "Epidermal Electronics," Science. 333:838-843.

Kim et al. (2012) "Flexible and stretchable electronics for biointegrated devices," Annu. Rev. Biomed. Eng. 14:113-128.

Kim et al. (Nov. 3, 2014) "Epidermal Electronics with Advanced Capabilities in Near-Field Communication," Small. 11(8):906-912.

Klosowicz et al. (2001) "Liquid-crystal thermography and thermovision in medical applications," Proc. SPIE 4535, Optical Sensing for Public Safety, Health, and Security. 4535:24-29.

Kodzwa et al. (2007) "Angular effects on thermochromic liquid crystal thermography," Exp. Fluids. 43:929-937.

Kohler et al. (1998) "Diagnostic value of duplex ultrasound and liquid crystal contact thermography in preclinical detection of deep vein thrombosis after proximal femur fractures," Arch. Orthop. Trauma Surg. 117:39-42.

Kramer et al. (2009) "Increased pain and neurogenic inflammation in mice deficient of neutral endopeptidase," Neurobiol. Dis. 35(2):177-83.

Kvandal et al. (2006) "Low-frequency oscillations of the laser Doppler perfusion signal in human skin," Microvascular Research. 72:120-127.

Lacour et al. (2004) "Design and performance of thin metal film interconnects for skin-like electronic circuits," IEEE Electr. Device. Lett. 25:179-181.

Larrañaga et al. (2012) "Heat Stress," In; Patty's Toxicology. 98:37-78.

Less et al. (1991) "Microvascular architecture in a mammary carcinoma: branching patterns and vessel dimensions," Cancer Research. 51:265-273.

Li et al. (2004) "Stretchability of thin metal films on elastomer substrates," Appl. Phys. Lett. 85:3435-3437.

Liao et al. (2012) "A 3-muhboxW CMOS Glucose Sensor for Wireless Contact-Lens Tear Glucose Monitoring," IEEE J. Solid State Circuits. 47:335-344.

Lindner (2004) "Microbubbles in medical imaging: Current applications and future directions," Nature Reviews Drug Discovery. 3:527-532.

Lossius et al. (1993) "Fluctuations in blood-flow to acral skin in humans—connection with heart-rate and blood-pressure variability," J. Physiol. 460:641-655.

Lu et al. (2012) "A thermal analysis of the operation of microscale, inorganic light-emitting diodes," Proceedings of the Royal Society A. 468:3215-3223.

Lu et al. (2012) "Highly Sensitive Skin-Mountable Strain Gauges Based Entirely on Elastomers," Adv. Funct. Mater. 22:4044-4050.

Lymberis (2010) "Advancced Wearable Sensors and Systems Enabling Personal Applications," In; Lecture Notes in Electrical Engineering: Wearable and Autonomous Biomedical Devices and Systems for Smart Environment. Eds.: Lay-Ekuakille et al. vol. 75. Springer. pp. 237-257.

Mangos et al. (1967) "Sodium Transport: Inhibitory Factor in Sweat of Patients with Cystic Fibrosis," Science. 158:135-136.

Mannsfeld et al. (2010) "Highly sensitive flexible pressure sensors with microstructured rubber dielectric layers," Nat. Mater. 9:859-864.

Marceau et al. (1983) "Pharmacology of kinins: their relevance to tissue injury and inflammation," Gen. Pharmacol. 14(2):209-29.

Martinez et al. (2007) "Patterned Paper as a Platform for Inexpensive, Low-Volume, Portable Bioassays," Angewandte Chemie International Edition. 46(8):1318-1320.

(56) References Cited

OTHER PUBLICATIONS

Martinez et al. (2008) "Simple Telemedicine for Developing Regions: Camera Phones and Paper-Based Microfluidic Devices for Real-Time, Off-Site Diagnosis," Analytical Chemistry. 80(10):3699-3707.
Martinez et al. (2010) "Diagnostics for the Developing World: Microfluidic Paper-Based Analytical Devices," Analytical Chemistry. 82(1):3-10.
Martinsen et al. (1999) "Measuring depth depends on frequency in electrical skin impedance measurements," Skin Research and Technology. 5(3):179-181.
Matzeu et al. (May 2015) "Advances in wearable chemical sensor design for monitoring biological fluids," Sensors and Actuators B. 211:403-418.
Mayrovitz et al. (2002) "Inspiration-induced vascular responses in finger dorsum skin," Microvasc. Res. 63:227-232.
McCartney et al. (2007) "Ultrasound Examination of Peripheral Nerves in the Forearm," Reg. Anesth. Pain Med. 32:434-439.
McDonald et al. (2002) "Poly(dimethylsiloxane) as a Material for Fabricating Microfluidic Devices," Accounts of Chemical Research. 35(7):491-499.
Mishra et al. (2005) "The Relevance of Sweat Testing for the Diagnosis of Cystic Fibrosis in the Genomic Era," Clin. Biochem. Rev. 26(4):135-153.
Moyer et al. (2012) "Correlation Between Sweat Glucose and Blood Glucose in Subjects with Diabetes," Diabetes Technology & Therapeutics. 14(5):398-402.
Mukerjee et al. (2004) "Microneedle Array for Transdermal Biological Fluid Extraction and In Situ Analysis," Sensors and Actuators A: Physical. 114(2-3):267-275.
Newman et al. (1984) "Liquid-crystal thermography in the evaluation of chronic back pain—a comparative-study," Pain. 20:293-305.
Nilsson et al. (1980) "Evaluation of a laser Doppler flowmeter for measurement of tissue blood flow," IEEE Transactions on Biomedical Engineering. 27:597-604.
Nitzan et al. (1986) "Theoretical-Analysis of the Transient Thermal Clearance Method for Regional Blood-Flow Measurement," Medical & Biological Engineering & Computing. 24:597-601.
Nitzan et al. (1988) "Simultaneous measurement of skin blood flow by the transient thermal-clearance method and laser Doppler flowmetry," Medical & Biological Engineering & Computing. 26:407-410.
Nopper et al. (2010) "Wireless Readout of Passive LC Sensors," IEEE Trans. Instrum. Meas. 59:2450-57.
Nordin (1990) "Sympathetic discharges in the human supraorbital nerve and their relation to sudo- and vasomotor responses," J. Physiol. 423:241-255.
Oberg (1990) "Laser-Doppler flowmetry," Critical Reviews in Biomedical Engineering. 18(2):125-163.
Oncescu et al. (Jun. 19, 2013) "Smartphone based health accessory for colorimetric detection of biomarkers in sweat and saliva," Lab Chip 13:3232-3238.
Paranjape et al. (2003) A PDMS dermal patch for non-intrusive transdermal glucose sensing. Sens. Actuat. A. 104:195-204.
Park et al. (2008) "The effect of heat on skin permeability," Int. J. Pharm. 359(1-2):94-103.
Pelrine et al. (2000) "High-field deformation of elastomeric dielectrics for actuators," Mater. Sci. Eng. C. 11:89-100.
Petrie et al. (1988) "How reproducible is bilateral forearm plethysmography?" British Journal of Clinical Pharmacology. 45:131-139.
Petrofsky (2012) "Resting blood flow in the skin: does it exist, and what is the influence of temperature, aging, and diabetes?" Journal of Diabetes Science and Technology. 6:674-685.
Pochaczevsky (1983) "The value of liquid-crystal thermography in the diagnosis of spinal root compression syndromes," Orthop. Clin. N. Am. 14:271-288.
Pochaczevsky et al. (1979) "Vacuum contoured, liquid-crystal, dynamic breast thermoangiography as an aid to mammography in the detection of breast-cancer," Clin. Radiol. 30:405-411.
Pochaczevsky et al. (1982) "Liquid crystal contact thermography of deep venous thrombosis," Am. J. Roentgenol. 138:717-723.
Pochaczevsky et al. (1982) "Liquid-crystal thermography of the spine and extremities—its value in the diagnosis of spinal root syndromes," J. Neurosurg. 56:386-395.
Polliack et al. (1997) "Sweat analysis following pressure ischaemia in a group of debilitated subjects," J. Rehabil. Res. Dev. 34(3):303-308.
Powers et al. (2009) :Rapid Measurement of Total Body Water to Facilitate Clinical Decision Making in Hospitalized Elderly Patients, J. Gerontol. A. Biol. Sci. Med. Sci. 64(6):664-9.
Prausnitz et al. (2008) "Transdermal drug delivery," Nature Biotechnology. 26(11):1261-1268.
Raamat et al. (2002) "Simultaneous recording of fingertip skin blood flow changes by multiprobe laser Doppler flowmetry and frequency-corrected thermal clearance," Microvascular Research. 64:214-219.
Rao et al. (2010) "Calibrations and the measurement uncertainty of wide-band liquid crystal thermography," Meas. Sci. Technol. 21(1):015105. pp. 1-8.
Ritz (2001) "Bioelectrical impedance analysis estimation of water compartments in elderly diseased patients: the source study," J. Gerontol. 56:M344-M348.
Robertson et al. (2010) "Variation in epidermal morphology in human skin at different body sites as measured by reflectance confocal microscopy," Acta Derm. Venereol. 90(4):368-73.
Roda et al. (Dec. 21, 2014) "A 3D-printed device for a smartphone-based chemilumin-escence biosensor for lactate in oral fluid and sweat," Analyst. 139:6494-6501.
Rogers et al. (2010) "Materials and mechanics for stretchable electronics," Science. 327:1603-1607.
Rose et al. (Nov. 11, 2014) "Adhesive RFID Sensor Patch for Monitoring of Sweat Electrolytes," IEEE Trans. Biomed. Eng. 62(6):1457-65.
Rosenbaum (2001) "Thermal properties and characterization of methane hydrates," M.S. thesis, University of Pittsburgh.
Sabatino et al. (2000) "A high-accuracy calibration technique for thermochromic liquid crystal temperature measurements," Exp. Fluids. 28:497-505.
Sage (2011) "Thermochromic liquid crystals," Liquid Crystals. 38:1551-1561.
Salvo et al. (2010) "A Wearable Sensor for Measuring Sweat Rate," IEEE Sens. J. 10:1557-1558.
Sandby-Moller et al. (2003) "Epidermal thickness at different body sites: Relationship to age, gender, pigmentation, blood content, skin type and smoking habits," Acta. Derm. Venereol. 83:410-413.
Sangkatumvong et al. (2011) "Peripheral vasoconstriction and abnormal parasympathetic response to sighs and transient hypoxia in sickle cell disease," Am. J. Respir. Crit. Care Med. 184:474-481.
Schrope et al. (1993) "Second harmonic ultrasonic blood perfusion measurement," Ultrasound in Medicine and Biology. 19:567-579.
Schwartz et al. (May 14, 2013) "Flexible polymer transistors with high pressure sensitivity for application in electronic skin and health monitoring," Nat. Commun. 4:1859. pp. 1-8.
Sekitani et al. (2008) "A rubberlike stretchable active matrix using elastic conductors," Science 321:1468-1472.
Sekitani et al. (2009) "Organic nonvolatile memory transistors for flexible sensor arrays," Science. 326:1516-1519.
Shen et al. (2006) "A genomewide scan for quantitative trait loci underlying areal bone size variation in 451 Caucasian families," J. Med. Genet. 43:873-880.
Shih et al. (2002) "Effect of effective tissue conductivity on thermal dose distributions of living tissue with directional blood flow during thermal therapy," International Communications in Heat and Mass Transfer. 29:115-126.
Shima et al. (1996) "An anatomical study on the forearm vascular system," J. Cranio. Maxill. Surg. 24:293-299.
Shpilfoygel et al. (2000) "X-ray videodensitometric methods for blood flow and velocity measurement: a critical review of literature," Medical Physics. 27:2008-2023.

(56) References Cited

OTHER PUBLICATIONS

Sieg et al. (2003) "Subcutaneous fat layer in different donor regions used for harvesting microvascular soft tissue flaps in slender and adipose patients," International Journal of Oral and Maxillofacial Surgery. 32:544-547.
Sikirzhytski et al. (2010) "Discriminant Analysis of Raman Spectra for Body Fluid Identification for Forensic Purposes," Sensors. 10(4):2869-2884.
Someya et al. (2005) "Conformable, flexible, large-area networks of pressure and thermal sensors with organic transistor active matrixes," Proc. Natl. Acad. Sci. USA. 102:12321-12325.
Son et al. (Mar. 30, 2014) "Multifunctional wearable devices for diagnosis and therapy of movement disorders," Nat. Nanotechnol. 9:397-404.
Sondheimer (1952) "The Mean Free Path of Electrons in Metals," Adv. Phys. 1:1-42.
Song et al. (1988) "A combined macro and microvascular model for whole limb heat transfer," J. Biomech. Eng. 110:259-268.
Stasiek et al. (2002) "Thermochromic liquid crystals applied for heat transfer research," Proceedings of the SPIE, vol. 4759:374-383.
Strommer et al. (2007) "Ultra-low Power Sensors with Near Field Communication for Mobile Applications," In; Wireless Sensor and Actor Networks. vol. 248. Springer. pp. 131-142.
Su et al. (2011) "A polymer stacking process with 3D electrical routings for flexible temperature sensor array and its heterogeneous integration," In; The 16th International Solid-State Sensors, Actuators and Microsystems Conference (Transducers), 2011. pp. 1396-1399.
Sun et al. (2009) "Inorganic islands on a highly stretchable polyimide substrate," J. Mater. Res. 24:3338-3342.
Sutera et al. (1993) "The History of Poiseuille's Law," Annu. Rev. Fluid Mech. 25:1-20.
Suzuki (1998) "Nickel and gold in skin lesions of pierced earlobes with contact dermatitis. A study using scanning electron microscopy and x-ray microanalysis," Arch. Dermatol. Res. 290:523-527.
Tee et al. (2012) "An electrically and mechanically self-healing composite with pressure- and flexion-sensitive properties for electronic skin applications," Nat. Nanotechnol. 7:825-832.
Ten Berge et al. (2011) "Perforating Veins: An Anatomical Approach to Arteriovenous Fistula Performance in the Forearm," European Journal of Vascular and Endovascular Surgery. 42:103-106.
Thalayasingam et al. (1989) "Thermal Clearance Blood-Flow Sensor Sensitivity, Linearity and Flow Depth Discrimination," Medical & Biological Engineering & Computing. 27:394-398.
Thomas et al. (1989) "Liquid-crystal thermography and c-reactive protein in the detection of deep venous thrombosis," Bri. Med. J. 299:951-952.
Thoresen et al. (1980) "Skin blood-flow in humans as a function of environmental-temperature measured by ultrasound," Acta Physiol. Scand. 109:333-341.
Togawa et al. (1994) "Non-contact imaging of thermal properties of the skin," Physiological Measurement. 15:291-298.
Van De Staak et al. (1968) "Measurements of Thermal Conductivity of Skin as an Indication of Skin Blood Flow," J. Invest. Dermatol. 51:149-154.
Varkey et al. (2011) "Human motion recognition using a wireless sensor-based wearable system," Pers. Ubiquit. Comput. 16(7):897-910.
Virkler et al. (2009) "Analysis of body fluids for forensic purposes: From laboratory testing to non-destructive rapid confirmatory identification at a crime scene," Forensci. Sci. Int. 188(1-3):1-17.
Wang et al. (2012) "Mechanics of Epidermal Electronics," Journal of Applied Mechanics. 79:031022.
Wang et al. (Jul. 21, 2013) "User-interactive electronic-skin for instantaneous pressure visualization," Nat. Mater. 12:899-904.
Wardell et al. (1993) "Laser Doppler perfusion imaging by dynamic light scattering," IEEE Transactions on Biomedical Engineering. 40:309-316.
Washburn (1921) "The Dynamics of Capillary Flow," Phys. Rev. 17(3):273.
Webb et al. (Feb. 6, 2015) "Thermal transport characteristics of human skin measured in vivo using ultrathin conformal arrays of thermal sensors and actuators," PLoS One. 10:e0118131. pp. 1-17.
Webb et al. (Oct. 30, 2015) "Epidermal devices for noninvasive, precise, and continuous mapping of macrovascular and microvascular blood flow," Sci Adv. 1(9):e1500701. pp. 1-13.
Webb et al. (Sep. 15, 2013) "Ultrathin conformal devices for precise and continuous thermal characterization of human skin," Nat. Mater. 12:938-944.
Weber et al. (2001) "Facilitated neurogenic inflammation in complex regional pain syndrome," Pain. 91(3):251-7.
Werner et al. (1992) "Measurement of the thermal diffusivity of human epidermis by studying thermal wave propagation," Physics in Medicine and Biology. 37:21-35.
Wilkinson et al. (2001) "Venous occlusion plethysmography in cardiovascular research: methodology and clinical applications," British Journal of Clinical Pharmacology. 52:631-646.
Windmiller et al. (Sep. 7, 2012) "Wearable Electrochemical Sensors and Biosensors: A Review," Electroanalysis. 25(1):29-46.
Wright et al. (2006) "Non-invasive methods and stimuli for evaluating the skin's microcirculation," Journal of Pharmacological and Toxicological Methods. 54:1-25.
Xiao et al. (1997) "Optothermal measurement of stratum corneum thickness and hydration-depth profile," In; The Proc. SPIE 2970, Lasers in Surgery: Advanced Characterization, Therapeutics, and Systems VII., 12 pgs.
Xiao et al. (2010) "Opto-thermal in-vivo skin hydration measurements—a comparison study of different measurement techniques," J. Phys. Conf. Ser. 214:012026. pp. 1-4.
Xiao et al. (2010) "Thermal diffusivity effect in opto-thermal skin measurements," J. Phys. Conf. Ser. 214:012027. pp. 1-4.
Xu et al. (Apr. 4, 2014) "Soft Microfluidic Assemblies of Sensors, Circuits, and Radios for the Skin," Science. 344:70-74.
Yamamoto et al. (1976) "Electrical properties of the epidermal stratum corneum," Medical and Biological Engineering. 14(2):151-158.
Yeo et al. (Feb. 26, 2013) "Multifunctional Epidermal Electronics Printed Directly Onto the Skin," Advanced Materials. 25:2773-2778.
Yu et al. (2012) "An Interstitial Fluid Transdermal Extraction System for Continuous Glucose Monitoring," J. Microelectromech. Syst. 21(4):917-925.
Zakharov et al. (2009) "A wearable diffuse reflectance sensor for continuous monitoring of cutaneous blood content," Physics in Medicine and Biology. 54:5301-5320.
Zamir et al. (2012) "Intrinsic microvasculature of the sciatic nerve in the rat," J. Peripher. Nerv. Syst. 17(4):377-84.
Zeng et al. (Jun. 18, 2014) "Fiber-Based Wearable Electronics: A Review of Materials, Fabrication, Devices, and Applications," Adv. Mater. 26:5310-5336.
International Search Report with Written Opinion corresponding to International Patent Application No. PCT/US2015/044573, dated Nov. 19, 2015, 8 pgs.
International Search Report with Written Opinion corresponding to International Patent Application No. PCT/US2015/044588, dated Jan. 7, 2016, 9 pgs.
International Search Report with Written Opinion corresponding to International Patent Application No. PCT/US2015/044638, dated Apr. 21, 2016, 23 pgs.
International Search Report with Written Opinion corresponding to International Patent Application No. PCT/US2015/053452, dated Mar. 10, 2016, 10 pgs.
Supplementary European Search Report corresponding to European Patent Application No. 15831510.1, dated Mar. 8, 2018.
U.S. Appl. No. 11/001,689, filed Dec. 1, 2004, 2006/0286488, Dec. 21, 2006, U.S. Pat. No. 7,704,684, Apr. 27, 2010.
U.S. Appl. No. 11/115,954, filed Apr. 27, 2005, 2005/0238967, Oct. 27, 2005, U.S. Pat. No. 7,195,733, Mar. 27, 2007.
U.S. Appl. No. 11/145,574, filed Jun. 2, 2005, 2009/0294803, Dec. 3, 2009, U.S. Pat. No. 7,622,367, Nov. 24, 2009.
U.S. Appl. No. 11/145,542, filed Jun. 2, 2005, 2006/0038182, Feb. 23, 2006, U.S. Pat. No. 7,557,367, Jul. 7, 2009.

(56) References Cited

OTHER PUBLICATIONS

U.S. Appl. No. 11/421,654, filed Jun. 1, 2006, 2007/0032089, Feb. 8, 2007, U.S. Pat. No. 7,799,699, Sep. 21, 2010.
U.S. Appl. No. 11/423,287, filed Jun. 9, 2006, 2006/0286785, Dec. 21, 2006, U.S. Pat. No. 7,521,292, Apr. 21, 2009.
U.S. Appl. No. 11/423,192, filed Jun. 9, 2006, 2009/0199960, Aug. 13, 2009, U.S. Pat. No. 7,943,491, May 17, 2011.
U.S. Appl. No. 11/465,317, filed Aug. 17, 2006.
U.S. Appl. No. 11/675,659, filed Feb. 16, 2007, 2008/0055581, Mar. 6, 2008.
U.S. Appl. No. 11/782,799, filed Jul. 25, 2007, 2008/0212102, Sep. 4, 2008, U.S. Pat. No. 7,705,280, Apr. 27, 2010.
U.S. Appl. No. 11/851,182, filed Sep. 6, 2007, 2008/0157235, Jul. 3, 2008, U.S. Pat. No. 8,217,381, Jul. 10, 2012.
U.S. Appl. No. 11/858,788, filed Sep. 20, 2007, 2008/0108171, May 8, 2008, U.S. Pat. No. 7,932,123, Apr. 26, 2011.
U.S. Appl. No. 11/981,380, filed Oct. 31, 2007, 2010/0283069, Nov. 11, 2010, U.S. Pat. No. 7,972,875, Jul. 5, 2011.
U.S. Appl. No. 12/372,605, filed Feb. 17, 2009.
U.S. Appl. No. 12/398,811, filed Mar. 5, 2009, 2010/0002402, Jan. 7, 2010, U.S. Pat. No. 8,552,299, Oct. 8, 2013.
U.S. Appl. No. 12/405,475, filed Mar. 17, 2009, 2010/0059863, Mar. 11, 2010, U.S. Pat. No. 8,198,621, Jun. 12, 2012.
U.S. Appl. No. 12/418,071, filed Apr. 3, 2009, 2010/0052112, Mar. 4, 2010, U.S. Pat. No. 8,470,701, Jun. 25, 2013.
U.S. Appl. No. 12/564,566, filed Sep. 22, 2009, 2010/0072577, Mar. 25, 2010, U.S. Pat. No. 7,982,296, Jul. 19, 2011.
U.S. Appl. No. 12/669,287, filed Jan. 15, 2010, 2011/0187798, Aug. 4, 2011, U.S. Pat. No. 9,061,494, Jun. 23, 2015.
U.S. Appl. No. 12/778,588, filed May 12, 2010, 2010/0317132, Dec. 16, 2010, U.S. Pat. No. 8,865,489, Oct. 21, 2014.
U.S. Appl. No. 12/844,492, filed Jul. 27, 2010, 2010/0289124, Nov. 18, 2010, U.S. Pat. No. 8,039,847, Oct. 18, 2011.
U.S. Appl. No. 12/892,001, filed Sep. 28, 2010, 2011/0230747, Sep. 22, 2011, U.S. Pat. No. 8,666,471, Mar. 4, 2014.
U.S. Appl. No. 12/916,934, filed Nov. 1, 2010, 2012/0105528, May 3, 2012, U.S. Pat. No. 8,562,095, Oct. 22, 2013.
U.S. Appl. No. 12/947,120, filed Nov. 16, 2010, 2011/0170225, Jul. 14, 2011, U.S. Pat. No. 9,057,994, Jun. 16, 2015.
U.S. Appl. No. 12/996,924, filed Dec. 8, 2010, 2011/0147715, Jun. 23, 2011, U.S. Pat. No. 8,946,683, Feb. 3, 2015.
U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/120,486, filed Aug. 4, 2011, 2011/0277813, Nov. 17, 2011, U.S. Pat. No. 8,679,888, Mar. 25, 2014.
U.S. Appl. No. 13/228,041, filed Sep. 8, 2011, 2011/0316120, Dec. 29, 2011.
U.S. Appl. No. 13/270,954, filed Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012, U.S. Pat. No. 9,442,285, Sep. 13, 2016.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/472,165, filed May 15, 2012, 2012/0320581, Dec. 20, 2012, U.S. Pat. No. 9,765,934, Sep. 19, 2017.
U.S. Appl. No. 13/486,726, filed Jun. 1, 2012, 2013/0072775, Mar. 21, 2013, U.S. Pat. No. 8,934,965, Jan. 13, 2015.
U.S. Appl. No. 13/492,636, filed Jun. 8, 2012, 2013/0041235, Feb. 14, 2013.

U.S. Appl. No. 13/549,291, filed Jul. 13, 2012, 2013/0036928, Feb. 14, 2013, U.S. Pat. No. 9,555,644, Jan. 31, 2017.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013, U.S. Pat. No. 9,691,873, Jun. 27, 2017.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/835,284, filed Mar. 15, 2013, 2014/0220422, Aug. 7, 2014.
U.S. Appl. No. 13/853,770, filed Mar. 29, 2013, 2013/0333094, Dec. 19, 2013, U.S. Pat. No. 9,554,484, Jan. 24, 2017.
U.S. Appl. No. 13/974,963, filed Aug. 23, 2013, 2014/0140020, May 22, 2014, U.S. Pat. No. 8,905,772, Dec. 9, 2014.
U.S. Appl. No. 14/033,765, filed Sep. 23, 2013, 2014/0092158, Apr. 3, 2014, U.S. Pat. No. 9,278,522, Mar. 8, 2016.
U.S. Appl. No. 14/140,299, filed Dec. 24, 2013, 2014/0163390, Jun. 12, 2014.
U.S. Appl. No. 14/155,010, filed Jan. 14, 2014, 2014/0191236, Jul. 10, 2014, U.S. Pat. No. 9,450,043, Sep. 20, 2016.
U.S. Appl. No. 14/173,525, filed Feb. 5, 2014, 2014/0216524, Aug. 7, 2014, U.S. Pat. No. 9,105,782, Aug. 11, 2015.
U.S. Appl. No. 14/209,481, filed Mar. 13, 2014, 2014/0373898, Dec. 25, 2014, U.S. Pat. No. 9,117,940, Aug. 25, 2015.
U.S. Appl. No. 14/220,910, filed Mar. 20, 2014, 2014/0374872, Dec. 25, 2014, U.S. Pat. No. 9,324,733, Apr. 26, 2016.
U.S. Appl. No. 14/220,923, filed Mar. 20, 2014, 2015/0001462, Jan. 1, 2015, U.S. Pat. No. 9,105,555, Aug. 11, 2015.
U.S. Appl. No. 14/246,962, filed Apr. 7, 2014, 2014/0361409, Dec. 11, 2014, U.S. Pat. No. 9,349,900, May 24, 2016.
U.S. Appl. No. 14/251,259, filed Apr. 11, 2014, 2014/0323968, Oct. 30, 2014.
U.S. Appl. No. 14/250,671, filed Apr. 11, 2014, 2014/0305900, Oct. 16, 2014, U.S. Pat. No. 9,496,229, Nov. 15, 2016.
U.S. Appl. No. 14/479,100, filed Sep. 5, 2014, 2015/0132873, May 14, 2015, U.S. Pat. No. 9,647,171, May 9, 2017.
U.S. Appl. No. 14/504,736, filed Oct. 2, 2014, 2015/0141767, May 21, 2015.
U.S. Appl. No. 14/521,319, filed Oct. 22, 2014, 2015/0181700, Jun. 25, 2015.
U.S. Appl. No. 14/532,687, filed Nov. 4, 2014, 2015/0080695, Mar. 19, 2015.
U.S. Appl. No. 14/599,290, filed Jan. 16, 2015, 2015/0207012, Jul. 23, 2015.
U.S. Appl. No. 14/686,304, filed Apr. 14, 2015, 2015/0290938, Oct. 15, 2015, U.S. Pat. No. 9,487,002, Nov. 8, 2016.
U.S. Appl. No. 14/706,733, filed May 7, 2015, 2015/0237711, Aug. 20, 2015.
U.S. Appl. No. 14/789,645, filed Jul. 1, 2015, 2016/0027737, Jan. 28, 2016, U.S. Pat. No. 9,515,025, Dec. 6, 2016.
U.S. Appl. No. 14/800,363, filed Jul. 15, 2015, 2016/0072027, Mar. 10, 2016, U.S. Pat. No. 9,601,671, Mar. 21, 2017.
U.S. Appl. No. 14/818,109, filed Aug. 4, 2015, 2016/0050750, Feb. 18, 2016.
U.S. Appl. No. 14/766,333, filed Aug. 6, 2015, 2015/0380355, Dec. 31, 2015, U.S. Pat. No. 9,613,911, Apr. 4, 2017.
U.S. Appl. No. 14/766,926, filed Aug. 10, 2015, 2016/0066789, Mar. 10, 2016.
U.S. Appl. No. 14/772,354, filed Sep. 2, 2015, 2016/0005700, Jan. 7, 2016, U.S. Pat. No. 9,875,974, Jan. 23, 2018.
U.S. Appl. No. 14/772,312, filed Sep. 2, 2015, 2016/0133843, May 12, 2016, U.S. Pat. No. 9,825,229, Nov. 21, 2017.
U.S. Appl. No. 14/944,039, filed Nov. 17, 2015, 2016/0136877, May 19, 2016.
U.S. Appl. No. 14/766,301, filed Dec. 24, 2015, 2015/0373831, Dec. 24, 2015.
U.S. Appl. No. 15/084,091, filed Mar. 29, 2016, 2016/0284544, Sep. 29, 2016, U.S. Pat. No. 9,761,444, Sep. 12, 2017.
U.S. Appl. No. 15/084,211, filed Mar. 29, 2016, 2016/0293794, Oct. 6, 2016, U.S. Pat. No. 9,768,086, Sep. 19, 2017.
U.S. Appl. No. 15/084,112, filed Mar. 29, 2016, 2016/0381789, Dec. 29, 2016.

(56) References Cited

OTHER PUBLICATIONS

U.S. Appl. No. 15/146,629, filed May 4, 2016, 2017/0020402, Jan. 26, 2017.
U.S. Appl. No. 15/339,338, filed Oct. 31, 2016, 2017/0200679, Jul. 13, 2017.
U.S. Appl. No. 15/349,525, filed Nov. 11, 2016, 2017/0128015, May 11, 2017.
U.S. Appl. No. 15/351,234, filed Nov. 14, 2016, 2017/0164482, Jun. 8, 2017.
U.S. Appl. No. 15/354,951, filed Nov. 17, 2016, 2017/0291817, Oct. 12, 2017.
U.S. Appl. No. 15/374,926, filed Dec. 9, 2016, 2017/0210117, Jul. 27, 2017.
U.S. Appl. No. 15/375,514, filed Dec. 12, 2016, 2017/0181704, Dec. 12, 2016.
U.S. Appl. No. 15/402,684, filed Jan. 10, 2017, 2017/0179100, Jun. 22, 2017.
U.S. Appl. No. 15/402,718, filed Jan. 10, 2017, 2017/0179085, Jan. 10, 2017.
U.S. Appl. No. 15/402,723, filed Jan. 10, 2017, 2017/0179356, Jun. 22, 2017.
U.S. Appl. No. 15/501,373, filed Feb. 2, 2017, 2017/0231571, Aug. 17, 2017.
U.S. Appl. No. 15/501,379, filed Feb. 2, 2017, 2018/0014734, Jan. 18, 2018.
U.S. Appl. No. 15/470,780, filed Mar. 27, 2017, 2017/0200707, Jul. 13, 2017.
U.S. Appl. No. 15/515,494, filed Mar. 29, 2017, 2017/0347891, Dec. 7, 2017.
U.S. Appl. No. 15/477,865, filed Apr. 3, 2017, 2017/0365557, Dec. 21, 2017.
U.S. Appl. No. 15/625,087, filed Jun. 16, 2017, 2018/0064377, Mar. 8, 2018.
U.S. Appl. No. 15/632,004, filed Jun. 23, 2017.
U.S. Appl. No. 15/640,206, filed Jun. 30, 2017, 2017/0309733, Oct. 26, 2017.
U.S. Appl. No. 15/578,602, filed Nov. 30, 2017.
U.S. Appl. No. 15/578,617, filed Nov. 30, 2017.
U.S. Appl. No. 15/741,081, filed Dec. 29, 2017.
U.S. Appl. No. 15/738,043, filed Dec. 19, 2017.
U.S. Appl. No. 15/861,257, filed Jan. 3, 2018.
U.S. Appl. No. 15/865,033, filed Jan. 8, 2018.
PCT/US16/35331, Jun. 1, 2016, WO 2016/196673, Dec. 8, 2016.
PCT/US16/35336, Jun. 1, 2016, WO 2016/196675, Dec. 8, 2016.
PCT/US16/40717, Jul. 1, 2016, WO 2017/004531, Jan. 5, 2017.
PCT/US16/40814, Jul. 1, 2016, WO 2017/004576, Jan. 5, 2017.

\* cited by examiner

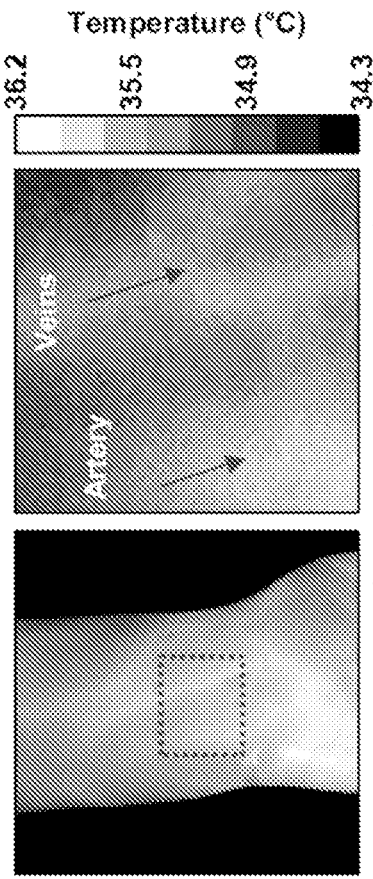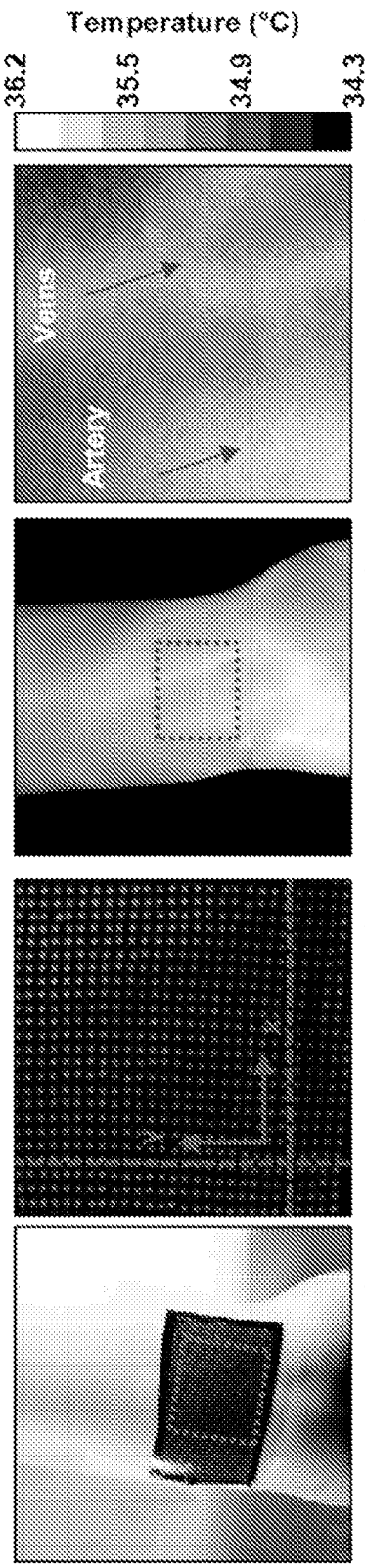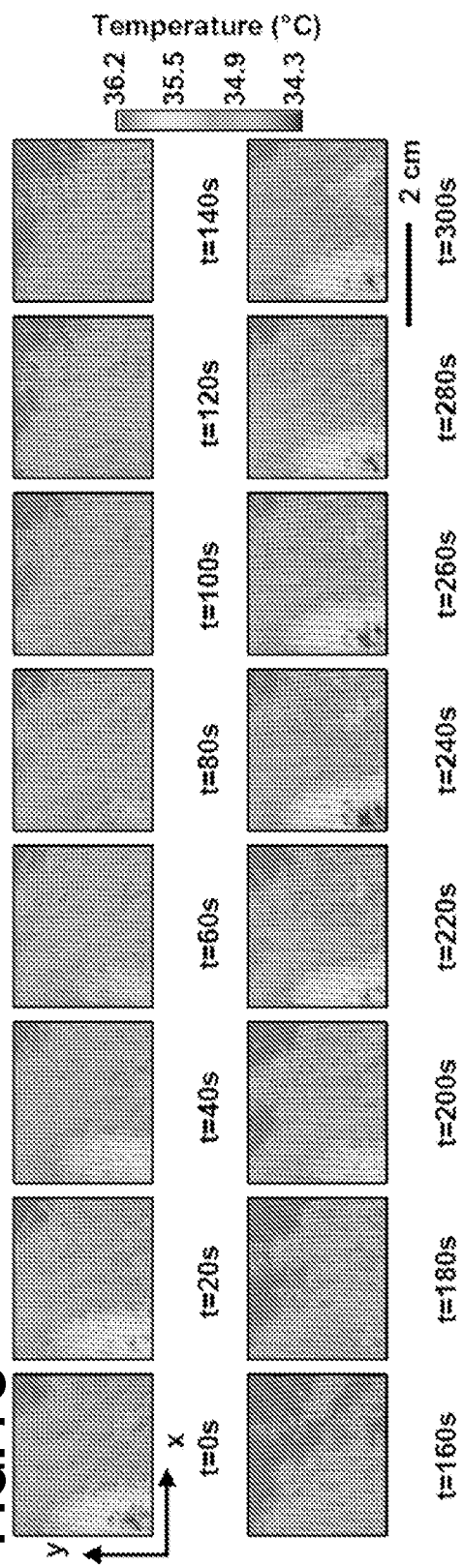
FIG. 7A  FIG. 7B  FIG. 7C
FIG. 7

- Syringe pump feed rate: 12 µL/hour (the value from reference)
- Feeding artificial sweat

A

B

C

A

| Type | Channel Width (mm) | Radius of Neutral Circle (mm) | Area (mm²) |
|---|---|---|---|
| A | 1.00 | 10.93 | 67.70 |
| B | 1.58 | 10.93 | 106.96 |
| C | 1.00 | 17.31 | 107.63 |
| D | 1.00 | 10.93 | 107.17 |

EPIDERMAL PHOTONIC SYSTEMS AND METHODS

CROSS-REFERENCE TO RELATED APPLICATIONS

This application is a U.S. National Stage Application under 35 U.S.C. 0.5371 of International Application No. PCT/US2015/044638, filed Aug. 11, 2015, which claims the benefit of and priority to U.S. Provisional Patent Application No. 62/035,823, filed Aug. 11, 2014, U.S. Provisional Patent Application No. 62/035,866, filed Aug. 11, 2014, and U.S. Provisional Patent Application No. 62/142,877, filed Apr. 3, 2015, each of which is hereby incorporated by reference in its entirety to the extent not inconsistent herewith.

STATEMENT REGARDING FEDERALLY SPONSORED RESEARCH OR DEVELOPMENT

This invention was made with governmental support under Grant N00014-10-1-0989 awarded by the Office of Naval Research. The government has certain rights in the invention.

BACKGROUND OF INVENTION

Wearable electronics and photonics are a class of systems with potential to broadly impact a range of technologies, industries and consumer products. Advances in wearable systems are driven, in part, by development of new materials and device architectures providing for new functionalities implemented using device form factors compatible with the body. Wearable consumer products are available, for example, that exploit small and portable electronic and/or photonic systems provided in body mounted form factors, such as systems building off of conventional body worn devices such as eye glasses, wrist bands, foot ware, etc. New device platforms are also under development to extend the range of wearable technology applications including smart textiles and stretchable/flexible electronic systems incorporating advanced electronic and photonic functionality in spatially complaint form factors compatible with low power operation, wireless communication and novel integration schemes for interfacing with the body. [see, e.g., Kim et al., Annu. Rev. Biomed. Eng. 2012.14; 113-128; Windmiller, et al., Electroanalysis; 2013, 25, 1, 29-46; Zeng et al., Adv. Mater., 2014, 26, 5310-5336; Ahn et al., J Phys. D: Appl. Phys., 2012, 45, 103001].

Tissue mounted systems represents one class of wearable systems supporting diverse applications in healthcare, sensing, motion recognition and communication. Recent advances in epidermal electronics, for example, provide a class of skin-mounted electronic systems provided in physical formats enabling mechanically robust and physically intimate contact with the skin. Certain classes of epidermal electronic systems have been developed, for example, combining high performance stretchable and/or ultrathin functional materials with soft elastic substrates implemented in device geometries useful for establishing and maintaining conformal contact with the soft, curvilinear and time varying surface of the skin. [see, e.g., US Publication No. 2013/0041235] W.-H. Yeo, Y.-S. Kim, J. Lee, A. Ameen, L. Shi, M. Li, S. Wang, R. Ma, S. H. Jin, Z. Kang, Y. Huang and J. A. Rogers, "Multifunctional Epidermal Electronics Printed Directly Onto the Skin," Advanced Materials 25, 2773-2778 (2013). Important to adoption of the emerging class of epidermal electronic systems is the continued development of devices supporting a wide range of applications for this technology including for personal healthcare assessment and clinical medicine.

It will be appreciated from the foregoing that tissue mounted systems are needed to support the rapidly emerging applications in wearable electronics. New epidermal systems are needed, for example, providing new sensing, readout and analysis modalities to support diverse technology applications in physiological and environmental sensing.

SUMMARY OF THE INVENTION

The invention provides systems and methods for tissue-mounted photonics. Devices of some embodiments implement photonic sensing and actuation in flexible and/stretchable device architectures compatible with achieving long term, mechanically robust conformal integration with a range of tissue classes, including in vivo biometric sensing for internal and external tissues. Tissue-mounted photonic systems of some embodiments include colorimetric, fluorometric and/or spectroscopic photonics structures provided in pixelated array formats on soft, elastomeric substrates to achieve spatially and/or or temporally resolved sensing of tissue and/or environmental properties, while minimize adverse physical effects to the tissue. Tissue-mounted photonic systems of some embodiments enable robust and convenient optical sensing modalities, including sensing compatible with optical readout using a mobile electronic devices such as using the camera and processor of a mobile phone or tablet computer. Tissue-mounted photonic systems of some embodiments have a low effective modulus and small thickness providing mechanical properties compatible with a range of deployment modes such as direct adhesion on the surface of a tissue and deployment using adhesives or intermediate bonding structures.

In one aspect, the invention provides a photonic device for interfacing with a tissue, the device comprising: (i) a flexible or stretchable substrate; and (ii) one or more photonic structures supported by the flexible or stretchable substrate for generating a photonic response corresponding to one or more tissue parameters or environmental parameters; wherein the flexible or stretchable substrate and the one or more photonic structures provide a net bending stiffness (and/or Young's modulus) such that the device is capable of establishing conformal contact with a surface of the tissue. In an embodiment, the device is for spatial and/or temporally characterizing tissue parameters or environmental parameters, for example, in connection with characterization of physiological, chemical and or environment properties of the tissue at, or below, the surface of the tissue and/or corresponding to materials derived from the tissue, e.g., biofluids. In an embodiment, for example, the device is for sensing or actuating the tissue. In an embodiment, for example, the device is for the device is for sensing or actuating an environment of the tissue, such as an ambient environment and/or an in vivo biological environment. In an embodiment, the photonic device is a tissue-mounted device, for example, a device that is conformally mounted and in physical contact with a tissue surface.

Tissue-mounted photonic systems and methods of the invention are capable of generating a range of photonic responses including photonic responses resulting from an external input, such a photonic response resulting from exposure of the device to electromagnetic radiation, for example, as provided by one or more optical sources (e.g., broad band (lamps, LEDs etc.) or narrow band (e.g. a laser)) or ambient light, in optical communication with the device.

Photonic responses include optical responses corresponding to electromagnetic radiation absorbed, scattered or emitted by the photonic structures. In an embodiment, for example, the photonic response corresponds to one or more of (i) wavelengths of light scattered, transmitted or emitted by the photonic structures; (ii) intensity of light scattered, transmitted or emitted by the photonic structures; (iii) spatial distribution of light scattered, transmitted or emitted by the photonic structures; (iv) phase of light scattered, transmitted or emitted by the photonic structures; and (v) one or more diffraction patterns of light scattered, transmitted or emitted by the photonic structures. In an embodiment, for example, the photonic response corresponds to a measurable change in one or more of: (i) wavelengths of light scattered, transmitted or emitted by the photonic structures; (ii) intensity of light scattered, transmitted or emitted by the photonic structures; (iii) spatial distribution of light scattered, transmitted or emitted by the photonic structures; (iv) phase of light scattered, transmitted or emitted by the photonic structures; and (v) one or more diffraction patterns of light scattered, transmitted or emitted by the photonic structures A wide range of photonic responses are compatible with the present photonic systems. In some embodiments, the photonic response includes spatial and or temporal information corresponding to tissue properties and/or environmental properties. Photonic responses of certain systems of the invention are spatially and/or temporally resolvable responses, for example, reflecting a spatially or temporally varying tissue parameter or environmental parameter. In an embodiment, for example, the photonic response is a colorimeteric response or fluorometric response, for example, corresponding to the optical characteristics of light scattered and/or emitted from the photonic structures. In an embodiment, for example, the photonic response is spectroscopic response. In an embodiment, for example, the photonic response results from a change in the spatial distribution, physical dimensions, phase or chemical composition of the photonic structures. In an embodiment, for example, the photonic response results from a distortion or displacement of the photonic structures in response to a change in the tissue parameters or environmental parameters.

Photonic responses of the present invention are compatible with a range of readout modalities including imaging-based optical readout. In an embodiment, for example, a photonic response generated by the present systems comprising electromagnetic radiation scattered, absorbed or emitted from the photonic structures is imaged on a camera or other imaging system, including a CCD, photodiode array or CMOS detector. In an embodiment, for example, the photonic response is measurable using a mobile electronic device, such a photonic response comprising electromagnetic radiation scattered, absorbed or emitted from the photonic structures that is imaged on a camera of a mobile electronic device. In some embodiments, for example, the photonic response is a diffraction pattern that is generated by the photonic structures, whereby features of the diffraction pattern correspond to changes in tissue parameters or environmental parameters. In an embodiment, a system of the invention optionally further comprises (i) an optical source for illuminating at least a portion of the photonic structures and/or (ii) an optical detector, such as a camera or other imaging system, for detecting electromagnetic radiation scattered, transmitted or emitted from the photonic structures. As used herein, scattered electromagnetic radiation is inclusive of scattering at any angle including forward and reverse scattering (e.g., reflection). In an embodiment, for example, the photonic response is compatible with colorimetric, fluorophoric and/or spectroscopic readout, for example, using a mobile electronic device.

In an embodiment, for example, the photonic response corresponds to one or more tissue parameters selected from the group consisting of: (i) temperature; (ii) hydration state; (iii) chemical composition of the tissue; (iii) chemical composition of a materials derived from the tissue; e.g. a biofluid; (iv) the composition and concentration of ions of a fluid from the tissue; (iv) pH of a fluid from the tissue; (v) the presence or absence of a biomarker; (vi) intensity of electromagnetic radiation exposed to the tissue; (vii) wavelength of electromagnetic radiation exposed to the tissue; and (vii) amount of an environmental contaminant exposed to the tissue. In an embodiment, for example, the photonic response corresponds to one or more environment parameters selected from the group consisting of: (i) intensity of electromagnetic radiation exposed to the device; (ii) wavelengths of electromagnetic radiation exposed to the device; (iii) amount of an environmental component exposed to the device; (iv) chemical composition of an environmental component exposed to the device; (v) amount of an environmental contaminant exposed to the device; (vi) chemical composition of an environmental contaminant exposed to the device. In an embodiment, the photonic response is an optical signal.

A wide range of photonic structures are useful in the present systems and methods. In an embodiment, for example, the one or more photonic structures optically absorb, scatter, transmit or emit electromagnetic radiation having wavelengths in the visible, ultraviolet or infrared regions of the electromagnetic spectrum. In an embodiment, use of visible region (e.g. 350 nm to 750 nm) and near-IR region (e.g., 750-1300 nm) of the electromagnetic spectrum light is preferred to minimize an potential adverse effects to the tissue. In an embodiment, the electromagnetic radiation exposed to the photonic device and/the electromagnetic radiation scatter or emitted from the photonic device is characterized by wavelengths selected over the range of 350 nanometers to 1300 nanometers, and optionally wavelengths selected over the range of 400 nanometers to 900 nanometers.

In an embodiment, for example, the one or more photonic structures are flexible or stretchable photonic structures, for example, exhibiting stretchability, without mechanical failure and/or degradation of optical properties, of greater than or equal to 5%, and greater than or equal 50% for some embodiments and greater than or equal 100% for some embodiments. In an embodiment, for example, the one or more photonic structures are microstructures (e.g., having physical dimensions selected from the range of 1 micron to 1000 microns) and/or nanostructures (e.g., having physical dimensions selected from the range of 1 nm to 1000 nm). In an embodiment, for example, the one or more photonic structures are characterized by an average modulus less than or equal to 100 MPa, optionally for some embodiments less than or equal 500 kPa. In an embodiment, for example, the one or more photonic structures are characterized by an average modulus selected over the range of 0.5 kPa to 100 MPa, optionally for some applications selected over the range of 0.5 kPa to 500 kPa. In an embodiment, for example, the one or more photonic structures are characterized by average lateral dimensions selected from the range of 10 µm to 1 cm and/or average thickness selected from the range of 1 µm to 1000 µm, optionally for some embodiments, average lateral dimensions selected from the range of 10 µm to 1000 µm and/or average thickness selected from the range of 1 µm to 100 µm. In an embodiment, for example, the one or more photonic structures are capable of mechanical deformation in response to a stimulus, such as a change in temperature. In an embodiment, for example, at least a portion of the one or more photonic structures are in fluid communication, thermal communication, optical communication, and/or electrical communication with the tissue. In an embodiment, for example, at least a portion of the one or more photonic structures are in physical contact with the surface of the tissue.

Useful photonic structures for some embodiments of the present systems and methods are spatially distributed in an array, such as an array with individual photonic structures individually in physical, optical or thermal contact with specific regions of the tissue surface. Photonic structures provided in an array form factor is useful in certain systems and methods to provide a photonic response characterizing spatial information corresponding to the tissue or environment, such as a spatial distribution of tissue parameters or environmental parameters with respect to a tissue surface. In an embodiment, for example, the array of photonic structures is a pixelated array; wherein each photonic structure independently corresponding to an individual position in the array. In an embodiment, for example, the array of photonic structures is a pixelated array, for example positions in the array individually addressed to specific regions of the tissue surface.

In an embodiment, for example, individual pixels or the array have an average lateral dimensions selected from the range of 10 µm to 1000 µm, optionally for some embodiments selected from the range of 100 µm to 500 µm and further optionally for some embodiments selected from the range of 200 µm to 500 µm. In an embodiment, for example, the individual pixels have an average thickness selected from the range of 1 µm to 100 µm, optionally for some embodiments selected from the range of 10 µm to 100 µm and further optionally for some embodiments selected from the range of 20 µm to 50 µm. In an embodiment, for example, the individual pixels are spaced from adjacent pixels in the array other by a distance selected from the range of 10 µm to 1000 µm, optionally for some embodiments a distance selected from the range of 100 µm to 1000 µm and further optionally for some embodiments a distance selected from the range of 250 µm to 500 µm. In an embodiment, for example, the pixelated array comprises 10 to 1,000,000 pixels, optionally for some embodiments 10 to 100,000 pixels. In an embodiment, for example, the pixelated array has a footprint selected from the range of 10 $mm^2$ to 2000 $cm^2$.

Photonic structures useful in the present systems and methods include structures incorporating optical indicators, such as colorimetric or fluorometric indicators, having optical properties that are useful for characterizing tissue parameters or environmental parameters. In an embodiment, for example, at least a portion of the pixels comprise a colorimetric indicator, fluorometric indicator or both, including device including pixels corresponding to different colorimetric and/or fluorometric indicators. The invention is compatible with a range of photonic structures incorporating indicators including embedded and/or encapsulated structures. In an embodiment, for example, the photonic structures are micro-encapsulated structures and/or nano-encapsulated structures, for example, having an indicator that is encapsulated by one or more encapsulation structures, such as laminating, embedding or encapsulation layers. In an embodiment, the micro-encapsulated structures and/or nano-encapsulated structures are in physical, thermal, optical or electrical contact with the tissue of a material(s) derived from the tissue, such as a biofluid.

In an embodiment, for example, at least a portion of the pixels comprise a colorimetric indicator that is a liquid crystal, an ionochromic dye, a pH indicator, a chelating agent, a fluorphore or a photosensitive dye. In an embodiment, for example, at least a portion of the pixels comprise a colorimetric indicator capable of generating a photonic response for characterizing a temperature, exposure to electromagnetic radiation or a chemical composition of a tissue or material derived from tissue. In an embodiment, for example, at least a portion of the pixels comprise a colorimetric indicator comprising a thermochromic liquid crystal that under goes a measurable change in the wavelength of light that is absorbed, transmitted or scattered upon a change of the tissue parameter. In an embodiment, for example, at least a portion of the pixels comprise a colorimetric indicator comprising chiral nematic liquid crystal that undergoes a measurable change in the wavelength of light that is absorbed, transmitted or scattered upon a change in temperature of the tissue.

In an embodiment, for example, at least a portion of the pixels comprise a colorimetric indicator comprising an ionochromic dye that under goes a measurable change in the wavelength of light that is absorbed, transmitted or scattered in response to a composition or property of the tissue or a material derived from the tissue such as a biological fluid. In an embodiment, for example, the composition or property of the biological fluid corresponds to a change in pH, concentration of free copper ion, or concentration of iron ion. In an embodiment, for example, at least a portion of the pixels comprise a colorimetric indicator that undergoes a measurable change in color in response to exposure to ultraviolet radiation. In an embodiment, for example, the photonic structures include colorimetric or fluorometric indicators that change optical properties upon contact with a biomarker in the tissue or in a material derived from the tissue such as a biological fluid In an embodiment, for example, the pixelated array further comprises one or more calibration pixels, such as dots having a fixed color.

A range of stretchable and flexible substrates are useful in embodiments of the present photonic devices and methods. In some embodiment, the substrate is a functional substrate. Use of low modulus and thin substrates are beneficial in some embodiments for achieving a conformal contact with tissue surface having complex morphologies without delamination and achieving a conformal contact without movement of the device relative to the contact surface of the tissue, for example, during movement of tissue. Use of selectively colored or optically opaque substrates are useful for providing contrast sufficient for effective optical readout, for example, via imaging using a mobile electronic device. Use of porous substrates and substrates having fluidic structures (e.g., active or passive fluidic channels) are beneficial for embodiments capable of characterizing properties of fluids from the tissue.

In an embodiment, for example, the substrate is optically opaque. In an embodiment, for example, the flexible or stretchable substrate incorporates one or more fluidic structures for collecting or transporting fluid from the tissue to the photonic structures. In an embodiment, for example, the flexible or stretchable substrate comprises an elastomer. In an embodiment, for example, the flexible or stretchable substrate is a low modulus rubber material or a low modulus silicone material. In an embodiment, for example, the flexible or stretchable substrate is a bioinert or biocompatible material. In an embodiment, for example, the flexible or stretchable substrate comprises a gas-permeable elastomeric sheet. In an embodiment, for example, the flexible or stretchable substrate has an average modulus less than or equal to 100 MPa, optionally for some embodiments less than or equal to 500 kPa, optionally for some embodiments less than or equal to 100 kPa. In an embodiment, for example, the flexible or stretchable substrate has an average modulus selected over the range of 0.5 kPa to 100 MPa, and optionally for some embodiments 0.5 kPa to 500 kPa, and optionally for some embodiments 0.5 kPa to 100 kPa. In an embodiment, for example, the flexible or stretchable substrate has an average thickness less than or equal to 3 mm, and for some applications less than or equal to 1000 microns. In an embodiment, for example, the flexible or stretchable substrate has an average thickness selected over the range of 1 to 3000 microns, and for some applications 1 to 1000 microns.

Photonic devices of the invention may further comprise a range of additional device components. In an embodiment, for example, the device further comprises one or more additional device components supported by the flexible or stretchable substrate, the device components selected from the group consisting of an electrode, strain gauge, optical source, temperature sensor, wireless power coil, solar cell, wireless communication component, photodiode, microfluidic component, inductive coil, high frequency inductor, high frequency capacitor, high frequency oscillator, high frequency antennae, multiplex circuits, electrocardiography sensors, electromyography sensors, electroencephalography sensors, electrophysiological sensors, thermistors, transistors, diodes, resistors, capacitive sensors, and light emitting diodes. In an embodiment, for example, the device further comprises one or more wireless communication antenna structures or near-field communication coils supported by the flexible or stretchable substrate. In an embodiment, for example, the device further comprises one or more single crystalline semiconductor structures supported by the flexible or stretchable substrate.

In an embodiment, for example, the device further comprises one or more optical components supported by the stretchable or flexible substrate, and optionally providing in optical communication of the photonic structures. In an embodiment, for example, the optical components are one or more of a light collecting optical component, a light concentrating optical component, a light diffusing optical component, a light dispersing optical component and a light filtering optical component. In an embodiment, for example, the optical components are one or more of a lens, a lens array, a reflector, an array of reflectors, a waveguide, an array of waveguides, an optical coating, an array of optical coatings, an optical filter, an array of optical filters, a fiber optic element and an array of fiber optic elements.

In some embodiment, the photonic structures are in physical contact with the substrate. Photonic devices of the invention include multilayer devices, for example, including one or more additional layer such as encapsulating layers at least partially encapsulating the photonic structures, and/or intermediate layers provided between the one or more photonic structures and the substrate. In an embodiment, the photonic structures are provided proximate to a neutral mechanical surface of the device. In an embodiment, for example, the photonic structures are positioned proximate to a neutral mechanical surface of the device, such as provided distance less than 2 mm, less than 10 µm, less than 1 µm, or less than 100 nm to a neutral mechanical surface. In an embodiment, for example, the thickness and/or physical properties (e.g., Young's modulus) of substrate and encapsulating layers are selected to position the photonic structure positioned proximate to a neutral mechanical surface of the device.

The device level mechanical, thermal, electronic and optical properties of the present photonic devices is important for supporting a range of technology applications. In an embodiment, for example, the device has a modulus within a factor of 1000, and optionally a factor of 10, of a modulus of the tissue at the interface with the device. In an embodiment, for example, the device has an average modulus less than or equal to 100 MPa, optionally for some embodiments less than or equal to 500 kPa, optionally for some embodiments less than or equal to 200 kPa and optionally for some embodiments less than or equal to 100 kPa. In an embodiment, for example, the device has an average modulus selected over the range of 0.5 kPa to 100 MPa, optionally for some embodiments selected over the range of 0.5 kPa to 500 kPa, optionally for some embodiments selected over the range of 1 kPa to 200 kPa.

Matching the physical dimensions and properties of the devices to that of the tissue is a useful design strategy in some embodiments to achieve robust conformal contact. In an embodiment, for example, the device has an average modulus equal to or less than 100 times, optionally equal to or less than 10 times, the average modulus of the tissue at the interface. In an embodiment, for example, the device has an average thickness less than or equal to 3000 microns, optionally for some embodiments less than or equal to 1000 microns. In an embodiment, for example, the device has an average thickness selected over the range of 1 to 1000 microns. In an embodiment, for example, the device has a net bending stiffness less than or equal to 1 mN m, optionally for some embodiments less than or equal to 1 nN m, optionally for some embodiments less than or equal to 0.1 nN m and optionally for some embodiments less than or equal to 0.05 nN m. In an embodiment, for example, the device has a net bending stiffness selected over the range of 0.01 nN m to 1 N m, optionally for some applications selected over the range of 0.01 to 1 nN m, and optionally for some embodiments selected over the range of 0.1 to 1 nN m. In an embodiment, for example, the device has an areal mass density less than or equal to 100 mg $cm^{-2}$, optionally for some applications less than or equal to 10 mg $cm^{-2}$. In an embodiment, for example, the device has an areal mass density selected over the range of 0.1 mg $cm^{-2}$ to 100 mg $cm^{-2}$, optionally for some applications elected over the range of 0.5 mg $cm^{-2}$ to 10 mg $cm^{-2}$. In an embodiment, the device is characterized by a stretchability greater than or equal to 5% and optionally for some applications 50% and optionally for some applications 100%, for example, by being able to undergo stretching to this extent without mechanical failure. In an embodiment, the device is characterized by a stretchability selected from the range of 5% to 200% and optionally for some applications 20% to 200%, for example, by being able to undergo stretching to this extent without mechanical failure.

The photonic systems of the invention are compatible with a range of tissue types including in vivo tissues, internal tissues and external tissues. In some embodiments, the tissue is skin, heart tissue, brain tissue, muscle tissue, nervous system tissue, vascular tissue, epithelial tissue, retina tissue, ear drum, tumor tissue, or digestive system structures. In some embodiments, for example, the device establishes conformal contact with the tissue when the device is placed in physical contact with the tissue, and wherein the conformal contact with the tissue in the biological environment is maintained as the tissue moves or when the device moves. The tissue may be of a subject that is undergoing treatment or diagnosis. In some embodiments, for example, the device is capable of establishing conformal contact with the tissue surface in the presence of a biofluid.

In an aspect, the invention provides a method of sensing one or more tissue parameters or environmental parameters, the method comprising the steps of: (i) providing the tissue of the subject; (ii) contacting a surface of the tissue with a photonic device, wherein the photonic device comprises: (1) a flexible or stretchable substrate; and (2) one or more photonic structures supported by the flexible or stretchable substrate for generating a photonic response corresponding to said one or more tissue parameters or environmental parameters; wherein the flexible or stretchable substrate and the one or more photonic structures provide a net bending stiffness (and/or Young's modulus) such that the device establishes conformal contact with a surface of the tissue; and (3) detecting the photonic response from the photonic device, thereby sensing the one or more tissue parameters or environmental parameters. Methods of this aspect may further include detecting the photonic response using a two-dimensional optical detector capable of spatially resolving the photonic response, such as a camera or other imaging device including using a mobile electronic device. Methods of this aspect may further include detecting the photonic response as a function of time. In an embodiment, for example, the step of measuring the photonic response from the photonic device comprises detecting electromagnetic radiation scattered or emitted by the one or more photonic structures. In an embodiment, for example, detecting electromagnetic radiation scattered or emitted by the one or more photonic structures is carried out using a mobile electronic device. Methods of this aspect may further comprise generating a detector signal corresponding to the photonic response using said optical detector. Methods of this aspect may further comprise analyzing the detector signal, thereby determining said one or more tissue parameters or environmental parameters.

Embodiments of this aspect include the step of establishing conformal contact with one or more surfaces of the tissue. In an embodiment, for example, the photonic device is provided in in conformal contact with tissue selected from the group consisting of: skin, heart tissue, brain tissue, muscle tissue, nervous system tissue, vascular tissue, epithelial tissue, retina tissue, ear drum, tumor tissue, and digestive system structures. In an embodiment, for example, the tissue is skin and wherein the device establishes conformal contact with the an outer surface of the epidermis. The methods of the invention include the step of contacting tissue of a subject with the photonic device, such as a human subject or other animal. In some embodiments, subjects of the present methods refer to a subject (1) having a condition able to be monitored, diagnosed, prevented and/or treated by administration of photonic device of the invention; or (2) that is susceptible to a condition that is able to be monitored, diagnosed, prevented and/or treated by administering a photonic device of the invention.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1.

FIG. 7. Application of an e-TLC thermal imaging device in a reactive hyperaemia test. a, Optical images of an e-TLC device on the wrist during an occlusion test after blood is released (left) with magnified view (right). b, Infrared image of the device (left) with magnified view (right). c, 3D rendering of spatial distributions of temperature determined with the e-TLC device at different times during and after occlusion (occlusion starts at t=0 s and ends at t=160 s). d, Line graphs of temperatures along the horizontal dashed red line in the right frame of a, at various times. e, Line graphs of temperatures along the vertical dashed red line in the right frame of a, at various times. f, Rate of blood flow through the ulnar artery determined by comparison of thermal models to experimental results. The key parameters include: the occlusion time (tocc)=160 s; time-to-peak-flow (tdw)=15 s; the baseline flow rate (w0)=30 mL/min; the occluded flow rate (ws)=1.5 mL/min; and the peak flow rate (wmax)=90 mL/min. g, Measured temperature rise at the surface of the skin above the ulnar artery during the occlusion along with results from finite element analyses (FEA) using the blood flow rate in frame f. The eight sub-frames correspond to the temperature histories of different points at the horizontal dashed red line in the right frame of a.

DETAILED DESCRIPTION OF THE INVENTION

Figure 1A:
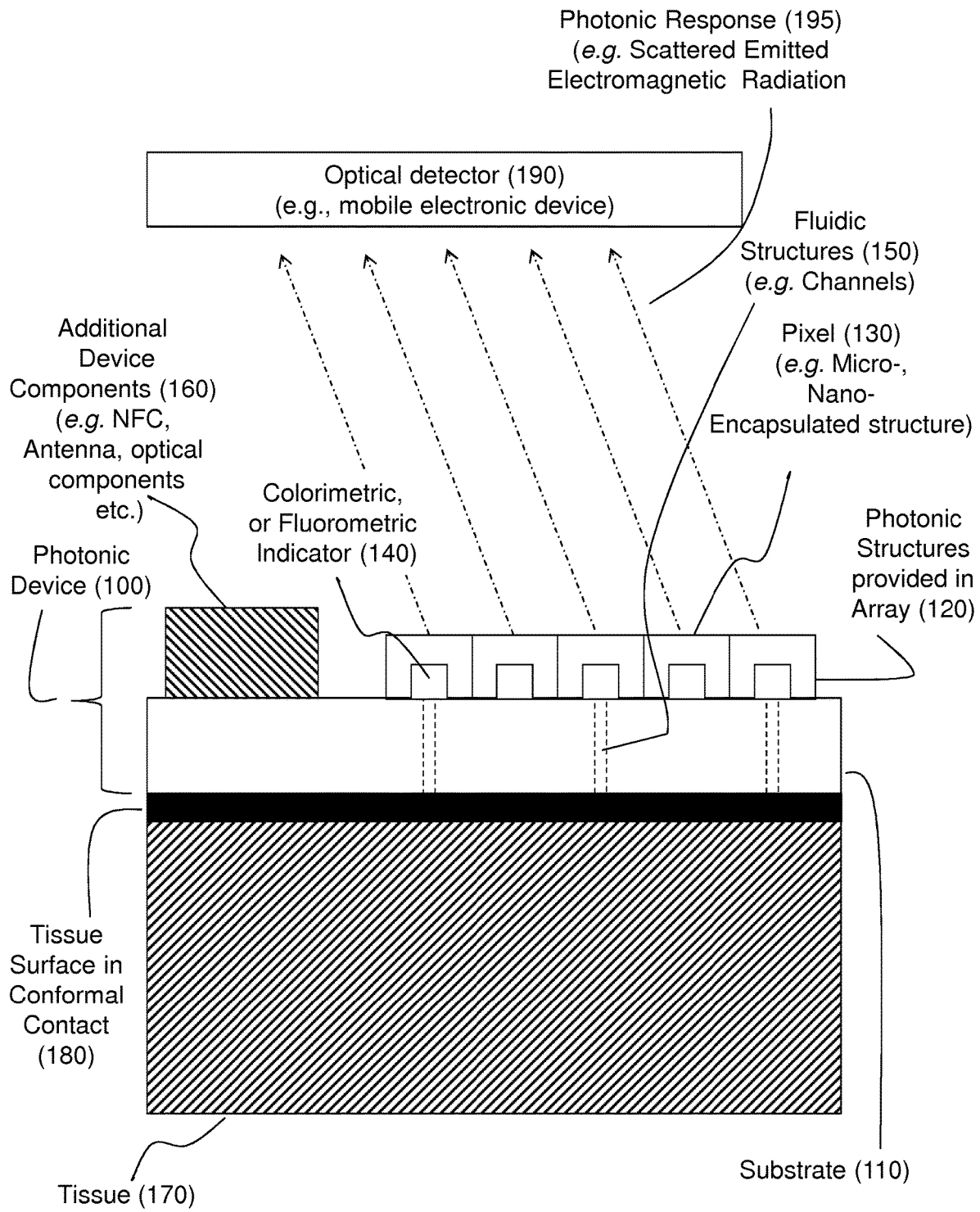
FIG. 1A shows an embodiment of a photonic device for interfacing with a tissue in a biological environment, including for example a tissue mounted device as shown in the Figure.

In general, the terms and phrases used herein have their art-recognized meaning, which can be found by reference to standard texts, journal references and contexts known to those skilled in the art. The following definitions are provided to clarify their specific use in the context of the invention.

"Functional substrate" refers to a substrate component for a device having at least one function or purpose other than providing mechanical support for a component(s) disposed on or within the substrate. In an embodiment, a functional substrate has at least one skin-related function or purpose. In an embodiment, a functional substrate of the present devices and methods exhibits a microfluidic functionality, such as providing transport of a bodily fluid through or within the substrate, for example via spontaneous capillary action or via an active actuation modality (e.g. pump, etc.). In an embodiment, a functional substrate has a mechanical functionality, for example, providing physical and mechanical properties for establishing conformal contact at the interface with a tissue, such as skin. In an embodiment, a functional substrate has a thermal functionality, for example, providing a thermal loading or mass small enough so as to avoid interference with measurement and/or characterization of a physiological parameter, such as the composition and amount of a biological fluid. In an embodiment, a functional substrate of the present devices and method is biocompatible and/or bioinert. In an embodiment, a functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another.

In some embodiments, a functional substrate that is mechanically matched to a tissue, such as skin, provides a conformable interface, for example, useful for establishing conformal contact with the surface of the tissue. Devices and methods of certain embodiments incorporate mechanically functional substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched functional substrate is characterized by one or more mechanical properties and/or physical properties that are within a specified factor of the same parameter for an epidermal layer of the skin, such as a factor of 10 or a factor of 2. In an embodiment, for example, a functional substrate has a Young's Modulus or thickness that is within a factor of 20, or optionally for some applications within a factor of 10, or optionally for some applications within a factor of 2, of a tissue, such as an epidermal layer of the skin, at the interface with a device of the present invention. In an embodiment, a mechanically matched functional substrate may have a mass or modulus that is equal to or lower than that of skin.

In some embodiments, a functional substrate that is thermally matched to skin has a thermal mass small enough that deployment of the device does not result in a thermal load on the tissue, such as skin, or small enough so as not to impact measurement and/or characterization of a physiological parameter, such as a characteristic of a biological fluid (e.g. composition, rate of release, etc.). In some embodiments, for example, a functional substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a functional substrate that is thermally matched to skin has a thermal mass low enough that is does not significantly disrupt water loss from the skin, such as avoiding a change in water loss by a factor of 1.2 or greater. Therefore, the device does not substantially induce sweating or significantly disrupt transdermal water loss from the skin.

In an embodiment, the functional substrate may be at least partially hydrophilic and/or at least partially hydrophobic.

In an embodiment, the functional substrate may have a modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

"Sensing" refers to detecting the presence, absence, amount, magnitude or intensity of a physical and/or chemical property, for example a tissue parameter or an environmental parameter. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material, environment or device component, such as a tissue or an environment. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a desired contour profile, for example a contour profile allowing for conformal contact with a surface having a pattern of relief features. In certain embodiments, a desired contour profile is that of skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Photonic devices of certain aspects are capable of establishing conformal contact with internal and external tissue. Photonic devices of certain aspects are capable of establishing conformal contact with tissue surfaces characterized by a range of surface morphologies including planar, curved, contoured, macro-featured and micro-featured surfaces and any combination of these. Photonic devices of certain aspects are capable of establishing conformal contact with tissue surfaces corresponding to tissue undergoing movement.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Tissue parameter" refers to a property of a tissue including a physical property, physiological property, electronic property, optical property and/or chemical composition. Tissue parameter may refer to a surface property, a sub-surface property or a property of a material derived from the tissue, such as a biological fluid. Tissue parameter may refer to a parameter corresponding to an in vivo tissue such as temperature; hydration state; chemical composition of the tissue; chemical composition of a fluid from said tissue; pH of a fluid from said tissue; the presence of absence of a biomarker; intensity of electromagnetic radiation exposed to the tissue; wavelength of electromagnetic radiation exposed to the tissue; and amount of an environmental contaminant exposed to the tissue. Photonic devices of some embodiments are capable of generating a photonic response that corresponds to one or more tissue parameters.

"Environmental parameter" refers to a property of an environment of a photonic device, such as a photonic device in conformal contact with a tissue. Environment parameter may refer to a physical property, electronic property, optical property and/or chemical composition or an environment, such as an intensity of electromagnetic radiation exposed to the device; wavelengths of electromagnetic radiation exposed to the device; a chemical composition of an environmental component exposed to the device; chemical composition of an environmental component exposed to the device; camount of an environmental contaminant exposed to the device; and/or chemical composition of an environmental contaminant exposed to the device. Photonic devices of some embodiments are capable of generating a photonic response that corresponds to one or more environmental parameters.

"Photonic response" refers to a response generated by one or more photonic structures of a photonic device of the invention. Photonic responses may correspond to one or more parameters including tissue parameters and/or environmental parameters. In some embodiments, a photonic response is an optical signal, such as a spatial and/or temporal resolvable optical signal. In some embodiments, a photonic response is a measurable change in one or more of: (i) wavelengths of light scattered, transmitted or emitted by said photonic structures; (ii) intensity of light scattered, transmitted or emitted by said photonic structures; (iii) spatial distribution of light scattered, transmitted or emitted by said photonic structures; (iv) phases of light scattered, transmitted or emitted by said photonic structures; and/or (v) diffraction pattern of light scattered, transmitted or emitted by said photonic structures. Photonic responses useful in certain embodiments include, for example, a spectroscopic response, a colorimeteric response or fluorometric response.

Figure 1B:
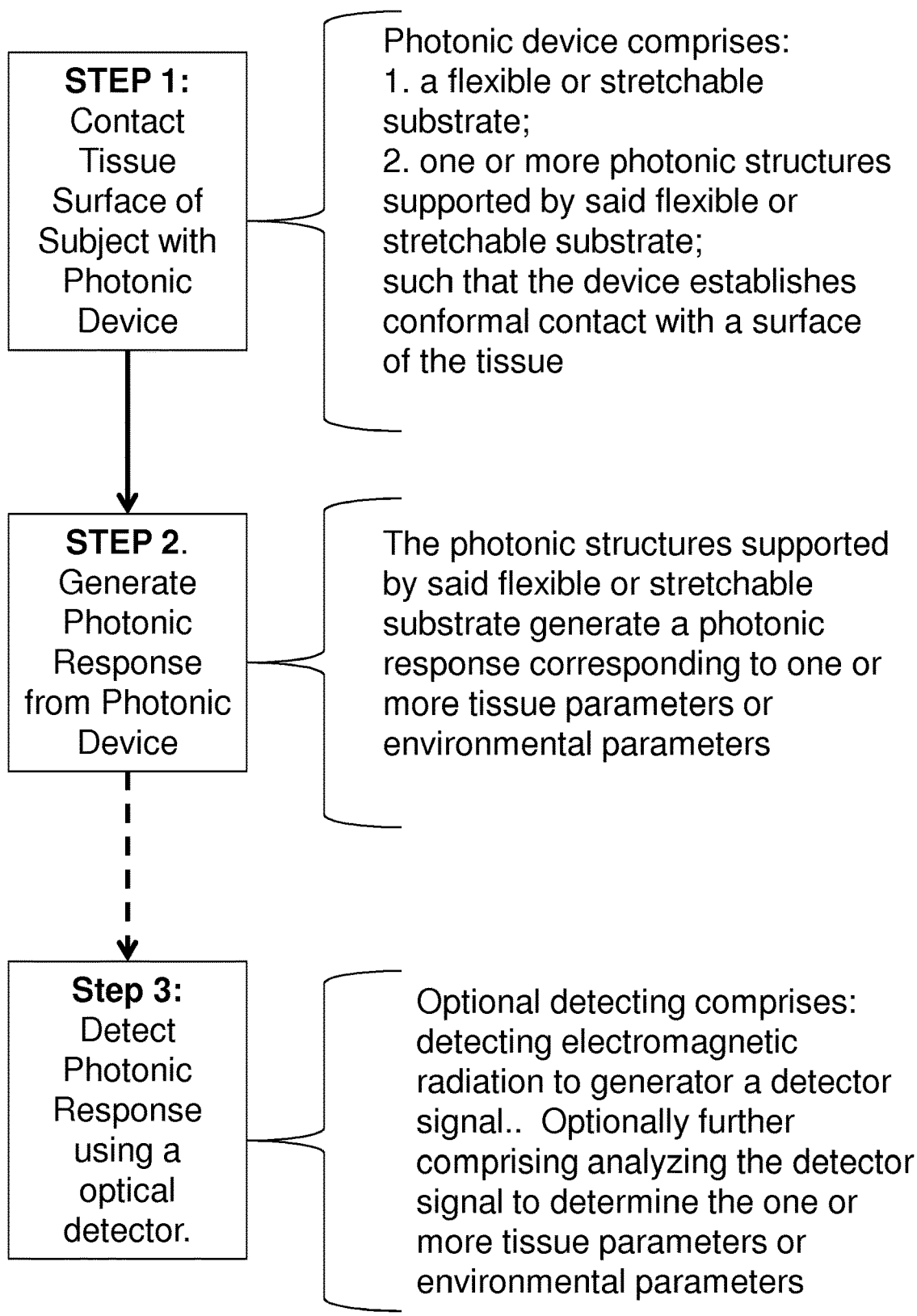
FIG. 1B shows an embodiment of a method of sensing one or more tissue parameters of a tissue of the subject or environmental parameters.

FIG. 1A shows an embodiment of a photonic device (100) for interfacing with a tissue in a biological environment, including for example a tissue mounted device as shown in the Figure. The photonic device (100) comprises a flexible, or stretchable substrate (110), and one or more photonic structures (120) supported by the substrate (110) for generating a photonic response corresponding to one or more tissue parameters or environmental parameters. In the embodiment shown in FIG. 1A, the photonic structures (120) are provided in an array, such as a pixelated two dimensional array. In this embodiment, the photonic structures (120) are comprised of micro-, or nan-encapsulated structures (130) that encapsulate colorimetric and/or fluorometric indicators (140), for example, that provide a change in one or more optical property in response to a change in a physical property, a physiological property or composition of the tissue (or a material derived from the tissue such as a biofluid) or a change in a physical property or composition of the environment of the device. As shown in this Figure, the substrate (110) is in conformal contact with a tissue surface (180) of a tissue (170). Optionally fluidic structures (150) are provided in the substrate (110) to provide for fluid communication and/or transport of fluid from the tissue surface (180) to at least portion of the photonic structures (120), in particular for some embodiments the encapsulated colorimetric and/or fluorometric indicators (140). Furthermore, additional device components (160) can be supported by substrate (160), such as wireless communication components including antenna and near field communication device elements, optical components, electrodes and electrode arrays, and semiconductor structures or devices. FIG. 1A also shows a, optical detector (190), such as a two dimensional detector, in optical communication with device (100) and capable of measuring the photonic response from said photonic structures (120). Optical detector (190) may be a camera or other imaging device, such as a camera on a mobile detect, capable of spatially and temporally resolving the photonic response from FIG. 1B shows an embodiment of a method of sensing one or more tissue parameters of a tissue of the subject or environmental parameters. In step 1, a tissue (170) is provided and contacted with the photonic device (100), such that conformal contact is established with a surface of the tissue. In some embodiment, the photonic device is provided in in conformal contact with tissue selected from the group consisting of: skin, heart tissue, brain tissue, muscle tissue, nervous system tissue, vascular tissue, epithelial tissue, retina tissue, ear drum, tumor tissue, or digestive system structures. In this embodiment, establishing conformal contact provides the device (and optionally the photonic structures thereof) in physical contact, thermal communication, optical communication, electrical communication, fluid communication or any combination of these. In step 2, a photonic response corresponding to one or more tissue parameters or environmental parameters is generated, such as a photonic response comprising an a spatially and temporally resolvable optical signal. In some embodiments, the photonic device (100) comprises a flexible or stretchable substrate (110); and one or more photonic structures (120) supported by the substrate (110). In step 3, a photonic response from the photonic device is detected using an optical detector. In an embodiment, the method comprises detecting electromagnetic radiation scattered or emitted by the one or more photonic structures, thereby generating a detector signal. Optionally, the detecting step of the electromagnetic radiation is carried out using a mobile electronic device. In an embodiment, the method further comprises analyzing the detector signal, thereby determining said one or more tissue parameters or environmental parameters.

The invention can be further understood by the following non-limiting examples.

Example 1: Epidermal Photonic Devices for Quantitative Imaging of Temperature and Thermal Transport Characteristics of the Skin Precision characterization of temperature and thermal transport properties of the skin can yield important information of relevance to both clinical medicine and basic research in skin physiology. Here, we describe an ultrathin, compliant skin-like, or 'epidermal', photonic device that combines colorimetric temperature indicators with wireless stretchable electronics for precision thermal measurements when softly laminated on the surface of the skin. The sensors exploit thermochromic liquid crystals (TLC) patterned into large-scale, pixelated arrays on thin elastomeric substrates; the electronics provide means for controlled, local heating by radio frequency (RF) signals. Algorithms for extracting patterns of color recorded from these devices with a digital camera, and computational tools for relating the results to underlying thermal processes near the surface of the skin lend quantitative value to the resulting data. Application examples include non-invasive spatial mapping of skin temperature with milli-Kelvin precision and sub-millimeter spatial resolution. Demonstrations in reactive hyperemia assessments of blood flow and hydration analysis establish relevance to cardiovascular health and skin care, respectively.

Spatio-temporal imaging of skin temperature offers experimental and investigational value for detection of breast cancers and other syndromes, as an adjunctive screening tool to mammography.[1-3] The required milli-Kelvin levels of precision and milli-meter scale resolution are most commonly achieved by use of sophisticated infrared digital imaging cameras. Widespread adoption of such technology is limited, however, by high capital costs, motion artifacts, and inability for use outside of clinical or laboratory settings. Other low cost thermography techniques has been exploited much earlier, for potential screening of deep venous thrombosis[4-7], breast cancer[8-10], spinal root syndromes[11,12], chronic back pain[13] and even pulmonological diagnostics.[14] Recent work[15,16] demonstrates that electronic temperature mapping devices can be constructed in ultathin, soft and compliant formats, sometimes referred to as 'epidermal' due to the similarity of their physical characteristics to those of the skin itself. These systems offer impressive capabilities that bypass many limitations of infrared cameras, but provide only modest spatial resolution and imaging fidelity, limited by multiplexing systems needed to address large sensor arrays. Untethered, wireless operation also demands data transmission components and power sources. Other stretchable smart skin devices that can monitor the vital health signals of the wearer with unprecedented function and comfort have been investigated intensively.[17-26] Here, we introduce a simple alternative that combines colorimetric readout and RF actuation for precision mapping of thermal characteristics of the skin. The sensors exploit thermochromic liquid crystals (TLC) patterned into large-scale, pixelated arrays on thin elastomeric substrates. Co-integration with electronics provides a means for controlled, local heating by radio frequency (RF) signals, to enable not only mapping of temperature but also intrinsic thermal constitutive properties. Uniform layers of TLCs in water-impermeable, non-stretchable thick plastic sheaths, and without electronics, have been explored for skin thermography,[27-29] but without the ability to conform sufficiently well to the curved, textured surface of the skin for accurate, reproducible measurements. Such devices also frustrate transepidermal water loss. They thermally load the skin, and cause irritation at the skin interface, thereby preventing reliable, accurate evaluation or use in continuous modes, over long periods of time. Thermochromic textiles are available for cosmetic and fashion purposes,[30-32] but their inability to maintain intimate contact with the skin and the limited capacity to use known thermochromic dyes for precision temperature evaluation prevent their use in the sorts of applications envisioned here. The devices reported here not only avoid these drawbacks, but they also allow precise measurement of thermal conductivity and thermal diffusivity through analysis of spatiotemporal images obtained during operation of integrated RF components. Conventional digital cameras and RF transmission systems enable simultaneous readout of thousands of pixels at resolutions that exceed those needed to image temperature and thermal property variations on the skin. The epidermal format induces minimal perturbations on the natural mechanical and thermal properties of the skin. Results presented in the following establish the foundational aspects in materials, mechanics and thermal physics for both electronically active and passive epidermal TLC (e-TLC) devices, including algorithms for extracting precision, calibrated data from color digital images. Demonstrations in reactive hyperemia assessments of blood flow, as it relates to cardiovascular health, and hydration analysis, as it relates to skin-care, provide two examples of use in clinically meaningful tests.

Figure 8:
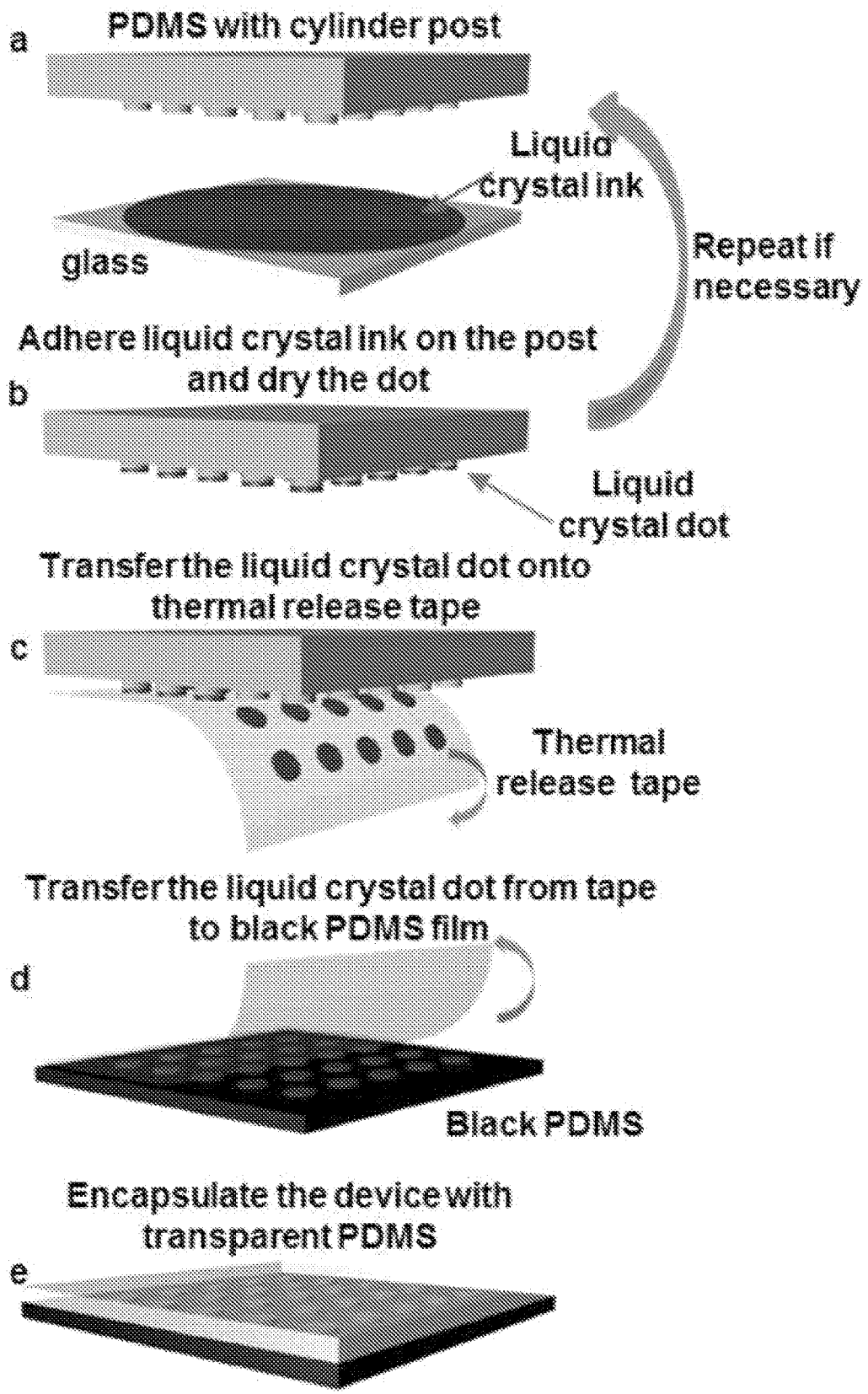
FIG. 8. Process for fabricating e-TLC devices. (a) A PDMS stamp with an array of posts embossed on its surface is 'inked' by bringing it into contact with a uniform layer of TLC aqueous slurry spin cast on a glass slide while still in wet state. The thickness of the ink was ~100 μm to ensure that the ink contacts on the top surfaces of the posts. (b) The inked TLC material on the PDMS stamp was allowed to dry in air for 15 minutes. The thickness of the dried film is ~15 μm. Additional 'inking' processes are repeated to achieve a final thickness of 25-30 μm. A typical TLC pixel is thickest in the center due to the hydrophobic nature of the PDMS surface and the large contact angle formed during the inking process. (c) Transfer printing allows delivery of the TLC to a piece of thermal release tape. (d) Transfer to the black PDMS substrate is enabled by heat activated release from the tape. (e) The device is encapsulated with a transparent layer of PDMS by spin casting.

The e-TLC thermal imagers use a multilayer design that includes (1) a thin (20 µm) black elastomeric membrane as a mechanical support and an opaque background for accurate colorimetric evaluation of the TLC materials, (2) an array of dots of TLC (i.e. pixels, with 25 µm thicknesses, and diameters of either 250 or 500 µm, spaced by 250 or 500 µm), with an optional interspersed array of dots with fixed colors (with 25 µm thicknesses, diameters of 400 µm, spaced by 600 µm) for calibration, both delivered to the surface of the black elastomer by transfer printing, (3) a thin (30 µm) overcoat of a transparent elastomer for encapsulation and (4) optional electronics in thin, stretchable configurations mounted on the back surface for active functionality described subsequently (details appear in FIG. 8 and Supplementary Note 1). The TLC material consists of microencapsulated chiral nematic liquid crystals. With increasing temperature, the phase varies from crystalline solid to sematic, cholestoric and, finally, isotropic liquid, all over a range of a few degrees, dictated by the chemistry.[33,34] In the cholestoric phase, light that reflects from the TLC pixels spans a narrow wavelength range defined by phase coherent interactions with the liquid crystal assemblies. Increases in temperature decrease the pitch, thereby leading to blueshifts in the peak wavelengths of this reflected light. This behavior provides the basis for colorimetric optical readout. Other phases have no chiral nematic orientation of molecular planes and thus do not yield any strong wavelength dependence to the reflection. The small sizes and large spacings of the TLC and calibration pixels, taken together with the low modulus, elastic properties of the substrate, encapsulation layer and electronics, yield soft, compliant mechanics in the overall e-TLC system. These properties yield devices are well suited for mounting on the skin.

Figure 2:
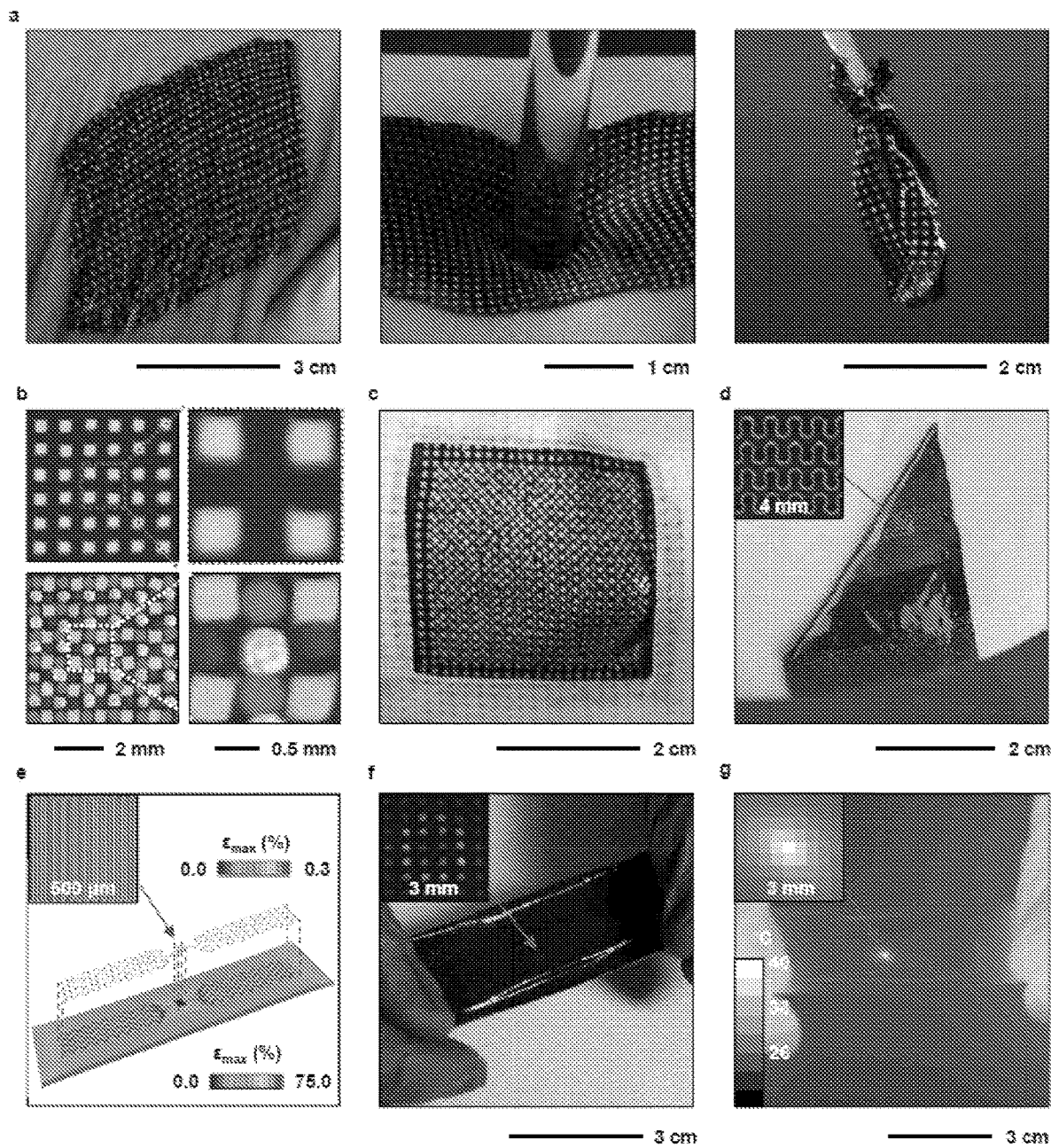
FIG. 2. Pictures, micrographs and design features of an 'epidermal' thermochromic liquid crystal (e-TLC) thermal imaging device. a, Picture of devices deformed by pinching the skin in a twisting motion (left), poking with a warm glass rod while on skin (middle) and collapsing under its own weight while free-standing (right). b, Magnified view of a device operating in the blue region of the spectrum, without (top) and with (bottom) integrated patterns of dots that have fixed colors for calibration. c, Picture of an e-TLC device with calibration system, operating the curved surface of the skin. d, Picture of a device that includes a radio frequency antenna and Joule heating element on its back surface, folded over and resting on palm, with an enlarged view of the serpentine antenna structure (inset). e, Schematic illustration of finite element modeling results for an e-TLC device with wireless heater under tensile strain, with magnified view of the Joule heating element (inset). f, Image of an active, wireless e-TLC device collected while exposed to RF power in air, with magnified view of the color changes induced by the heater (inset). g, Infrared image of the same device under similar conditions, with magnified view in the region of the heater (inset).

FIG. 2a shows an e-TLC on the skin of the forearm when twisted and gently poked with a mildly heated rod. Low interfacial stresses that follow from the low effective modulus and small thickness of the device enable adequate adhesion through van der Waals interactions alone. The collapse of a free-standing device under its own weight, as in the right frame, provides qualitative evidence of these mechanical characteristics. FIG. 2b shows a pair of magnified images of e-TLC devices; those on the bottom include interspersed color calibration pixels consisting of red, green and blue dye in a non-toxic acrylic base (aqueous dispersion of organic pigment and acrylic polymer, Createx). A completed device of this latter type placed on the curved surface of the back of the hand appears in FIG. 2c. As previously mentioned, the backside of the black elastomer substrate provides a mounting location for stretchable electronics. The image in FIG. 2d shows an example of an e-TLC device with a wireless system integrated in this way, for remote delivery of controlled levels of heat. The folded configuration reveals part of the serpentine antenna structure (inset). An illustration of this system, in the form of three dimensional finite element analysis (3D-FEA), appears in FIG. 2e. The antenna captures incident radio frequency (RF) energy to power a Joule heating element (inset, FIG. 2e). The result provides well-defined, localized increases in temperature, as revealed in the pattern of colors in the TLC pixels of FIG. 2f and the infrared images of FIG. 2g. As described subsequently, the results from measurements under such conditions allow determination of the thermal conductivity and thermal diffusivity of the skin.

Figure 3:
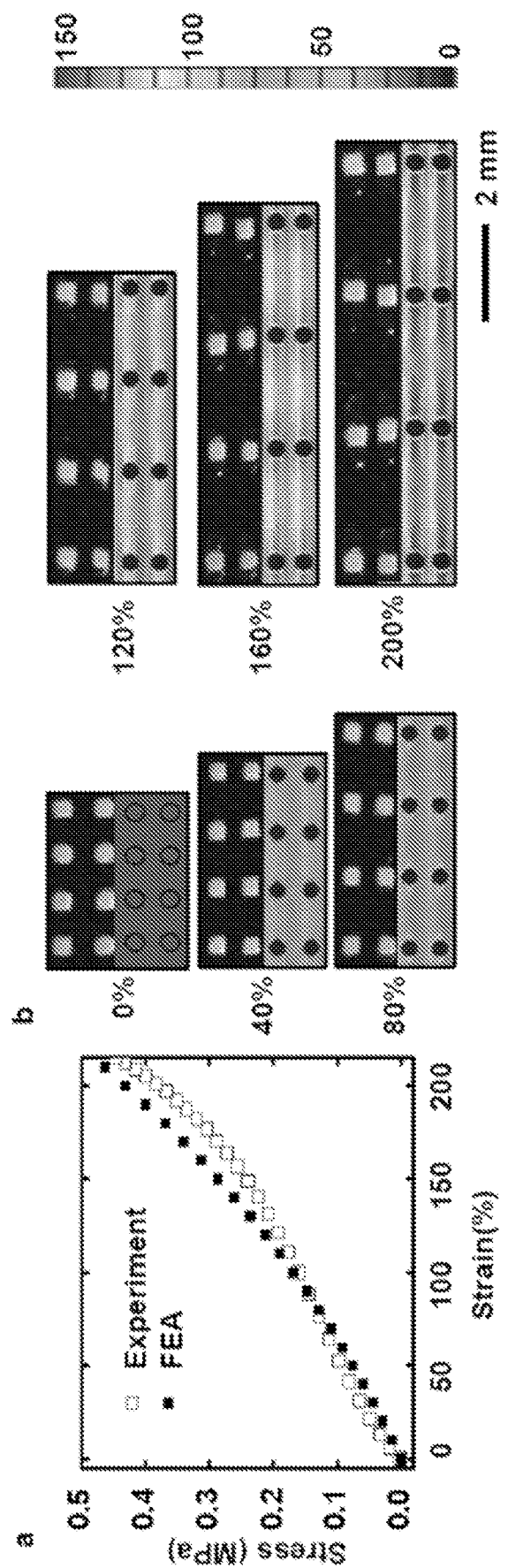
FIG. 3. Experimental and computational studies of the mechanical properties of e-TLC devices. a, Measurements and theoretical calculations of stress-strain responses of a device. b, Comparison between images and three dimensional finite element modeling of a representative region of e-TLC device under different levels of tensile strain.
Figure 9:
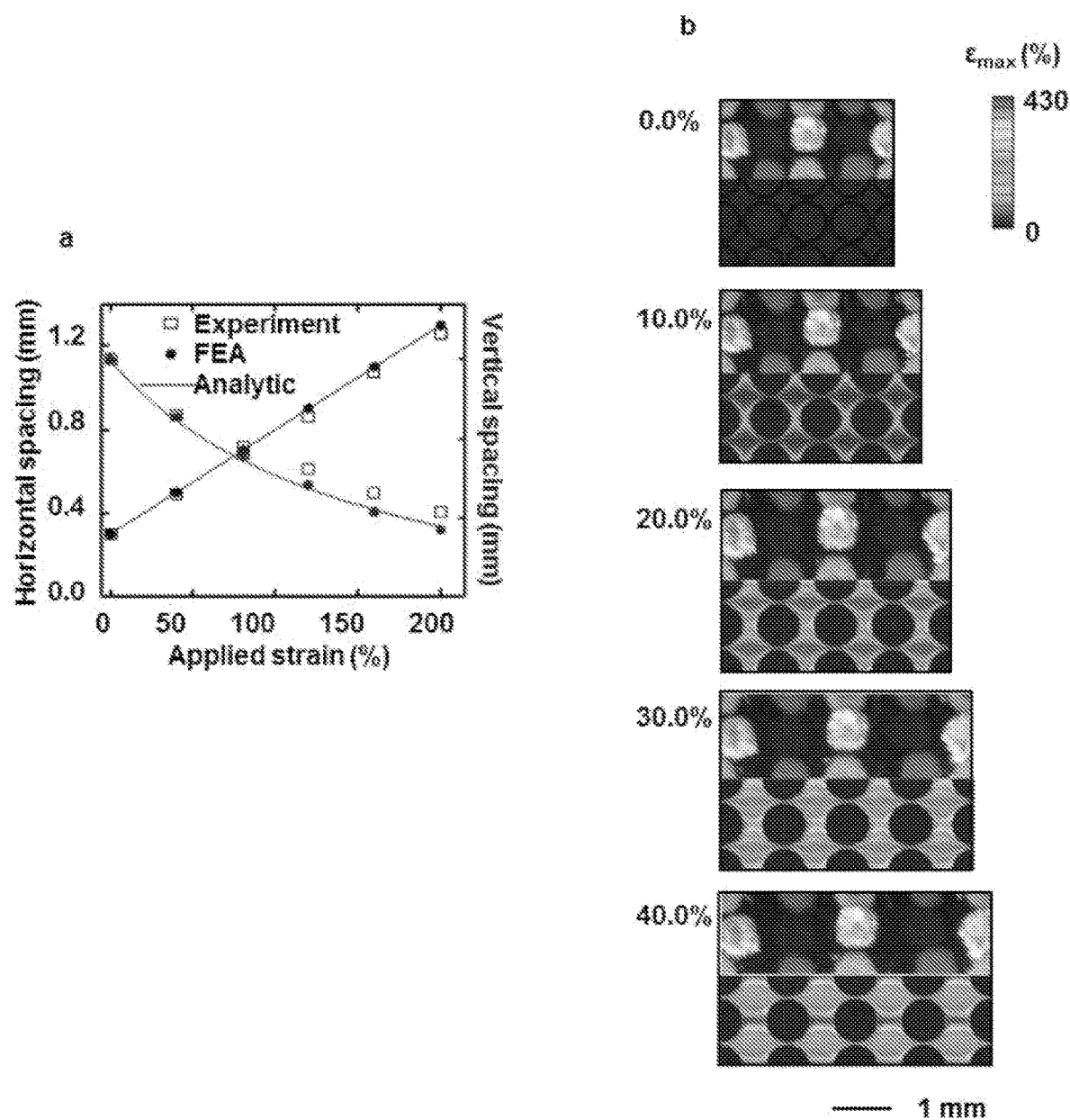
FIG. 9. Mechanical response of an e-TLC device to uniaxial strain. (a) Experimental, analytical and finite element modeling results for the change in horizontal and vertical spacings between adjacent pixels under different levels of tensile strain. (b) Comparison between images and three dimensional finite element modeling of a representative region of an e-TLC device that incorporates color calibration pixels under different levels of tensile strain.
Figure 10:
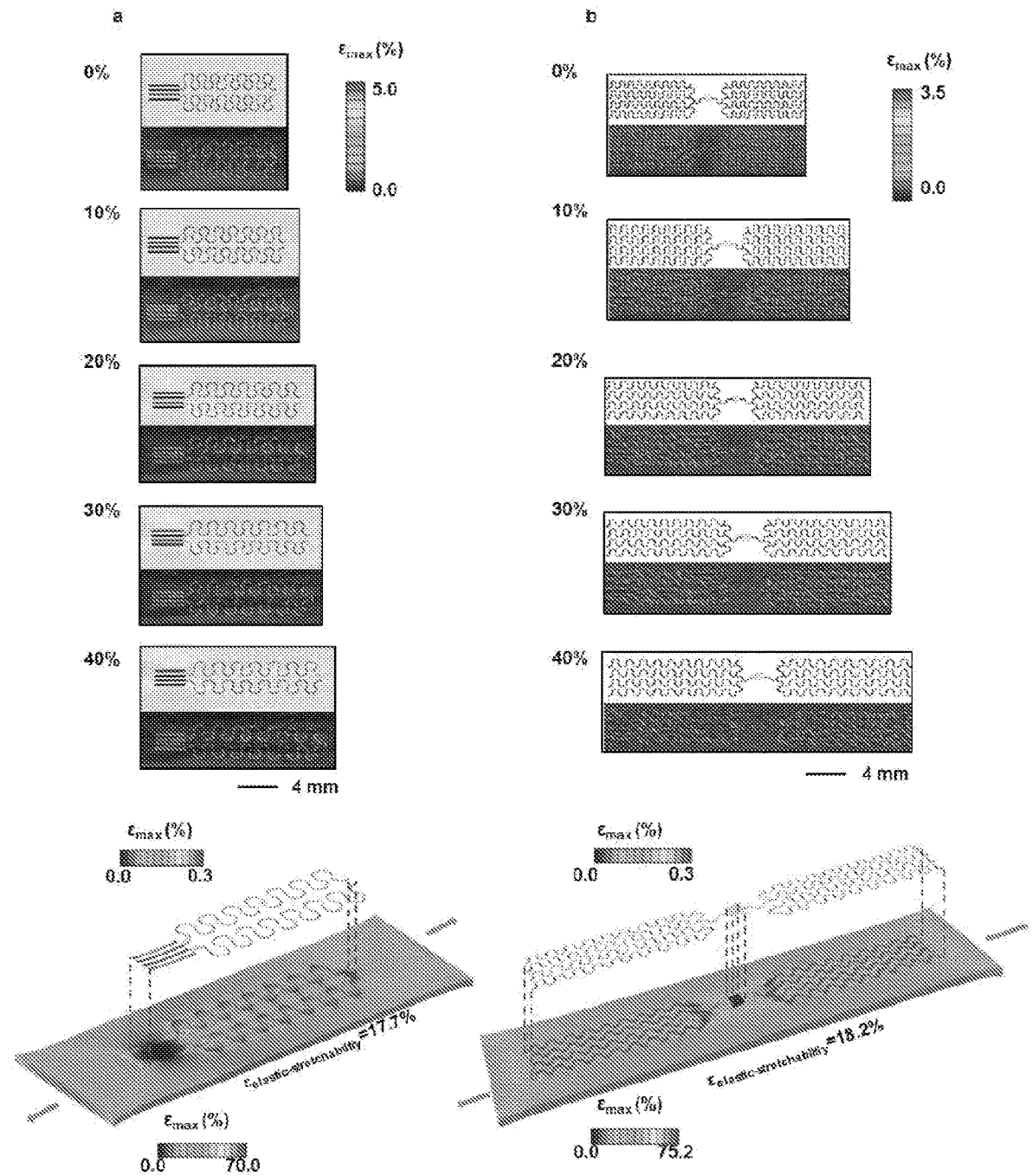
FIG. 10. Experimental and computational studies of the mechanical properties of Joule heater element. (a) Comparison between experimental images and three dimensional finite element modeling of a wired Joule heating element under different levels of tensile strain, and strain distribution computed for the case of stretching to 50%. (b) Comparison between experimental images and three dimensional finite element modeling of a wireless Joule heater under different levels of tensile strain, and strain distribution computed for the case of stretching to 50%.
Figure 11:
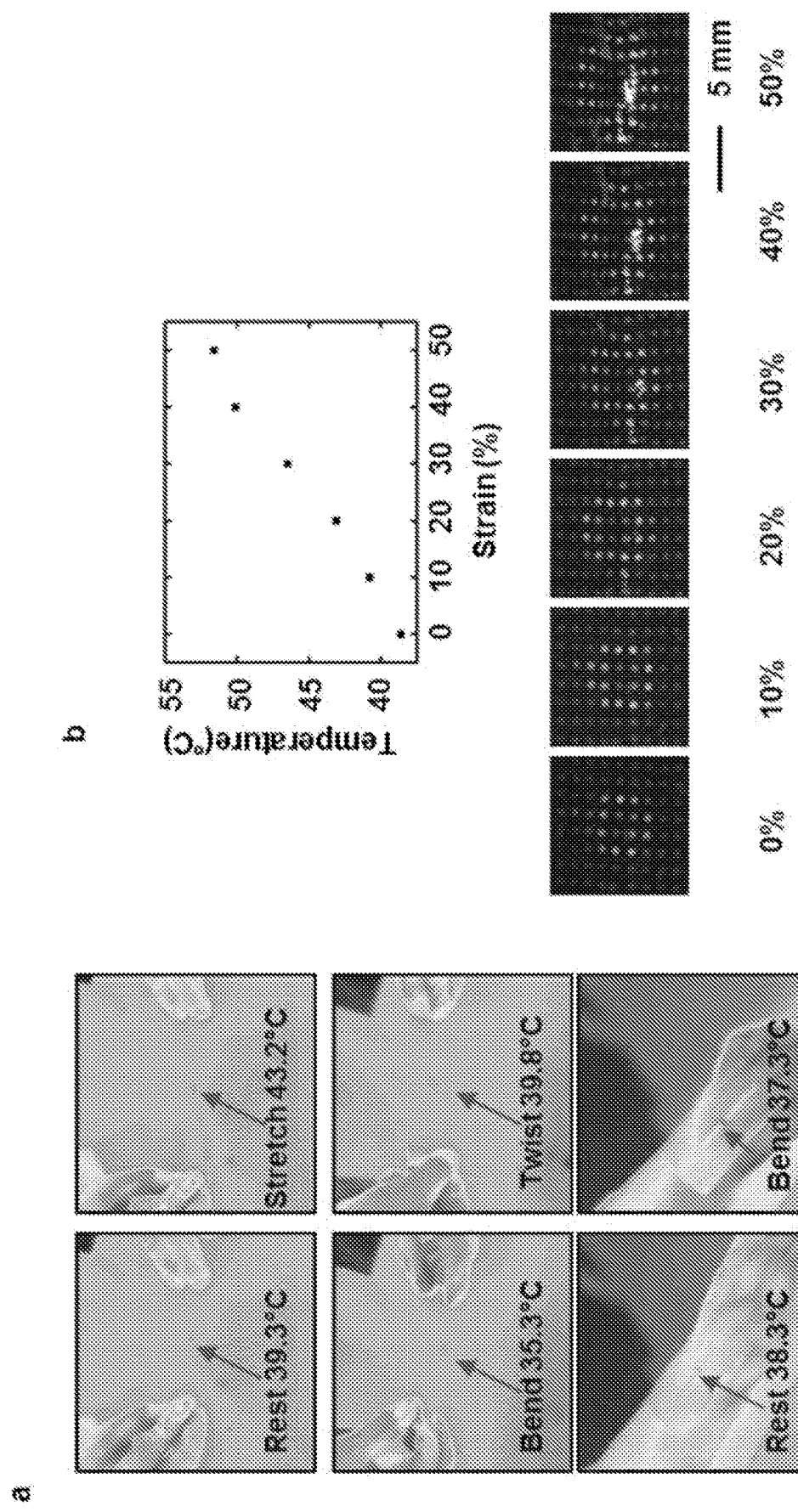
FIG. 11. Experimental studies of the effect of strain on the efficiency of wireless Joule heating. (a) Infrared temperature measurements for a wireless Joule heater under exposure to RF energy while mechanically deformed in different ways, both in air and on skin. (b) Measurements at different levels of tensile strain with corresponding images.

A key design goal is to produce e-TLC systems that induce minimal perturbations to the skin, thereby avoiding irritation, enhancing wearability and ensuring accurate measurement capabilities. The mechanical and thermal properties are particularly important in this context. Experimental and theoretical studies of the former reveal low modulus, elastic characteristics over large ranges of strain. FIG. 3a shows the stress/strain responses of an e-TLC device under static uniaxial testing. The results agree well with the predictions of 3D-FEA. In particular, the TLC pixels (~221 MPa) and elastomeric substrate (~131 kPa) yield an effective modulus (~152 kPa and 178 kPa from 3D-FEA and experiment, respectively) that is only slightly larger (by 16-35%) than the intrinsic value associated with the bare elastomer, and is comparable to that of the epidermis itself. The TLC pixels experience ultra-low strain (e.g., <2%) even under extreme stretching (e.g., 200%), as shown in FIG. 3b. Negligible deformations of the TLC pixels, as observed in experiment and FEA (FIG. 3b), allow approximations for simple, but quantitatively accurate, analytical solutions of the mechanics (see Supplementary Note 2 and FIG. 9a). The thicknesses, bending stiffnesses, effective moduli and stretchability of these devices are 50 μm, 3.0 nN·m, 178 kPa and beyond 200%, respectively; these characteristics are superior than those of typical, commercially available TLC sheets (Hallcrest) whose corresponding properties of ~125 μm, 570,000 nN·m, 3.3 GPa and ~5% (Hallcrest). The differences are significant, at a qualitative level of importance for deployment on the skin. In particular, the collective mechanical characteristics allow largely unconstrained natural motions of the skin, including wrinkling and stretching even in challenging regions such as the knees and elbows. Addition of calibration pixels reduces the stretchability and increases the modulus (FIG. 9b), but retain elastic strain levels (50%) that exceed those that can be tolerated by the epidermis (linear response to tensile strain up to 15%, nonlinear to 30%, and rupture at >30%[35]). Incorporating a wireless electronic heating system further reduces the accessible strain, but with an elastic stretchability of nearly 20%, which is useful for many applications (see FIG. 10).[36,37] Although the characteristics of the antenna change with mechanical deformation, experiments indicate that uniaxial stretching (up to 50%) does not disrupt the overall function or the efficiency of power harvesting (see FIG. 11); bending decreases the efficiency only slightly.

Figure 12:
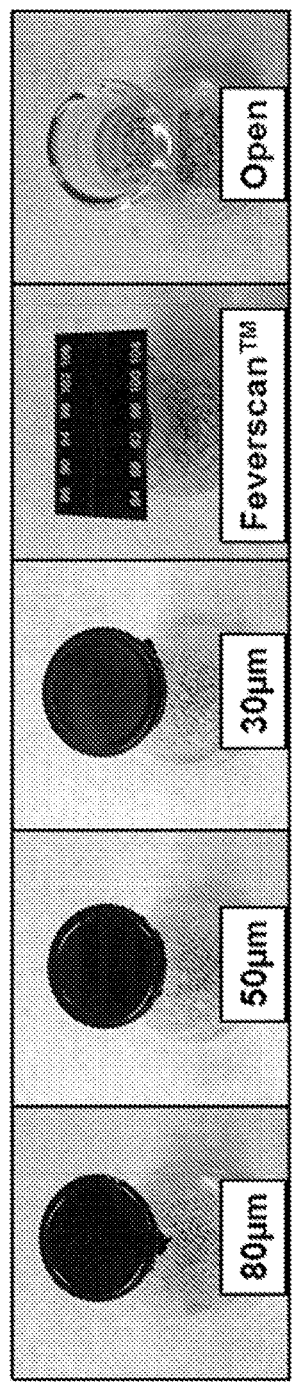
FIG. 12. Water permeability test. (a) Images of the experimental set-ups for measurement of water permeation according to ASTM E96-95 guidelines, and (b) Results of the change in weight as a function of time associated with water uptake by the dessicant, for e-TLC devices with different thicknesses and for a commercial TLC strip.
Figure 12:
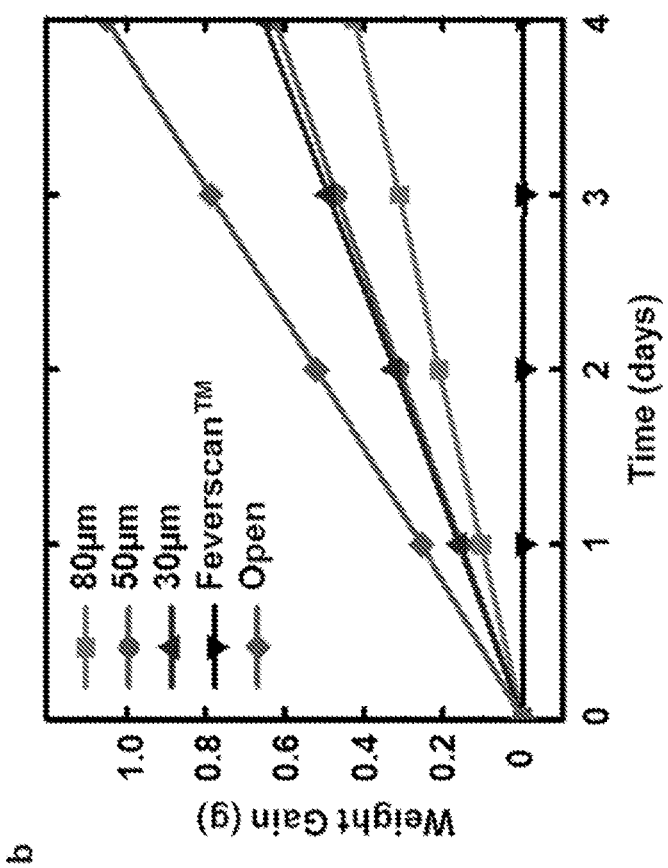
Figure 13:
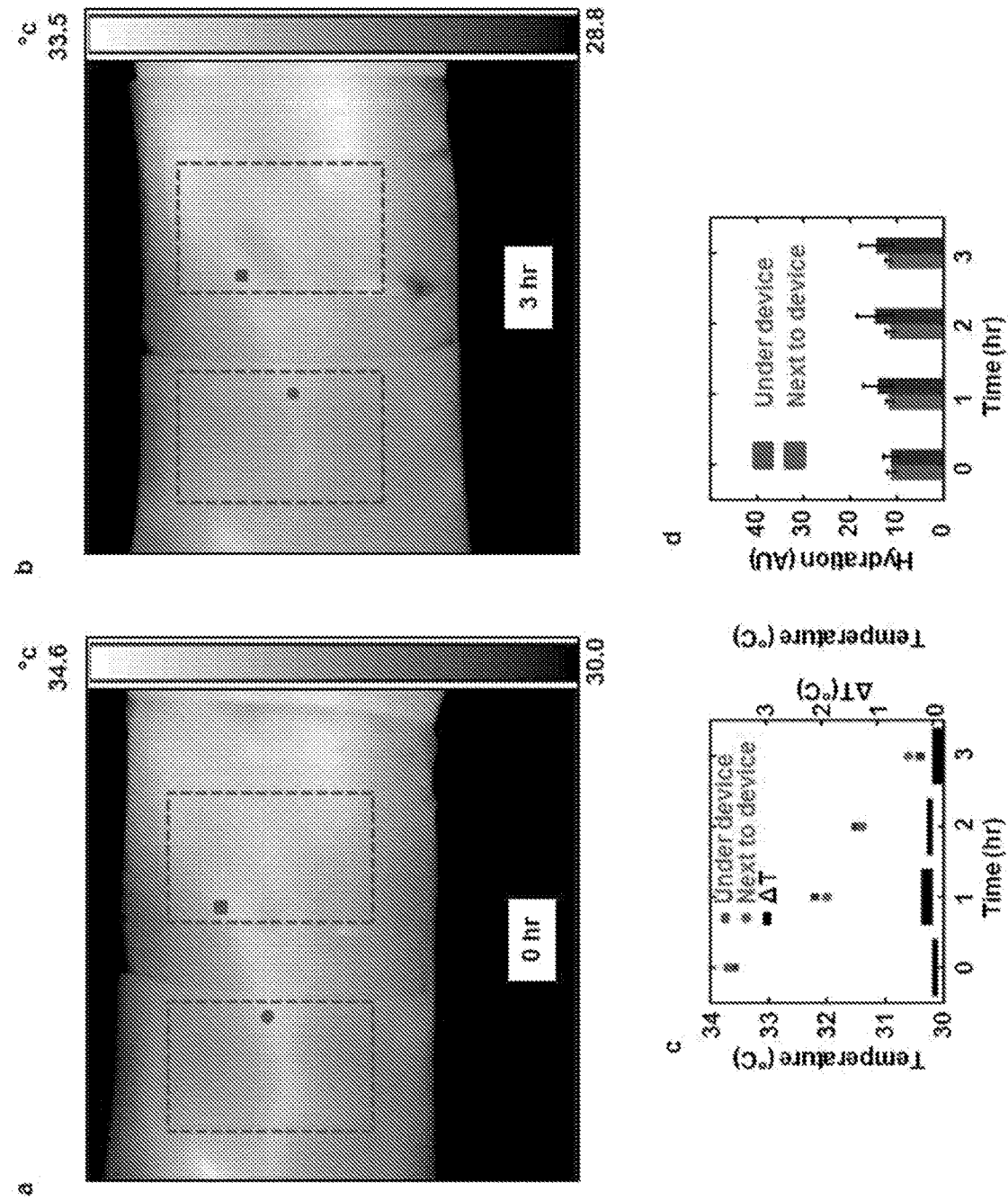
FIG. 13. Effect of e-TLC operation on temperature and hydration of the skin. (a) Infrared image captured immediately after mounting an e-TLC device on the wrist. (b) Infrared image captured 3 hours after mounting. For both (a) and (b), the data indicate that the average temperatures at the regions of the device are the same as those adjacent to the device. (c) Temperature difference between a point near the device and a point underneath the device shows no obvious increase during the three hour operation. (d) Hydration level read from a commercial hydration meter shows a maximum increase of about 25% after 3 hours operation on a very dry skin.
Figure 14:
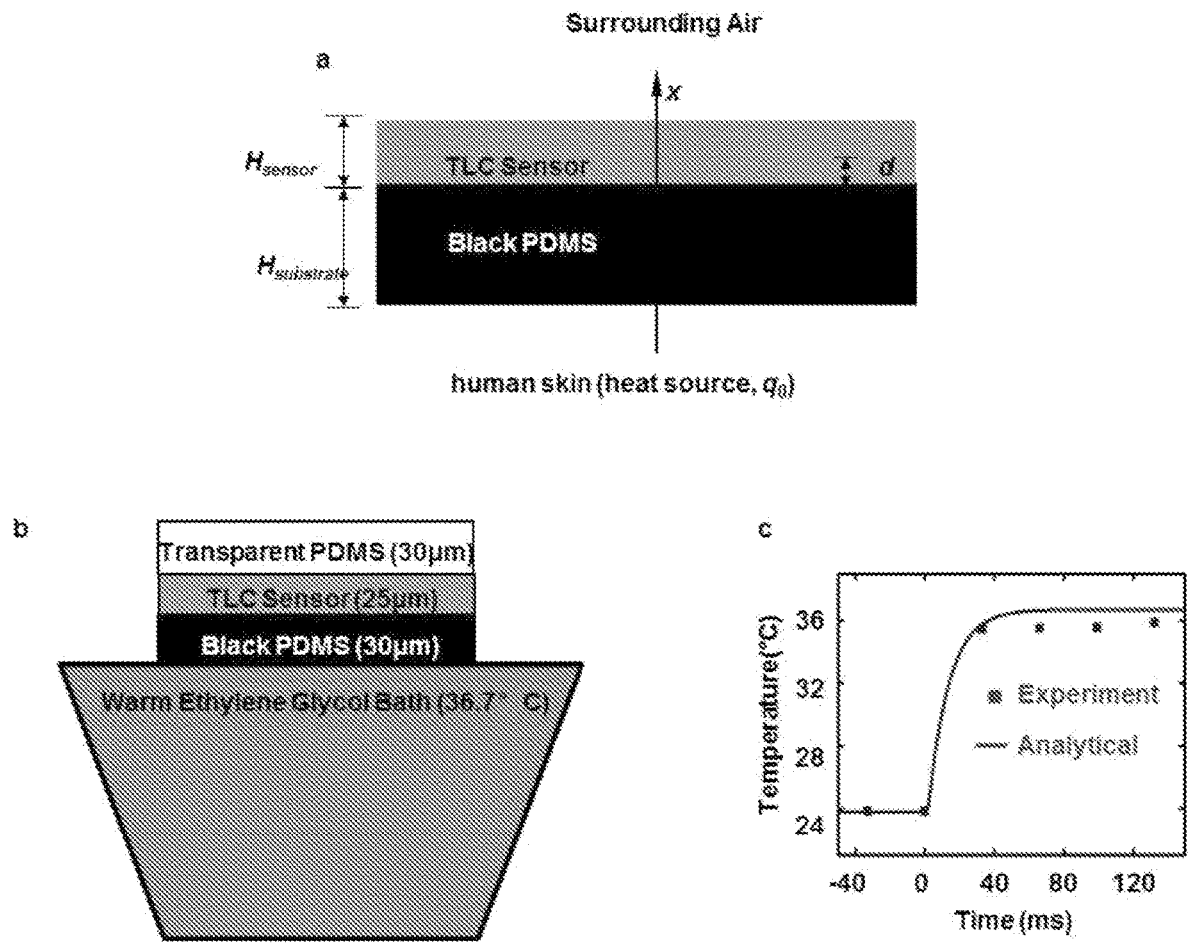
FIG. 14. Sensor response time. (a) Layers used in analytical modeling to determine sensor response time on skin. (b) Experimental setup for measuring sensor response time. A warm ethylene glycol bath, which has similar thermal properties to skin, is in contact with the e-TLC device from the back surface. (c) Experimental sensor response time captured by high speed camera, and corresponding analytic predictions based on a one-dimensional heat conduction model. In experiment, the time required for the sensor to reach 90% of the total temperature change is achieved in one frame which is approximate 33 ms for the case of 30 μm black PDMS and 25 μm liquid crystal.

The thermal characteristics of the systems define the thermal load on the skin, as well as the overall time response. For an active e-TLC device, the thermal mass per unit area is ~7.7 mJ·cm$^{-2}$·K$^{-1}$ (Supplementary Note 3). This value corresponds to an equivalent of skin thickness of ~20 μm, i.e. only 25% of the thickness of the epidermis itself.[38] Water vapor permeability test on e-TLC and Feverscan™ strip devices (Supplementary Note 4 and FIG. 12) has revealed that e-TLC devices provide minor moisture barrier for operation on skin. Decreasing the thickness of the device increases the water permeation, as expected (see FIG. 12b). Additional increases can be achieved by microstructuring, i.e. introducing arrays of holes or pores. The small thermal mass and high water permeability minimize changes in skin temperature and hydration level induced by presence of the device. Temperatures measured with an infrared camera on the forearm adjacent to an e-TLC and directly underneath it (FIG. 13a-c) show minimal differences. The effects of the device on skin hydration (FIG. 13d-e) are also small. A mounted 80 μm thick e-TLC on well hydrated skin (~35) leads to a small percentage increase in hydration (7.5%) after 3 hours. For an otherwise identical set of testing conditions, the Feverscan™ strip led to a ~100% increase in hydration. For monitoring of transient processes, the time response of the system is important. With geometries and materials investigated here, the response time for an e-TLC device is dominated by the thickness and thermal properties of the black elastomer substrate. Transient measurements reveal response times of less than ~30 ms (Supplementary Note 5), consistent with estimates developed using analytical models (FIG. 14). The intrinsic switching times for most TLC materials are ~3-10 ms.[39-42]

Figure 15:
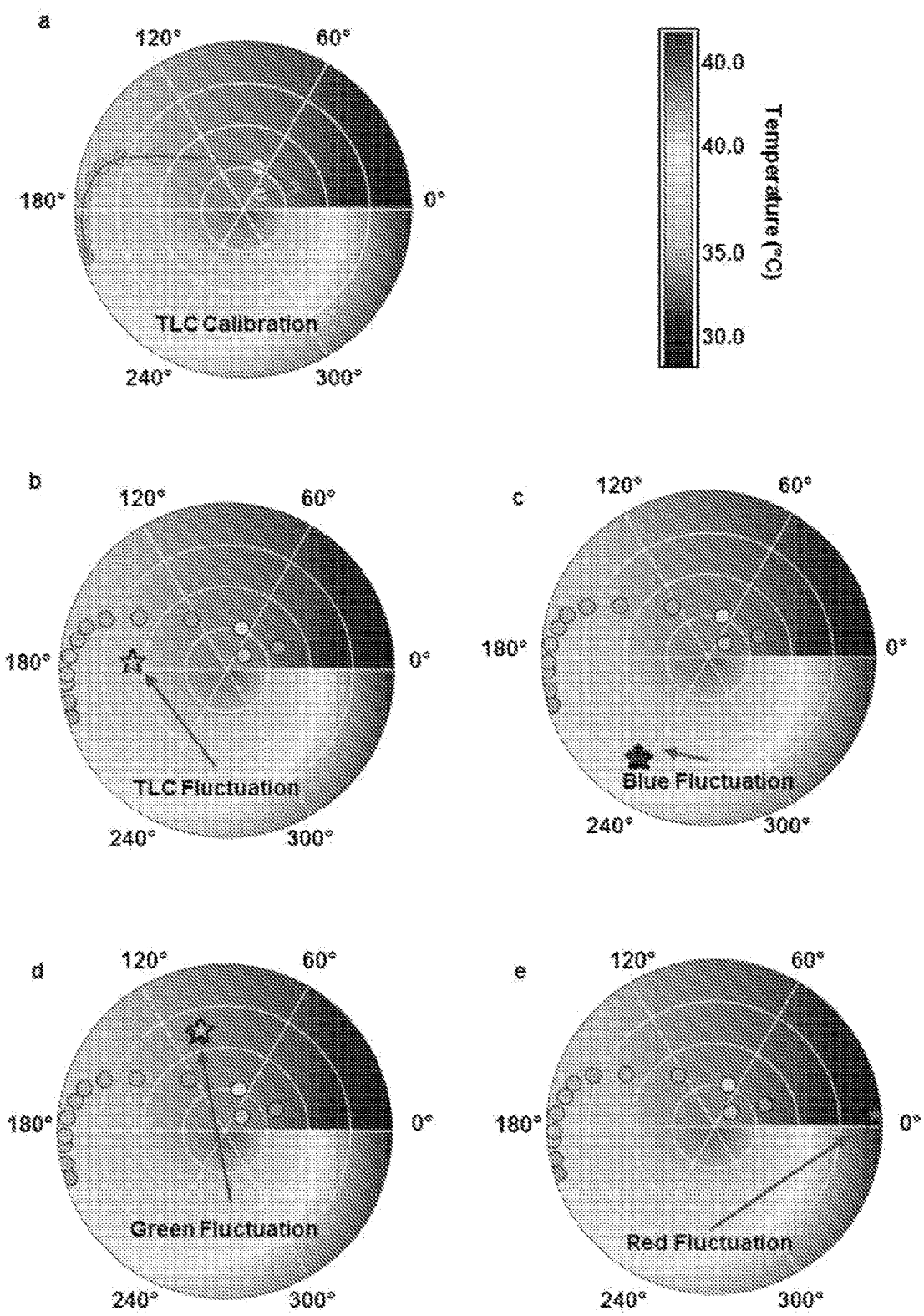
FIG. 15. Noise and uncertainty examined using temperature insensitive acrylic colors. (a) TLC color-temperature calibration plotted in the hue/saturation space. Symbols are located at positions corresponding to the hue/saturation values of the TLC during calibration runs, as indicated with their hue values. Temperatures are calculated with a two dimensional linear fit and are represented by a color gradient. (b) Temporal fluctuation in the color of the TLC, when held at a nominally fixed temperature. (c) Temporal fluctuation of the blue calibration color at fixed temperature. (d) Temporal fluctuation of the green calibration color at fixed temperature. (e) Temporal fluctuation of the red calibration color at fixed temperature.

Reflection mode spectroscopic characterization (Zeiss Axio Observer D1) of the steady-state response of the TLC material to changes in temperature between 32° C.-39° C. show expected behaviors, as in FIG. 4a. With proper calibration, described next, the temperature extracted from the hue and saturation values determined using a typical digital camera (Canon 5D Mark II) with the e-TLC device held at a nominally constant temperature exhibits a standard deviation of ~30 mK over a measurement time of 760 s. This value is comparable to that observed from temperature readings simultaneously determined with an infrared camera (~50 mK) (FIG. 4b). The measurement precision is, then, at least ±50 mK under these experimental conditions Equivalent temperatures extracted from analysis of color recorded at the calibration pixels (red, green, blue) show fluctuations with similar magnitudes, as summarized in FIG. 4c. These observations suggest that the process of image capture and color analysis enables levels of precision that are comparable to those of infrared cameras, not limited by the physics of the TLC. Detailed calibration plots and information on temperature extraction appear in FIG. 15.

Analysis of hue/saturation/value data obtained from the digital camera represents the simplest and most straightforward analysis approach. Sophisticated algorithms based on computer vision techniques are advantageous, however, not only for color determination but for full pixelated analysis of complete e-TLC devices. FIG. 4d illustrates an example of a process that exploits computer vision code (OpenCV), in which an image of an e-TLC device that consists of a 7×7 pixel array undergoes a set of color extraction and data transformation steps (details in Supplementary Note 6). A Gaussian filter first reduces noise through smoothing to yield a gray scale rendering for use with an adaptive threshold that compensates for illumination non-uniformities. The output is a binary mask containing value "1" at bright areas and "0" elsewhere. A two-step erode/dilate process eliminates small speckles that arise from defects. A full list of contours can be extracted from this "clean" image, in which each contour bounds a single pixel in the array. An enclosing circle function uses the contours as inputs to define the pixel positions, for extraction of color information from the original, unprocessed image. A typical calibration that relates hue and saturation values extracted in this manner to temperature evaluated with an infrared camera appears in FIG. 4e. The biggest advantage of using hue/saturation/value (HSV) color space instead of red/green/blue (RGB) is that the color information is encoded only in two (hue and saturation), rather than three (red, green and blue) channels. These two values are comparatively resilient to changes in lightning levels since that information is stored separately in the value channel. Any possible hue/saturation combination can be represented by a point in polar coordinates where radial coordinate corresponds to saturation and angular one to hue. The positions of the calibration set are marked with the dots painted with the corresponding hue. These points define the temperature calibration surface by means of two dimensional linear fit. The results allow any hue/saturation combination to be assigned to a temperature value, as indicated in the plot using a color gradient.

Scaled use of this process is summarized in FIG. 4f. Here, a full e-TLC device on a portion of the wrist where near-surface veins are located reveals corresponding variations in temperature of the epidermis. The hue values across the e-TLC yield three dimensional temperature contour plots that reflect the blood vessels with high spatial resolution (FIG. 4g). A direct comparison with temperature distributions measured in the same region with an infrared camera (FIG. 4h) exhibits excellent agreement. Plots of the temperature extracted from these two sets of results at the locations indicated by the dashed red lines in FIG. 4g,h appear in FIG. 4i. These results suggest suitability of e-TLC systems for mapping of vascular distributions in applications such as screening for deep venous thrombosis, without the need for costly infrared camera systems.

Figure 5:
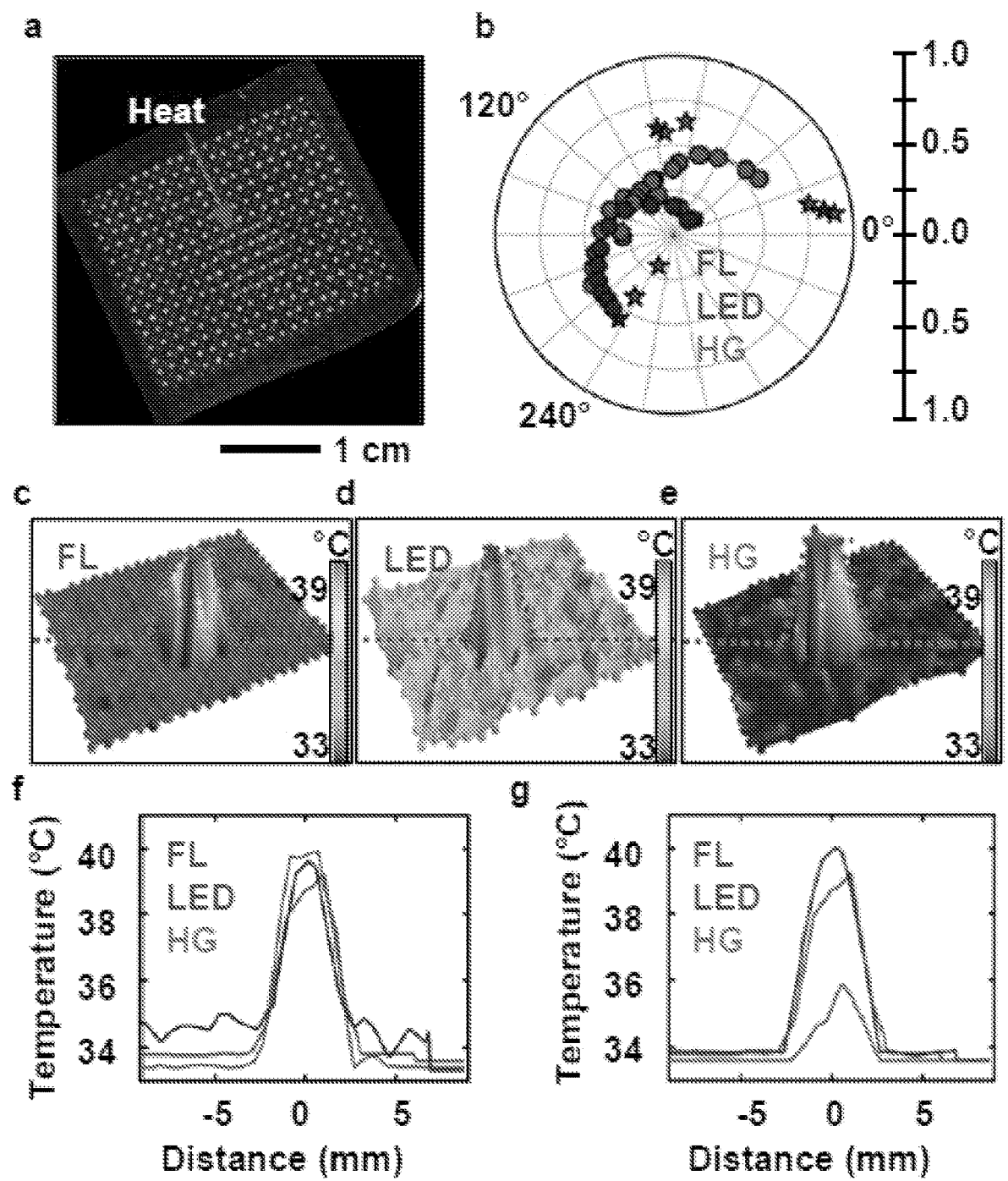
FIG. 5. Temperature analysis with an e-TLC device that incorporates an array of color calibration pixels co-located with sensing pixels, evaluated under different illumination conditions. a, Image of a device immediately after local heating at the center of the array. b, Hue and saturation values extracted for the calibration (stars) and sensing pixels (dots; red—illumination with a fluorescent light; blue—illumination with a light emitting diode; green—illumination with a halogen lamp). 3D rendering of color-corrected temperatures determined with c, white fluorescent light (FL), d, white light-emitting diode (LED), e, halogen light (HG). f, Line graphs of results collected along the dashed lines shown in c-e. g, Results similar to those in f, but without color correction.

In such practical situations, the lighting conditions can strongly affect the precision and accuracy of the temperature determination.[43-46] In particular, the hue and saturation depend on the type of light source used for illumination. The color calibration pixels provide a means to compensate for such effects, since their known colors are influenced by the lighting in the same way as the TLC. As a result, it should be possible to develop algorithms that account for shifts in the apparent colors of these calibration pixels and yield a set of numerical compensations that can restore their actual, known colors. Applying the same compensations to the TLC pixels will serve as the basis for a temperature evaluation process that is independent of illumination conditions, within some reasonable range. Effects of three different lightning conditions appear in FIG. 5. Red, green and blue color calibration pixels, interspersed across the entire device, are present in this active e-TLC sample. FIG. 5a presents an image of the device, with circles that indicate the positions of the TLC pixels. A Joule heating element is present in the center region. Fluorescent, light emitting diode (LED) and halogen (FIGS. 5c, 5d and 5e) light sources provide a range of practical examples. The corresponding temperature calibration data appear in FIG. 5b. The circles correspond to the hue/saturation values of TLC pixels recorded at different temperatures to define calibration fits for specific light sources. The stars delineate the effect of illumination on the colors of the calibration pixels. Red, green and blue calibration pixels are located at ~5°, ~100° and ~240°, respectively. Since these colors are known, data from them allow extraction of compensation factors for any given lighting condition. Applying the results to measurements of TLC pixels dramatically reduce the sensitivity of the temperature detection process to lightning source. FIG. 5f presents computed temperatures evaluated along lines that pass through the central region while the Joule element is activated. The results are comparable for all three lighting sources. To demonstrate the importance of proper calibration, FIG. 5g summarizes data that exploit the fluorescent temperature fit for all lighting conditions explored here. Significant discrepancies occur, as might be expected due to the different color temperatures of the halogen and LED sources. The resulting discrepancies in temperature readings are reflected not only in the temperature maxima, but also the temperature profiles, shapes and noise levels, which again emphasize the importance of proper calibration and potential for compensation approaches.

Figure 6:
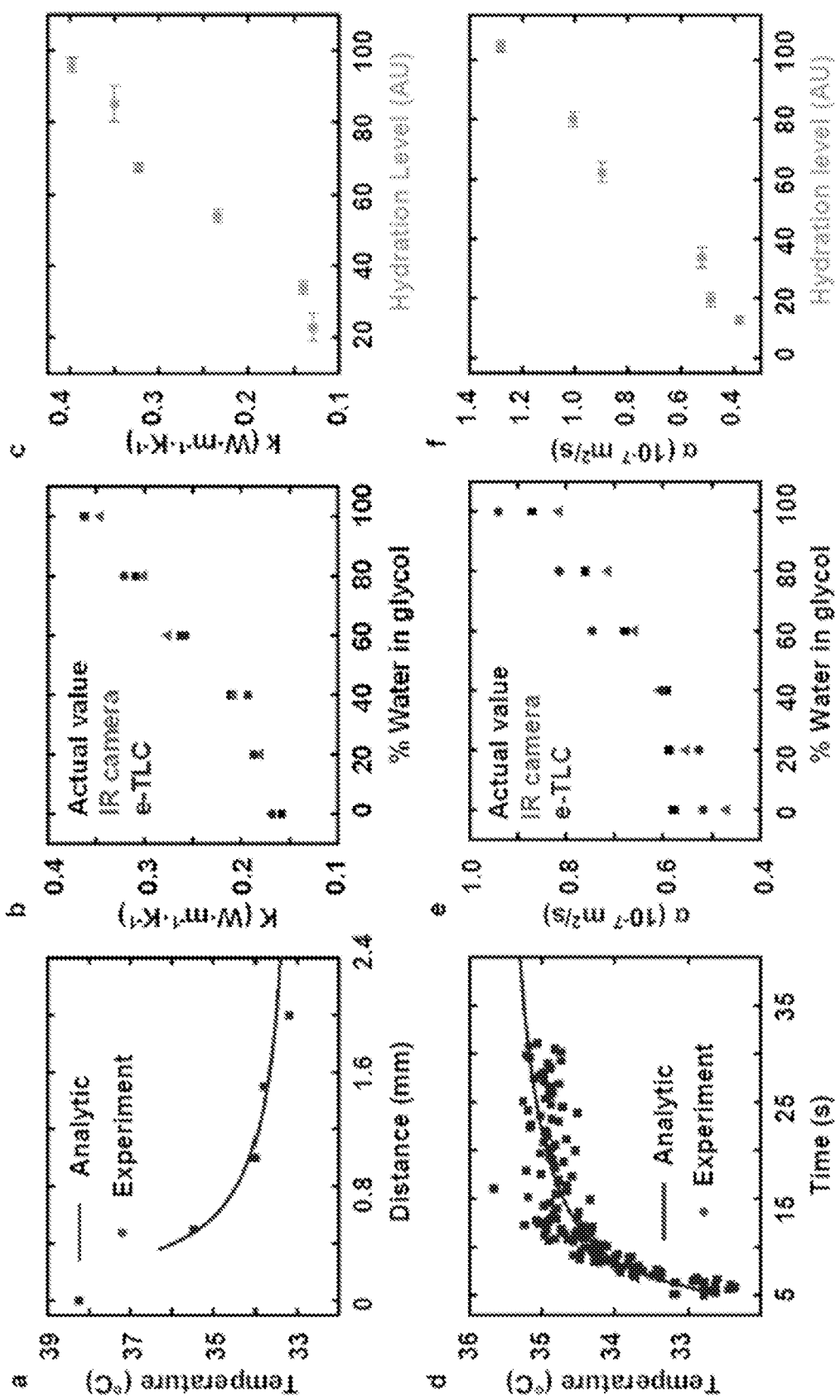
FIG. 6. Determination of thermal conductivity and thermal diffusivity of the skin using active e-TLC devices. a, Example of temperatures (symbols) as a function of distance from the position of local heating in an active e-TLC device and corresponding best fit modeling results (analytic; line), for determining the thermal conductivity. b, Thermal conductivity of water/ethylene glycol solutions evaluated using an active e-TLC device, with comparison to values obtained from the literature and from analysis of temperatures determined with an infrared camera. c, Thermal conductivities measured with an active e-TLC device on the skin at different levels of hydration, separately measured with a commercial moisture meter. The error bars represent average standard deviations of measurements obtained with the moisture meter. d, Example of temperatures (symbols) as a function of time for a location near a wireless heater in an active e-TLC device, and corresponding best fit modeling results (analytic; line) for determining the thermal diffusivity. e, Thermal diffusivity of water/ethylene glycol solutions evaluated using an active e-TLC device, with comparison to values obtained from the literature and from analysis of temperatures determined with an infrared camera. f, Thermal diffusivities measured with an active, wireless e-TLC device on the skin at different levels of hydration, separately measured with a commercial moisture meter. The error bars represent average standard deviations of measurements obtained with the moisture meter.
Figure 16:
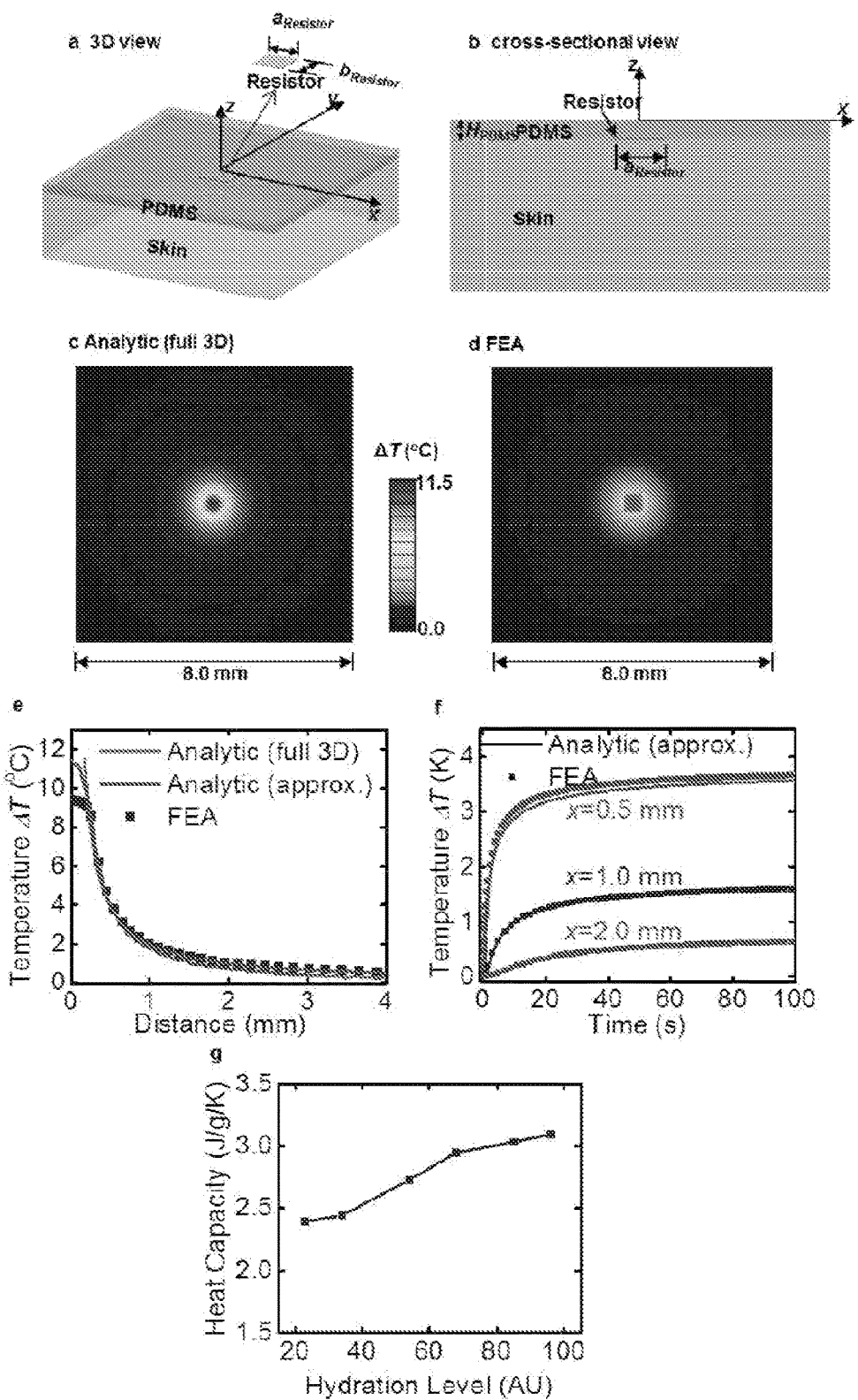
FIG. 16. Finite element models that allow determination thermal conductivity and diffusivity from data collected using active e-TLC devices. (a) A 3D view of a model with a Joule heater embedded between an e-TLC device and the skin. (b) A cross-sectional view of a model with a Joule heater embedded between an e-TLC device and the skin. (c) Analytical model of the spatial decay in temperature at steady state during operation of the Joule heater. (d) Corresponding finite element modeling results. (e) Analytical and finite element model of the spatial temperature decay with a wired Joule heater operation along one dimension. (f) Analytical and finite element model of the temporal temperature rise with a wireless Joule heater operation for locations away from the heater. (g) Skin heat capacity inferred from the skin thermal conductivity and diffusivity values in FIG. 6.

As suggested by the active e-TLC results in FIG. 5, the local Joule heating element enables additional measurement capabilities. In particular, spatial and temporal variations in temperature at locations near this heater can be used, with thermal models, to extract the thermal conductivity and diffusivity of the skin. Increases in temperature of a few ° C. can be sufficient for accurate evaluation. The thermal conductivity (k) can be determined by comparing measured steady state distributions in temperature to axis-symmetric thermal conduction models (see Supplementary Note 7). Calculations based on this model suggest spatial decays in temperature ($T_{sensor-layer}$) that vary as 1/r (except the central sensor), which can be written as $$T_{sensor-layer} \approx T_\infty + \frac{Q}{2\pi kr}, \quad (1)$$

where r is the distance from the heat source, Q is the heat generated by the Joule heating element, and $T_\infty$ is the temperature of surrounding air. An example appears in FIG. 6a, with details in FIG. 16a,b,e. Calibration can be performed through measurements of materials with known properties (FIG. 6b). FIG. 6c indicates excellent correspondence between thermal conductivity of the skin evaluated with an active e-TLC and hydration levels determined with a moisture meter (Delfin MoistureMeterSC) that relies on electrical impedance. The quantitative values of k fall within a range that is consistent literature values determined by subcutaneous thermocouples and high speed radiometer etc.[47] By simplifying the heating element as a point heat source turning on at time t=0, the transient temperature variation can be analytically solved as (see Supplementary Note 8)

$$T_{Sensor-layer}(t) \approx T_\infty + \frac{Q}{2\pi kr}\text{erfc}\left(\frac{r}{\sqrt{4\alpha t}}\right), \quad (2)$$

where α is the thermal diffusivity of the skin, and erfc (x) is the complementary error function. Therefore, transient temperature data associated with activation or deactivation of the Joule heating element can be used to determine thermal diffusivity, α, as illustrated in FIG. 6d (see FIG. 16a,b,f). As with conductivity, the device can be calibrated using samples with known diffusivity (FIG. 6e). Here, a wireless active e-TLC system serves as the measurement vehicle. The time dependence of the temperature, rather than the absolute values, is sufficient for extraction of diffusivity. The device operates at frequencies of ~2 GHz with maximum power inputs of ~2.5 W/kg for the subject of the studies described here (i.e. one third of the power limit recommended by the Federal Communications Commission's guidelines). The values also correspond closely to the hydration level, as shown in FIG. 6f. As with k, the values of a are consistent with literature reports based on techniques such as opto-thermal measurement.[48] The values of k and a can be combined to yield the product of the density (ρ) and heat capacity (c) of skin, based on the relation (cp=k/α). The calculations (See FIG. 16g) show that the heat capacity increases slightly with the increase of hydration level (assuming that ρ is approximately constant), which is consistent with expectation since the heat capacity (~4.2 J/g/K) of water is larger than the human tissue (e.g., ~3.7 J/g/K for dermis, ~2.3 J/g/K for fat).[49]

Figures 7D, 7E, 7F, 7G:
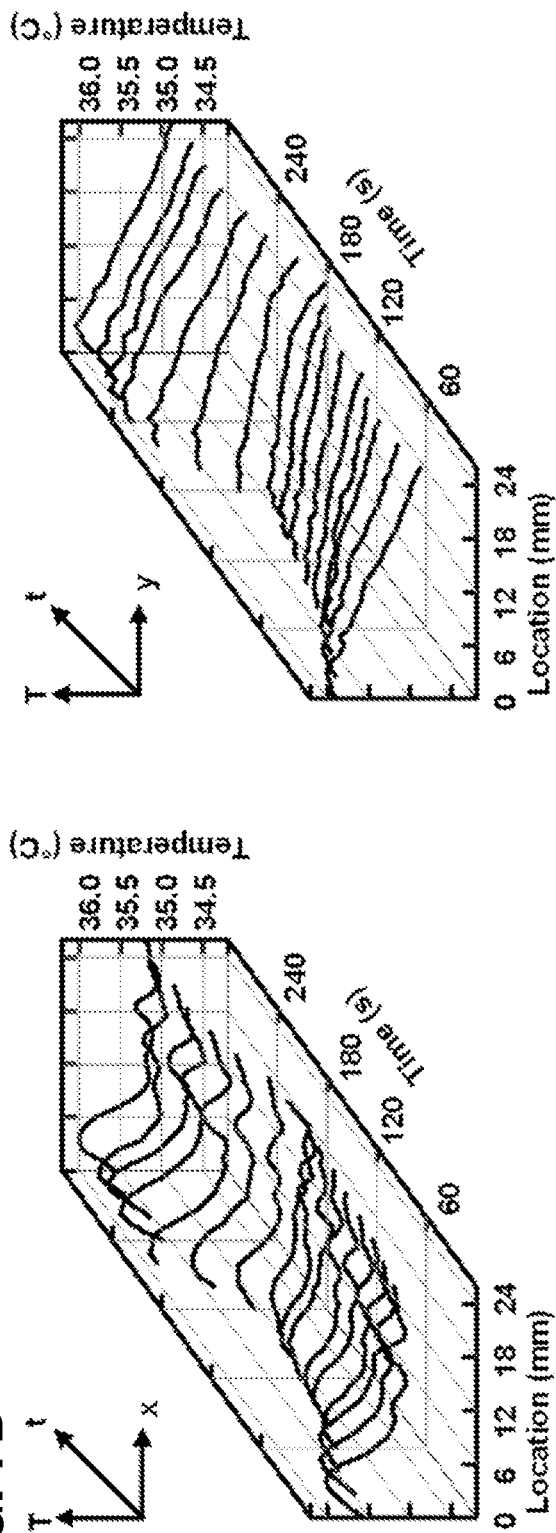
Figure 17:
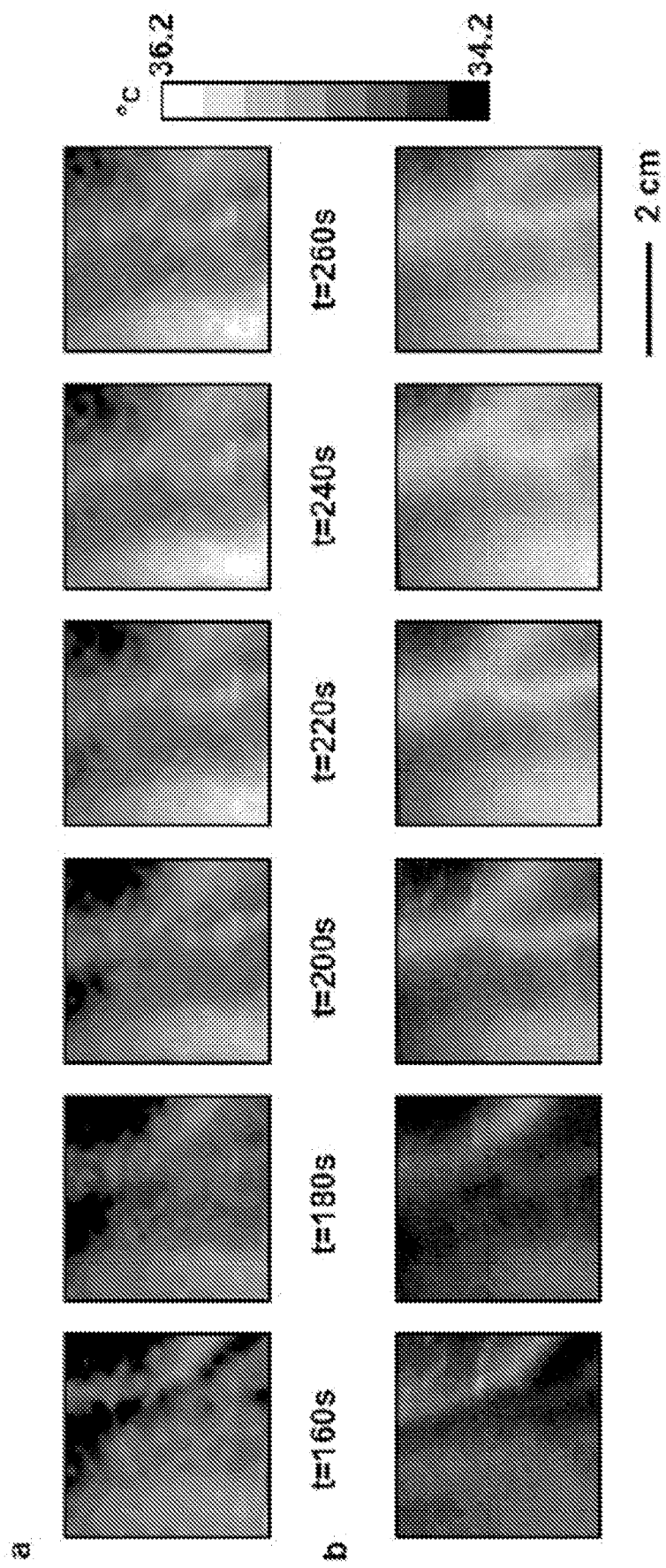
FIG. 17. Comparison of an e-TLC thermal imaging device and infrared camera measurement in a reactive hyperaemia test. (a) Spatial distributions of temperature determined with the e-TLC device at representative times from t=1605 to t=2605 at an interval of 20 s. (b) Spatial distributions of temperature determined with the infrared camera at representative times from t=1605 to t=2605 at an interval of 20 s.
Figure 18:
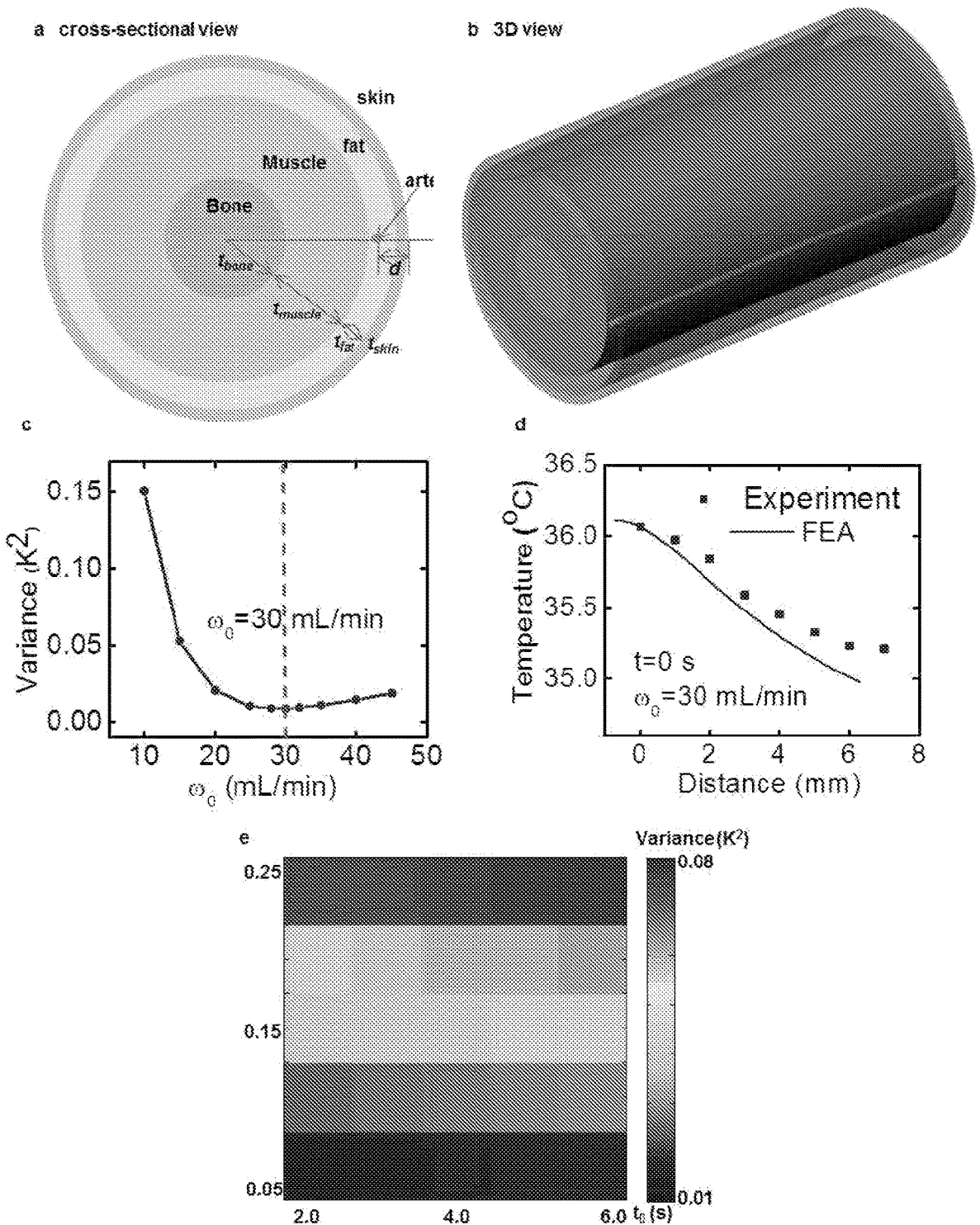
FIG. 18. Schematic illustration of the thermal conduction model that determines the blood flow rate during occlusion. (a) Cross-sectional view and (b) three-dimensional view of the wrist model; (c) Temperature variance of FEA and experiment versus the baseline flow rate; (d) Experimental results of the steady-state temperature as a function of the distance from the artery, as compared to the FEA calculations using the baseline flow rate of 30 mL/min; (e) Distribution of temperature variance in the space of parameters, $\alpha$ and $\tau_0$, during stage II of occlusion.

Spatio-temporal mapping even with passive e-TLC systems yields useful information on blood circulation,[50,51] maximal percentage increase in blood flow rate after occlusion,[52] and duration of reactive hyperaemia.[53] Measurements of temperature fluctuations above the ulnar artery and adjacent veins serve as an important part of a reactive hyperaemia protocol. Here, the flow of blood is temporarily occluded by a pressure cuff on the upper arm, followed by abrupt release. FIGS. 7a and 7b summarize results of measurements performed with an e-TLC device and an infrared camera. FIG. 7c presents representative frames of temperature distributions captured at 20 s intervals throughout the experiment. Occlusion, which begins at t=0 s, causes the temperature of the skin above the ulnar artery and adjacent areas to decrease drastically owing to lack of incoming blood flow and loss of heat to the environment. The minimum temperature is achieved at t=160 s; at this time, the occlusion is released and blood flow resumes. Sharp temperature increases occur in areas above the blood vessels, as shown in FIG. 7c, until the temperature stabilizes. The responses of pixels across the array of the e-TLC vary widely depending on their distance from the blood vessels. The maximum temperature fluctuations are ~1.2° C. and occur immediately above the ulnar artery; the minimum temperature fluctuations are ~0.4° C. and occur at locations away from near-surface blood vessels. Direct comparisons of spatio-temporal variations in temperature obtained from the e-TLC show quantitative agreement with results from an infrared camera (FIG. 17). FIGS. 7d and 7e highlight temperature variations along horizontal and vertical lines illustrated in the right image of FIG. 7a. A thermal model of the human wrist (Supplementary Note 9 and FIG. 18) that accounts for both the time-dynamic effect of occlusion and the thermal diffusion from the ulnar artery can capture the effects revealed in the measurements (FIG. 7f, g) and enable extraction of additional physiological information. The temporal variation of blood flow can be described with a piecewise, exponential type function,[54,55] corresponding to the three stages of the process: pre-occlusion, vascular occlusion, and reperfusion. The parameters characterizing this piecewise function can be determined by minimizing the average differences between the temperature-time profiles predicted by the model and those measured by the e-TLC device, during each stage. FIG. 7g shows that the calculated temperature history based on the thermal model agrees with experiment at all six of the pixels near the artery (i.e., distance <6 mm). Due to simplifying assumptions in the models, the FEA does not quantitatively capture the overshoot behavior observed in the two nearest sensors. Discrepancies at the two most distant sensors can be attributed to the neglect of heating associated with a nearby vein (~13 mm from the artery) in the model. For vessel diameters and depths that lie within reported ranges (Supplementary Note 9), the peak blood flow velocity after occlusion is calculated to be 58.8 cm/s, representing a three-fold increase over the baseline of 19.6 cm/s, with reactive hyperemia duration of 144 s. These values match those reported in the literature for a person with low cardiovascular risk.[52,53]

The epidermal photonic systems, as embodied by the e-TLC devices introduced here, are useful for characterization of the skin and, by extension, important parameters relevant in determining cardiovascular health and physiological status. These same capabilities are also useful in wound treatment and monitoring during a healing process, cancer screening, core body temperature assessments and others of clinical relevance. In all cases, the ability to wear the devices continuously, over days or weeks, and to perform readout and power delivery via a conventional smartphone, represent uniquely enabling features for some embodiments. Photonic operation in the red and near infrared enable use in near-surface implantable diagnostics.

References

1 Arora, N. et al. Effectiveness of a noninvasive digital infrared thermal imaging system in the detection of breast cancer. *Am. J. Surg.* 196, 523-526, (2008).
2 Kennedy, D. A., Lee, T. & Seely, D. A Comparative Review of Thermography as a Breast Cancer Screening Technique. *Integr. Cancer Ther.* 8, 9-16, (2009).
3 Kerr, J. Review of the effectiveness of infrared thermal imaging (thermography) for population screening and diagnostic testing of breast cancer. *NZHTA Tech Brief Series* 3 (2004).
4 Pochaczevsky, R., Pillari, G. & Feldman, F. Liquid crystal contact thermography of deep venous thrombosis. *Am. J. Roentgenol.* 138, 717-723 (1982).
5 Thomas, E. A., Cobby, M. J. D., Davies, E. R., Jeans, W. D. & Whicher, J. T. Liquid-crystal thermography and c-reactive protein in the detection of deep venous thrombosis. *Bri. Med. J.* 299, 951-952 (1989).
6 Cameron, E. W., Sachdev, D., Gishen, P. & Martin, J. F. Liquid-crystal thermography as a screening-test for deep-vein thrombosis in patients with cerebral infarction. *Eur. J. Clin. Invest.* 21, 548-550 (1991).
7 Kohler, A., Hoffmann, R., Platz, A. & Bino, M. Diagnostic value of duplex ultrasound and liquid crystal contact thermography in preclinical detection of deep vein thrombosis after proximal femur fractures. *Arch. Orthop. Trauma Surg.* 117, 39-42 (1998).
8 Davison, T. W. et al. Detection of breast-cancer by liquid-crystal thermography—preliminary report. *Cancer* 29, 1123 (1972).
9 Pochaczevsky, R. & Meyers, Vacuum contoured, liquid-crystal, dynamic breast thermoangiography as an aid to mammography in the detection of breast-cancer. *Clin. Radiol.* 30, 405-411 (1979).
10 Bakan, J. A. & Schaab, C. K. Liquid-crystal microcapsule medical device used for thermographic examination of the human female breast. *Appl. Biochem. and Biotech.* 10, 289-299 (1984).
11 Pochaczevsky, R. The value of liquid-crystal thermography in the diagnosis of spinal root compression syndromes. *Orthop. Clin. N. Am.* 14, 271-288 (1983).
12 Pochaczevsky, R., Wexler, C. E., Meyers, P. H., Epstein, J. A. & Marc, J. A. Liquid-crystal thermography of the spine and extremities—its value in the diagnosis of spinal root syndromes. *J. Neurosurg.* 56, 386-395 (1982).
13 Newman, R. I., Seres, J. L. & Miller, E. B. Liquid-crystal thermography in the evaluation of chronic back pain—a comparative-study, *Pain* 20, 293-305 (1984).
14 Klosowicz, S. J., Jung, A. & Zuber, J. Liquid-crystal thermography and thermovision in medical applications. Pulmonological diagnostics in *P. Soc Photo-Opt. Ins.* 4535, 24-29 (2001).
15 Kim, D.-H. et al. Epidermal Electronics. *Science* 333, 838-843 (2011).
16 Webb, R. C. et al. Ultrathin conformal devices for precise and continuous thermal characterization of human skin. *Nat. Mater.* 12, 938, (2013).
17 Sekitani, T. et al. A rubberlike stretchable active matrix using elastic conductors. *Science* 321, 1468 (2008).
18 Sekitani, T. et al. Organic nonvolatile memory transistors for flexible sensor arrays. *Science* 326, 1516 (2009).
19 Mannsfeld, S. C. B. et al. Highly sensitive flexible pressure sensors with microstructured rubber dielectric layers. *Nat. Mater.* 9, 859-864 (2010).
20 Kim, D.-H. et al. Epidermal Electronics. *Science* 333, 838-843 (2011).
21 Tee, B. et al. An electrically and mechanically self-healing composite with pressure- and flexion-sensitive properties for electronic skin applications. *Nat. Nanotechnol.* 7, 825-832 (2012).
22 Kaltenbrunner, M. et al. An ultra-lightweight design for imperceptible plastic electronics. *Nature* 499, 458 (2013).
23 Schwartz, G. et al. Flexible polymer transistors with high pressure sensitivity for application in electronic skin and health monitoring. *Nat. Commun.* 4, 1859 (2013).
24 Wang, C. et al. User-interactive electronic-skin for instantaneous pressure visualization. *Nat. Mater.* 12, 899-904 (2013).
25 Xu, S. et al. Soft Microfluidic Assemblies of Sensors, Circuits, and Radios for the Skin. *Science* 344, 70-74 (2014).

26 Son, D. et al. Multifunctional wearable devices for diagnosis and therapy of movement disorders. *Nat. Nanotechnol.* 9, 397-404 (2014).

27 Brull, S. J. et al. Comparison of crystalline skin temperature to esophageal temperatures during anesthesia. *Anesthesiology*, 73(3A), A472 (1990).

28 Ikeda, T. et al. Influence of thermoregulatory vasomotion and ambient temperature variation on the accuracy of core-temperature estimates by cutaneous liquid crystal thermometers. *Anesthesiology*, 86, 603 (1997).

29 Wisniewski, C. M. A comparison of esophageal temperature readings and liquid crystal temperature readings in the pediatric population. *CRNA Masters Thesis*. (1991).

30 Aitken, D. et al. Textile applications of thermochromic systems. *Rev. Prog. Coloration* 26, 1-8 (1996).

31 Chowdhury, M. A. et al. Application of thermochromic colorants on textiles: temperature dependence of colorimetric properties. *Color. Technol.* 129, 232-237 (2012).

32 Chowdhury, M. A. et al. Photochromic and thermochromic colorants in textile applications. *J. Eng. Fiber. Fabr.* 9, 107-123 (2014).

33 Dolphin, D., Muljiani, Z., Cheng, J. & Meyer, R. B. Low-temperature chiral nematic liquid-crystals derived from beta-methylbutylaniline. *J. Chem. Phys.* 58, 413-419 (1973).

34 Sage, I. Thermochromic liquid crystals. *Liquid Crystals* 38, 1551-1561 (2011).

35 Arumugam, V., Naresh, M. D. & Sanjeevi, R. Effect of strain-rate on the fracture-behavior of skin. Journal of Biosciences. *J. Biosciences* 19, 307-313 (1994).

36 Davis, J. R. *ASM Specialty Handbook: Copper and Copper Alloys*. (ASM International, 2001).

37 William, F. R., Leroy, D. S. & Don, H. M. *Mechanics of Materials*. (Jon Wiley & Sons, 1999).

38 Sandby-Moller, J., Poulsen, T. & Wulf, H. C. Epidermal thickness at different body sites: Relationship to age, gender, pigmentation, blood content, skin type and smoking habits. *Acta. Derm-Venereol.* 83, 410-413 (2003).

39 Kakade, V. U., Lock, G. D., Wilson, M., Owen, J. M. & Mayhew, J. E. Accurate heat transfer measurements using thermochromic liquid crystal. Part 1: Calibration and characteristics of crystals. *Int. J. of Heat. Fluid Fl.* 30, 939-949 (2009).

40 Stasiek, J. A. & Kowalewski, T. A. Thermochromic liquid crystals applied for heat transfer research. *Opto-Electron. Rev.* 10, 1-10 (2002).

41 Rao, Y. & Zang, S. Calibrations and the measurement uncertainty of wide-band liquid crystal thermography. *Meas. Sci. Technol.* 21 (2010).

42 Ireland, P. T. & Jones, T. V. The response-time of a surface thermometer employing encapsulated thermochromic liquid-crystals. *J. Phys. E. Sci. Instrum.* 20, 1195-1199 (1987).

43 Farina, D. J., Hacker, J. M., Moffat, R. J. & Eaton, J. K. Illuminant invariant calibration of thermochromic liquid-crystals. *Exp. Therm. Fluid. Sci.* 9, 1-12 (1994).

44 Anderson, M. R. & Baughn, J. W. Liquid-crystal thermography: Illumination spectral effects. Part 1—Experiments. *J. Heat. Trans-T. Asme* 127, 581-587 (2005).

45 Sabatino, D. R., Praisner, T. J. & Smith, C. R. A high-accuracy calibration technique for thermochromic liquid crystal temperature measurements. *Exp. Fluids.* 28, 497-505 (2000).

46 Kodzwa, P. M., Jr. & Eaton, J. K. Angular effects on thermochromic liquid crystal thermography. *Exp. Fluids.* 43, 929-937 (2007).

47 Cohen, M. L. Measurement of thermal-properties of human-skin-review. *J. Invest Dermatol.* 69, 333-338, (1977).

48 Xiao, P., Cui, Y., Ciortea, L. I., Berg, E. P. & Imhof, R. E. Opto-thermal in-vivo skin hydration measurements—a comparison study of different measurement techniques. *J. Phys. Conf. Ser.* 214, 012026, (2010).

49 Fiala, D., Lomas, K. J. & Stohrer, M. A computer model of human thermoregulation for a wide range of environmental conditions: the passive system. *J. Appl. Physiol.* 87, 1957-1972 (1999).

50 Holowatz, L. A., Thompson-Torgerson, C. S. & Kenney, W. L. The human cutaneous circulation as a model of generalized microvascular function. *J. App. Physiol.* 105, 370-372 (2008).

51 Gorbach, A. M. et al. Infrared imaging of nitric oxide-mediated blood flow in human sickle cell disease. *Microvasc. Res.* 84, 262-269 (2012).

52 Huang, A. L. et al. Predictive value of reactive hyperemia for cardiovascular events in patients with peripheral arterial disease undergoing vascular surgery. *Arterioscl. Throm. Vasc.* 27, 2113-2119 (2007).

53 Ishibashi, Y. et al. Short duration of reactive hyperemia in the forearm of subjects with multiple cardiovascular risk factors. *Circ. J.* 70, 115-123 (2006).

54 Akhtar, M. W., Kleis, S. J., Metcalfe, R. W. & Naghavi, M. Sensitivity of Digital Thermal Monitoring Parameters to Reactive Hyperemia. *J. Biomech. Eng-T. Asme.* 132 (2010).

55 Deshpande, C. *Thermal analysis of vascular reactivity MS thesis*, Texas A&M University (2007).

Methods

Fabrication of e-TLC Thermal Imaging Devices.

The fabrication (details in FIG. 8) began with spin-coating and curing a thin (20 µm) layer of poly(dimethylsiloxane) (PDMS, Sylgard 184, 40:1 mixing ratio) mixed with Iron Oxide Pigment Black 11 (The Earth Pigments Company, LLC) on a substrate of poly(ethyleneterephlatate) (PET). A PDMS stamp with arrays of square posts (each post, 0.5 mm×0.5 mm over an area of 15 cm$^2$; see Supplementary Note 1a) was contacted against a layer of micro-encapsulated thermochromic liquid crystals (Hallcrest SSN33R5W). Removing the stamp and drying it in air resulted in the formation of a solid layer of e-TLC material with an average thickness of 25 µm on the raised regions. A thermal release tape (Nitto Denko REVALPHA 90° C.) facilitated transfer of this material from the stamp to the surface of the black PDMS film. The device was completed by spin-coating and curing a thin (30 µm) layer of transparent PDMS on top of the structure, as an encapsulant. Fabrication of the wireless heater for the active e-TLC devices began with spin-coating of a thin film of polyimide (Sigma Aldrich) on a sacrificial layer of poly(methylmethacrylate) (PMMA; 100 nm, MicroChem) on a silicon wafer. Metal-evaporation (Cr/Au, 5 nm/50 nm), photolithography and wet-etching defined the serpentine structure for the Joule heater. Additional polyimide spin-coating, oxygen reactive ion etching and metal deposition for contacts, interconnects, and antenna circuits completed the wireless system. Dissolving the PMMA and then physically transferring the electronic structure to the back side of the e-TLC device completed the fabrication.

Device Calibration and Test for Noise Level.

An e-TLC device was placed on a metal plate with black matt finish on a hotplate. Two white fluorescent light sources were placed on opposite sides of the device for illumination in a manner that avoided specular reflection. A digital camera (Canon Mark||5D) and an infrared camera (FLIR ExaminIR) placed side-by-side were focused on the same area of the device at a distance of ~30 cm. The angle between the cameras and each of the light sources was ~90 degrees. The device was heated to 40° C. on the hotplate and then the hotplate was turned off. During the cooling process, high resolution images were collected every 10 seconds with the digital camera; the infrared camera captured frames at a rate of 12.5 s$^{-1}$. The process of cooling from 40° C. to 32° C. lasted about 20 minutes. The color information of the TLC was extracted from 33° C. to 39° C. with steps of 0.5° C. The set of algorithms developed to accomplish this task are based on computer vision OpenCV (http://opencv.org/) library. The main functions are (in alphabetic order) "adaptiveThreshold", "cvtColor", "dilate", "drawContours", "erode", "findContours", "GaussianBlur", "getStructuringElement", "imread", "inRange", "matchShapes", "minEnclosingCircle", "threshold". In HSV color space, the light intensity information is stored in the "value" channel and is completely separated from the color information which is encoded in the "hue" and the "saturation" channels. Hue and saturation are, therefore, a natural basis for temperature calibration since they are not strongly affected by the change in illumination intensity. Temperature calibration was constructed by means of two dimensional linear fit. The core function used in the process is "lstsq" from linear algebra module of Numerical Python (http://www.numpy.org/). Any combination of hue/saturation values can be assigned to a temperature value. Even for materials that are not temperature sensitive like the calibration color pixels, their hue/saturation can be treated as a specific temperature for consistency of analysis. To test the noise level and precision of the system, the hotplate temperature was set at a fixed value; temporal fluctuations of TLC color, calibration dot color and infrared emission were recorded using the two cameras over a period of 15 minutes. The color changes were converted to temperature fluctuation and compared to infrared fluctuation directly.

Reactive Hyperemia Test.

A volunteer (female, 27 years old) reclined in a chair with her left forearm secured gently to an arm rest using Velcro strips to reduce movement. A pressure cuff was secured around the subject's left bicep. An e-TLC device was placed on the skin of the left wrist approximately above the ulnar artery. Applying puffs of compressed air ensured full, conformal contact. Infrared and digital cameras placed 30 cm above the subject's left wrist were focused on the location of the device while illuminated with white fluorescent lights. The subject was instructed to relax for 5 minutes. The cuff was inflated to a pressure of 250 mm Hg for 160 seconds. Continuous high resolution color images and infrared temperature measurements were then collected with the two cameras as the occlusion started and was then released. The total during of the measurement period was 300 seconds.

Thermal Conductivity/Diffusivity and Hydration Measurements.

Thermal conductivity was determined by analyzing the spatial distribution of temperature for a few seconds immediately after activation of a Joule heater in an active e-TLC device. To validate the computational models, an active e-TLC device was floated on the surface of a mixture of ethylene glycol/water preheated to ~33° C. A constant voltage supplied to the e-TLC Joule heating element created a steady state temperature rise of a few degrees at the location of the heater. Images were then collected with a digital and infrared camera set up above the device with only white fluorescent light sources. The spatial decay of temperature in the e-TLC was recorded by analysis of images from the infrared camera and from color images of the device. The same experiment was performed on a volunteer's forearm skin. Here, different hydration levels were achieved by applying various amounts of lotion to the measurement location, prior to application of the active e-TLC device. Immediately after image capture, the e-TLC device was removed and a hydration meter was used to determine the actual moisture level (averaged from 5 readings). Measurements of thermal diffusivity used a wireless, active e-TLC, with a transmission antenna located ~10 cm away and adjusted to achieve a peak change in temperature of a few degrees (RF power below 2.5 W/kg at frequencies between 1.95-2.35 GHz, tuned to match the response of the receiver antenna on the e-TLC). Both digital and infrared cameras were focused on the device with a distance of 30 cm. Videos with 60 second duration recorded the changes in temperature associated with activation and de-activation of the heater. The experiment was validated using the ethylene glycol/water system, and then repeated on skin with different hydration levels, in procedures otherwise similar to those for the thermal conductivity measurements.

Supplementary Note 1a: Fabrication Procedure for PDMS Post Stamp Used for Inking Liquid Crystal 1. Clean a 3" Si wafer (Acetone, IPA->Dry 5 min at 110° C.).
2. Spin coat SU8 50 (microchem, 1000 rpm for 30 s, anneal 65° C. 10 min 95° C. 30 min)
3. Pattern SU8 with 365 nm optical lithography through iron oxide mask (Karl Suss MJB3) develop in SU8 developer
4 post exposure bake at 65° C. 1 min 95° C. 10 min
5. STS ICP RIE silicon etch SF6 20 s at 20 w CF4 10 s at 0w for 250 cycles to achieve a hole depth of around 400 um
6. Mold the silicon template with PDMS Supplementary Note 1 b: Fabrication Procedure for a Single Heater with Wired and Wireless Design Prepare Polymer Base Layers 1. Clean a 3" Si wafer (Acetone, IPA->Dry 5 min at 110° C.).
2. Spin coat with PMMA (poly(methyl methacrylate), spun at 3,000 rpm for 30 s)
3. Anneal at 180° C. for 10 min.
4. Spin coat with polyimide (PI, poly(pyromellitic dianhydride-co-4,4'-oxydianiline), amic acid solution, Sigma-Aldrich, spun at 4,000 rpm for 30 s for wired design and 1,000 rpm for 30 s for wireless design).
5. Anneal at 110° C. for 30 s.
6. Anneal at 150° C. for 5 min.
7. Anneal at 250° C. under vacuum for 1 hr.

Deposit First Metallization

8. E-beam 5/50 nm Cr/Au.
9. Pattern photoresist (PR; Clariant AZ5214, 3000 rpm, 30 s) with 365 nm optical lithography through iron oxide mask (Karl Suss MJB3).

Develop in aqueous base developer (MIF 327).

10. Etch Au with TFA Au etchant (Transene).
11. Etch Cr with CR-7 Cr Mask Etchant (Cyantek).
12. Remove PR w/ Acetone, IPA rinse.
13. Dry 5 min at 150° C.

Isolate First Metallization and Pattern Via Holes

14. Spin coat with PI.
15. Anneal at 110° C. for 30 s.
16. Anneal at 150° C. for 5 min.

17. Anneal at 250° C. under vacuum for 1 hr.
18. Pattern photoresist (PR; Clariant AZ4620, 3000 rpm, 30 s) with 365 nm optical lithography through iron oxide mask (Karl Suss MJB3). Develop in aqueous base developer (AZ 400K, diluted 3:1).
19. Reactive ion etch (RIE; March CS-1701, 50 mTorr, 20 sccm O2, 150 W, 35 min).

Deposit Second Metallization
20. E-beam 5/500 nm Cr/Au for wired design or 5/1600 nm Cr/Cu for wireless design.
21. Pattern PR AZ5214.
22. Etch Au with TFA Au etchant or etch Cu with TFA Cu etchant.cs
23. Etch Cr with Cr Mask Etchant.
24. Remove PR w/ Acetone, IPA rinse.
25. Dry 5 min at 150° C.

Isolate Entire Device
26. Spin coat with PI.
27. Anneal at 110° C. for 30 s.
28. Anneal at 150° C. for 5 min.
29. Anneal at 250° C. under vacuum for 1 hr.
30. Pattern PR AZ4620.
31. RIE (50 mTorr, 20 sccm O2, 150 W, 35 min for wired design and 120 min for wireless design).

Release and Transfer
32. Release w/ boiling Acetone.
33. Transfer to water soluble tape.
34. E-beam 3/30 nm Ti/SiO2.
35. Transfer to back of e-TLC device.
36. Bond thin, flexible cable (Elform, HST-9805-210) using hot iron with firm pressure for wired heater Supplementary Note 2: Analytic Solution of Spacing of e-TLC Dots During Uniaxial Stretching The deformation of an e-TLC device under uniaxial stretching (along horizontal direction) is analyzed to determine the change of spacing between pixels associated with the applied strain ($\in$). The e-TLC material (~221 MPa) is much stiffer than the elastomeric substrate (~131 kPa), and therefore undergoes negligible deformation, as evidenced by the experiment images of FEA results in FIG. 3b. The stretching deformation is, as a result, mainly accommodated by the soft substrate material. For pixels (in diameter of $d_{TLC}$) with an initial spacing $\Delta_0$, the horizontal spacing ($\Delta_{horizontal}$) after deformation is given by $$\Delta_{horizontal} = \Delta_0 + (\Delta_0 + d_{TLC})\in \quad (S1)$$

The vertical spacing ($\Delta_{vertical}$) decreases due to the Poisson effect. For sparsely distributed pixels (e.g., $d_{TLC} < \Delta_0$) the mechanical constrains associated with the e-TLC on the transverse compression can be neglected, such that the vertical spacing ($\Delta_{vertical}$) after deformation can be approximated as $$\Delta_{vertical} = \frac{\Delta_0 + d_{TLC}}{\sqrt{1+\varepsilon}} - d_{TLC}. \quad (S2)$$

Note that the transversely compressive strain of the soft substrate, due to stretching ($\in$), is given by $\in_{compression} = 1-(1+\in)^{-1/2}$, since it is nearly incompressible (i.e., Poisson ratio v=0.5). For $\Delta_0=0.3$ mm, $d_{TLC}=0.2$ mm as adopted in experiments, the analytic results in FIG. 9a, based on Eqs. (S1) and (S2), agree well with the experiment and FEA results.

Supplementary Note 3: Thermal Mass Calculation of e-TLC Device

The thermal mass of the devices are determined for 20 μm silicone and black iron oxide substrate and 30 μm transparent silicone substrate. The devices have an overall aerial coverage of ~15 cm². The calculated thermal masses that follow are given as thermal mass per unit area of skin. The device construction for the TCR device contains approximately 8.7 ng·cm$^{-2}$ of Au, 56 μg·cm$^{-2}$ of PI, 55.8 μg·cm$^{-2}$ of Cu, 0.64 mg·cm$^{-2}$ of black iron oxide powder, 4.18 mg·cm$^{-2}$ of silicone substrate, ~0.61 mg·cm$^{-2}$ of liquid crystal materials (Hallcrest, density 0.97 g·cm$^{-3}$). The material contributions to aerial thermal mass are: 21.48 μJ·cm$^{-2}$·K$^{-1}$ from Cu, 64.4 μJ·cm$^{-2}$·K$^{-1}$ from PI, 0.42 mJ·cm$^{-2}$·K$^{-1}$ from black iron oxide, ~1.09 mJ·cm$^{-2}$·K$^1$ from liquid crystal (Hallcrest, specific heat Specific heat 1.8 J·g$^{-1}$·K$^{-1}$), 6.11 mJ·cm$^{-2}$·K$^{-1}$ from the silicone backing (calculate values) and negligible from Au. This results overall device aerial thermal masses of ~7.7 mJ·cm$^{-2}$·K$^{-1}$. The thermal mass of skin depends on the water content where thermal mass increases with skin hydration and water content[2]. For hydrated skin, the heat capacity is approximately 3.7 J·cm$^{-3}$·K-1, and the device aerial thermal mass of 7.7 mJ·cm$^{-2}$·K$^{-1}$ is equivalent to the aerial thermal mass of skin with a thickness of 20.8 μm.

Supplementary Note 4: Water Vapor Permeability Test

Water permeability tests followed the ASTM E96-95 standard, and involved evaluation of e-TLC devices (thicknesses of 80 μm, 50 μm and 30 μm) and a commercial Feverscan™ device (LCR Hallcrest; polyester covering film ~75 μm, liquid crystal layer ~10-50 μm, black backing layer ~10-20 μm and graphic print layer ~10-20 μm). The experiments involved sealing the tops of identical jars, each containing a fixed amount of desiccant (97% anhydrous calcium sulfate and 3% cobalt chloride), with the devices under test. Control samples consist of jars without any seal on top. Diffusion of water vapor through the devices from the surrounding ambient air causes increases in weight, due to uptake by the desiccant. All jars were placed in a room that has consistent temperature (~22° C.) and humidity (~50%). The weight gain of each jar was recorded at the same time of day on a balance that has precision of 0.1 mg. By this test, after a 4-day period, the weight of the jar sealed by the Feverscan™ remains unchanged, consistent with negligible water permeation. By contrast, weight of the jar with the 80 μm e-TLC device increases by an amount that is nearly half (41%) of that compared to the control. The 50 μm and 30 μm e-TLC devices exhibit weight increases that are greater than half of the control, i.e. 60% and 62%, respectively. These results indicate that our formulation of PDMS, at the thicknesses used in our devices, provide only minor barriers to moisture, particularly when compared to conventional analogs.

Supplementary Note 5: Sensor Response Time

The TLC dot array is embedded in between two PDMS layers. The thickness and thermal properties of the black PDMS substrate and the TLC layer will both determine the heat transfer rate from the skin to the top of TLC layer. The effect from the top encapsulation elastomer is neglected to simplify the model.

A warm ethylene glycol bath heats up the entire device from the backside of black PDMS substrate. The in-plane dimensions of the elastomer layer are much larger than its thickness such that the heat flux is mainly along the thickness direction, which can be represented by a one-dimensional heat transfer model described elsewhere.[1]

The sensor response time is defined by the time at which the sensor temperature increase $T_{sensor}$ reaches 90% of $T_0$. For 30 μm black PDMS and 25 μm TLC layer as used in the experiment, the response time is predicted to be ~30 ms.

These agree reasonably well with the experimentally measured sensor response time (for $T_{sensor}=0.9\ T_0$) of 33 ms.

Supplementary Note 6: Color and Temperature Extraction Process

The only parts of TLS sensor that are temperature sensitive are the liquid crystal dots. Finding them in the image and separating from black elastomer background is necessary first stage in temperature extraction process. This is a typical computer vision problem (OpenCV http://opencv.org/). The essential steps of the process are illustrated in FIG. 4a. First frame show the original picture of 7×7 area of the sensor array. Second is the output of Gaussian filter which reduce noise through image smoothing. Gray scale (third frame) format is required input for adaptive threshold (fourth frame). Adaptive threshold is the robust algorithm that is aware of the illumination non-uniformity at different parts of the image. The output is the binary mask containing value "1" at bright areas and "0" elsewhere. Small speckles from the defects are visible here as well. They are removed with the two step erode/dilate process. Erode (fifth frame) shrink the white areas in frame four by removing few pixels at the border. Due to the small size of the defects they vanish completely. Dilate step (sixth frame) expand the white regions back restoring area of interest by adding the same amount of pixels removed in the previous step. List of contours can be extracted from this "clean" image (seventh frame). Every contour is enclosing a single temperature sensitive dot. The shape of the dot is closely reminiscent to circle. The obvious choice for dots position detection is the OpenCV's "enclosing circle" function which take a contour as an input. Last frame is the superposition of the original image and the set of corresponding positions (red dots) and enclosing circles (cyan rings).

Typical output of the digital camera is red-green-blue (RGB) color map. Intensities of all colors are affected by illumination conditions during the experiment. Converting to hue-saturation-value (HSV) color space make analysis more resilient to the change in lightning due to the fact that intensity now is encoded in value channel and color is in hue and saturation channels. In order to track the color change only hue and saturation are of interest. FIG. 4b show the calibration we use to convert the colors into temperature. The dots plotted are positioned at corresponding hue/saturation values and painted with their hue value. Background is the temperature evaluated from them with two dimensional linear fit.

Supplementary Note 7: Steady-State Thermal Conduction Model for Prediction of Thermal Conductivity A Cartesian coordinate system is set such that the origin is located at the center of the top surface of PDMS, as shown in FIGS. 15a and 15b, where the schematic illustrations of the device geometry, from both the 3D and cross-sectional views, are presented. FEA indicates that the ultrathin e-TLC dots (~20 μm) have negligible effects on the temperature distributions, and thus are not considered in the analytic model. The skin layer (homogenized from real skin and the underlying tissues, with the thickness >2 mm) are usually much thicker than the PDMS layer (with a thickness of ~60 μm), such that it can be considered as infinitely thick. The steady-state heat conduction equation is $\partial^2 T/\partial x^2 + \partial^2 T/\partial y^2 + \partial^2 T/\partial z^2 = 0$ for both the PDMS and skin, where T is the temperature. The square shaped resistor ($a_{Resistor} \times b_{Resistor}$) serves as the heat source, with the heat generation Q that pumps into the PDMS and skin. This can be modeled as a surface heat flux ($q_0 = Q/(a_{Resistor} b_{Resistor})$) for the bilayer system, i.e., $q_0 = q_{zPDMS}|_{z=-H_{PDMS}} - q_{zSkin}|_{z=-H_{PDMS}}$ for the region occupied by heat source. The free, top surface of the PDMS has natural convection with the surrounding air ($T_\infty$), i.e., $q_{zPDMS}|_{z=0} = h(T-T_\infty)$, with h denoting the heat transfer coefficient. The continuity conditions include $[T]=0$ and $[q_z]=0$ across the PDMS/skin interface, where $[\ ]=0$ stands for the jump across the interface. By adopting the approach of double Fourier transform, the temperature at the sensor plane ($z=-H_{sensor}$) is obtained as $$T_{Sensor\text{-}layer} = T_\infty + \frac{4q_0}{\pi^2 k_{PDMS}} \cdot \int_0^\infty \cos(\omega x) d\omega \int_0^\infty \frac{\sin\frac{a_{Resistor}\omega}{2} \sin\frac{b_{Resistor}\zeta}{2} \left( \frac{e^{\eta H_{Sensor}} + \frac{k_{PDMS}\eta - h}{k_{PDMS}\eta + h} e^{-\eta H_{Sensor}}}{} \right) \cos(\zeta y) d\zeta}{\omega \zeta \eta \left[ \left(1 + \frac{k_{Skin}}{k_{PDMS}}\right) e^{\eta H_{PDMS}} - \frac{k_{PDMS}\eta - h}{k_{PDMS}\eta + h}\left(1 - \frac{k_{Skin}}{k_{PDMS}}\right) e^{-\eta H_{PDMS}} \right]},$$

(S3)

where the subscripts 'PDMS' and 'skin' denote the PDMS and skin, respectively; k is the thermal conductivity. Eq. (S3) corresponds to the temperature solution of the forward thermal conduction problem, given the thermal conductivity of the skin layer. The parameters adopted in experiments include $a_{Resister}=b_{Resister}=0.5$ mm, $h=5$ W·m$^{-2}$K$^{-1}$, $H_{sensor}=30$ μm, $H_{PDMS}=60$ μm, $k_{PDMS}=0.16$ W·m$^{-1}$K$^{-1}$, and the thermal diffusivity $\alpha_{PDMS}=1.07$ m$^2$·s$^{-1}$. For a representative value of $k_{skin}=0.31$ W·m$^{-1}$K$^{-1}$ and Q=3.8 mW, the distribution of temperature at the sensor plane, as given by Eq. (S3), is shown in FIG. 15c, which agrees reasonably well with FEA results (FIG. 15d). The temperature profile along the x axis (in FIG. 15e) is in quantitative agreement with the FEA results. The relatively large discrepancy at the center region is mainly attributed to the assumption of homogenious heat generation $q_0$ through the entire heater, adopted for the aim of model simplification. FIG. 15e also shows the temperature gradient is obvious in the region within a distance of ~4 mm from the heater center. For the sensors far from the heater (0.5 by 0.5 mm), the temperature distribution can be approximated by the simple solution of a point heat source, i.e., $$T_{Sensor\text{-}layer} \approx T_\infty + \frac{Q}{2\pi k_{Skin} r},$$

(S4)

where the ultrathin PDMS layer is neglected, and $r=\sqrt{x^2+y^2}$ is the in-plane distance from the origin. FIG. 15e demonstrates that this approximate solution has very good accuracy for $r \geq a_{Resister}/2$. This simplified solution is adopted to predict the thermal conductivity of skin by fitting the temperature data from the e-TLC device, as shown in FIG. 6a for an example with $T_\infty=33.9°$ C. and Q=3.83 mW. FIG. 6b demonstrates the prediction of thermal conductivity for the calibration experiment, in which the water/ethylene glycol solutions with different mixing ratios are adopted to mimic real skin in different hydration levels. The thermal conductivities predicted by the current model agree fairly well with those reported in the literature (MEGlobal, Ethylene Glycol Product Guide).

Supplementary Note 8: Transient Thermal Conduction Model for Prediction of Thermal Diffusivity To simplify the analyses for the transient thermal conduction problem, we continue to assume that the heater is a point heat source. Consider that the heater is turned on at time t=0, the induced transient temperature solution is given by $$T_{Sensor-layer}(t) \approx T_\infty + \frac{Q}{2\pi k_{skin} r} \text{erfc}\left(\frac{r}{\sqrt{4\alpha_{skin} t}}\right), \quad (S5)$$

where $\alpha_{skin}$ is the thermal diffusivity of the skin, and erfc(x) is the complementary error function. For the representative value of $k_{skin}$=0.31 W·m$^{-1}$K$^{-1}$, $\alpha_{skin}$=1.14 m$^2$·s$^{-1}$, and Q=3.8 mW, the time dynamic temperature given by Eq. (S5) agree remarkably well with FEA results, as shown in FIG. 15f, for three different points (with a distance of 0.5, 1.0 and 2.0 mm from the origin).

Based on Eq. (S5), we can determine the thermal diffusivity based on the transient temperature data from the e-TLC device, even when the power is unknown (e.g., when the wireless system is adopted to power the heater). FIG. 6d gives an example of temperature profile at the sensor with a distance of 0.5 mm from the heater, where the analytic curve with the thermal diffusivity of 0.43×10$^{-7}$ m$^2$/s gives the best match with the experimental data. FIG. 6e demonstrates the predictions of thermal diffusivity for the calibration experiment, which agree reasonably well with those reported in the literature (MEGlobal, Ethylene Glycol Product Guide).

Supplementary Note 9: Mathematical Modeling of Reactive Hyperemia

A two-dimensional (2D), transient, heat transfer model of human wrist was developed, which considers the various tissues surrounding the ulnar artery, and quantitatively characterizes the heat exchange between the blood flow and the surrounding tissues. FIGS. 17a and 17b show the schematic illustration of the tissue geometry, in which a circular cross section is adopted for the wrist to simplify the analyses. The blood at body temperature flows through the circular artery embedded in the fat layer, heating the surrounding tissues. The heat exchange between the blood flow and the fat layer across the artery wall is described with a heat convection model[2], which assumes the exchanged heat flux (q) to be proportional to the blood flow rate, i.e.

$$q = \frac{\rho_b c_{pb} \omega_b(t)}{\pi D_{artery}} (T_{body} - T_s), \quad (S6)$$

where $\rho_b$, $c_{pb}$, $\omega_b(t)$ are the density, specific heat capacity, and time-dependent flow rate of the blood; $D_{artery}$ is the diameter of the artery; $T_{body}$ and $T_s$ are the body temperature, and the temperature of fat at the artery wall, respectively. Due to the heating of the blood flow, the temperature distributes non-uniformly in these tissues, which is governed by the temporal heat conduction equation of $$\rho_j c_j \frac{\partial T_j}{\partial t} = k_j \left(\frac{\partial^2 T_j}{\partial x^2} + \frac{\partial^2 T_j}{\partial y^2} + \frac{\partial^2 T_j}{\partial z^2}\right)(j = 1 \ldots 4),$$

with the subscript representing different tissues (with skin as j=1, fat as j=2, muscle as j=3, and bone as j=4). The free, outer surface of the skin has natural convection with air, which usually cools down the skin due to a lower room temperature than body temperature. The interior bone layer is assumed to maintain the core-temperature (close to the body temperature $T_{body}$).

The modeling of occlusion involves two steps, starting from the simulation of the steady-state heat conduction in the various tissues due to constant heating of blood flow, corresponding to the stage of pre-occlusion (Stage I). With the steady-state solution as an input, we further simulate the temporal changes in temperature distributions due to the application and release of occlusion, corresponding to the stage of vascular occlusion (Stage II) and reperfusion (Stage III), respectively. Based on previous experimental data, the temporal variation of blood flow during these different stages can be well described by the following piecewise function[2,3]

$$\omega_b^I(t) = \omega_0, \quad t \leq t_{occ,st} \quad (S7)$$

$$\omega_b^{II}(t) = (\omega_0 - \omega_s)\exp(-t/\tau_0) + \omega_s, \quad t_{occ,st} < t \leq t_{occ,end}$$

$$\omega_b^{III}(t) = \begin{cases} (\omega_{max} - \omega_s)\sin^2\left[\frac{\pi(t - t_{occ,end})}{(2t_{dw})}\right] + \omega_s, & t_{occ,end} < t \leq (t_{occ,end} + t_{dw}) \\ (\omega_{max} - \omega_f)\exp\left[\frac{-(t - t_{occ,end} - t_{dw})}{\tau_h}\right] + \omega_0, & t > (t_{occ,end} + t_{dw}) \end{cases},$$

where $\omega_0$ represents the baseline blood flow; $\omega_s$ is the blood perfusion after the occlusion is applied for a sufficiently long time, 160 s in the case of experiments here; $\omega_{max}$ is the maximum hyperemic blood flow; $\tau_0$ is a time constant depicting the falling speed of blood flow after occlusion is applied; $t_{dw}$ is the time required to reach the maximum hyperemic blood flow after the release of occlusion; $\tau_h$ indicates the rate at which the blood flow returns to the baseline value during the reperfusion; $t_{occ,st}$ and $t_{occ,end}$ denote the starting and ending times of the occlusion, respectively. Except for $t_{occ,st}$ and $t_{occ,end}$, which are known in experiments ($t_{occ,st}$=0 s, $t_{occ,end}$=160 s), there are six parameters in this model of reactive hyperemia which can be varied to simulate the temperature history of blood perfusion. The aim of the thermal analyses is to obtain an optimized set of parameters that can minimize the average difference between the simulations and experiment data of temperature-time profile at those sensors with a distance ≤7 mm from the artery (FIG. 7g). The baseline blood flow $\omega_0$ does not involve the occlusion process, and therefore can be determined using the temperature value measured before the occlusion (Stage I). The blood flow $\omega_s$ and time parameter $\tau_0$ (only related to Stage II) are determined by the measured temperature-time profile during Stage II, and the other three parameters ($\omega_{max}$, $t_{dw}$ and $\tau_h$) are determined by the data during Stage III. In total, there are six parameters in our simulations, i.e., $\omega_0$, $\alpha=\omega_s/\omega_0$, $\beta=\omega_{max}/\omega_0$, $\tau_0$, $t_{dw}$ and $\tau_h$, whose ranges are listed in Supplementary Table 1, based on reported experiments[2,3].

Finite element analyses (FEA) were adopted to solve the above transient heat transfer equation, and determine the temperature distribution numerically. 4-node linear heat transfer elements were used, and refined meshes were adopted to ensure the accuracy. The boundary conditions include the prescribed temperature (T=$T_{body}$) in the bone layer, the heat convection at the artery wall with blood flow of body temperature (i.e., Eq. (S6)), and the natural convection at the outer surface of skin with air of room temperature (~27.0° C.). The geometric and thermal-physical properties of various tissues are given in Supplementary Table 2. For the reactive hyperemia model described above, the baseline blood flow rate is determined as $\omega_0$=30 mL/min (19.6 cm/s for a vessel diameter of 1.8 mm), which could minimize the difference between FEA and experiment, i.e., the variance, as shown in FIG. 17c. Based on $\omega_0$=30 mL/min, the calculated temperature decay from the artery at the steady state indeed agree well with experiment data (FIG. 17d). To minimize the temperature variance during stage II (FIG. S10e), the blood flow $\omega_s$ and time parameter $\tau_0$ are determined as $\omega_s$=1.5 mL/min and $\tau_0$=2 s. Similarly, the other three parameters corresponding to stage III can be obtained as $\omega_{max}$=90 mL/min (58.8 cm/s), $t_{dw}$=15 s and $\tau_h$=35 s. For this set of parameters, the temperature-time profile obtained from FEA agrees reasonably well with the experiment results (FIG. 6g) for all the sensor points close to the artery.

SUPPLEMENTARY TABLE 1

The parameter range in the model of reactive hyperemia for simulations.

| | $\omega_0$ (mL/min) | $\alpha = \omega_s/\omega_0$ | $\beta = \omega_{max}/\omega_0$ | $T_0$ (s) | $t_{dw}$ (s) | $T_h$ (s) |
|---|---|---|---|---|---|---|
| Range | [10, 45] | [0.05, 0.25] | [3, 10] | [2, 6] | [15, 45] | [35, 75] |

SUPPLEMENTARY TABLE 2

The geometric and thermal-physical properties of various tissues for the wrist, where t denotes the thickness, D is the diameter of the artery, and d is the depth of the artery.

| Parameter | Skin | Fat | Muscle | Bone | Blood |
|---|---|---|---|---|---|
| $\rho$ (kg/m$^3$)$^{(2, 4)}$ | 1085 | 850 | 1085 | 1357 | 1069 |
| $c_p$ (J/kg/K) $^{(2, 4)}$ | 3680 | 2300 | 3768 | 1700 | 3659 |
| k (W/m/K) $^{(5-7)}$ | 0.47 | 0.16 | 0.42 | 0.75 | / |
| t (mm) $^{(5-7)}$ | 1.0 | 4.4 | 13.6 | 10.0 | / |
| D (mm) $^{(8)}$ | / | / | / | / | 1.8 |
| d (mm) $^{(9, 10)}$ | / | / | / | / | 2.2 |

References

1 Webb, R. C. et al. Ultrathin conformal devices for precise and continuous thermal characterization of human skin. *Nat. Mater.* 12, 938, (2013).

2 Deshpande, C. Thermal analysis of vascular reactivity MS thesis, Texas A&M University, (2007).

3 Akhtar, M. W., Kleis, S. J., Metcalfe, R. W. & Naghavi, M. Sensitivity of digital thermal monitoring parameters to reactive hyperemia. *J. Biomech. Eng-T. Asme.* 132, 051005, (2010)

4 Fiala, D., Lomas, K. J. & Stohrer, M. A computer model of human thermoregulation for a wide range of environmental conditions: The passive system. *J. App. Physiol.* 87, 1957-1972 (1999).

5 Song, W. J., Weinbaum, S., Jiji, L. M. & Lemons, D. A combined macro and microvascular model for whole limb heat transfer. *J. Biomech. Eng-T. Asme.* 110, 259-268 (1988).

6 Sieg, P., Hakim, S. G., Bierwolf, S. & Hermes, D. Subcutaneous fat layer in different donor regions used for harvesting microvascular soft tissue flaps in slender and adipose patients. *Int. J. Oral. Max. Surg.* 32, 544-547 (2003).

7 Shen, H. et al. A genomewide scan for quantitative trait loci underlying areal bone size variation in 451 Caucasian families. *J. Med. Genet.* 43, 873-880 (2006).

8 Shima, H., Ohno, K., Michi, K. I., Egawa, K. & Takiguchi, R. An anatomical study on the forearm vascular system. *J. Cranio. Maxill. Surg.* 24, 293-299 (1996).

9 McCartney, C. J. L., Xu, D., Constantinescu, C., Abbas, S. & Chan, V. W. S. Ultrasound Examination of Peripheral Nerves in the Forearm. *Region. Anesth. Pain. M.* 32, 434-439 (2007).

10 Kathirgamanathan, A., French, J., Foxall, G. L., Hardman, J. G. & Bedforth, N. M. Delineation of distal ulnar nerve anatomy using ultrasound in volunteers to identify an optimum approach for neural blockade. *Eur. J. Anaesth.* 26, 43-46 (2009).

Example 2: Stretchable, Wireless Sensors and Functional Substrates for Epidermal Characterization of Sweat This Example introduces materials and architectures for ultrathin, stretchable wireless sensors that mount on functional elastomeric substrates for epidermal analysis of biofluids. Measurement of the volume and chemical properties of sweat via dielectric detection and colorimetry demonstrates some capabilities. Here, inductively coupled sensors comprising LC resonators with capacitive electrodes show systematic responses to sweat collected in microporous substrates. Interrogation occurs through external coils placed in physical proximity to the devices. The substrates allow spontaneous sweat collection through capillary forces, without the need for complex microfluidic handling systems. Furthermore, colorimetric measurement modes are possible in the same system by introducing indicator compounds into the depths of the substrates, for sensing specific components ($OH^-$, $H^+$, $Cu^+$, and $Fe^{2+}$) in the sweat. The complete devices offer Young's moduli that are similar to skin, thus allowing highly effective and reliable skin integration without external fixtures. Experimental results demonstrate volumetric measurement of sweat with an accuracy of 0.06 µL/mm$^2$ with good stability and low drift. Colorimetric responses to pH and concentrations of various ions provide capabilities relevant to analysis of sweat. Similar materials and device designs can be used in monitoring other body fluids.

1. Introduction

Emerging wearable sensor technologies offer attractive solutions for continuous, personal health/wellness assessment,[1,2] forensic examination[3] patient monitoring[4,5] and motion recognition.[6,7] Recent advances in epidermal electronics[8] provide classes of skin-mounted sensors and associated electronics in physical formats that enable intimate, conformal contact with the skin. The soft, non-irritating nature of this contact yields an interface that simultaneously provides high precision, accurate measurement of biophysiological parameters, such as temperature,[9] hydration,[10] strain,[11] and biopotential.[12] Such epidermal sensors are ultrathin, breathable and stretchable, with mechanical and thermal properties that closely match to the skin itself, to enable effective skin integration with minimum constraints on natural processes. The results provide unique capabilities in long-term, reliable health monitoring.

An important measurement mode in such devices may involve the analysis of body fluids (blood, interstitial fluid, sweat, saliva, and tear), to gain insights into various aspects of physiological health.[13-16] Such function in wearable sensors, generally, and epidermal electronics in particular, is relatively unexplored. Existing devices either use complex microfluidic systems for sample handling[17-20] or involve purely concentration-based measurement without sample collection and storage, or access to parameters related to quantity and rate.[21-23] In addition, mechanical fixtures, straps and/or tapes that are typically required to maintain contact of these devices with the skin do not lend themselves well to continuous, long term monitoring without discomfort.[24] In the following, a set of materials and device architectures that provide advanced capabilities in this area is reported. The key concept involves the use of functional soft substrates to serve as a means for microfluidic collection, analysis and presentation to co-integrated electronic sensors and/or external camera systems. The pores of these substrates spontaneously fill with body fluids that emerge from the skin, where they induce colorimetric changes in the substrate and alter the radio frequency characteristics of integrated electrical antenna structures. The results offer valuable insights into the properties and volume of sweat, and their relationships to fluctuations in body temperature,[25] fluid and electrolyte balance,[26] and disease state.[27] The devices also eliminate the need for direct skin-electrode contacts, thereby minimizing irritation that can be caused by contact between the skin and certain metals,[28] while at the same time enabling repeated use of a single device with minimal noise induced by motion artifacts. The sensors exploit inductive coupling schemes, without on-chip detection circuits but with some potential for compatibility using near-field communication systems that are found increasingly in portable consumer electronic devices. The entire sensing system offers flexible and stretchable mechanics, with form factors that approach those of epidermal electronics.

2. Results and Discussion

Figure 19:
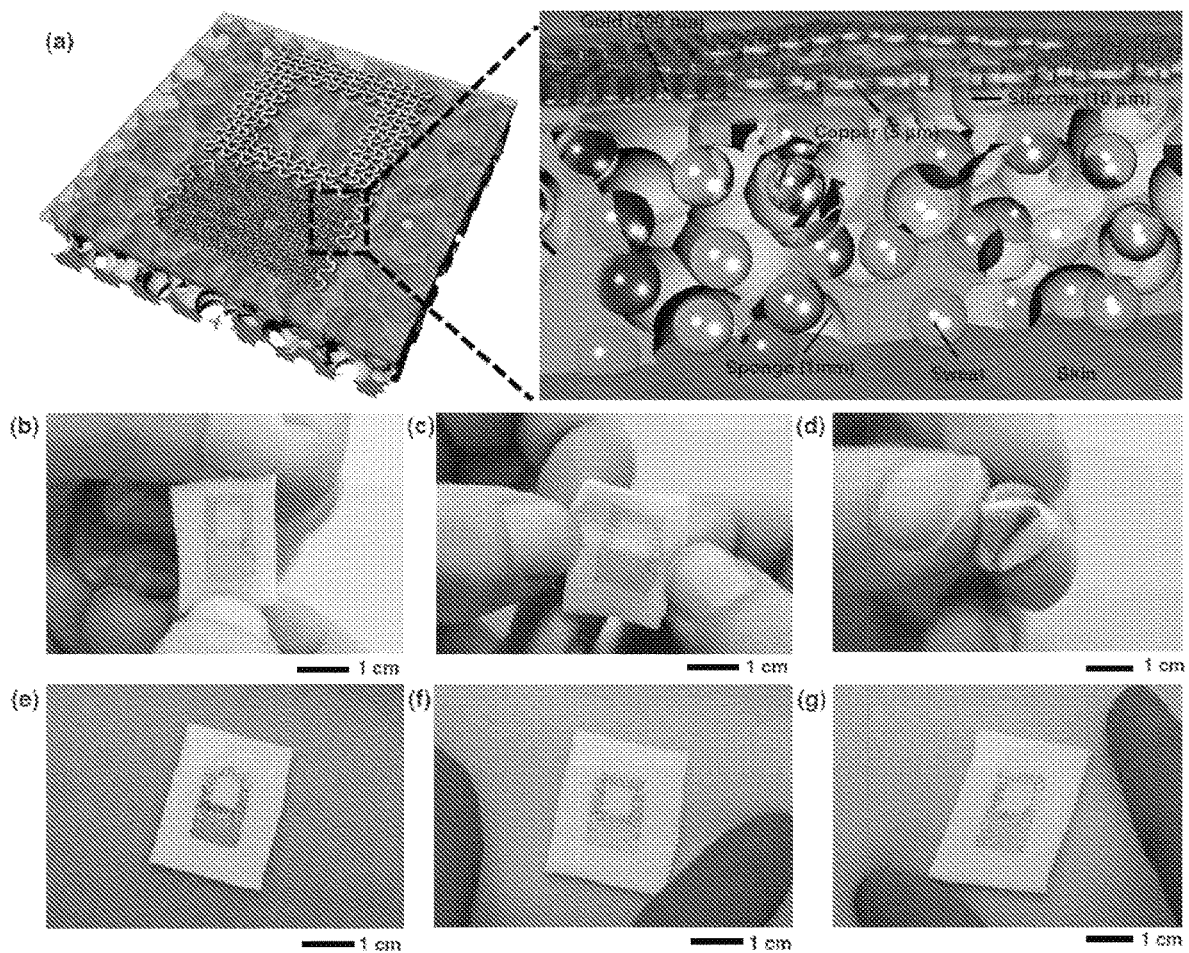
FIG. 19. (a) Schematic illustration of a passive wireless capacitive sensor designed for sensing of sweat from the surface of the skin. Pictures of a device in (b) longitudinal and (c) latitudinal states of deformation, and crumpled between the fingers (d). Pictures of a device mounted on the skin in (e) undeformed, (f) uniaxially stretched and (g) biaxially stretched configurations.

FIG. 19a shows images and schematic illustrations of a typical device (22×28 mm² for the surface area of the substrate, and 10×15 mm² for the dimension of the sensor) that includes an inductive coil and a planar capacitor formed with interdigitated electrodes. The coil consists of four turns of thin copper traces in a filamentary serpentine design that affords both flexibility and stretchability. The width of the trace is 140 μm, and the lengths of the inner and outer turns are 4.8 and 9.5 mm, respectively. The electrodes consist of serpentine wires (50 μm in width) that have lengths between 6.5 to 8.4 mm, to form 9 digits with a digit-to-digit spacing of 600 μm. The dielectric properties of the microporous supporting substrate strongly influence the capacitance of the structure.

Figure 23:
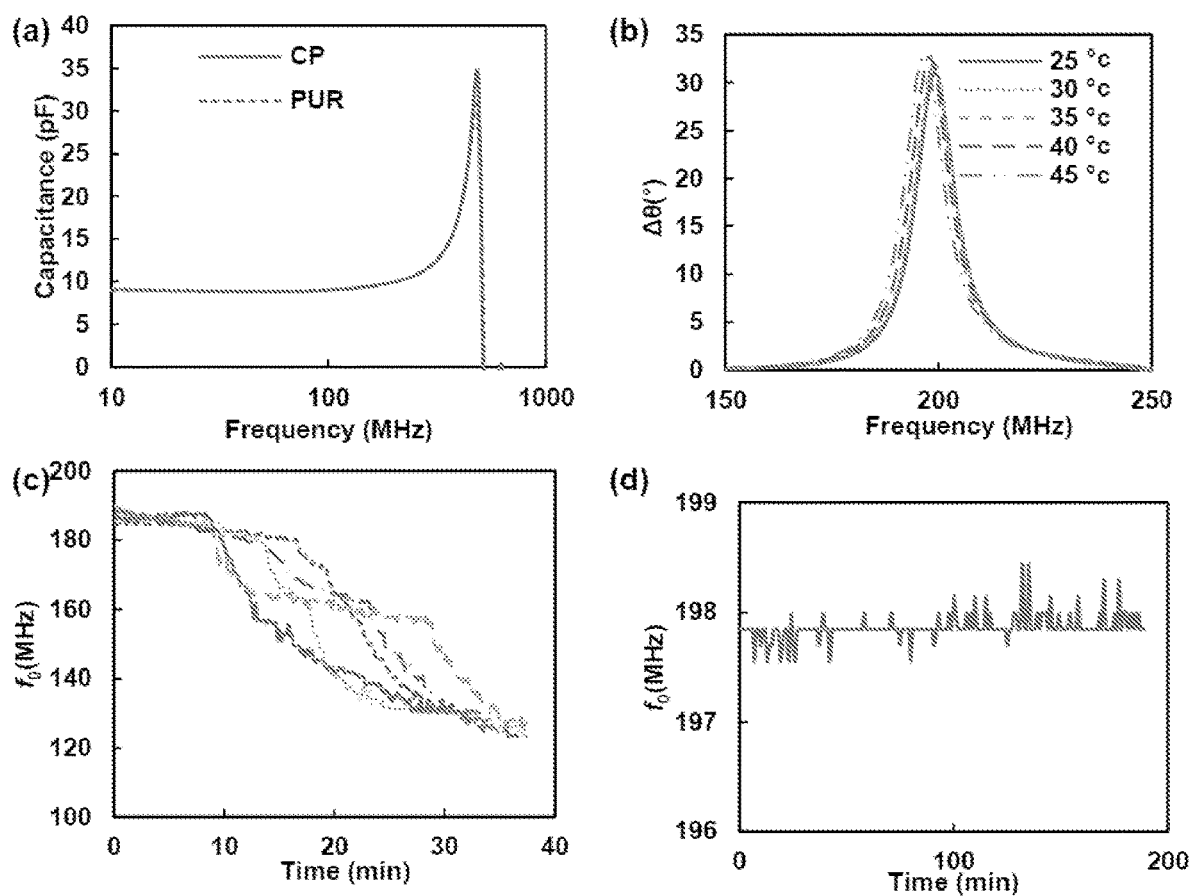
FIG. 23. (a) Capacitance values of a coaxial cable probe when in contact with sensors on CP and PUR substrates injected with 0.6 mL buffer solution. (b) Stability of a sweat sensor at temperatures from 25 to 45° C. (c) Time variation of $f_0$ for a sweat sensor on a silicone substrate in response to the injection of 0.6 mL buffer solution. (d) Drift and stability of a sensor output at dry state over an extended period of 3 hours.

In this way, the sweat sensor enables capacitive detection of the change of the dielectric properties of the substrate as its pores fill with biofluids (e.g. sweat). An external primary coil generates a time varying electromagnetic field that induces a current flow within the sensor. The impedance of the sensor is then determined by the amount of sweat within the substrate; this impedance influences that of the primary coil placed in proximity to the device. The resonance frequency ($f_0$) of the sensor can be determined from the frequency of a phase dip (or a peak in the phase difference, $\Delta\theta$, obtained from the subtraction of the phase of the primary coil with and without the sensor underneath) in the phase-frequency spectrum of the primary coil.[29-32] At measurement frequencies examined here (100 to 200 MHz), free water molecules are under the influence of δ relaxation.[33] The responses of the functional polymer substrates only involve contributions from induced charges. The movement of the water molecules and dynamics of the induced charges are sufficiently fast to respond to the external electromagnetic field. As a result, the combined dielectric properties of substrate and the sweat exhibit an invariant dielectric response over a wide range of frequencies (FIG. 23(a)). For present purposes, the frequency-dependence in the dielectric properties of the substrate can be ignored.

The sensor offers mechanical properties (elastic modulus ≈80 kPa) similar to those of the skin.[34] The thickness of the substrate (1 mm), along with its lateral dimensions and porosity define the amount of fluid that it can capture. The devices exhibit robust, elastic behavior under axial stretching (FIGS. 19b and 19c) and other more complex modes of deformation (FIG. 19d). Attachment of the sensor onto the skin (FIG. 1e) using a thin layer of commercial spray-on bandage as adhesive leads to reversible skin/sensor bonding that can withstand significant extension and compression of the skin with sufficient mechanical strength to prevent delamination (FIGS. 19f and 19g).

In vitro experiments involve slow introduction of 0.6 mL of buffer solution (phosphate buffered saline, Sigma-Aldrich Corporation, St. Louis, Mo., USA) onto the substrates with a syringe pump, over the course of ≈40 minutes (FIG. 20d). The resonance frequency of the sensor ($f_0$), as measured by the shift of the phase peak of a primary coil placed in proximity to the device (FIG. 20c), decreases with increasing buffer solution content in the substrate. This response reflects increases in the permittivity due to replacement of air with buffer solution in the pores of the substrate, leading to an increase in the capacitance of the interdigitated electrodes associated with their proximity to the substrate. For a typical porous polyurethane (PUR) (PUR permittivity=7,[35] PUR substrate permittivity=1.42 at 0.93 porosity in air) (FIG. 20a), $f_0$ shifts from 195.3 to 143.3 MHz in this experiment (FIG. 20d). Drying of the sensor in air at room temperature leads to the recovery of $f_0$, eventually to the original value (195.3 MHz) over a period of ≈6 hours, indicating a reversible response with relative insensitivity to residual salt that might remain in the substrate.

Assessment of performance with human subjects involves use of sensors on cellulose paper (CP) and silicone substrates attached to the arms of two volunteers. Reference substrates made of the same materials with similar sizes placed in close proximity to the sensors provide means for determining the accuracy and establishing a calibrated response (FIG. 20b). The monitoring includes measuring the value of $f_0$ of the sensors and the weight of the reference substrates every 5 min for a period of 2 hours. The results indicate that $f_0$ is inversely proportional to the weight of the reference sensor, such that the response can be calibrated with any two measured weights. The calibrated results closely follow weight changes of 0.4 (FIG. 20e) and 0.2 g (FIG. 20f) in the reference substrates, corresponding to 0.4 and 0.2 mL of sweat over the sensing areas.

Figure 20:
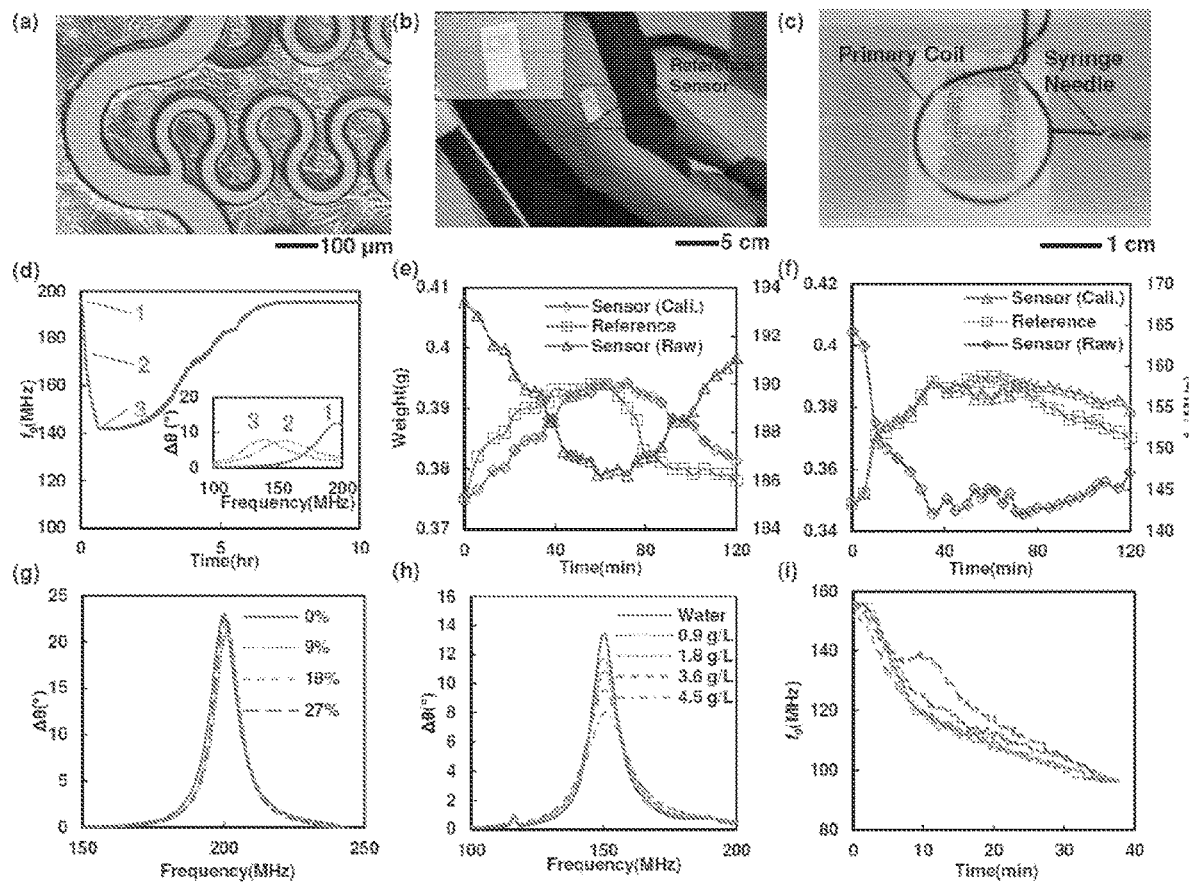
FIG. 20. (a) Scanning electron micrograph of a sensor on a PUR substrate coated with a thin silicone film; the regions colorized in yellow represent the interdigitated gold electrodes. (b) Picture of a sweat sensor and a reference sensor on the arm of a volunteer for in-vivo testing. (c) Picture of a sweat sensor underneath a primary coil. A syringe needle inserted into the sensor delivers controlled amounts of a buffer solution through a syringe pump. (d) Representative data showing the response of the sensor (resonant frequency, $f_0$) as a function of time after introduction of 0.6 mL buffer solution (labeled 1). The initial response (labeled 2) corresponds to wicking of the solution into the porous substrate, to yield a stable overall shift in $f_0$ (labeled 3). As the solution evaporates over the next several hours, $f_0$ recovers to approximately the initial value. The inset shows the phase difference measured by the primary coil at the three time points indicated in the main frame. (e, f) Results of testing on two volunteers, with comparisons to changes in weight evaluated using similar porous substrates (without detection coils) placed next to the sensors. Both $f_0$ and the weight of the sensors calibrated from $f_0$ are shown, along with comparison to the weight of the reference substrates. (g) Phase response of a sensor under biaxial strain from 0 to 27%. (h) Phase response as a function of concentration of sodium chloride, from 0 to 4.5 g/L. (i) Change in $f_0$ of a sweat sensor on a CP substrate as a function of time during controlled injection of 0.6 mL buffer solution.
Figure 24:
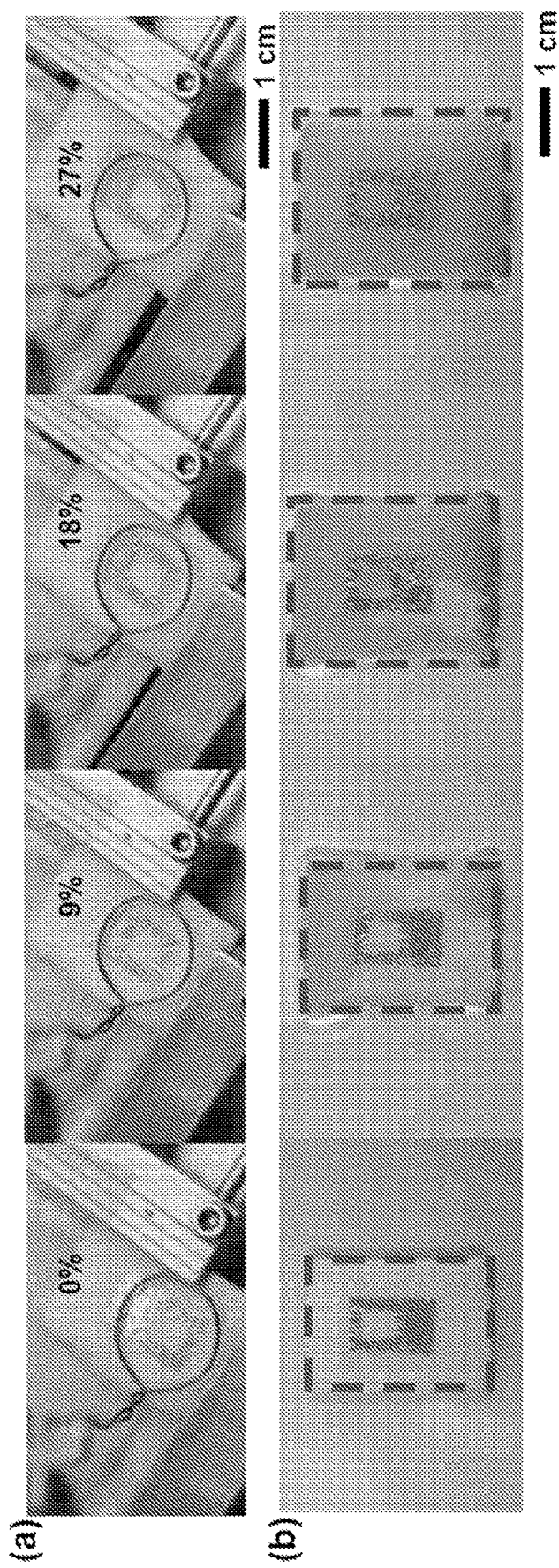
FIG. 24. (a) A sensor is biaxially stretched by two perpendicular stretchers at a strain from 0 to 27%. (b) Expansion of the surface area of the sensor in response to water absorption.

Dimensional changes associated with deformation of the skin or swelling of the device caused by sweat absorption could, conceivably, lead to changes in $f_0$. Strain induced effects can be examined by biaxially stretching a device and measuring $f_0$ at various states of deformation (FIG. 24(a)). The results show changes of only ≈0.9 MHz for biaxial strains of 27% (FIG. 20g) that are comparable to those caused by the absorption of water (FIG. 24(b)). The modest changes in $f_0$ under biaxial stretching may be attributed to the symmetric design of the sensor coil as well as mutual compensation of the changes in lengths and spacings of the interdigitated electrodes. The effects of temperature are also small. In particular, data indicate (FIG. 23(b)) that $f_0$ shifts from 199.25 MHz to 196.63 MHz when the temperature is changed from 25 to 45° C. Finally, although the salinity and ionic content of the sweat may lead to changes in both conductivity and permittivity, experiments with buffer solutions having various concentrations of sodium chloride (0 to 4.5 g/L) reveal only small variations in $f_0$ ($\approx$0.6 MHz; FIG. 20$h$).

The sensors exhibit excellent repeatability and are suitable for repeated use. Multiple (i.e. five) measurements using sensors on CP and silicone substrates serve as demonstrations. Between each measurement, immersion in water followed by drying on a hot plate regenerates the devices. The changes in $f_0$ are repeatable for experiments that involve injection of 0.6 mL buffer solution (FIGS. 20$i$ and 23($c$)). The average change in $f_0$ is 58.3 MHz with a standard deviation of 1.1 MHz for the sensor on CP; the corresponding values for silicone are 60.1 MHz and 3.6 MHz, respectively. The changes in $f_0$ undergo different temporal patterns, as might be expected due to the differences in chemistry, microstructure and pore geometry for these two substrates. Measurements over 3 hours show no drifts in $f_0$ (FIG. 23($d$)). The noise levels are <0.7 MHz; this parameter, together with an average change of $f_0$ of 58.3 to 60.1 MHz for 0.6 mL buffer solution over a surface area of 22×28 mm$^2$, suggests a measurement accuracy of $\approx$0.06 mL/mm$^2$.

Figure 21:
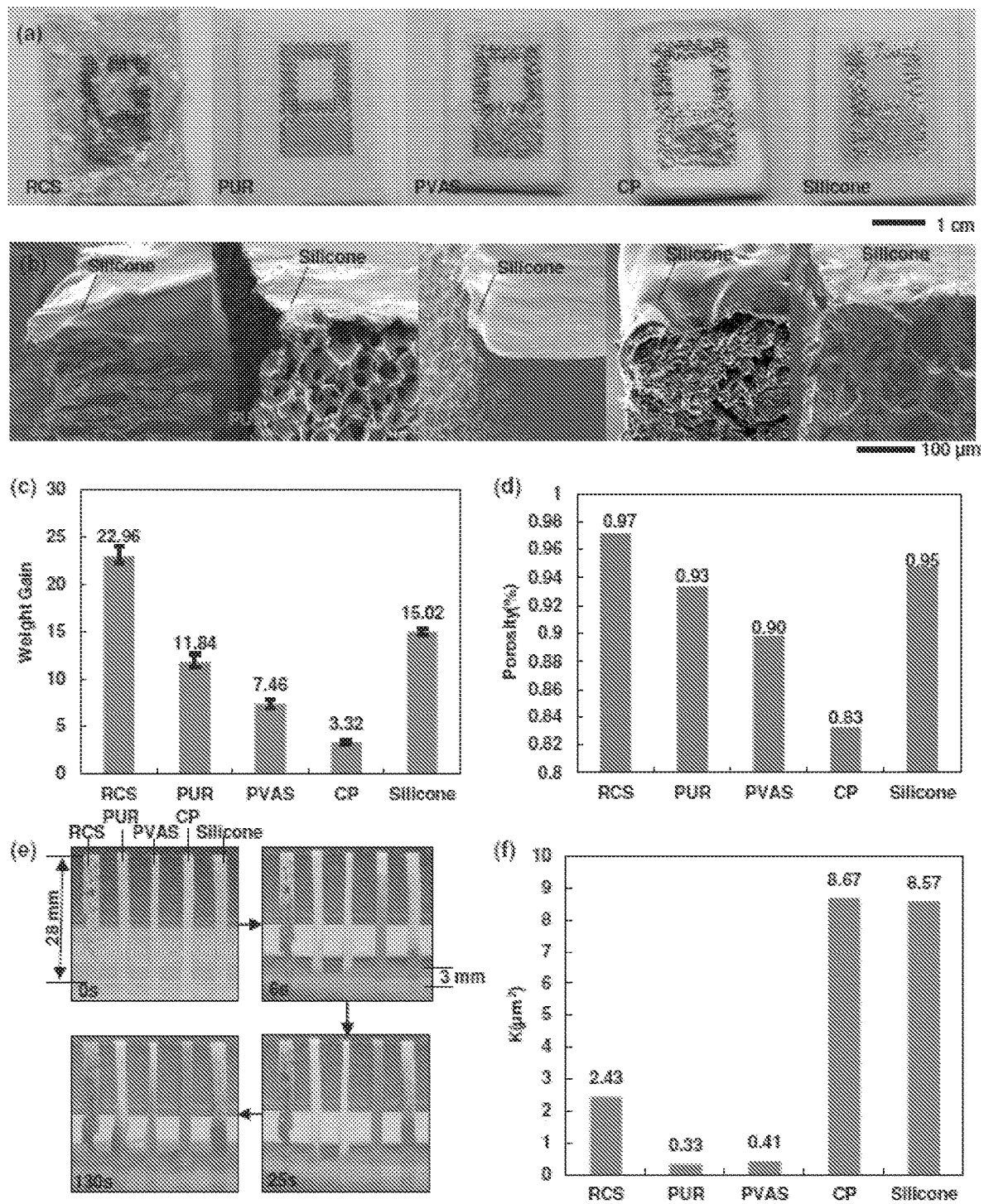
FIG. 21. (a) Wireless sweat sensors based on different porous substrates. (b) SEM images of the substrates coated with thin layer of silicone to facilitate chemical bonding between the sensors and the substrates. (c) Weight gain of different substrate materials associated with immersion in water. (d) Porosity of the substrate materials. (e) Images of strips of the substrate materials when partially immersed into water with red dye. (f) Water permeability of the substrate materials.

The coil structures can be mounted onto various types of functional substrates. Demonstrated examples include recycled cellulose sponge (RCS), polyurethane sponge (PUR), polyvinyl alcohol sponge (PVAS), cellulose paper (CP), and silicone sponge (FIG. 21$a$). Cutting with a hot-wire device (PUR, silicone) or with a razor blade (other) yields the appropriate lateral dimensions and thicknesses. Spin-coated silicone films with accurately controlled thickness ($\approx$10 μm; FIG. 21$b$) enable strong bonding between each of these functional substrates and the sensors through surface chemical functionalization, while preventing direct contact between the sensors and the sweat. Relative characteristics in water absorption are also important to consider, as described in the following.

Figure 25:
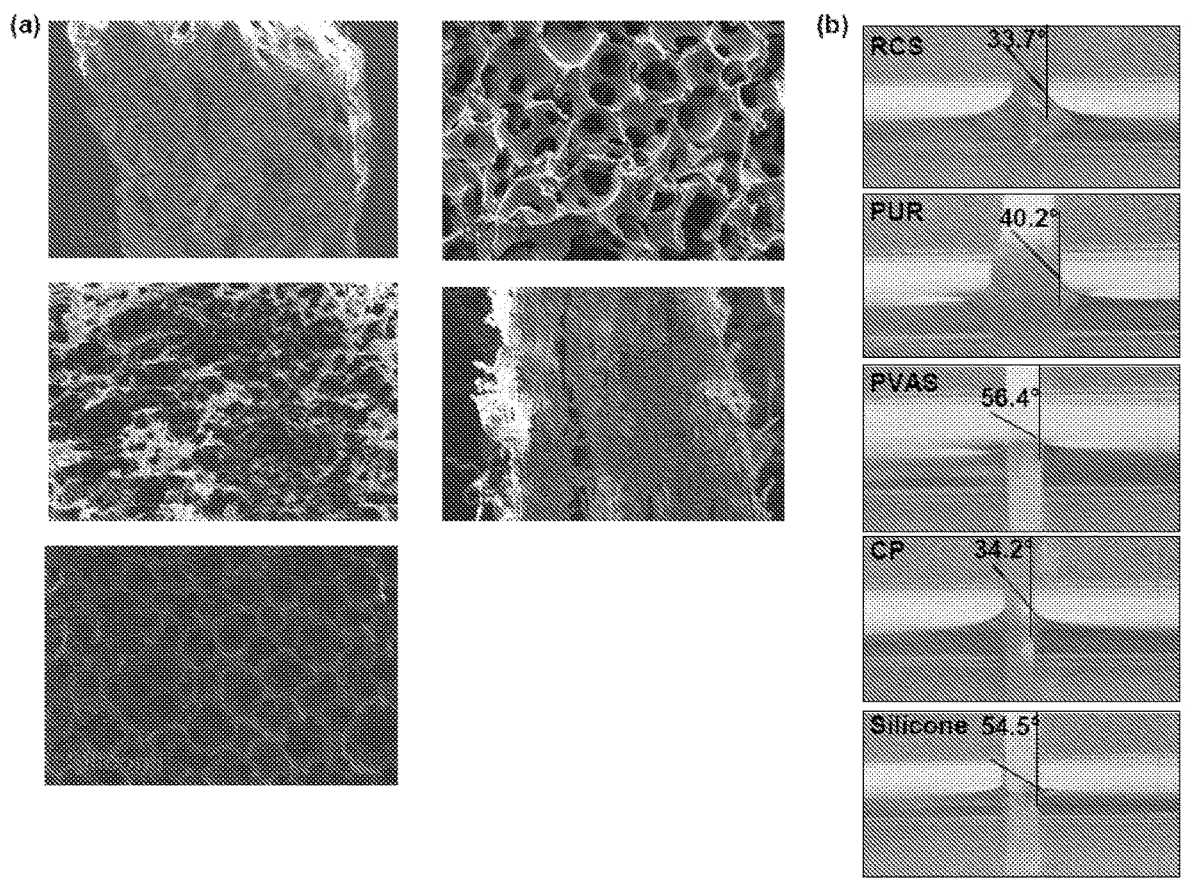
FIG. 25. (a) SEM images of porous materials, showing that the pores of PUR and Silicone dressing are uniform and that the pores of RCS, PVAS, and CP are amorphous. (b) Contact angle measurements performed by partially immersing strips of the porous materials into water dyed with red color, and recording the angle at the interface of two materials.

The percentage gain in weight of the various porous materials after immersion in water defines their ability to hold fluids; the results are $\approx$2300% (RCS), $\approx$1200% (PUR), $\approx$750% (PVAS), $\approx$350% (CP), and $\approx$1500% (silicone) (FIG. 21$c$). These data, together with measured volume changes yield the porosity levels: 0.97 (RCS), 0.93 (PUR), 0.90 (PVAS), 0.83 (CP) and 0.95 (silicone) (FIG. 21$d$). The water permeability can be determined from the capillary water absorption rate by combining Darcy's law[36] and the Hagen-Poiseuille equation.[37] Strips of the substrates (3 mm in width and 28 mm in length) are partially immersed into water with red dye (3 mm under the water). A camera enables measurements of changes in height of the absorbed water as a function of time (FIG. 21$e$). The CP material exhibits the fastest absorption rate (complete filling in $\approx$6 s), followed by the RCS ($\approx$25 s). The PUR shows the smallest rate, with an increase in height of 8.3 mm over 130 s. These rates depend strongly on the pore size and degree of interconnectedness and on the contact angle. The latter can be determined optically (FIG. 25($b$)); the former can be obtained by scanning electron microscopy (FIG. 25($a$)) or by calculation and measurement of the height of absorbed water at a long period of time (details in supporting information). The permeability of the five substrates are 2.4 (RCS), 0.3 (PUR), 0.4 (PVAS), 8.7 (CP), and 8.6 (silicone) μm$^2$ (FIG. 21$f$).

Figure 22:
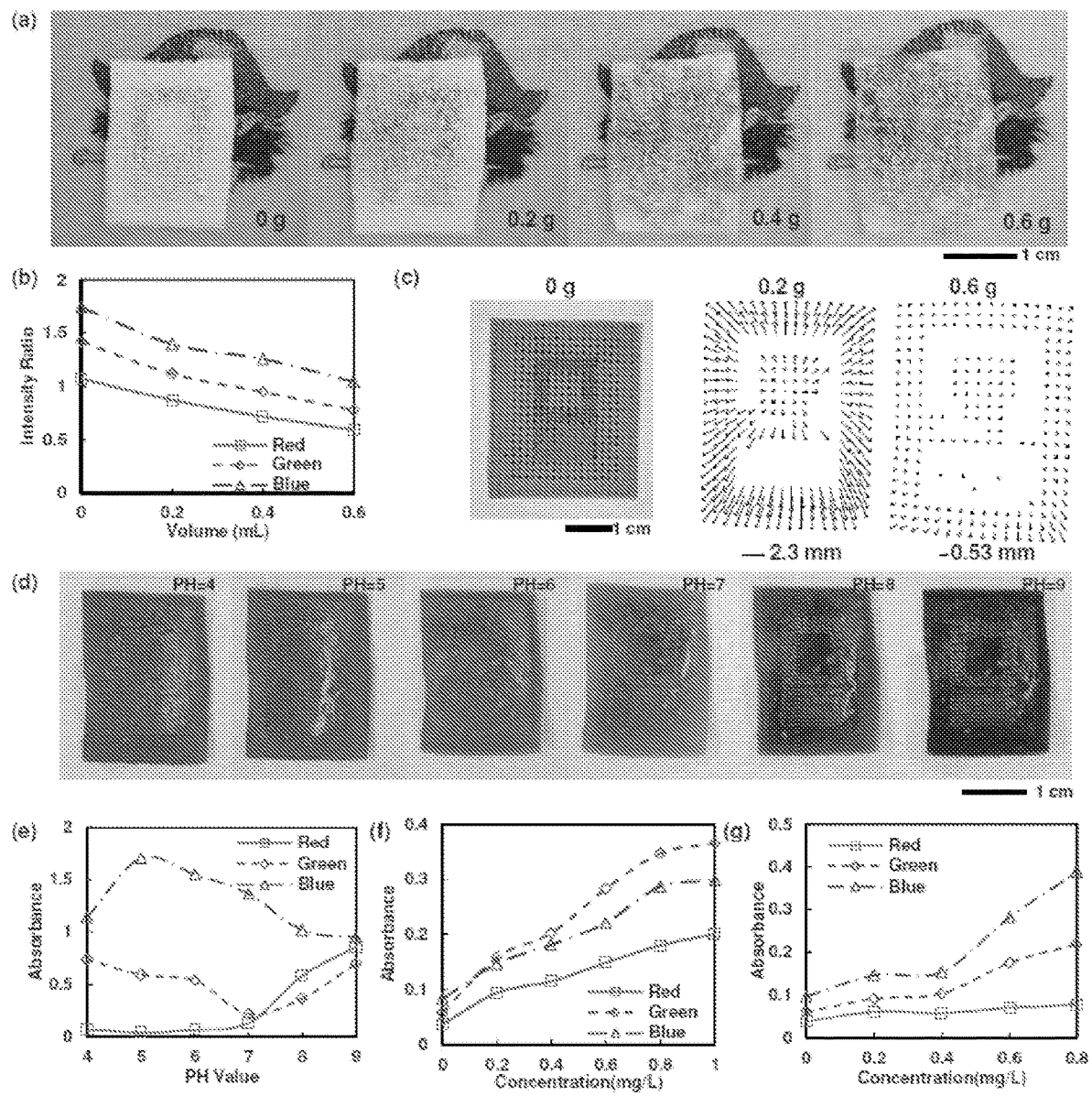
FIG. 22. (a) Images that illustrate a simple colorimetric detection scheme, based on systematic increases in transparency with water absorption. (b) The ratio of RGB intensity for a sensor like the one illustrated in (a), as a function of water absorption. (c) An image and vector diagrams corresponding to a sensor and its expansion due to water absorption. (d) Series of pictures of a sensor doped with a pH indicator, each collected with absorbed water at a different pH value. (e) Absorbance of RGB channels at different pH values. (f) Absorbance of RGB channels at different copper concentrations. (g) Absorbance of RGB channels at different iron concentrations.

In addition to dielectric response, absorption of water changes both the transparency, due to index matching effects, and the overall dimensions, due to swelling (FIGS. 22$a$ and 22$c$). These effects can be used as additional measurement parameters to complement the electrical data described previously. The optical behavior can be illustrated by placing a sensor on a region of the skin with a temporary tattoo pattern. Continuous introduction of a buffer solution, up to a total of 0.6 mL, leads to increasing levels of transparency. Selected regions of the images in FIG. 22$a$ can be used to obtain RGB (red, green, and blue) intensities at different locations. The resulting data (FIG. 22$b$) indicate that the water content is inversely proportional to the ratio of the RGB intensity on the sensor and the skin. The water also induces changes in the lateral dimensions. These changes can be measured by optically tracking the displacements of an array of opaque dots (Cr, by electron beam evaporation through a shadow mask) on the device (FIG. 22$c$). The results indicate a large displacement response to introduction of 0.2 mL of the buffer solution ($\approx$2.3 mm dot displacement), but with diminishing response for an additional 0.4 mL ($\approx$0.5 mm dot displacement). Nevertheless, these motions, which may be limited by mechanical constraints associated with mounting on the skin, might have some utility in measuring sweat loss.

Figure 4:
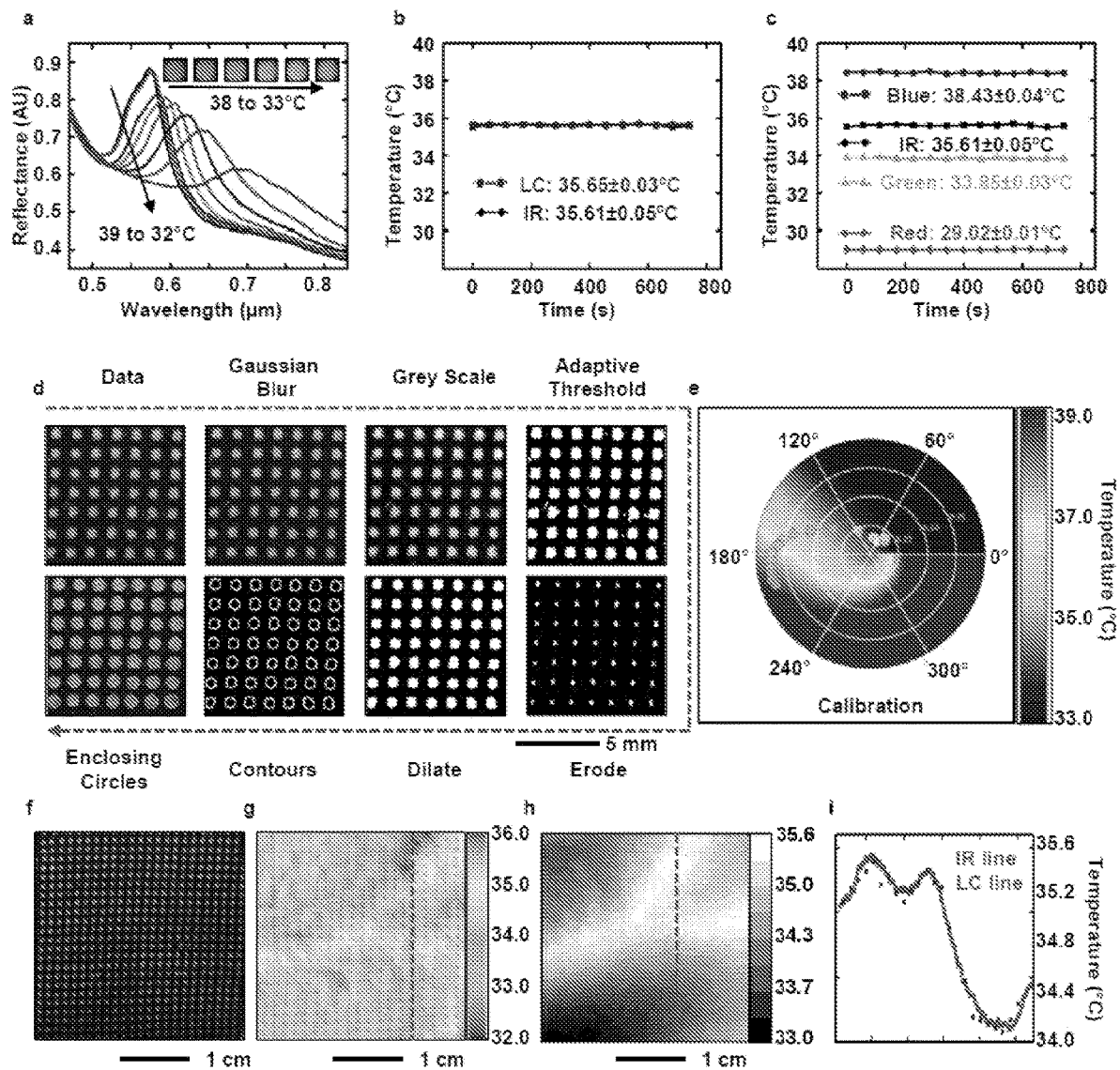
FIG. 4. Calibration and use of e-TLC devices for precision thermal imaging on the skin. a, Reflectance measured at a single pixel from 32° C. to 39° C. and corresponding images for 33° C. to 38° C. (inset). b, Temporal variations in temperature extracted from digital color analysis of an e-TLC held, nominally, at a constant temperature. c, Temporal variations in apparent temperature determined from color analysis of calibration pixels in an e-TLC device. Frames b and c also show results obtained with an infrared camera. d, Illustration of the steps for processing digital images of e-TLC devices, demonstrated on a representative 7×7 array of pixels. e, Color-temperature calibration determined using hue analysis. f, Images of a e-TLC device that consists of an 26×26 array of pixels, conformally mounted on the wrist. g, 3D rendering of the temperature distribution extracted from the color information obtained by hue value analysis of digital images of the device. h, 2D rendering of temperature captured by an infrared camera at the same time and at the same location as in g. i, Line-cut temperature profiles extracted from the data of g and h.
Figure 26:
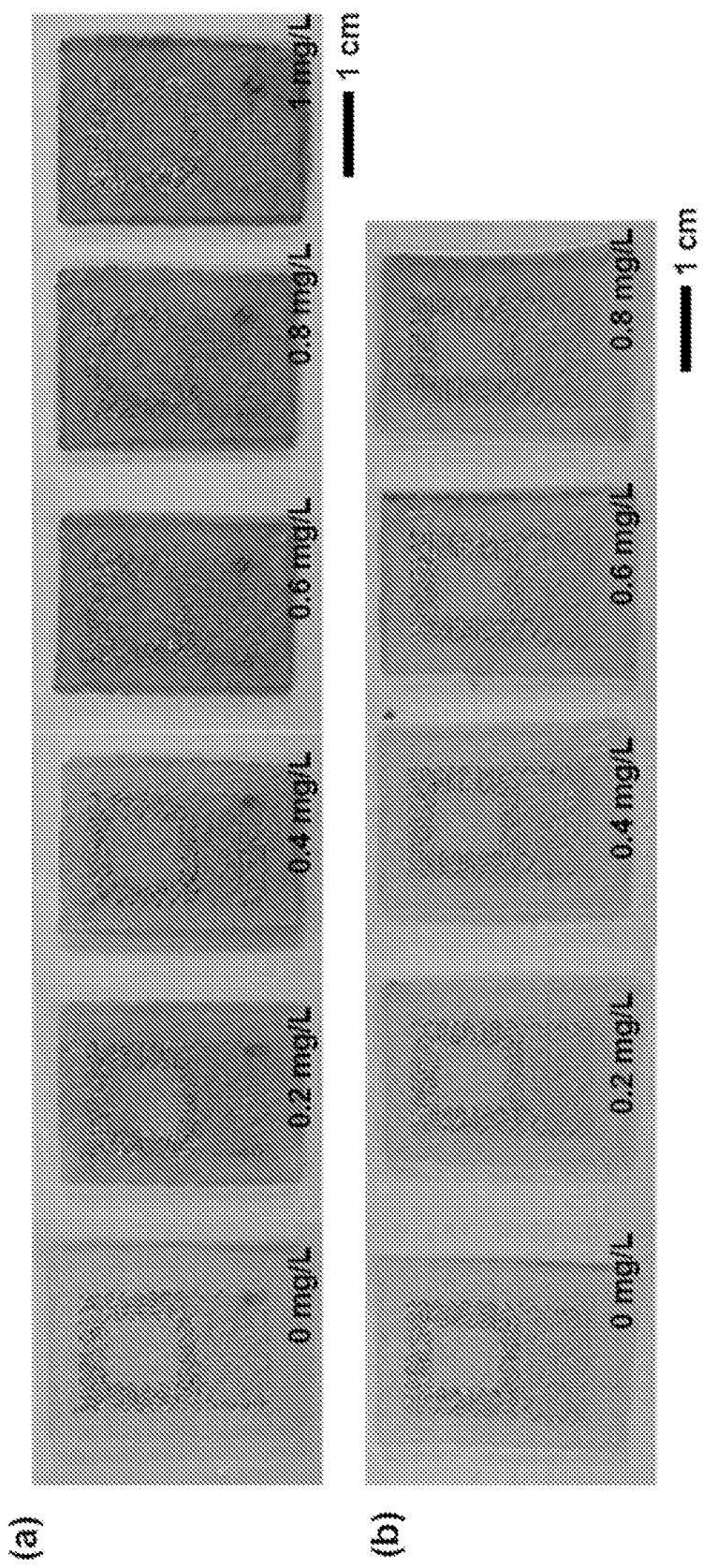
FIG. 26. (a) Color changes in the sensor when the free copper concentration changes from 0 to 1 mg/L, (b) Color changes in the sensor when the iron concentration changes from 0 to 0.8 mg/L.

The substrates can be rendered more highly functional, from an optical standpoint, by introduction of chemicals or immobilized biomolecules. Resulting interactions with the sweat can be evaluated through electrical dielectric measurement or simply colorimetric detection. For example, silicone substrates doped with colorimetric indicators render sensitivity to relevant biophysical/chemical parameters, such as pH values (FIG. 22$d$), free copper concentrations (FIG. 26($a$)), and iron concentrations (FIG. 26($b$)). To demonstrate pH detection, standard buffer solutions with pH values from 4 to 9 are introduced into a substrate that is dyed with a mixture of several different pH indicators (bromothymol blue, methyl red, methyl yellow, thymol blue, and phenolphthalein). These chemicals reversibly react with free —OH groups and/or protons in the buffer solutions, leading to changes in absorption spectra. Accordingly, the substrate undergoes a series of color changes that reveal the pH values (FIG. 4$d$). In addition, buffer solutions with copper (FIG. 26($a$)) and iron (FIG. 26($b$)) at physiological concentrations (0.8 to 1 mg/L) can also be detected using similar colorimetric schemes. The intensities of individual colors (red, green, and blue) extracted from the images determine changes in analyte concentrations (FIGS. 22$e$, 22$f$ and 22$g$). This type of strategy has potential utility when used in combination with the sorts of wireless schemes introduced here. For example, near field communication[38] enabled devices such as cellphones also offer digital image capture capabilities, for simultaneous colorimetric measurement.

3. Conclusions

The results presented here provide materials and design strategies for integrating flexible and stretchable wireless sensors on functional substrates. Demonstrated devices intimately mounted on the skin enable non-invasive, wireless quantification of sweat loss as well as colorimetric detection of sweat composition. Similar strategies can be used to develop sensors for monitoring a range of key parameters associated not only with sweat but with other body fluids.

4. Experimental Section

Figure 27:
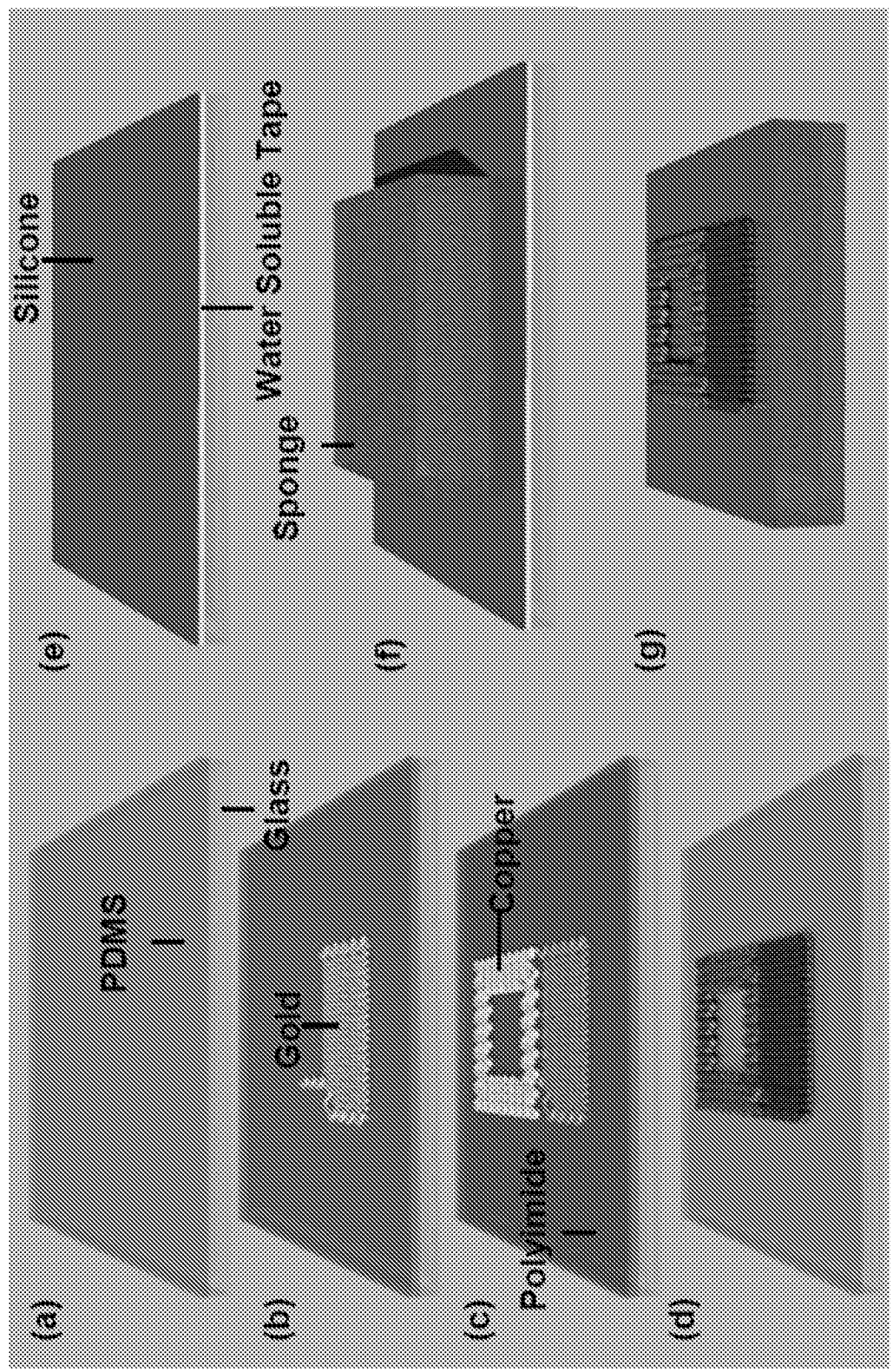
FIG. 27. (a)-(g) Fabrication processes for a wireless sweat sensor.

To fabricate the device, a layer of polydimethylsiloxane (PDMS, 20 μm thick) is first spin-coated onto a glass slide (FIG. 27($a$)). Curing the PDMS at 120° C. for 10 min and treating its surface with reactive ion etching (RIE) for 5 min (20 sccm O$_2$, 300 mTorr pressure, 150 W power) allows conformal spin-coating of a layer of polyimide (PI; 1 μm thick) on top. A bilayer of chrome (5 nm) and gold (200 nm)

deposited by electron beam (ebeam) evaporation is photolithographically patterned to form serpentine interdigitated electrodes (FIG. 27(b)). An additional spin-coated PI (1 μm) layer electrically insulates the surfaces of the electrode patterns, while selective regions on the PI layer are etched by RIE for electrical contact between the electrode and serpentine coils formed by patterning a layer of ebeam deposited copper (6 μm) (FIG. 27(c)). The entire patterns are encapsulated by another spin-coated PI layer (1 μm). Patterned RIE yields an open mesh layout, capable of release onto the surface of a target substrate by use of water-soluble tape (Aquasol ASWT-2, Aquasol Corporation, North Tonawanda, N.Y., USA). To prepare the functional substrates, a layer of uncured silicone (10 μm thick) is spin-coated onto a water soluble tape fixed on its edges to a glass slide by Scotch tape. Pre-curing the silicone at 150° C. for 1 min transforms the liquid precursor into a tacky, soft solid (FIG. 27(e)). Placing the substrates on the silicone film with gentle pressure allows the partially cured film to crosslink with porous structures on the surface. The silicone and the substrates are then fully cured at 120° C. to achieve robust bonding (FIG. 27(f)). The resulting structure is removed from the glass, and rinsed with water to remove the water soluble tape. Deposition of $Ti/SiO_2$ (5/60 nm) onto the exposed backside of the sensor facilitates chemical bonding to the PDMS film on the functional substrates after UV ozone activation. Dissolving the water soluble tape yields an integrated device with excellent levels of mechanical stretchability and flexibility (FIG. 27(g) and FIG. 19b). The functional substrates can be immersed into colorimetric indicators, followed by baking at 100° C. on a hotplate to dry the devices.

Five hydrophilic porous substrates serve as the sweat absorption materials, including Whatman GB003 cellulose paper (GE Healthcare Life Sciences, Pittsburgh, Pa., USA), Scotch-Brite recycled cellulose sponge (3M Cooperation, St. Paul, Minn., USA), polyvinyl alcohol sponge (Perfect & Glory Enterprise Co., Ltd., Taipei), Kendall hydrophilic polyurethane foam dressing (Covidien Inc., Mans-feld, MA, USA), and Mepilex silicone foam dressing (Mölnlycke Health Care AB, Sweden). For colorimetric detection, a universal pH indicator (pH 2-10) (Ricca Chemical, Arlington, Tex., USA) yields responses to buffer solutions with well-defined pH (Sigma-Aldrich Corporation, St. Louis, Mo., USA). Colorimetric copper and iron ion detection is enabled by a copper color disc test kit (CU-6, Hach Company, Loveland, Colo., USA) and an iron color disc test kit (IR-8, Hach Company, Loveland, Colo., USA), while standard stock solutions of copper and iron (Hach Company, Loveland, Colo., USA) are diluted to achieve different ion concentrations.

The sensors can be integrated onto the skin. Briefly, spray bandage (Nexcare No Sting Liquid Bandage Spray, 3M Cooperation, St. Paul, Minn., USA) is first applied onto the corresponding skin region. Evaporation of the solvent results in a tacky, water-permeable film that does not significantly influence the transdermal water loss from the skin and provides sufficient adhesion to fix the sweat sensors onto the skin. The sensor is then applied to the skin with continuous pressure over several seconds. The bonding is reversible, but is sufficiently strong to accommodate heavy sweating and shear forces.

The electrical responses of the sensors are evaluated using a HP 4291A impedance analyzer (Agilent Technologies, Santa Clara, Calif., USA) with a frequency range from 1 MHz to 1.8 GHz. The analyzer connects to a one-turn hand-wound copper primary coil whose resonance frequency is significantly different from the sweat sensor. The coil is placed 2 mm away from the sweat sensor during the measurement. However, small variations in the distance between the coil and the sweat sensor are tolerable, with negligible effects on the results. A xyz mechanical stage and a rotational platform allow manual adjustment of the position and orientation of the primary coil relative to the sweat sensor. The primary coil provides a time varying electromagnetic field that induces alternating voltages in the sweat sensor. Changes of sweat content within the substrate of the sensor lead to changes in the capacitance of the sweat sensor and its $f_0$. A syringe pump (KD Scientific Inc., Holliston, Mass., USA) is used to deliver buffer solutions to the sensors during the in vitro experiments. The sweat sensors with a CP substrate and a silicone porous material are mounted on the arms of two volunteers for 2 hour in vivo testing, with reference substrates of the same materials and sizes placed in close proximity to the sweat sensors (FIG. 20b). For the first hour, the volunteers exercise continuously to generate sweat, and then stop to rest for the second hour. During the measurement, the sweat sensors remain on the skin, while the reference sensors are peeled off every 5 min to record their weight using a precise balance and reattached back to the same positions afterwards.

The absorbance values are estimated from the digital images by accessing the RGB (red, green, blue) values of the selected regions on the experimental images using ImageJ.[39] The average RGB values are determined from multiple pixels enclosed within a rectangular frame drawn by ImageJ with a plugin called, "measure RGB". The Absorbance (A) defined as the negative log of the transmittance ($I_n/I_{blank}$), is then calculated using the following formula:

$$A = -\log(I_n/I_{blank}) \quad (1)$$

in which $I_n$ denotes the R, G or B values for the functional substrates and $I_{blank}$ the R, G, or B value for the background, both obtained from the experimental images.

References

[1] M. Chan, EstC, J.-Y. Fourniols, C. Escriba, E. Campo, Artif. Intell. Med. 2012, 56, 137.
[2] A. Lay-Ekuakille, S. Mukhopadhyay, A. Lymberis, in Wearable and Autonomous Biomedical Devices and Systems for Smart Environment, Vol. 75, Springer, Berlin Heidelberg, 237.
[3] A. J. Bandodkar, A. M. O'Mahony, J. Ramirez, I. A. Samek, S. M. Anderson, J. R. Windmiller, J. Wang, Anal. 2013, 138, 5288.
[4] P. Bonato, IEEE Eng. Med. Biol. Mag. 2010, 29, 25.
[5] P. M. Deshmukh, C. M. Russell, L. E. Lucarino, S. N. Robinovitch, Enhancing clinical measures of postural stability with wear-able sensors, presented at Engineering in Medicine and Biology Society (EMBC), 2012 Annual International Conference of the IEEE, Aug. 28, 2012-Sep. 1, 2012.
[6] J. Varkey, D. Pompili, T. Walls, Pers. Ubiquit. Comput. 2011, 16, 897.
[7] J. R. Windmiller, J. Wang, Electroanal. 2013, 25, 29.
[8] D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, Science 2011,333, 838.
[9] R. C. Webb, A. P. Bonifas, A. Behnaz, Y. Zhang, K. J. Yu, H. Cheng, M. Shi, Z. Bian, Z. Liu, Y. S. Kim, W. H. Yeo, J. S. Park, J. Song, Y. Li, Y. Huang, A. M. Gorbach, J. A. Rogers, Nat. Mater. 2013, 12, 938.

[10] X. Huang, H. Cheng, K. Chen, Y. Zhang, Y. Liu, C. Zhu, S. C. Ouyang, G. W. Kong, C. Yu, Y. Huang, J. A. Rogers, IEEE Trans. Biomed. Eng. 2013, 60, 2848.

[11] N. Lu, C. Lu, S. Yang, J. Rogers, Adv. Funct. Mater. 2012, 22, 4044.

[12] W.-H. Yeo, Y.-S. Kim, J. Lee, A. Ameen, L. Shi, M. Li, S. Wang, R. Ma, S. H. Jin, Z. Kang, Y. Huang, J. A. Rogers, Adv. Mater. 2013, 25, 2773.

[13] K. Virkler, I. K. Lednev, Forensci. Sci. Int. 2009, 188, 1.

[14] T. L. Guidotti, J. McNamara, M. S. Moses, Indian J. Med. Res. 2008, 128, 524.

[15] V. Sikirzhytski, K. Virkler, I. K. Lednev, Sensors 2010, 10, 2869.

[16] S. Hu, J. A. Loo, D. T. Wong, Proteomics 2006, 6, 6326.

[17] P. Salvo, F. Di Francesco, D. Costanzo, C. Ferrari, M. G. Trivella, D. De-Rossi, IEEE Sens. J. 2010, 10, 1557.

[18] Y. Haixia, L. Dachao, R. C. Roberts, X. Kexin, N. C. Tien, J. Micro-electromech. Syst. 2012, 21, 917.

[19] A. Lay-Ekuakille, S. Mukhopadhyay, S. Coyle, F. Benito-Lopez, R. Byrne, D. Diamond, in Wearable and Autonomous Biomedical Supporting Information 1. Methods for Determination of Weight Gain, Porosity, and Permeability The percentage weight gain (W %) of the substrates can be obtained by measuring the weight of the materials in dry ($W_{dry}$) and water-saturated ($W_{sat}$) states. Thus, W % can be expressed as.

$$W\% = \frac{W_{sat} - W_{dry}}{W_{dry}} \times 100\% \quad (1)$$

The porosity ($\phi$) of the materials is determined by the volume of pores ($V_{pores}$) to the total volume of the medium ($V_{bulk}$), is thus defined by $$\phi = \frac{V_{pores}}{V_{bulk}} = \frac{(W_{sat} - W_{dry})/\rho_{water}}{(W_{sat} - W_{dry})/\rho_{water} + W_{dry}/\rho_{bulk}} \quad (2)$$

where, $\rho_{water}$ and $\rho_{bulk}$ are the density of the water and the substrate materials, respectively.

To obtain the water permeability of the substrates, the Darcy law[1], which describes the water flow in porous materials, can be used. It is found that the pressure gradient ($\nabla P$) that causes the water to flow in the porous materials can be described by $$\nabla P = \frac{\mu}{K}q \quad (3)$$

where q is the volume average velocity (or flux), which represents discharge per unit area, with units of length per time. The factor K is the permeability of the material and $\mu$ the viscosity of the water. Determination of $\nabla P$ typically involves an experimental setup containing two chambers with well-controlled pressures. An alternative method uses the Hagen-Poiseuille equation[2] to determine $\nabla P$ by considering the porous materials as bundles of capillaries. As a result, the pressure gradient can be further expressed as:

$$\nabla P = \frac{\Delta P}{L} = \frac{8\mu Q}{\pi R^4} \quad (4)$$

where $\Delta P$ is the pressure loss, L the length of the pipe, $\mu$ the dynamic viscosity, Q the volumetric flow rate (volume of fluid passing through the surface of the pipe per unit time), R the radius of the capillaries. Combing Eq. (3) and Eq. (4) yields $$\frac{\mu}{K}q = \frac{8\mu Q}{\pi R^4} \quad (5)$$

Here, $Q/\pi R^2$ represents the interstitial velocity of the flow, while q represents the superficial velocity of the flow. As a result, the ratio between $Q/\pi R^2$ and q is equivalent to the porosity of the materials $$\phi = \left(\frac{Q/\pi R^2}{q}\right).$$

Thus, Eq. (5) can be further simplified as $$R^2 = \frac{8K}{\phi} \quad (6)$$

The linear momentum balance of the flow within a capillary tube can be expressed as $$\frac{2\sigma\cos(\theta)}{R} = \rho g h + \frac{8\mu h h'}{R^2} + \rho \frac{d(hh')}{dt} \quad (7)$$

where terms from left to right refer to the capillary pressure, the hydrostatic pressure, the viscous pressure loss, and the inertia terms, respectively. In Eq. (7), σ is the surface tension of water, h is the height of water in the capillary tube at time t, and θ is the contact angle at the interface of the capillary tube and the water. As the porous materials may not have uniform R (especially for the porous materials with amorphous pores), such as RCS, PVAS, and CP in FIG. 25(a), it is possible to replace R in Eq. (7) with a more general term $R_s$, which represents the static radius of the porous materials and can be obtained from the equilibrium height ($h_{eq}$) in the static case (height of the absorbed water in the porous materials when t reaches ∞). The static radius $R_s$ can be calculated from $$h_{eq} = \frac{2\sigma\cos(\theta)}{R_s \rho g} \quad (8)$$

As a result, Eq. (7) can be further expressed as $$\frac{2\sigma\cos(\theta)}{R_s} = \rho g h + \frac{8\mu h h'}{R_s^2} + \rho \frac{d(hh')}{dt} \quad (9)$$

by considering a flow regime where the influence of inertia as well as the influence of gravity can be neglected[3,4].

Thus, Eq. (8) can be simplified to $$\frac{2\sigma\cos(\theta)}{R_s} = \frac{8\mu hh'}{R_s^2} \quad (10)$$

or $$\frac{hdh}{dt} = \frac{\sigma\cos(\theta)}{4\mu} \quad (11)$$

Solving this ordinary differential equation with the initial condition h(0)=0 leads to the Lucas-Washburn equation [4].

$$h^2 = \frac{\sigma R_s \cos(\theta)}{2\mu} t \quad (12)$$

According to Eq. (6), Eq. (12) can be further expressed as $$h^2 = \frac{\sigma R_s \cos(\theta)}{2\mu} t \cong \frac{4\sigma\cos(\theta)}{\mu} \frac{K}{\phi R_s} t \quad (13)$$

As a result, the permittivity (K) can then be determined using the following equation $$K = \frac{h^2 \mu \phi R_s}{4\sigma\cos(\theta)t} \quad (14)$$

where h, t, $\phi$, and $R_s$ of individual materials can all be experimentally determined, as summarized in Table 3.

TABLE 3

Parameters of the porous materials used for functional substrates

| Materials | W % | $\rho_{bulk}$ (g/cm³) | $\phi$ | h (m) | t (s) | $R_s$ (m) | K (µm²) |
|---|---|---|---|---|---|---|---|
| RCS | 2296 | 1.5 | 0.97 | 0.025 | 25 | 2.52E-5 | 2.43 |
| PUR | 1184 | 1.2 | 0.94 | 0.008 | 130 | 1.52E-4 | 0.33 |
| PVAS | 746 | 1.2 | 0.90 | 0.013 | 130 | 6.34E-5 | 0.41 |
| CP | 332 | 1.5 | 0.83 | 0.025 | 6 | 2.50E-5 | 8.67 |
| Silicone | 1502 | 1.2 | 0.95 | 0.025 | 70 | 1.78E-4 | 8.57 |

2. Experiments for Determination of Weight Gain, Porosity, and Permeability $R_s$ can be determined from the $h_{eq}$ measurement, in which 50 cm strips of the porous materials are partially immersed into the water (approximately 1 cm strip in the water), while the heights of the water in the strips after one day immersion are measured. As PUR and silicone have more uniform pore sizes (FIG. 25(a)), their $R_s$ can also be determined by measuring the radii of 10 pores in their SEM images and taking the average numbers. The contact angle θ can be measured through the analysis of images taken by a camera on the interface of water and the porous materials (FIG. 25(b)). The relation between h and t can be obtained using video captured throughout the process of water absorption.

References

[1] N. Fries, Capillary Transport Processes in Porous Materials: Experiment and Model, Cuvillier.
[2] S. P. Sutera, R. Skalak, Annu. Rev. Fluid Mech. 1993, 25, 1.
[3] E. W. Washburn, Phys. Rev. 1921, 17, 273.
[4] A. Hamraoui, T. Nylander, J. Colloid Interf. Sci. 2002, 250, 415.

Example 3: Epidermal Microfluidic Sweat Patch

This Example discloses an epidermal microfluidic sweat patch incorporating at least one microfluidic channel and a plurality of colorimetric indicators disposed within cavities of the patch. The patch optionally includes a near-field communication coil.

Table 4 shows concentrations of parameters and chemical species relevant to sweat monitoring.

TABLE 4

Parameters and chemical species relevant to sweat monitoring.

| Constituents | Median Concentration | Range |
|---|---|---|
| Sweat gland density | 100 pores/cm² | 50~300 pores/cm² |
| Sweat rate | 50 µL/hour · cm² | 12-120 µL/hour · cm² |
| pH | | 4.0-6.8 |
| Glucose | 0.17 mM | 5.6 µM-2.2 mM |
| Lactic acid | 14 mM | 3.7-50 mM |
| Chloride | 23 mM | 0.02-280 mM |
| Sodium ion | 31 mM | 0.11-390 mM |

Figure 28:
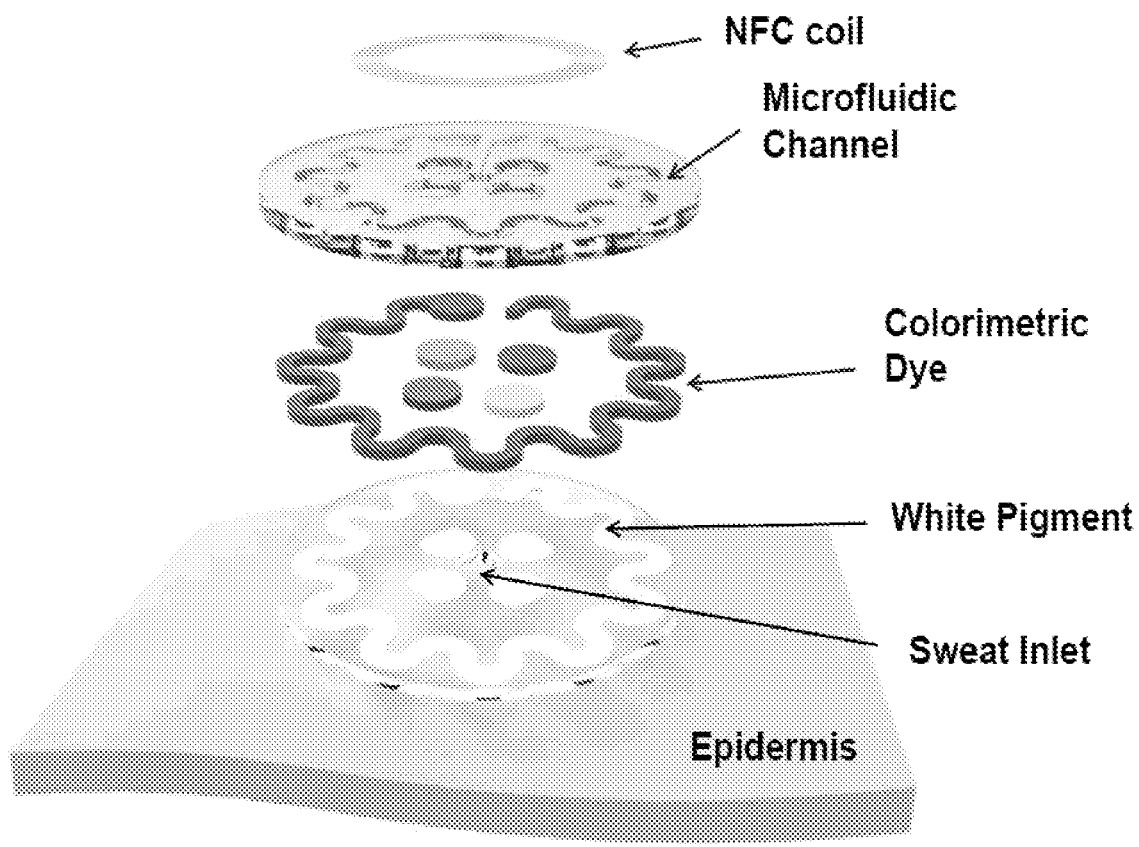
FIG. 28. Exploded view of a colorimetric sensor comprising a near-field communication coil.
Figure 29:
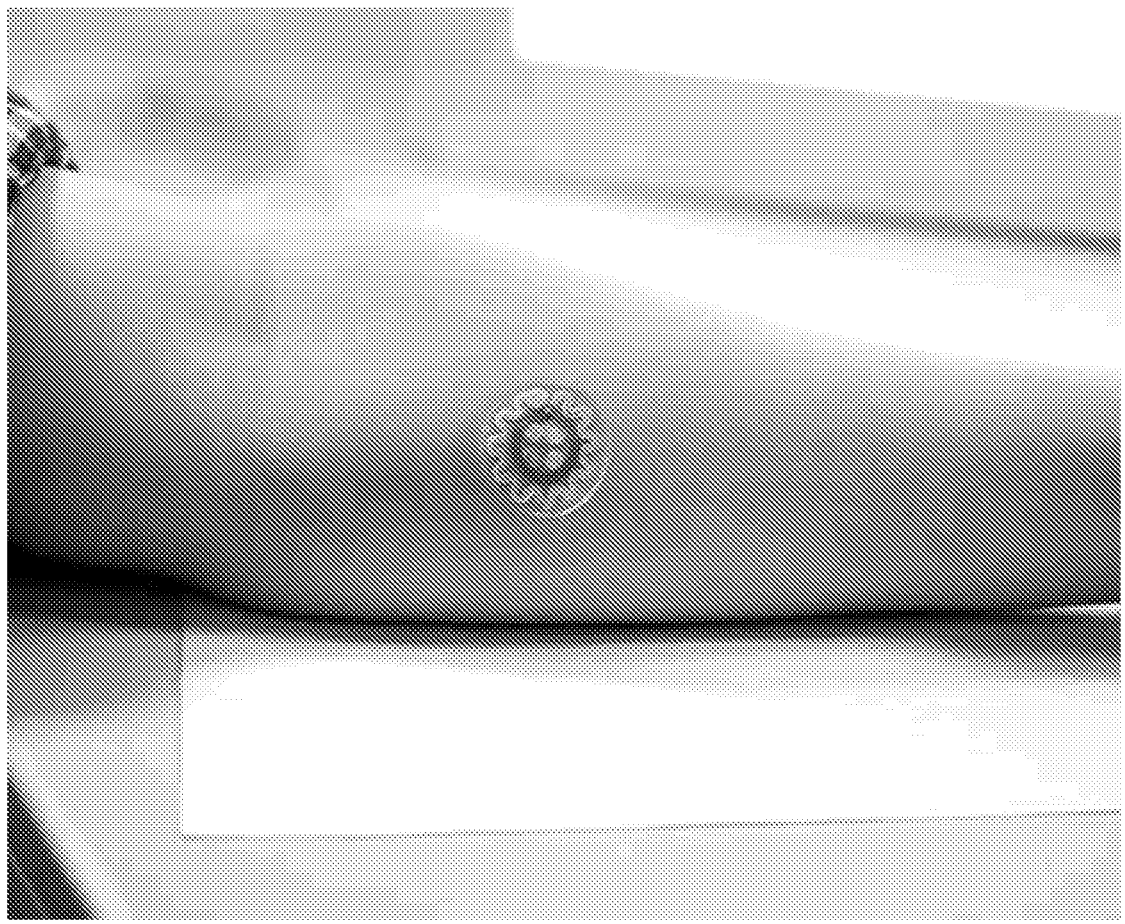
FIG. 29. Photograph of the device of FIG. 46 adhered to the skin of a subject.

FIG. 29 shows an exploded view of a colorimetric sensor comprising a near-field communication coil. FIG. 29 is a photograph of the device of FIG. 28 adhered to the skin of a subject.

Figure 30:
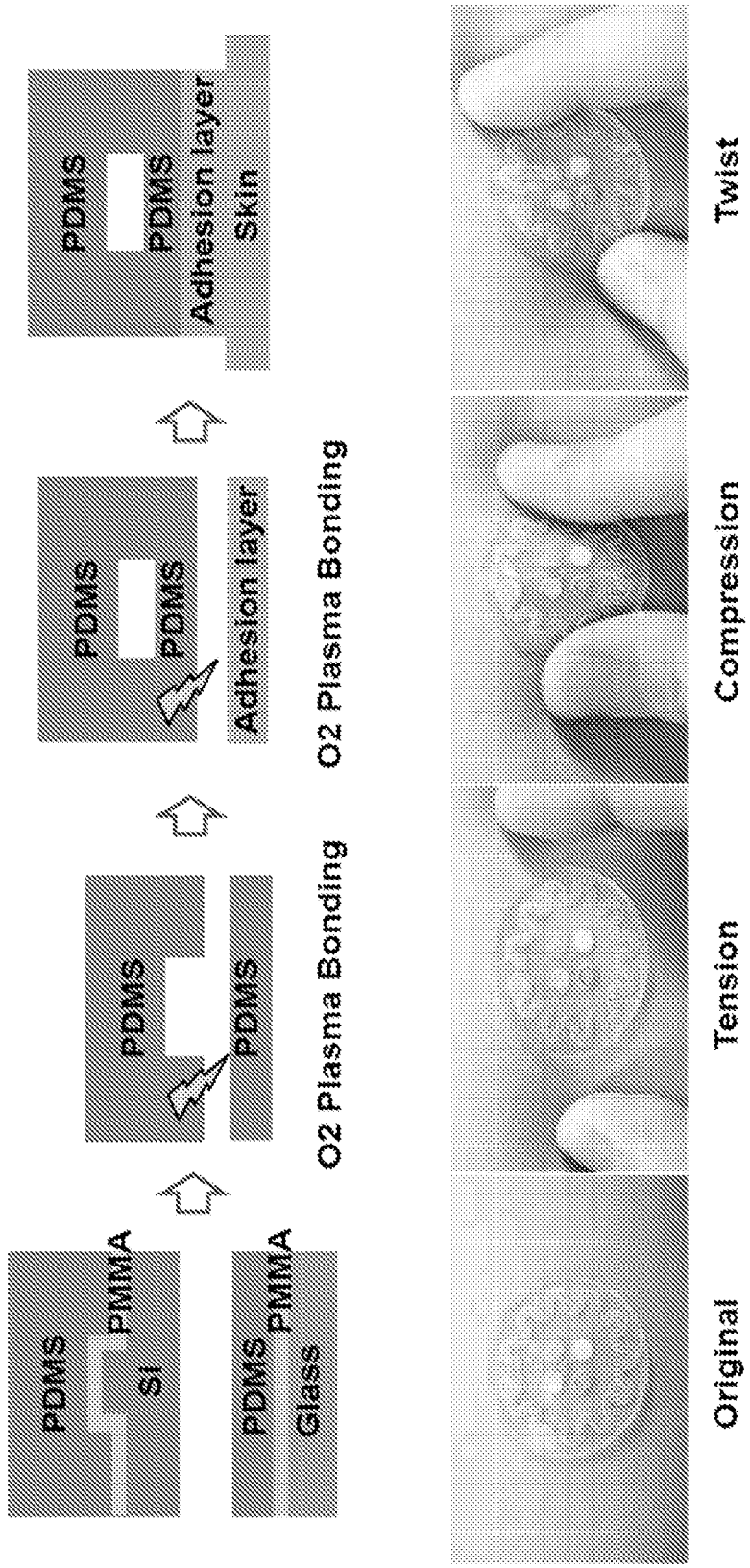
FIG. 30. Fabrication method and adhesion test on skin.

FIG. 30 illustrates a fabrication method for a sweat patch and an adhesion test on skin.

Figure 31:
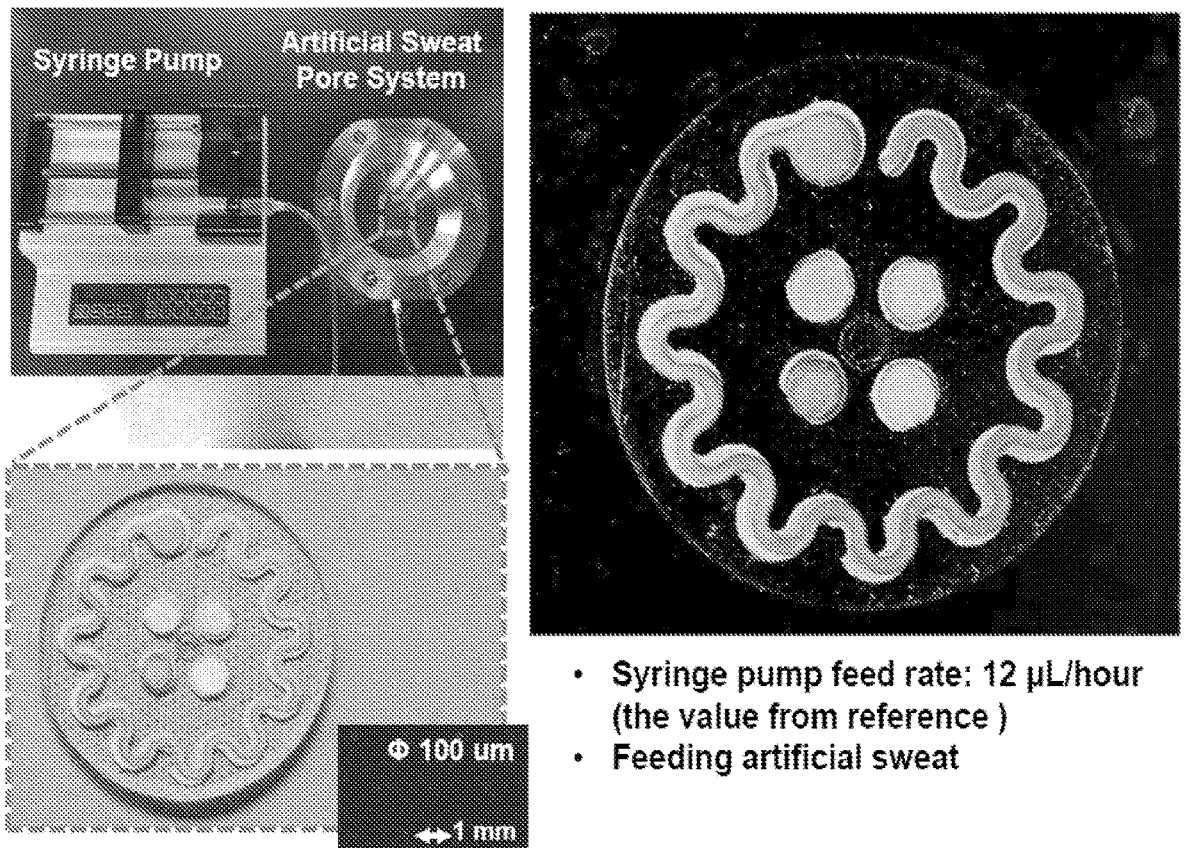
FIG. 31. Artificial sweat pore test using a syringe to feed artificial sweat at a rate of 12 μL/hr.

FIG. 31 illustrates an artificial sweat pore test using a syringe to feed artificial sweat at a rate of 12 µL/hr.

Figure 32:
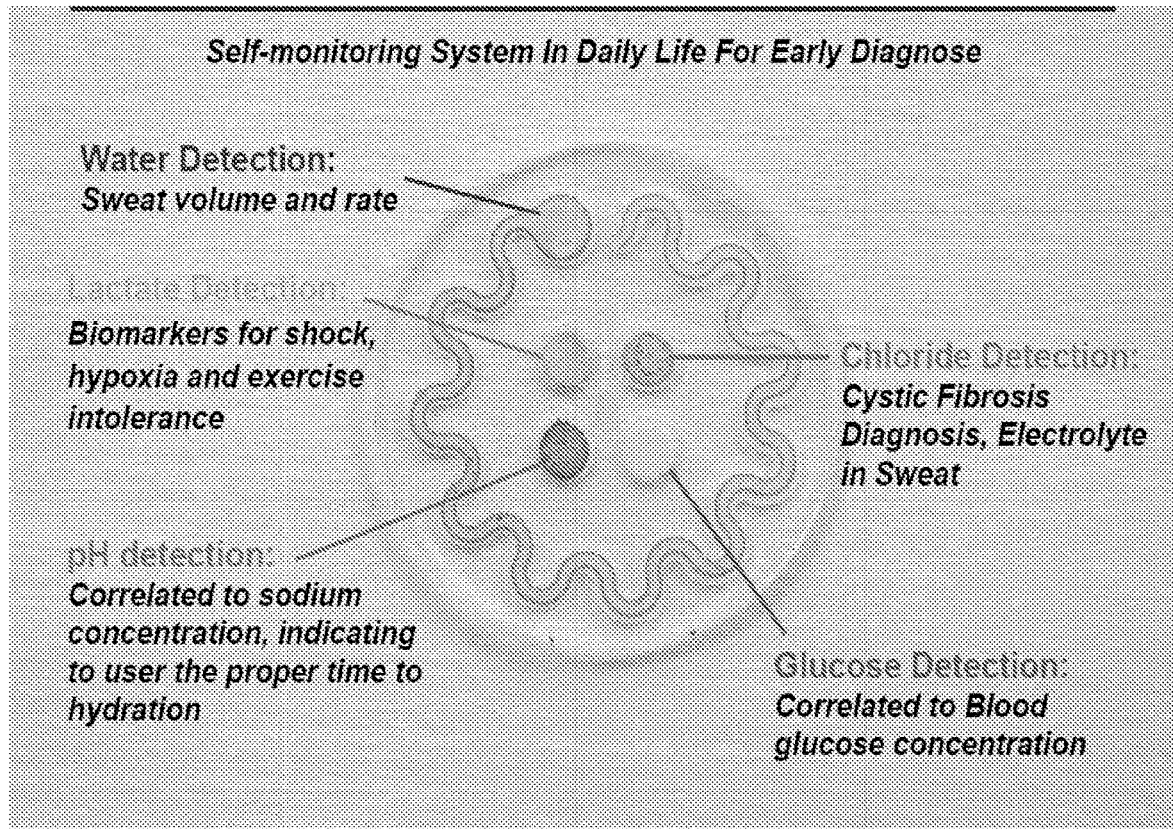
FIG. 32. Colorimetric detection of various biomarkers using a sweat sensor for self-monitoring and early diagnosis.
Figure 33:
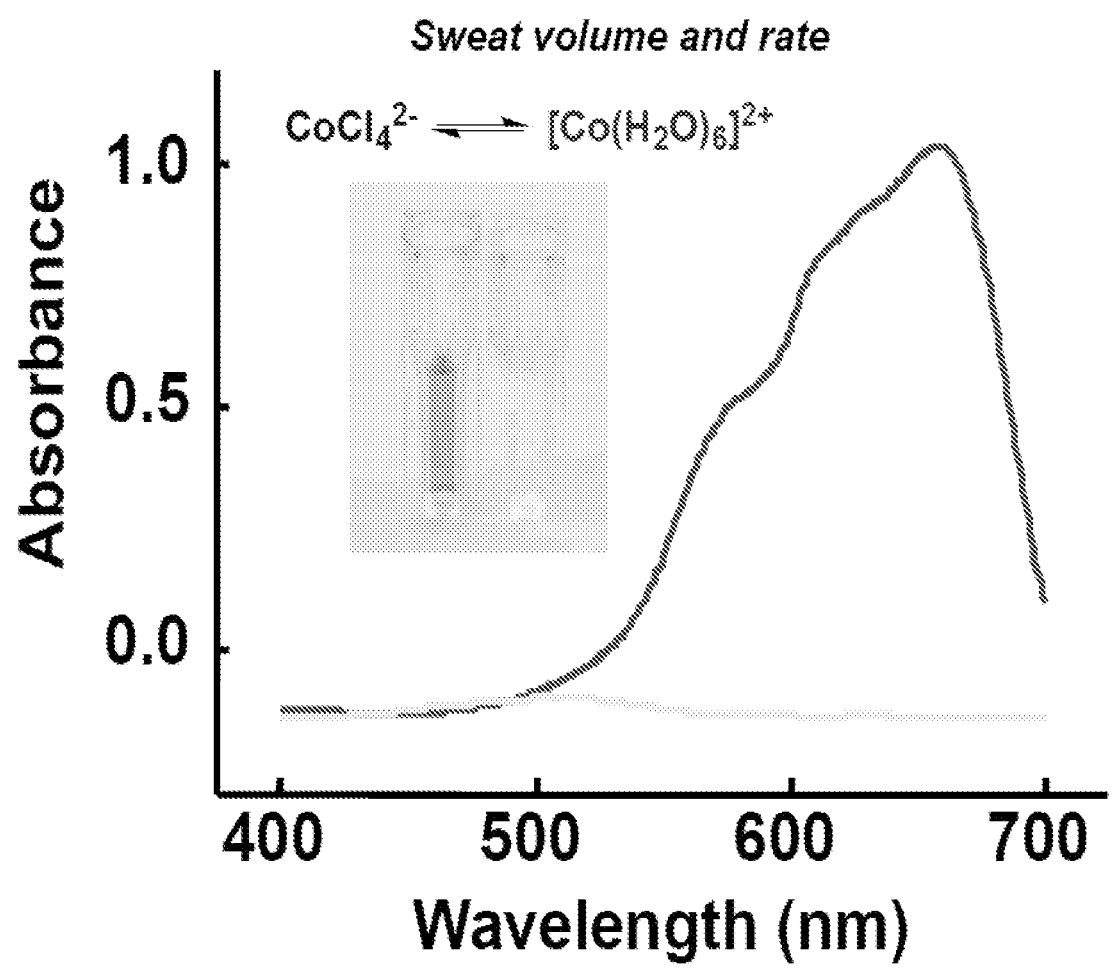
FIG. 33. Absorbance spectrum illustrating the color change of a reactant that may be used to determine sweat volume and rate.
Figure 34:
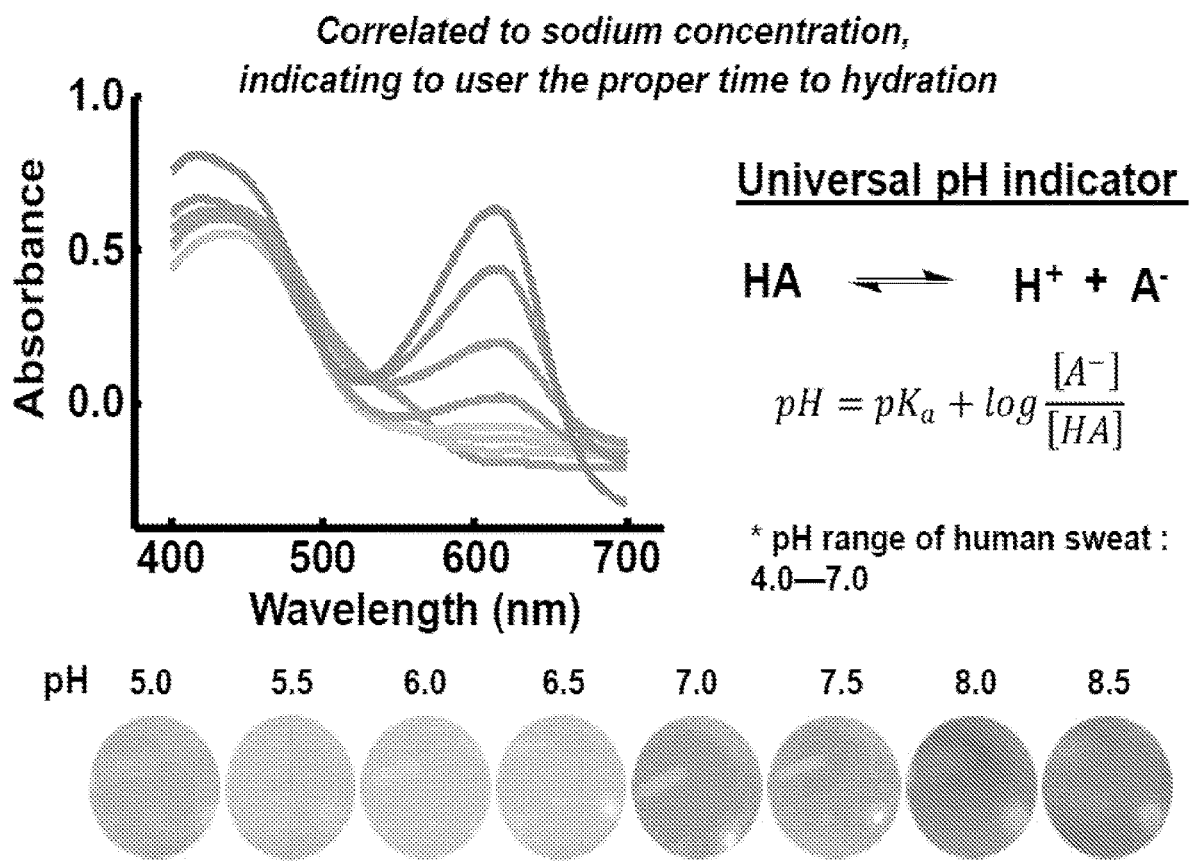
FIG. 34. Absorbance spectrum and legend illustrating the color change of a reactant(s) that may be used to determine sweat pH, which may be correlated with sodium concentration, indicating to a user the proper time to hydrate.
Figure 35:
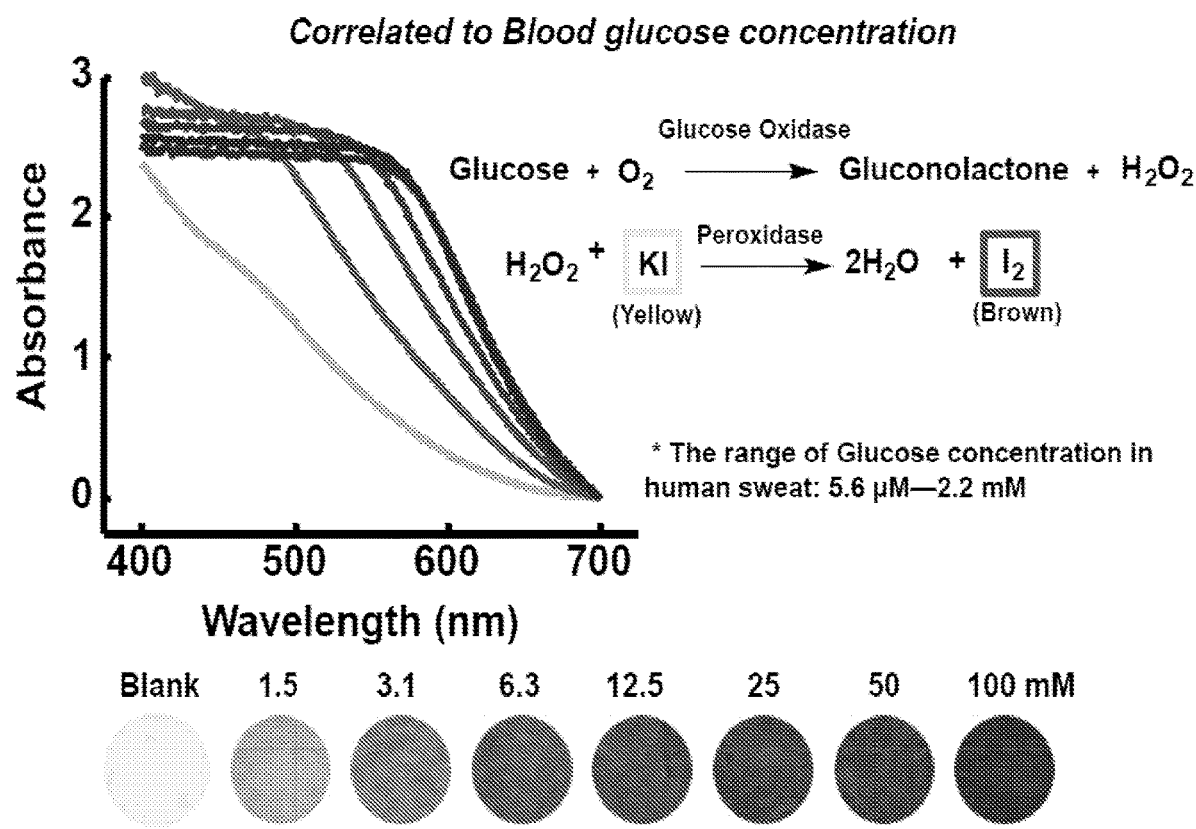
FIG. 35. Absorbance spectrum and legend illustrating the color change of a reactant(s) that may be used to determine glucose concentration in sweat, which may be correlated with blood glucose concentration.
Figure 36:
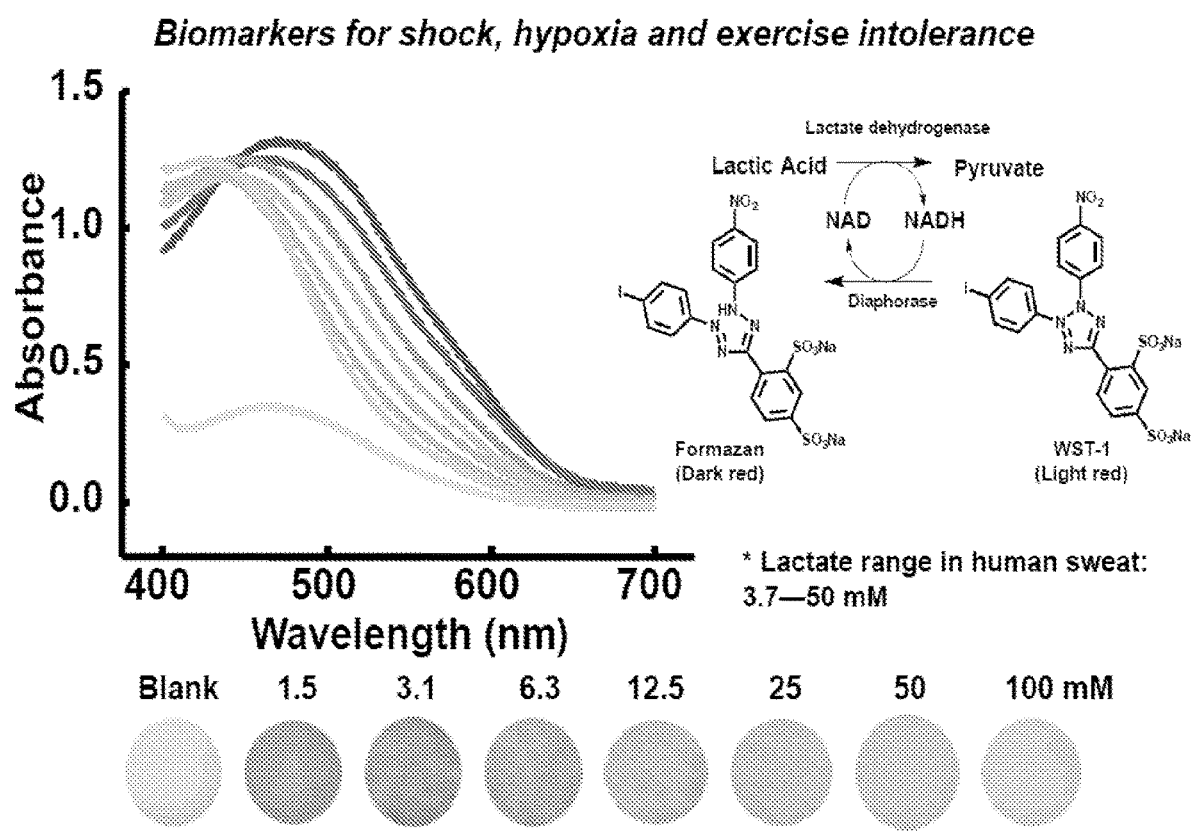
FIG. 36. Absorbance spectrum and legend illustrating the color change of a reactant(s) that may be used to determine lactate concentration in sweat, which may provide an indication of shock, hypoxia and/or exercise intolerance.

FIG. 32 shows a sweat patch incorporating colorimetric detection of various biomarkers for self-monitoring and early diagnosis. For example, FIG. 33 shows an absorbance spectrum illustrating the color change of a reactant that may be used to determine sweat volume and rate. FIG. 34 shows an absorbance spectrum and legend illustrating the color change of a reactant(s) that may be used to determine sweat pH, which may be correlated with sodium concentration, indicating to a user the proper time to hydrate. FIG. 35 shows an absorbance spectrum and legend illustrating the color change of a reactant(s) that may be used to determine glucose concentration in sweat, which may be correlated with blood glucose concentration. FIG. 36 shows an absorbance spectrum and legend illustrating the color change of a reactant(s) that may be used to determine lactate concentration in sweat, which may provide an indication of shock, hypoxia and/or exercise intolerance.

Figure 37:
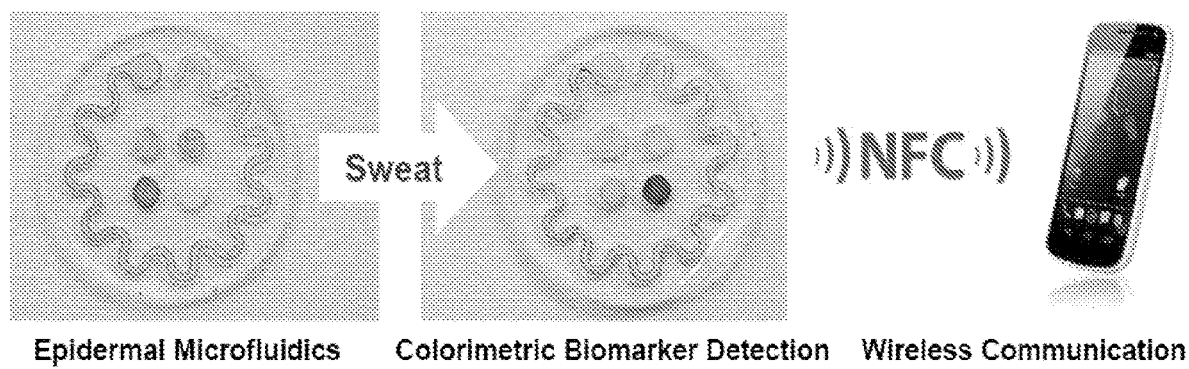
FIG. 37. A sweat sensor incorporating colorimetric biomarker indicators provides qualitative and quantitative data that may be observed by the naked eye and/or wirelessly observed by a detection device, such as a smartphone.

As shown in FIG. 37, a sweat sensor incorporating colorimetric biomarker indicators provides qualitative and quantitative data that may be observed by the naked eye and/or wirelessly observed by a detection device, such as a smartphone.

Example 4: Sweat Patches

Overview

Provided herein are epidermal microfluidic sweat patches for daily wear as personal healthcare monitoring systems that are highly conformable and stretchable. The patches allow for the non-invasive determination of sweat rate, sweat volume, and biomarker concentration, thereby providing clinically reliable information. This technology relates to self-diagnostic systems for monitoring an individual's health state by tracking color changes of indicators within the devices by the naked eye or with a portable electronic device (e.g., a smartphone). By monitoring changes over time or trends, the disclosed devices may provide early indications of abnormal conditions.

The disclosed sweat sensor enables detection of sweat volume and rate, as well as concentration of biomarkers in sweat (e.g., pH, glucose, lactate, chloride, creatinine and ethanol) via various quantitative colorimetric assays. In an embodiment, the colorimetric indicators are incorporated into a polydimethysiloxane (PDMS) substrate because PDMS is a silicon-based organic polymer approved for a wide range of medical applications, including contact lenses and medical devices.

Epidermal Microfluidics

Figure 39:
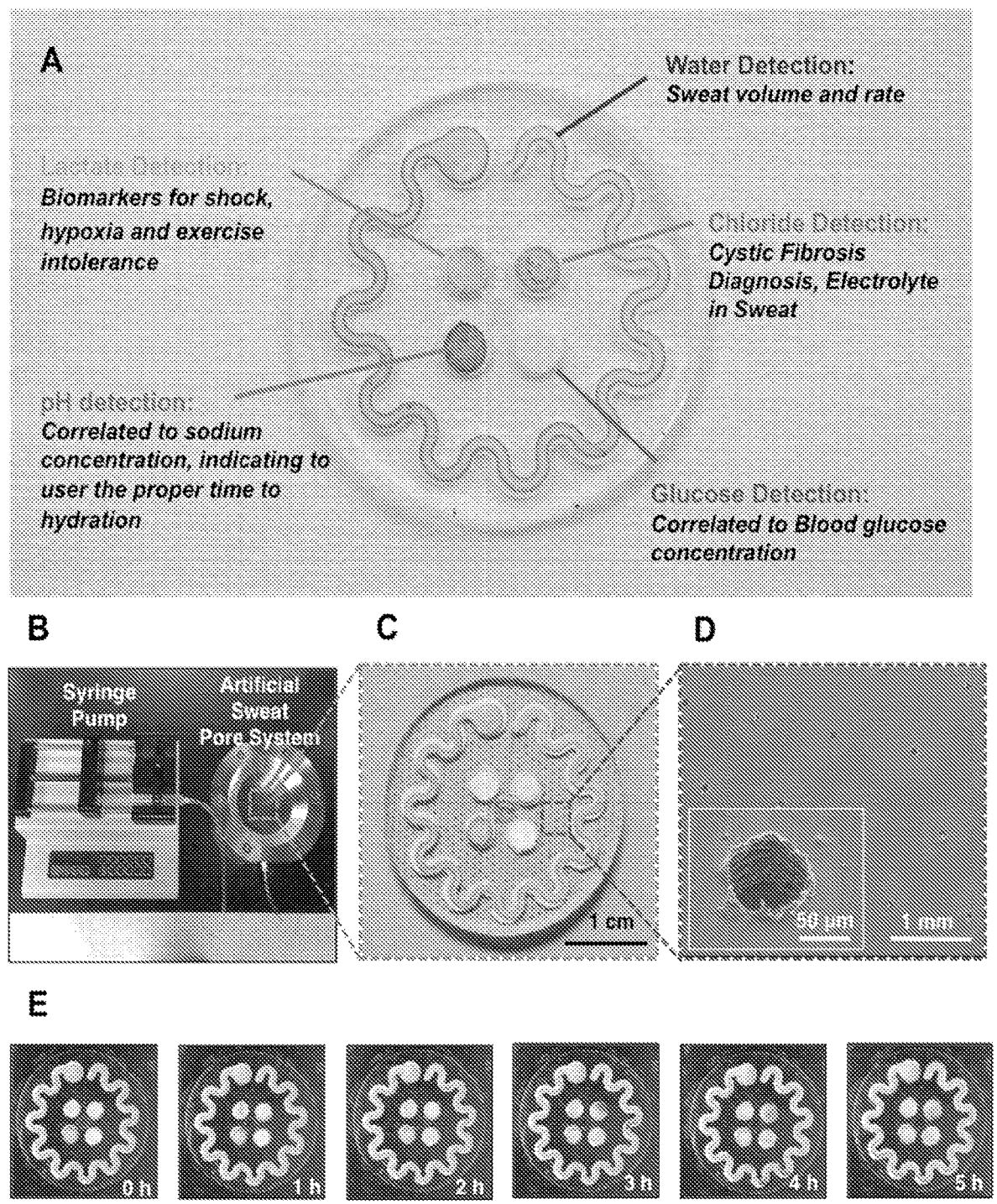
FIG. 39. (A) Picture of fabricated epidermal sweat sensor indicating informative detection schemes for sweat analysis. (B) In vitro artificial sweat pore system set up. (C) Optical image of sweat sensor applied on artificial pore membrane. (D) Scanning electron microscopy (SEM) image of the artificial pore membrane. Inset shows magnified image of single pore. (E) Representative images of sweat patch on the artificial sweat pore system while mimicking sweating events for 5 h. Sweat flowed continuously in the microfluidic systems along with color change accordingly.

Microfluidic analytical devices for sweat monitoring were developed based on a 2D channel system within poly (dimethylsiloxane) (PDMS) without pumps, valves, or fluid detectors. The chemical and physical characteristics of PDMS made it suitable for epidermal applications. For example, PDMS is optically transparent, elastomeric, non-toxic, chemically inert toward most reagents, and possesses a low surface energy.[1] The fabricated epidermal sweat patch was composed of four individual quantitative colorimetric detection reservoirs and an orbicular outer-circle serpentine fluidic channel (FIG. 39A). Each of the biomarker detection reservoirs holds 4 µL while the orbicular water detection channel contains 24 µL. The sample inlet located at the bottom of the device (0.5 cm$^2$) may cover about 50 sweat glands, thus introducing sweat into the device, filling the detection reservoirs, and allowing sweat to flow through the outer-circle channel for approximately 6 hours calculated based on an average sweat rate of 12 µL/hour·cm$^2$ for humans. Due to the interfacial permeability of PDMS, which is impermeable to liquid water but permeable to gases, the water loss of the sweat patch was moderate (3% of the total volume during the sensor life-time). The device was 3 cm in diameter and 500 µm in thickness constructed with PDMS consisting of 30:1 (v/v) base:curing agent resulting in a modulus of 145 kPa. The mass of the device was ~970 mg.

Figure 38:
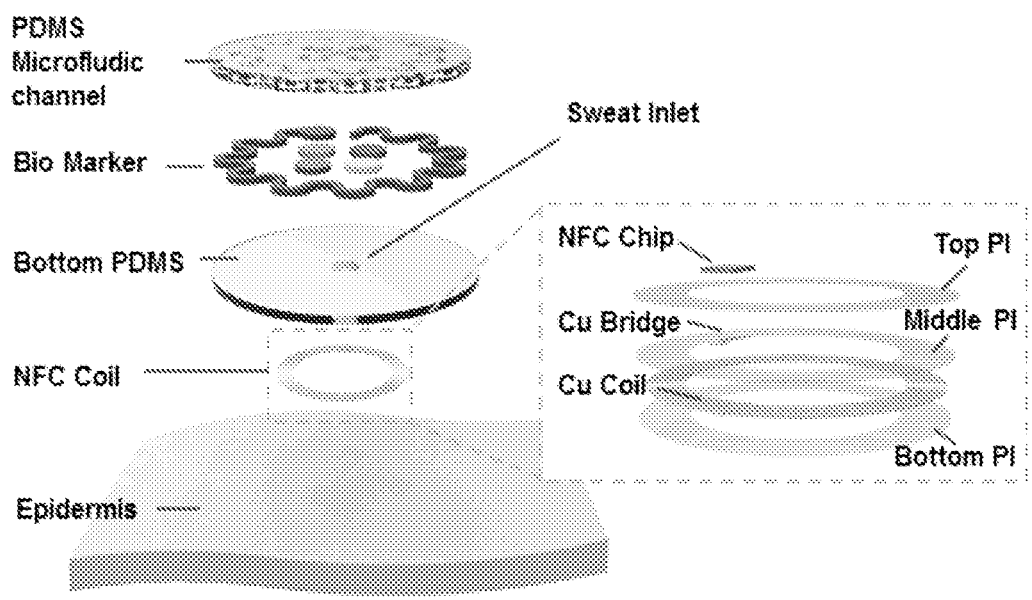
FIG. 38. (A) Schematic illustration of an epidermal microfluidic sweat sensor providing information of sweat volume and rate as well as concentration of biomarkers in sweat incorporated with wireless communication electronics. (B) Fabrication process for flexible and stretchable epidermal microfluidics. (C) Pictures of fabricated sweat sensors mounted on the skin under various mechanical stresses.
Figure 38:
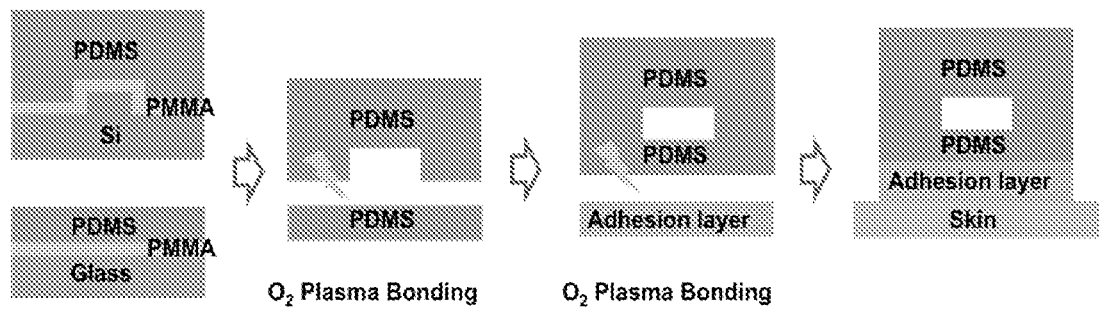
Figure 38:
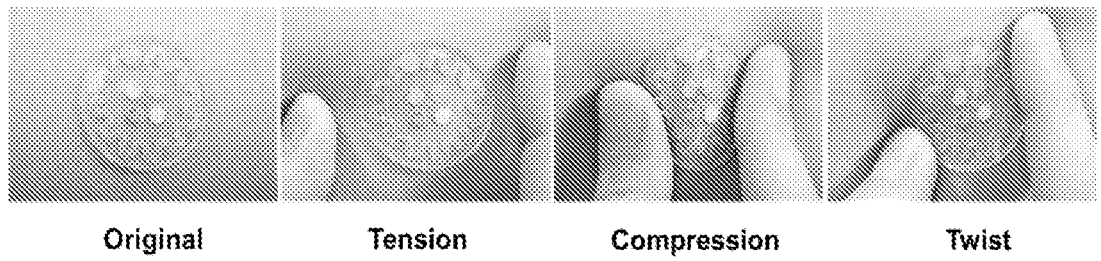

The epidermal microfluidic sweat sensors were fabricated using soft lithography. The schematic illustration and fabrication processes are shown in FIG. 38. A master device was prepared from a silicon wafer by photolithography and dip-etching to generate a reverse image having 300 µm deep channels. To produce replicas, the mixture of 30:1 (v/v) base:curing agent of PDMS was poured over the master that was coated with a thin layer of poly(methyl methacrylate) (PMMA) and cured at 70° C. for 1 h. Once the PDMS was fully cured, the replica was released from the master. The prepared replica was then sealed with a PDMS film by oxygen plasma bonding for 1 min to activate surface silanol groups to form siloxane bonds. Finally, the fabricated microfluidic devices were attached to a commercial medical dressing (i.e., Tegederm®) via oxygen plasma bonding and applied on the skin surface. This epidermal microfluidic sweat-monitoring device was able to withstand significant tension, compression, and twist of the skin while maintaining sufficient adhesion (FIG. 38C).

Quantitative Colorimetric Detection of Biomarkers

The colorimetric determination holds great advantages for diagnosis in quantitative analysis. In this sweat sensor, four colorimetric analyses were introduced for biomarkers being able to self-diagnosis and monitor a variety of medical conditions. Each detection reservoir represented a different analyte for determination of (1) water (for sweat volume and rate evaluation), (2) pH, (3) glucose, (4) lactate, and (5) chloride concentrations.

Figure 40:
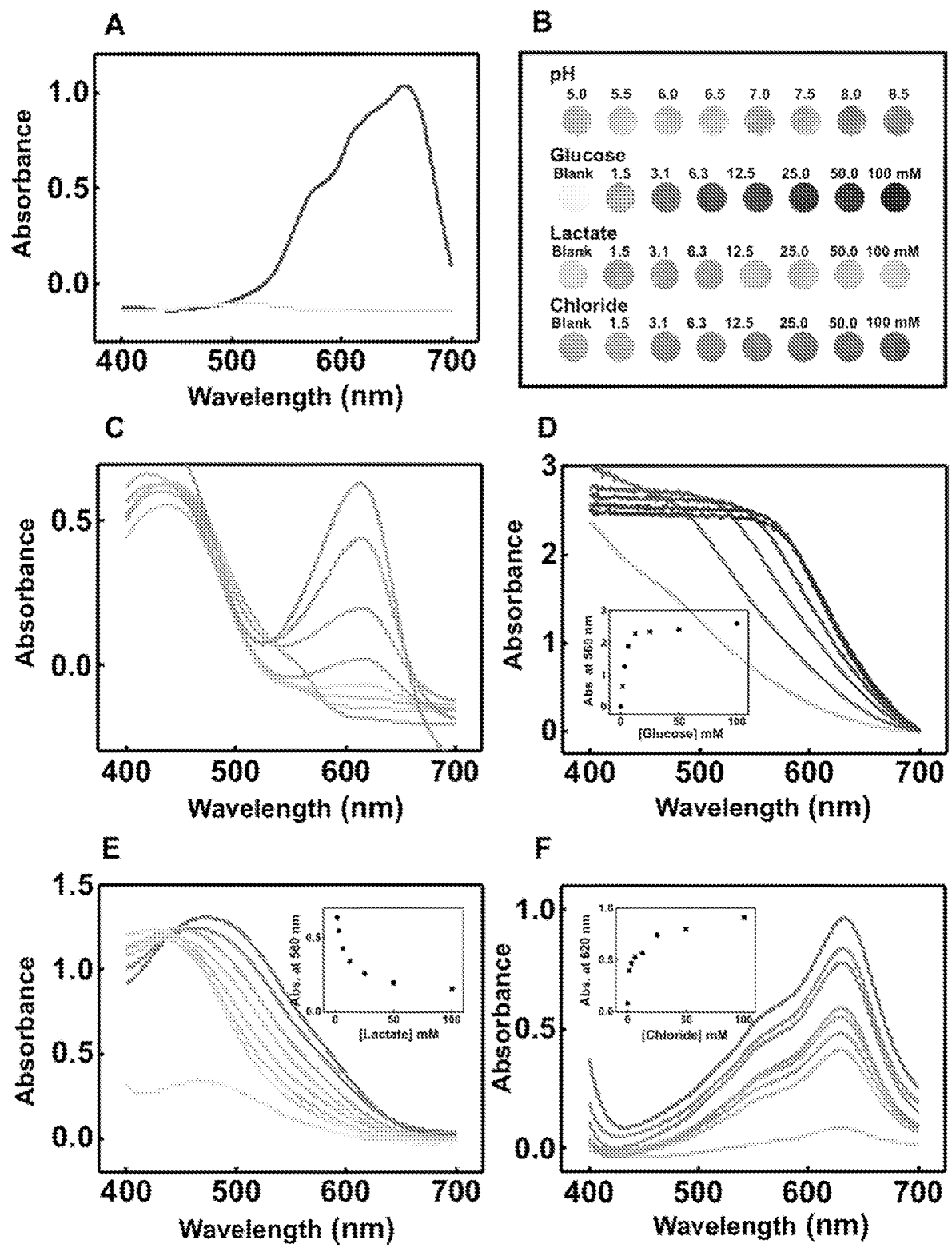
FIG. 40. Analytical colorimetric detections and respective UV-Vis spectrums of biomarkers in sweat. (A) Spectrum of anhydrous (blue) and hexahydrate (pale pink) cobalt (II) chloride. The presented color in the spectrum corresponds to the observed color with naked eye. (B) Optical images of resulted color change of the filter papers as a function of various pH values and analyte concentrations. (C) Spectrum of universal pH assay with various buffer solutions in the range of pH 5.0-8.5. (D-F) Spectrum of biomarkers in sweat as a function of concentration of analytes: glucose (D), lactate (E) and chloride (F). The presented color for each spectrum corresponds to exhibited color on paper-based colorimetric results, which is presented in image (B). Insets indicate calibration curves of respective analytes corresponding with concentration in the optical images (B). All spectra were determined at room temperature.

Thermal regulation and dehydration are highly related to sweat rate and volume and thus continuous monitoring is a vital tool for assessing health states of individuals and providing information relating to electrolyte balance and rehydration. The orbicular channel in the sweat sensor was coated with cobalt (II) chloride (i.e., $CoCl_2$) contained in a polyhydroxyethylmethacrylate hydrogel (pHEMA) matrix. As the sweat is introduced into the channel the blue colored anhydrous cobalt (II) chloride reacts with water turning into hexahydrate cobalt chloride (i.e., $CoCl_2.6H_2O$) presenting a pale purple color (FIG. 40A). By determining the distance of color change within the channel during a certain period of time, the sweat rate and volume could be assessed.

Not only physical sweat analysis, but chemical detection of biomarkers in sweat is essential. In some embodiments, quantitative colorimetric assays were demonstrated with paper-based reservoirs individually located in the middle of the sweat sensor. Filter paper was chosen as a matrix material among other materials (e.g., hydrogel, sol-gel, and agarose gel) since the hydrophilic cellulose fibers wicked biofluids at a fast absorption rate, as well as provided a solid support for assay reagent and allowed clear contrast regarding color changes.[2] A colorimetric sweat sensor was developed that consisted of four biomarker detection reservoirs: pH, glucose, lactate, and chloride.

The pH value of sweat has been known to exhibit a proportional relationship with sweat rate and sodium ion concentration. As an indicator of proper hydration time for a user, sweat pH was determined using a universal pH indicator consisting of various pH dyes (e.g., bromothymol blue, methyl red, and phenolphthalein), which covers a wide range of pH values. While the sweat was introduced in the reservoir, the pH indicator changed color based on the ratio of weak acid and its conjugate base form of the indicator based on the Henderson-Hasselbalch equation. The color change was observed according to various pH values of buffer solution in a medically reliable range (i.e., pH 4.0-7.0) as shown in FIG. 40B and its respective spectrum is presented in FIG. 40C.

Glucose concentration in the sweat is one of the most biomarkers for monitoring health state, especially playing a crucial role for improving diabetes treatment. In this device, the glucose was detected based on an enzymatic reaction that governed the selectivity of the measurement. Physically immobilized glucose oxidase produced hydrogen peroxide associated with oxidation of glucose and reduction of oxygen, next, iodide was oxidized to iodine by peroxidase, which was also contained in the paper-based reservoir.[3] Therefore, a color change was observed from yellow to brown, the respective colors of iodide and iodine, to indicate the concentration of glucose.[3] The color change illustrating the glucose concentration is presented in FIG. 40B as well as the respective spectrum in FIG. 40D. Thus, this device may warn of abnormal blood glucose concentrations for not only diabetes patients but also prediabetes and healthy persons by correlating perspiration glucose concentration in a completely noninvasive manner on a daily basis.[4]

The sweat lactate concentration is an indicator of exercise intolerance, tissue hypoxia, pressure ischemia, and even pathological conditions (e.g., cancer, diabetes, and lactate acidosis).[5] Lactate is produced by anaerobic energy metabolism from the eccrine gland, so lactate concentration in perspiration is a good criterion for determining individuals' abilities to endure rigorous exercise, especially for athletes and military personnel, and/or severe physical activity while on life support.[6] Enzymatic reactions between lactate and co-factor NAD[+] by lactate dehydrogenase and diaphorase allowed a color change of a chromogenic reagent (i.e., Formazan dyes) resulting in an orange color. As shown in FIGS. 22B and 22E, the color change within the detection reservoir was observed with regard to the concentration of lactate within the medically relevant range of 1.5-100 mM.

The representative sweat tests rely on determination of chloride ion concentration in perspiration. These tests may diagnosis cystic fibrosis (CF) since excreted chloride content increases when there are defective chloride channels in sweat glands.[7] Additionally, the level of chloride is considered to be an index of hydration. Accordingly, the level of chloride in sweat was determined using colorimetric detection by competitive binding between $Hg^{2+}$ and $Fe^{2+}$ with 2,4,6-tris(2-pyridiyl)-s-triazine (TPTZ). In the presence of chloride ion, iron ion prefers to bind with TPTZ while $Hg^{2+}$ participates as $HgCl_2$, which results in a color change from transparent to blue binding with respective metal ions. The quantitative colorimetric results are shown in FIGS. 40B and 40F.

Not only the biomarkers mentioned above, but copper ion, iron ion, and ethanol concentrations in sweat may also be detected by colorimetric assay. The trace copper ion in sweat was determined using a 1,2-bicinchoninate acid (BCA). The copper complex with BCA exhibited an intense purple color demonstrating a quantitative color change from 0 to 1 mg/mL.[8] Similarly, iron ions were detected by a colored complex formed with 1,10-phenanthroline in the range of 0-0.8 mg/L.[8b] Additionally, colorimetric detection of ethanol was demonstrated using an enzymatic reaction consisting of alcohol dehydrogenase, peroxidase, and formazan dye.

Collectively, these quantitative colorimetric analyses provide pre-diagnostic information of multiple biomarkers in sweat. By combining the colorimetric devices with telemedicine technology, this sweat patch could provide a user-friendly self-monitoring system for daily wear.

Telemedicine Technologies

Figure 41:
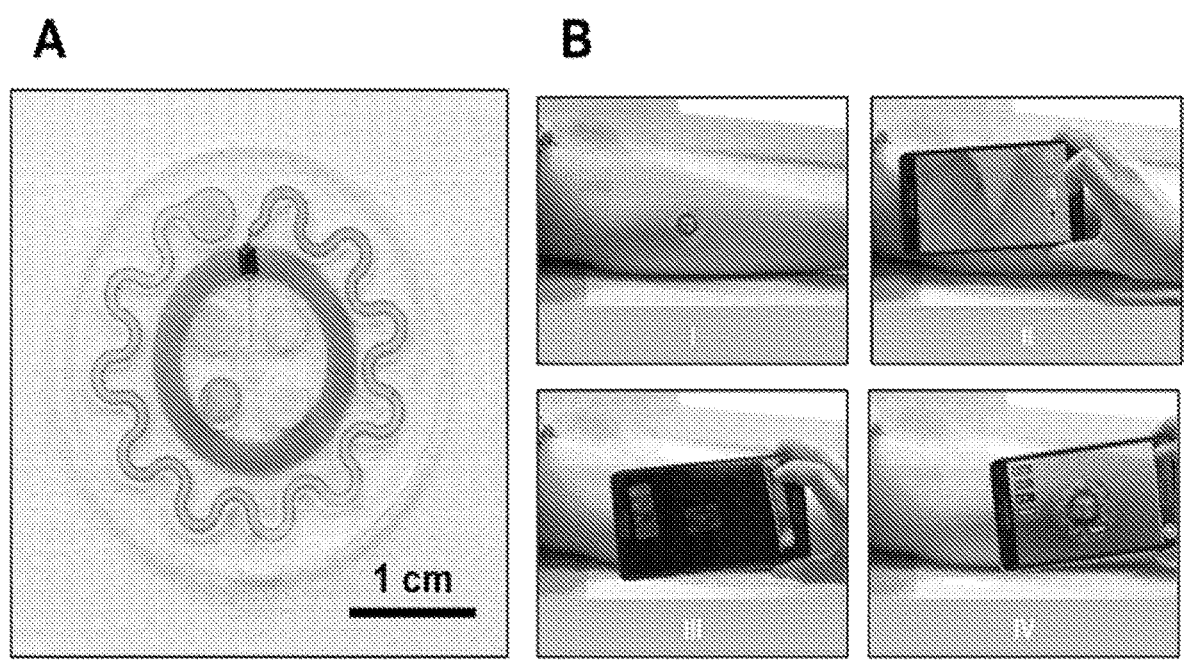
FIG. 41. (A) An image of fabricated sweat sensor incorporated with near-field communication electronics. (B) Demonstration pictures of wireless communication via smartphone. The RGB information was determined using an android image analysis app.

In order to provide personalized clinical health care with a smartphone, near field communication (NFC) electronics were applied to the sweat patch. The NFC communication devices were fabricated with an ultrathin construction using ultralow modulus materials, which enable wireless communication under extreme deformations in daily usage.[9] The NFC coils were incorporated on the sweat patch as shown in FIG. 41A. The biomedical information of sweat is quantitatively analyzed by taking images of the sweat sensor showing the color changes of the reservoirs (FIG. 41B). Using wireless NFC electronics to communicate to a smartphone permits the images to be examined based on an RGB digital color specification, converted into health informatics (e.g., concentration of biomarkers) and optionally transmitted from an individual's smartphone to medical staff or a medical records database.

References

1. McDonald, J. C.; Whitesides, G. M., Poly(dimethylsiloxane) as a Material for Fabricating Microfluidic Devices. Accounts of Chemical Research 2002, 35 (7), 491-499.
2. Martinez, A. W.; Phillips, S. T.; Whitesides, G. M.; Carrilho, E., Diagnostics for the Developing World: Microfluidic Paper-Based Analytical Devices. Analytical Chemistry 2010, 82 (1), 3-10.
3. (a) Martinez, A. W.; Phillips, S. T.; Butte, M. J.; Whitesides, G. M., Patterned Paper as a Platform for Inexpensive, Low-Volume, Portable Bioassays. Angewandte Chemie International Edition 2007, 46 (8), 1318-1320; (b) Martinez, A. W.; Phillips, S. T.; Carrilho, E.; Thomas, S. W.; Sindi, H.; Whitesides, G. M., Simple Telemedicine for Developing Regions: Camera Phones and Paper-Based Microfluidic Devices for Real-Time, Off-Site Diagnosis. Analytical Chemistry 2008, 80 (10), 3699-3707.
4. Moyer, J.; Wilson, D.; Finkelshtein, I.; Wong, B.; Potts, R., Correlation Between Sweat Glucose and Blood Glucose in Subjects with Diabetes. Diabetes Technology & Therapeutics 2012, 14 (5), 398-402.
5. (a) Polliack, A.; Taylor, R.; Bader, D., Sweat analysis following pressure ischaemia in a group of debilitated subjects. J Rehabil Res Dev 1997, 34 (3), 303-308; (b) Biagi, S.; Ghimenti, S.; Onor, M.; Bramanti, E., Simultaneous determination of lactate and pyruvate in human sweat using reversed-phase high-performance liquid chromatography: a noninvasive approach. Biomedical Chromatography 2012, 26 (11), 1408-1415.
6. Jia, W.; Bandodkar, A. J.; Valdes-Ramirez, G.; Windmiller, J. R.; Yang, Z.; Ramirez, J.; Chan, G.; Wang, J., Electrochemical tattoo biosensors for real-time noninvasive lactate monitoring in human perspiration. Anal Chem 2013, 85 (14), 6553-60.
7. Mishra, A.; Greaves, R.; Massie, J., The Relevance of Sweat Testing for the Diagnosis of Cystic Fibrosis in the Genomic Era. The Clinical biochemist. Reviews/Australian Association of Clinical Biochemists. 2005, 26 (4), 135-153.
8. (a) Brenner, A. J.; Harris, E. D., A quantitative test for copper using bicinchoninic acid. Anal Biochem 1995, 226 (1), 80-4; (b) Huang, X.; Liu, Y. H.; Chen, K. L.; Shin, W. J.; Lu, C. J.; Kong, G. W.; Patnaik, D.; Lee, S. H.; Cortes, J. F.; Rogers, J. A., Stretchable, Wireless Sensors and Functional Substrates for Epidermal Characterization of Sweat. Small 2014, 10 (15), 3083-3090.
9. Kim, J.; Banks, A.; Cheng, H. Y.; Xie, Z. Q.; Xu, S.; Jang, K. I.; Lee, J. W.; Liu, Z. J.; Gutruf, P.; Huang, X.; Wei, P. H.; Liu, F.; Li, K.; Dalal, M.; Ghaffari, R.; Feng, X.; Huang, Y. G.; Gupta, S.; Paik, U.; Rogers, J. A., Epidermal Electronics with Advanced Capabilities in Near-Field Communication. Small 2015, 11 (8), 906-912.

Example 5: Additional Sweat Patches

Figure 42:
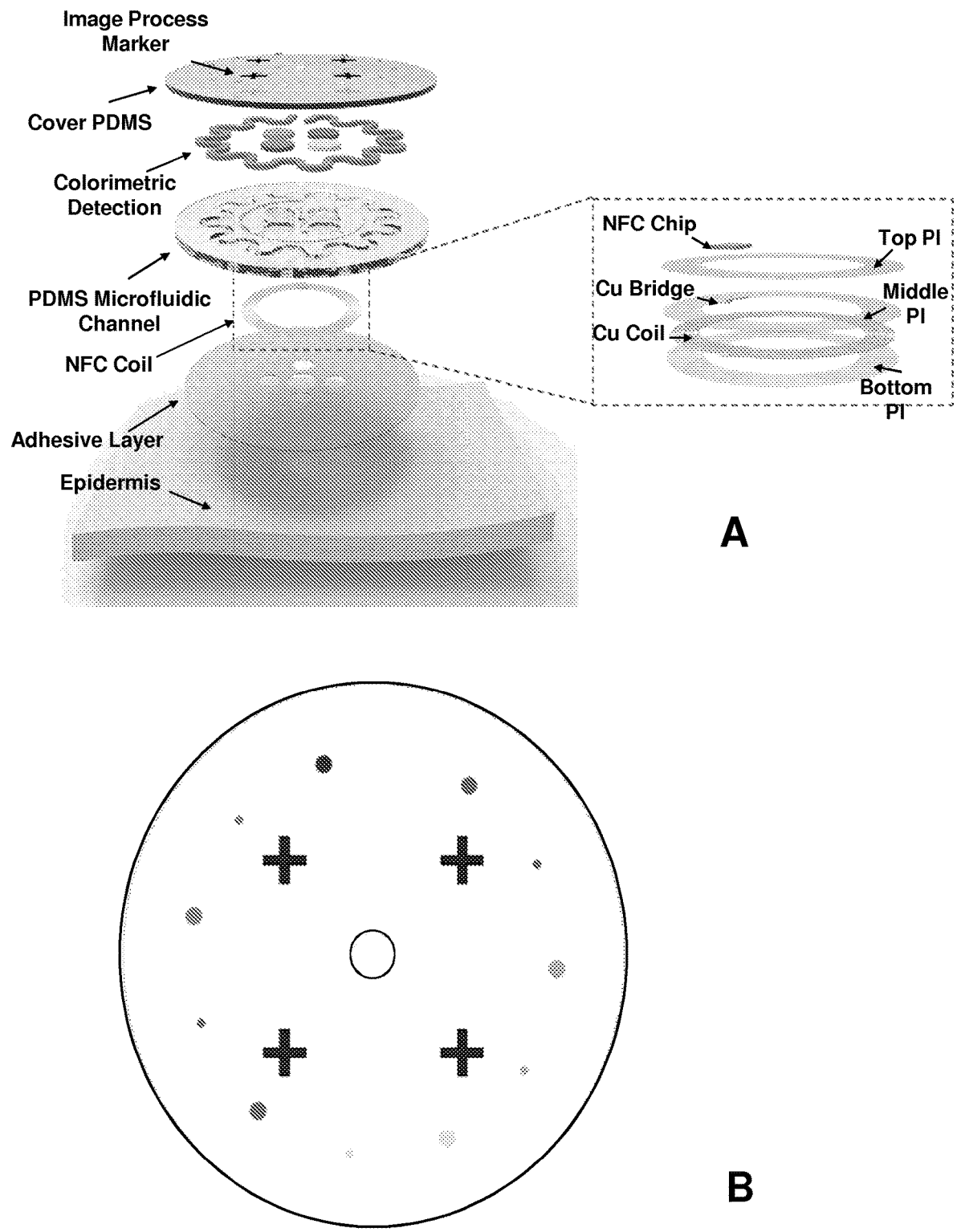
FIG. 42. (A) Schematic illustration of an epidermal microfluidic sweat sensor providing information on sweat volume and rate as well as concentration of biomarkers in sweat incorporated with wireless communication electronics and an adhesive layer. (B) Schematic illustration of image process markers applied to an epidermal microfluidic sweat sensor.

FIG. 42(A) shows a schematic illustration of an epidermal microfluidic sweat sensor providing information on sweat volume and rate as well as concentration of biomarkers in sweat incorporated with wireless communication electronics and an adhesive layer for adhering the sensor to the epidermis of a subject. FIG. 42(B) shows a schematic illustration of image process markers applied to an epidermal microfluidic sweat sensor. Image process markers are laminated on or disposed in a top layer of the sensor for white balance and color calibration, which enables the sensors to function under various light conditions. The image process markers also provide a reference for device orientation and a borderline for color change within a channel.

Figure 43:
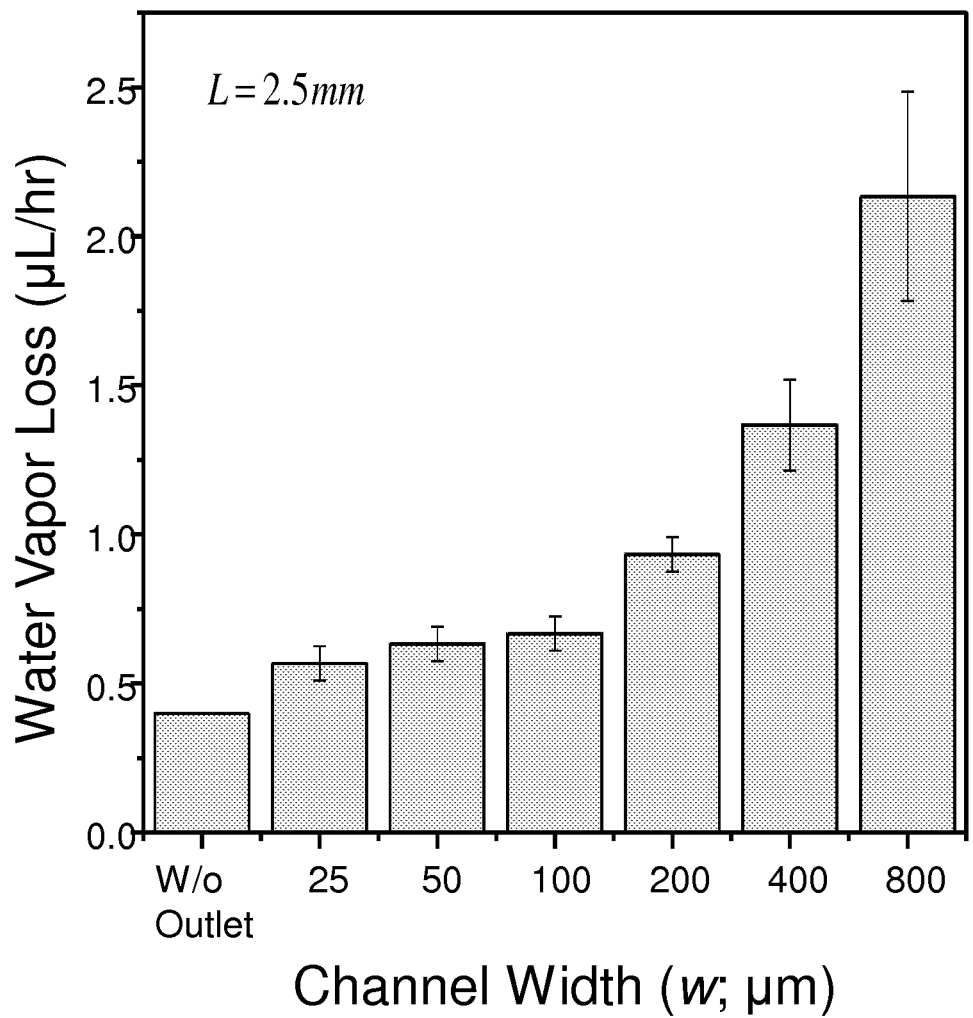
FIG. 43. Graphical representation of water loss as a function of outlet channel (A) width and (B) length.
Figure 43:
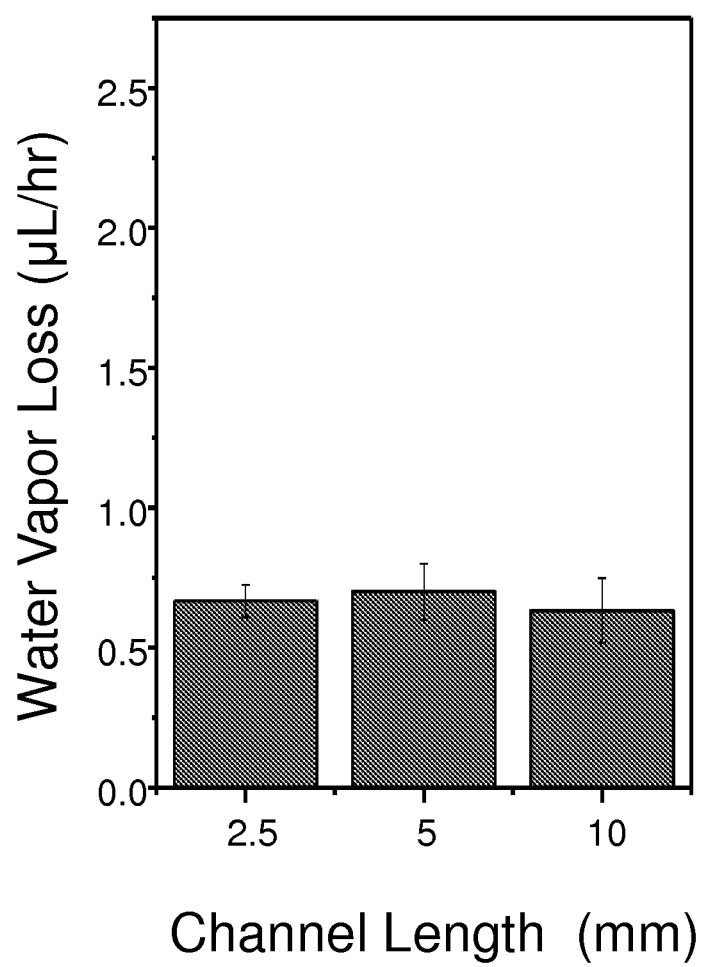
Figure 44:
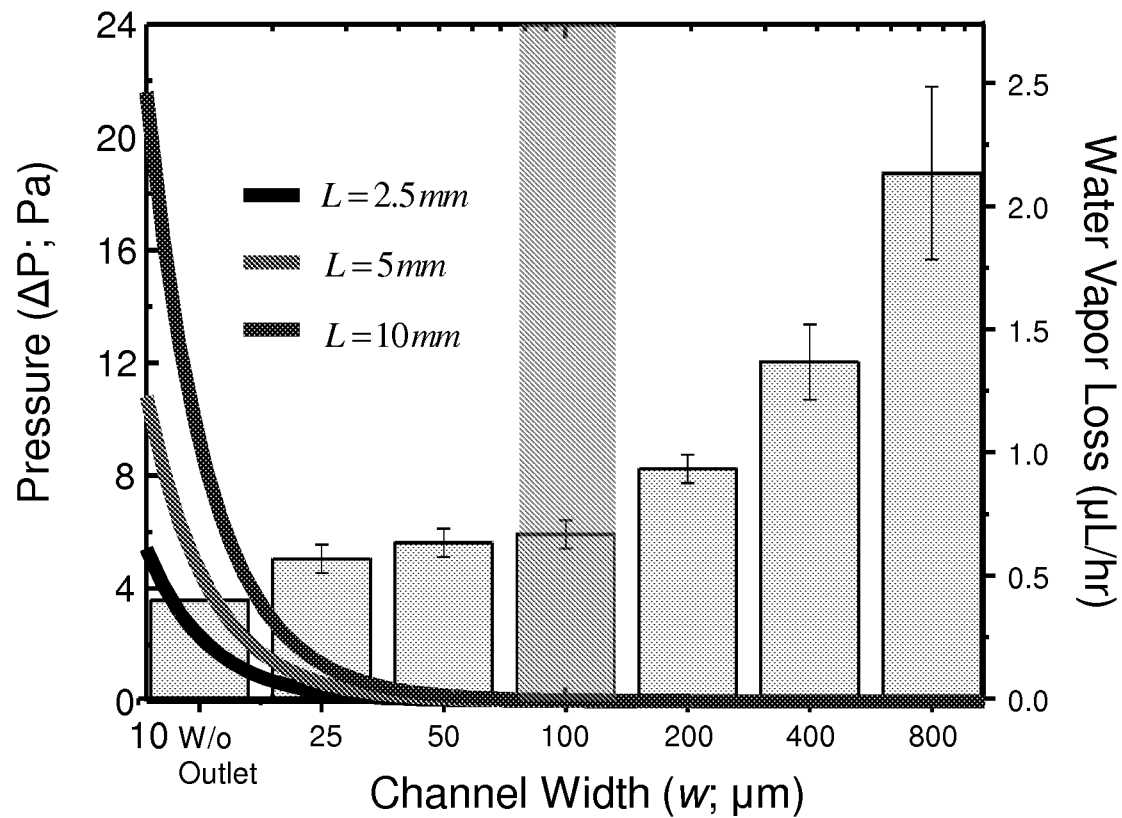
FIG. 44. Graphical representation of back pressure inside a channel showing that shorter outlet channels and larger channel widths produce lower back pressures.

FIG. 43 provides graphical representations of water loss as a function of outlet channel (A) width and (B) length. Smaller channel widths generally lead to a lower rate of water vapor loss than larger channel widths, but channel length does not significantly affect the rate of water vapor loss. FIG. 44 provides a graphical representation of back pressure inside a channel showing that shorter outlet channels and larger channel widths produce lower back pressures. At a channel width of 100 µm, back pressure became negligible for all channel lengths studied. The following equation was used to calculate the theoretical pressure in the channel:

$$\Delta P \approx \frac{8L(w+h)^2}{w^3 h^3} \frac{\mu M}{\rho} \frac{\dot{V}_{inlet} P_0}{RT} \quad (15)$$

where h=300 μm, M=29E-3 Kg/mol, ρ=1.2 Kg/m³, μ=1.8E-5 Pa·s, $P_0$=1E5 Pa, $V_{in}$=15 μL/hour, R=8.314 J/(mol·K), T=300 K.

Figure 45:
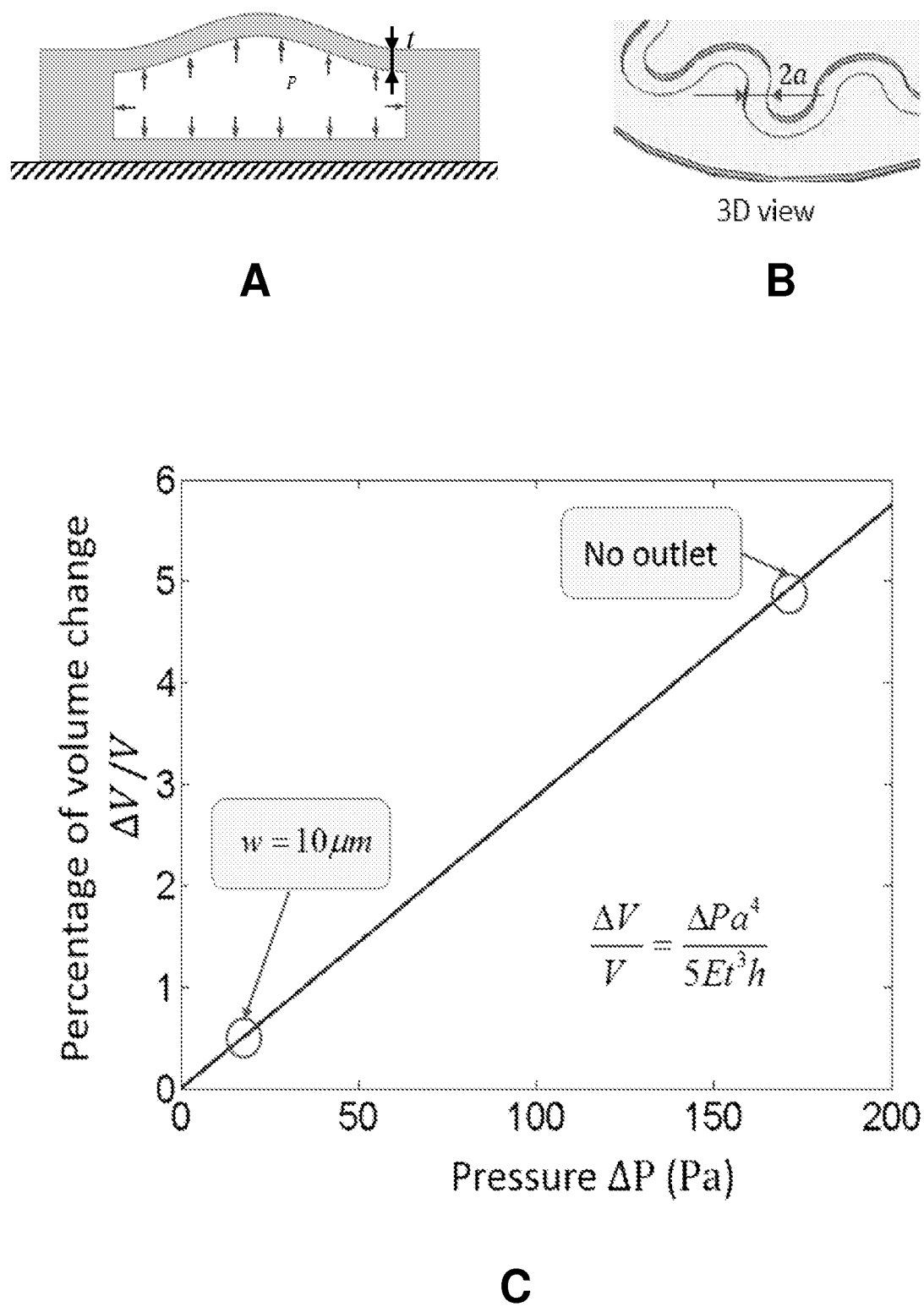
FIG. 45. (A) Schematic illustration of a cross section of a microfluidic channel deformed due to pressure. (B) Schematic illustration of a top perspective view of a section of an epidermal microfluidic sweat sensor showing a width of the microfluidic channel. (C) Graphical representation of deformation shown as volume change due to pressure.

FIG. 45 shows a schematic illustration of a cross section of a microfluidic channel deformed due to pressure (A) and a top perspective view of a section of an epidermal microfluidic sweat sensor showing a width of the microfluidic channel (B), as well as a graphical representation of deformation shown as volume change due to pressure. The volume change was calculated using:

$$\frac{\Delta V}{V} = \frac{\Delta P a^4}{5 E t^3 h} \quad (16)$$

where 2a=1 mm, t=100 μm, E=145 KPa and v=0.5. At an outlet width greater than 10 μm, a pressure-induced volume change can be avoided.

Figure 46:
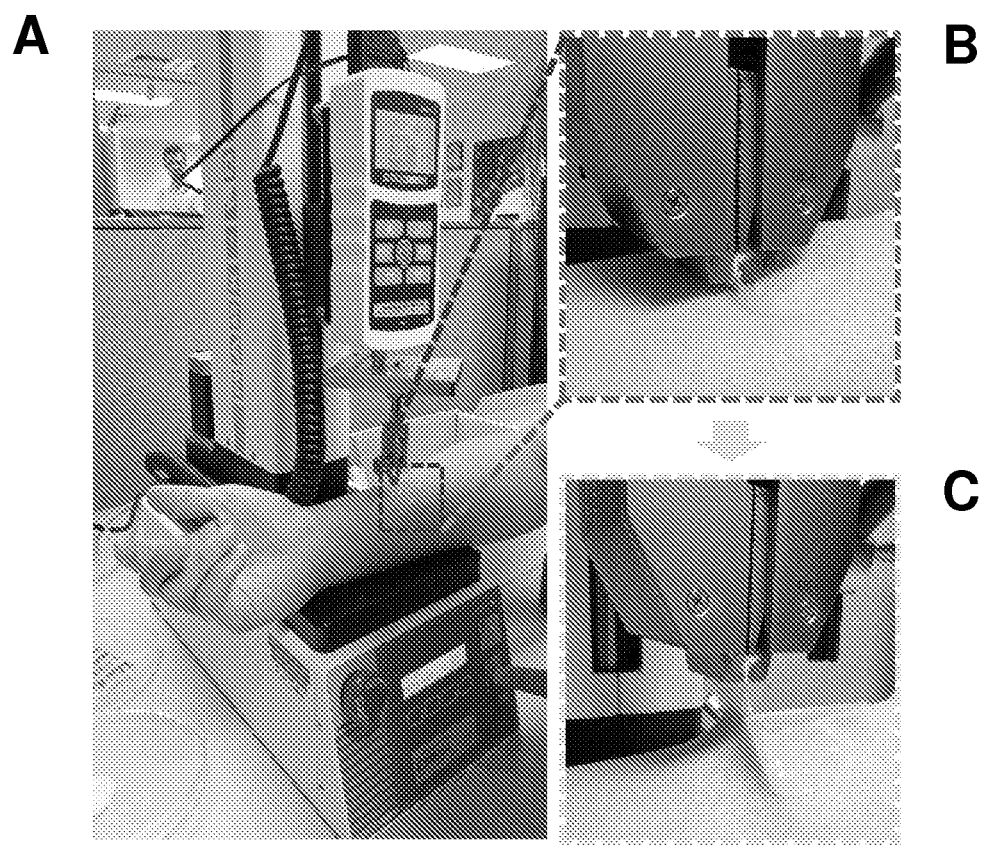
FIG. 46. (A) Experimental set-up for 90° peel adhesion property testing (standard ISO 29862:2007) using a force gauge (Mark-10, Copiague, N.Y.). Images of (B) holding devices adhered on the skin with a force gauge and (C) peeling devices at an angle of 90°. (D) Force measurement while displacing the device at a rate of 300 mm/min indicated by the gray region where peeling occurs. Determined average peeling force is 5.7 N.
Figure 46:
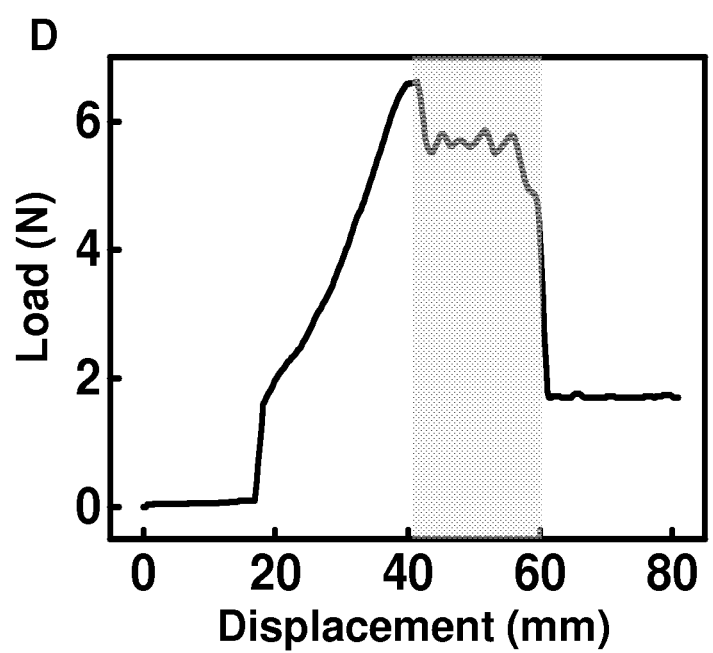

To harvest biofluids using pump-less microfluidics, sufficient adhesion force is required to drive fluid into the microfluidics system. The disclosed microfluidic devices demonstrate great adhesion on the epidermis facilitated by medical-grade adhesives (e.g., Tagaderm®). FIG. 46 shows an experimental set-up for 90° peel adhesion property testing (standard ISO 29862:2007) using a force gauge (Mark-10, Copiague, N.Y.) (A). A holding devices is adhered on the skin with a force gauge (B) and devices are peeled at an angle of 90° (C.). The force measurement while displacing the device at a rate of 300 mm/min is shown graphically in (D) and the area where peeling occurs is indicated by the gray region. The average peeling force was determined to be 5.7 N. Thus, the disclosed microfluidic sweat sensors may be bonded to the epidermis of a subject with an adhesion force in the range from 1 N to 10 N, or 2 N to 8 N, or 3 N to 6 N.

Figure 47:
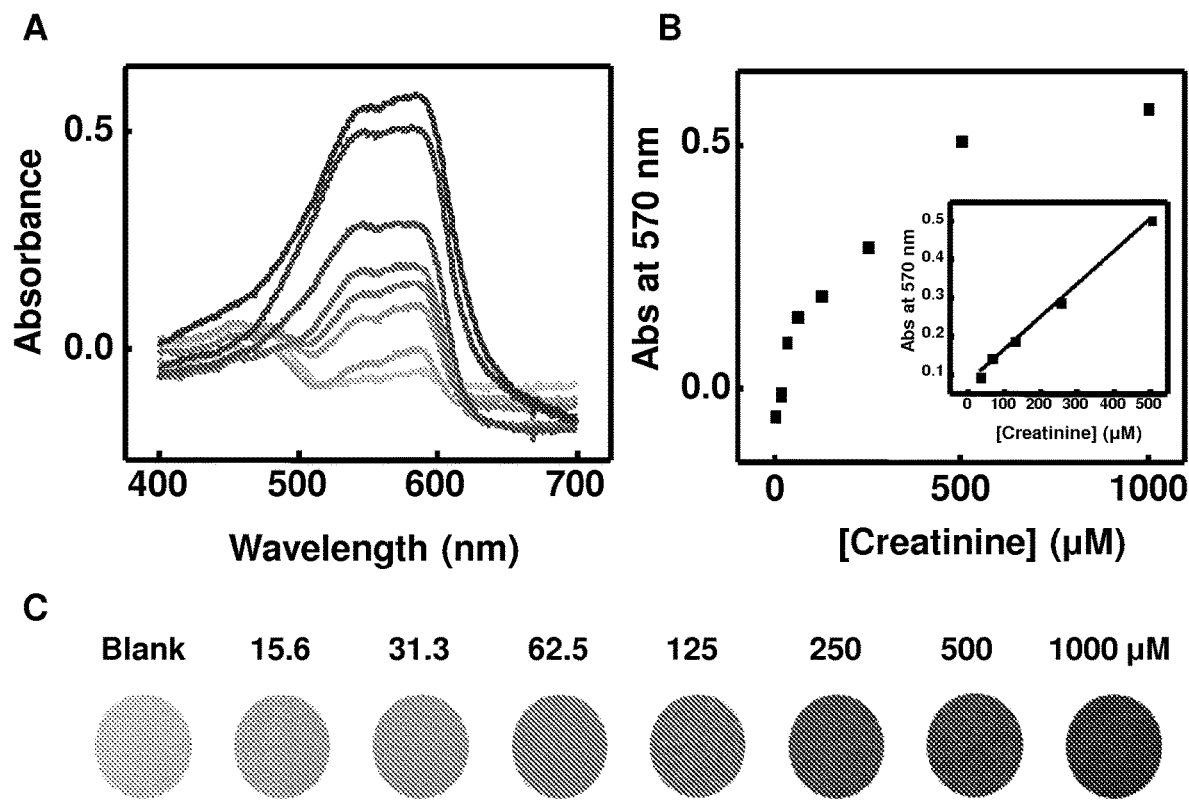
FIG. 47. Colorimetric determination of creatinine. (A) UV-VIS spectrum with various creatinine concentrations (i.e., 15-1000 µM) and (B) constructed calibration based on this spectrum. The presented color for each spectrum corresponds to exhibited color on paper-based colorimetric detection reservoirs as a function of creatinine concentration, which is presented in optical image (C).

FIG. 47 illustrates one example of colorimetric determination of creatinine. A UV-VIS spectrum illustrating various creatinine concentrations (i.e., 15-1000 μM) is shown in (A) and a constructed calibration curve based on this spectrum is shown in (B). The presented color for each spectrum corresponds to exhibited color on paper-based colorimetric detection reservoirs as a function of creatinine concentration, which is presented in optical image (C). This colorimetric analysis is based on an enzymatic reaction using a mixture of creatinine amidohydrolase, creatine amidinohydrolase and sarcosine oxidase. Reaction of creatinine with this enzyme mixture generates hydrogen peroxide proportional to the concentration of creatinine in biological fluids. The hydrogen peroxide concentration is determined colorimetrically by the chromogen 2,5-dichloro-2-hydroxybenzenesulfonic acid and 4-amino-phenazone in a reaction catalyzed by horseradish peroxidase.

Figure 48:
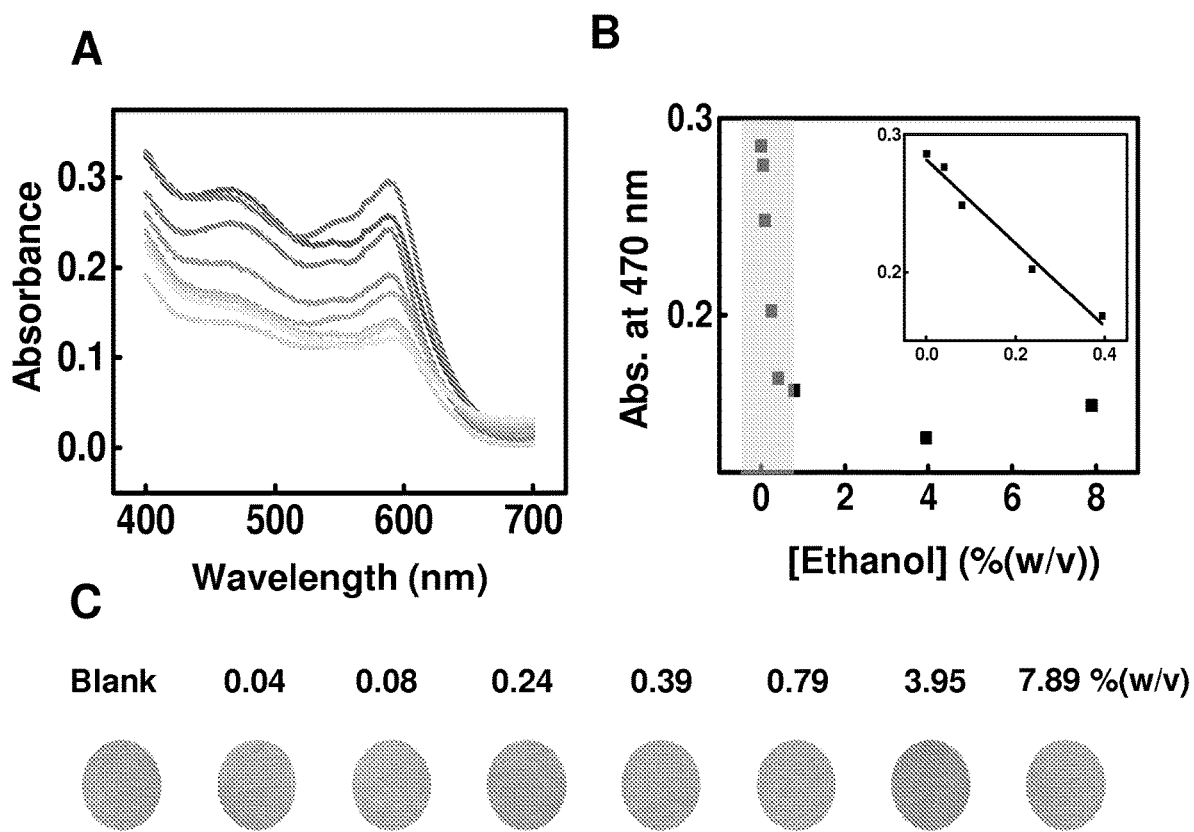
FIG. 48. Colorimetric determination of ethanol. (A) UV-VIS spectrum with various ethanol concentrations (i.e., 0.04-7.89% (w/v)) and (B) constructed calibration based on this spectrum. The presented color for each spectrum corresponds to exhibited color on paper-based colorimetric detection reservoirs as a function of ethanol concentration, which is presented in optical image (C).

FIG. 48 illustrates one example of colorimetric determination of ethanol. Ethanol is detected via reaction with alcohol dehydrogenase in the presence of formazan dye. A UV-VIS spectrum illustrating various ethanol concentrations (i.e., 0.04-7.89% (w/v)) is shown in (A) and a constructed calibration curve based on this spectrum is shown in (B). The presented color for each spectrum corresponds to exhibited color on paper-based colorimetric detection reservoirs as a function of ethanol concentration, which is presented in optical image (C).

Figure 49:
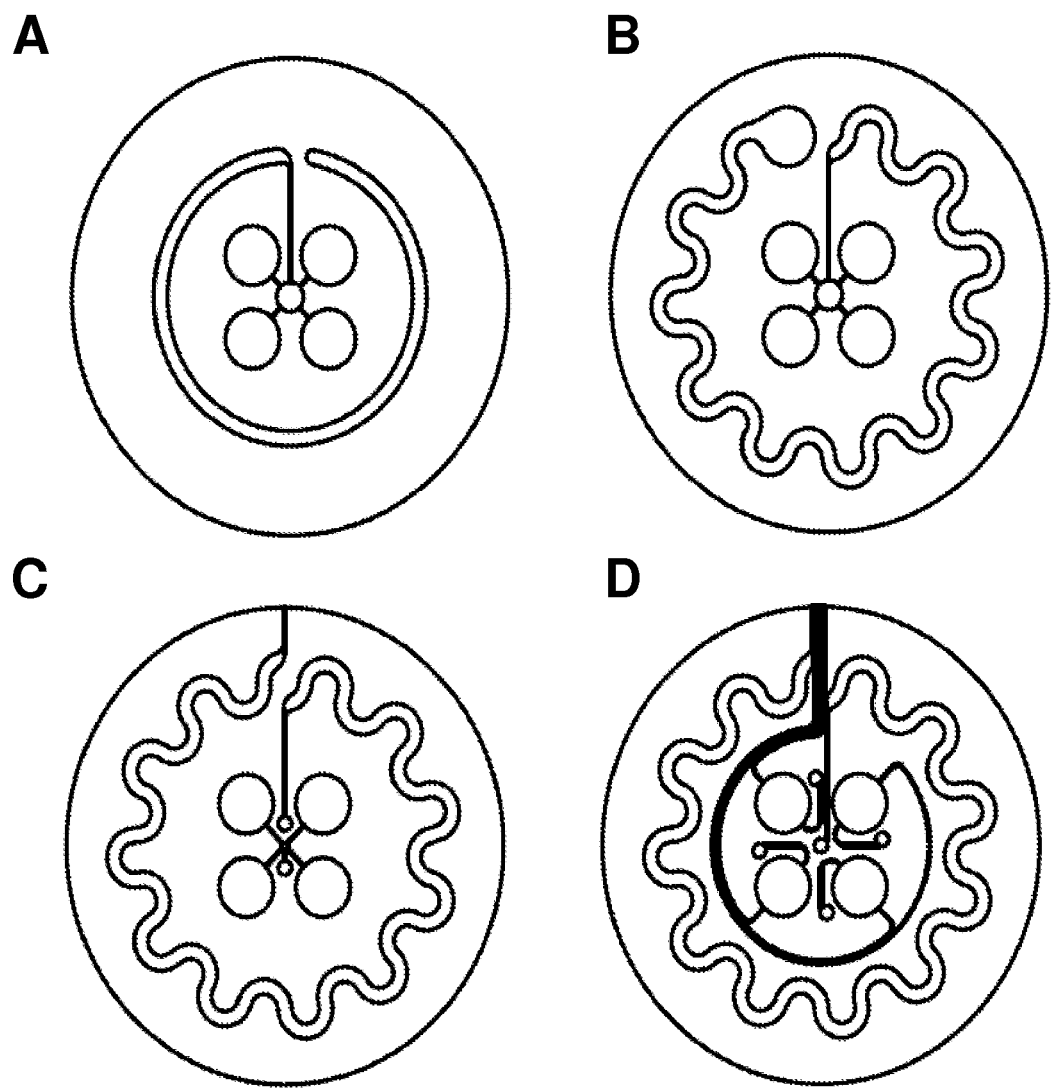
FIG. 49. Various microfluidic sweat sensor designs.
Figure 50:
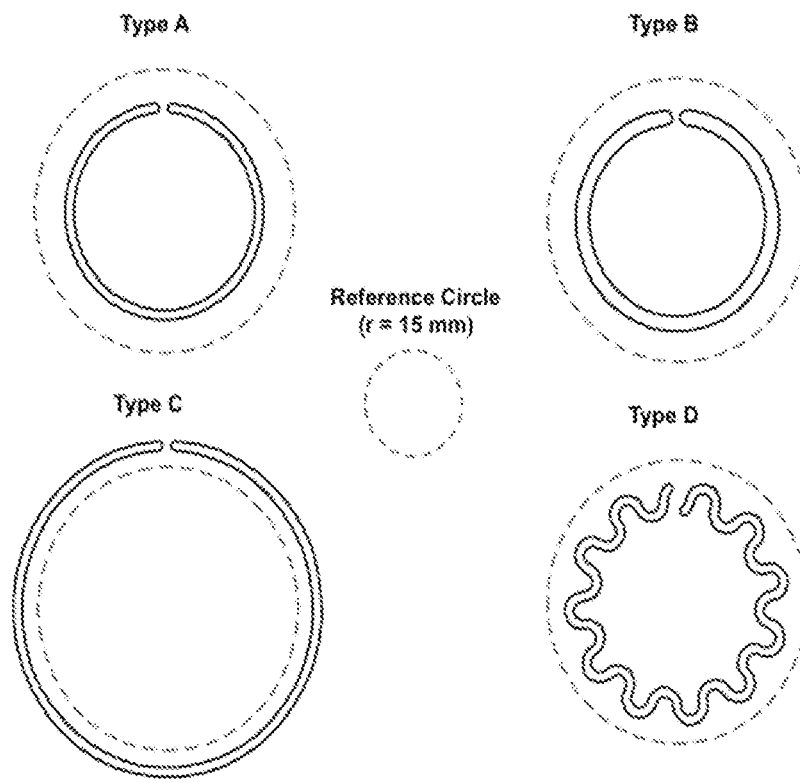
FIG. 50. Various types of orbicular channel designs and respectively calculated channel properties.

FIG. 49 shows various microfluidic sweat sensor designs including four individual quantitative colorimetric detection reservoirs and an orbicular outer-circle fluidic channel. In some embodiments, a single microfluidic channel is in fluidic communication with all of the colorimetric detection reservoirs and an orbicular fluidic channel. In an other embodiment, one microfluidic channel transports fluids from the epidermis of a subject to the colorimetric detection reservoirs and a second microfluidic channel transports fluids from the epidermis of the subject to the orbicular fluidic channel (C). In another embodiment, each colorimetric detection reservoir and the orbicular microfluidic channel may be independently connected to a microfluidic channel that transports fluid from the epidermis of a subject. Optionally, each of the colorimetric detection reservoirs may comprise an outlet to a channel that allows vapor to escape to the surrounding environment. As shown in (D), the outlet channel may be tapered to increase in volume nearer the outlet to the surrounding environment, thereby accommodating larger quantities of vapor without increasing back pressure within the outlet channel. In any of the embodiments disclosed, the orbicular fluidic channel may be circular or serpentine and the orbicular fluidic channel may have a sealed distal end, optionally including a reservoir, or an outlet to the surrounding environment. As shown in FIG. 50, a serpentine orbicular fluidic channel provides a greater area and channel volume than a circular orbicular fluidic channel while controlling for channel width and height to avoid collapse of the channel. For example, a serpentine channel may provide an increased area of up to 58% compared to a circular channel having an identical channel width. An increased area of the orbicular channel increases the amount of time a microfluidic sweat sensor can be used for monitoring a subject without being replaced or dried.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A photonic device for interfacing with a skin tissue comprising:
   a flexible or stretchable substrate;
   one or more microfluidic channels incorporated through or in the flexible or stretchable substrate for transporting a biological fluid that is sweat released from sweat glands in the skin through or within said flexible or stretchable substrate, said microfluidic channels fluidically connected to:
      a sweat inlet formed from the flexible or stretchable substrate for receiving sweat released by sweat glands in the skin; and
      one or more detection reservoirs for receiving sweat from said microfluidic channels, wherein the one or more detection reservoirs are embedded in or supported by the flexible or stretchable substrate; and
   one or more photonic structures supported by said flexible or stretchable substrate for generating a photonic response corresponding to one or more parameters of the sweat detected by the one or more detection reservoirs;
   wherein said flexible or stretchable substrate and said one or more photonic structures provide a net bending stiffness such that the device is capable of establishing conformal contact with a surface of the tissue.

2. The device of claim 1, wherein said device further comprises an optical detector to spatially characterize said one or more parameters.

3. The device of claim 1, said device further comprises an optical detector to temporally characterize said one or more tissue parameters or environmental parameters.

4. The device of claim 1, wherein said device further comprises an optical sensor for sensing one or more tissue parameters.

5. The device of claim 1, wherein said device further comprises an electromagnetic radiation element for actuating the tissue.

6. The device of claim 1, said device further comprises an optical sensor for sensing one or more environmental parameters.

7. The device of claim 1, wherein said photonic response corresponds to one or more parameters selected from the group consisting of:
   (i) wavelengths of light scattered, transmitted or emitted by said photonic structures;
   (ii) intensity of light scattered, transmitted or emitted by said photonic structures;
   (iii) spatial distribution of light scattered, transmitted or emitted by said photonic structures;
   (iv) phases of light scattered, transmitted or emitted by said photonic structures; and
   (v) one or more diffraction patterns of light scattered, transmitted or emitted by said photonic structures.

8. The device of claim 1, wherein said photonic response is a spectroscopic response.

9. The device of claim 1, wherein said photonic response is a colorimeteric response or fluorometric response.

10. The device of claim 1, wherein said photonic response results from a change in a spatial distribution, physical dimensions, phase or chemical composition of said photonic structures.

11. The device of claim 1, wherein said photonic response results from a distortion or displacement of said photonic structures in response to a change in said parameters.

12. The device of claim 1, further comprising a mobile electronic device to detect said photonic response.

13. The device of claim 1, wherein said photonic response corresponds to one or more tissue parameters selected from the group consisting of:
   (i) temperature;
   (ii) hydration state;
   (iii) chemical composition of the tissue;
   (iv) chemical composition of a fluid from said tissue;
   (v) pH of a fluid from said tissue;
   (vi) the presence or absence of a biomarker;
   (vii) intensity of electromagnetic radiation exposed to the tissue;
   (viii) wavelength of electromagnetic radiation exposed to the tissue; and
   (ix) amount of an environmental contaminant exposed to the tissue.

14. The device of claim 1, wherein said photonic response corresponds to one or more environment parameters selected from the group consisting of:
   (i) intensity of electromagnetic radiation exposed to the device;
   (ii) wavelengths of electromagnetic radiation exposed to the device;
   (iii) amount of a composition of an environmental component exposed to the device;
   (iv) chemical composition of an environmental component exposed to the device;
   (v) amount of an environmental contaminant exposed to the device; and
   (vi) chemical composition of an environmental contaminant exposed to the device.

15. The device of claim 1, wherein said one or more photonic structures optically absorb, scatter, transmit or emit electromagnetic radiation having wavelengths in the visible, ultraviolet or infrared regions of the electromagnetic spectrum.

16. The device of claim 1, wherein said one or more photonic structures are flexible or stretchable photonic structures.

17. The device of claim 1, wherein said one or more photonic structures are microstructures, nanostructures or both.

18. The device of claim 1, wherein said one or more photonic structures are spatially distributed in an array.

19. The device of claim 18, wherein said array is a pixelated array; wherein each photonic structure provides an individual pixel independently corresponding to an individual position in said array.

20. The device of claim 19, wherein individual pixels have average lateral dimensions selected from the range of 10 μm to 1 cm.

21. The device of claim 19, wherein individual pixels have an average thickness selected from the range of 1 μm to 1000 μm.

22. The device of claim 19, wherein said pixelated array comprises 10 to 100,000 pixels.

23. The device of claim 19, wherein said pixelated array has a footprint selected from the range of 10 $mm^2$ to 2000 $cm^2$.

24. The device of claim 19, wherein at least a portion of said pixels comprise micro-encapsulated structures or nano-encapsulated structures.

25. The device of claim 19, wherein at least a portion of said pixels comprise a colorimetric indicator, fluorometric indicator or both.

26. The device of claim 19, wherein at least a portion of said pixels comprise a colorimetric indicator that is a liquid crystal, an ionochromic dye, a pH indicator, a chelating agent, a fluorphore or a photosensitive dye.

27. The device of claim 19, wherein at least a portion of said pixels comprise a colorimetric indicator that undergoes a measurable change in an optical property in response to a change in temperature, exposure to electromagnetic radiation or upon exposure to a chemical composition.

28. The device of claim 19, wherein at least a portion of said pixels comprise a colorimetric indicator comprising a thermochromic liquid crystal that under goes a measurable change in the wavelength of light that is absorbed, transmitted or scattered upon a change of said tissue parameter.

29. The device of claim 19, wherein at least a portion of said pixels comprise a colorimetric indicator comprising chiral nematic liquid crystal that under goes a measurable change in the wavelength of light that is absorbed, transmitted or scattered upon a change in temperature of said tissue.

30. The device of claim 19, wherein at least a portion of said pixels comprise a colorimetric indicator comprising an ionochromic dye that undergoes a measurable change in the wavelength of light that is absorbed, transmitted or scattered in response to a composition or property of a biological fluid from said tissue.

31. The device of claim 30, wherein said composition or property of the biological fluid corresponds to pH, concentration of free copper ion, or concentration of iron ion.

32. The device of claim 19, wherein at least a portion of said pixels comprise a colorimetric indicator that undergoes a measurable change in color in response to exposure to ultraviolet radiation.

33. The device of claim 19, wherein said pixelated array further comprises one or more calibration pixels.

34. The device of claim 33, wherein said calibration pixels comprise dots having a fixed color.

35. The device of claim 1, wherein said substrate is optically opaque.

36. The device of claim 1, wherein the flexible or stretchable substrate is a functional substrate.

37. The device of claim 1, wherein the flexible or stretchable substrate comprises an elastomer.

38. The device of claim 1, wherein the flexible or stretchable substrate is a bioinert or biocompatible material.

39. The device of claim 1, wherein the flexible or stretchable substrate comprises a gas-permeable elastomeric sheet.

40. The device of claim 1, wherein the flexible or stretchable substrate has an average modulus less than or equal to 100 MPa.

41. The device of claim 1, wherein the flexible or stretchable substrate has an average modulus selected over the range of 0.5 kPa to 100 MPa.

42. The device of claim 1, wherein the flexible or stretchable substrate has an average thickness less than or equal to 3 mm.

43. The device of claim 1, wherein the flexible or stretchable substrate has an average thickness selected over the range of 1 to 3000 microns.

44. The device of claim 1, further comprising one or more additional device components supported by said flexible or stretchable substrate, said device components selected from the group consisting of an electrode, strain gauge, optical source, temperature sensor, wireless power coil, solar cell, wireless communication component, photodiode, microfluidic component, inductive coil, high frequency inductor, high frequency capacitor, high frequency oscillator, high frequency antennae, multiplex circuits, electrocardiography sensors, electromyography sensors, electroencephalography sensors, electrophysiological sensors, thermistors, transistors, diodes, resistors, capacitive sensors, and light emitting diodes.

45. The device of claim 1 further comprising one or more wireless communication antenna structures or near-field communication coils supported by said flexible or stretchable substrate.

46. The device of claim 1 further comprising one or more single crystalline semiconductor structures supported by said flexible or stretchable substrate.

47. The device of claim 1, comprising a multilayer device wherein said one or more photonic structures are at least partially encapsulated by a barrier layer.

48. The device of claim 1, wherein the device has a modulus within a factor of 1000 of a modulus of the tissue at the interface with the device.

49. The device of claim 1, wherein the device has an average modulus less than or equal to 100 MPa.

50. The device of claim 1, wherein the device has an average modulus selected over the range of 0.5 kPa to 100 MPa.

51. The device of claim 1, wherein the device has an average modulus equal to or less than 100 times the average modulus of the tissue at the interface.

52. The device of claim 1, wherein the device has an average thickness less than or equal to 3000 microns.

53. The device of claim 1, wherein the device has an average thickness selected over the range of 1 micron to 3000 microns.

54. The device of claim 1, wherein the device has a net bending stiffness less than or equal to 1 mN m.

55. The device of claim 1, wherein the device has a net bending stiffness selected over the range of 0.1 nN m to 1 N m.

56. The device of claim 1, wherein the device has an areal mass density less than or equal to 100 mg cm$^{-2}$.

57. The device of claim 1, wherein the device has an areal mass density selected over the range of 0.1 mg cm$^{-2}$ to 100 mg cm$^{-2}$.

58. The device of claim 1, wherein the device is characterized by a stretchability greater than or equal to 5%.

59. The device of claim 1, wherein the device is characterized by a stretchability selected from the range of 5% to 200%.

60. The device of claim 1, wherein the device establishes conformal contact with the skin when the device is placed in physical contact with the skin, and wherein the conformal contact with the skin in the biological environment is maintained as the skin moves or when the device moves.

61. A method of sensing one or more sweat parameters, said method comprising the steps of:
providing a skin tissue of a subject;
contacting an epidermal surface of said skin tissue with a photonic device, wherein said photonic device comprises:
a flexible or stretchable substrate;
one or more microfluidic channels incorporated in or through the flexible or stretchable substrate for transporting a biological fluid that is sweat released from sweat glands in the skin through or within said flexible or stretchable substrate, said microfluidic channels fluidically connected to:

a sweat inlet formed from the flexible or stretchable substrate for receiving sweat released by sweat glands in the skin; and one or more detection reservoirs for receiving said sweat from said microfluidic channels, wherein the one or more detection reservoirs are embedded in or supported by the flexible or stretchable substrate; and one or more photonic structures supported by said flexible or stretchable substrate for generating a photonic response corresponding to said one or more tissue parameters of the sweat detected by the one or more detection reservoirs;

wherein said flexible or stretchable substrate and said one or more photonic structures provide a net bending stiffness such that the device establishes conformal contact with a surface of the tissue; and detecting said photonic response from said photonic device using an optical detector, thereby sensing said one or more sweat parameters.

62. The method of claim 61, wherein said step of detecting said photonic response from said photonic device comprises detecting electromagnetic radiation scattered or emitted by said one or more photonic structures.

63. The method of claim 61, wherein detecting electromagnetic radiation scattered or emitted by said one or more photonic structures is carried out using a mobile electronic device.

64. The method of claim 61, further comprising generating a detector signal corresponding to the photonic response using said optical detector.

65. The method of claim 61, further comprising analyzing the detector signal, thereby determining said one or more tissue parameters or environmental parameters.

66. The device of claim 1, wherein said one or more detection reservoirs are formed in said flexible or stretchable substrate and said one or more photonic structures comprise a colorimetric indicator of the detection reservoir, a fluorometric indicator of the detection reservoir, or both.

67. The device of claim 66, wherein said one or more microfluidic channels are fluidically connected to an orbicular fluidic channel having a circular or a serpentine geometry.

68. The device of claim 67, comprising a plurality of detection reservoirs.

69. The device of claim 66, further comprising an outlet channel fluidically connected to each of said detection reservoirs at an inlet end and extending to an outlet end for a vapor to escape from said detection reservoirs to a surrounding environment.

70. The device of claim 69, wherein said outlet has a tapered geometry for increased volume toward the outlet end.

* * * * *